United States Patent
Shandler et al.

(10) Patent No.: US 9,789,164 B2
(45) Date of Patent: Oct. 17, 2017

(54) PEPTIDES COMPRISING NON-NATURAL AMINO ACIDS AND METHODS OF MAKING AND USING THE SAME

(71) Applicant: Longevity Biotech, Inc., Philadelphia, PA (US)

(72) Inventors: Scott Shandler, Philadelphia, PA (US); Samuel H. Gellman, Madison, WI (US); John M. Gledhill, Devon, PA (US)

(73) Assignee: LONGEVITY BIOTECH, INC., Philadelphia, PA (US)

(*) Notice: Subject to any disclaimer, the term of this patent is extended or adjusted under 35 U.S.C. 154(b) by 0 days.

(21) Appl. No.: 14/776,566

(22) PCT Filed: Mar. 17, 2014

(86) PCT No.: PCT/US2014/030527
§ 371 (c)(1),
(2) Date: Sep. 14, 2015

(87) PCT Pub. No.: WO2014/145718
PCT Pub. Date: Sep. 18, 2014

(65) Prior Publication Data
US 2016/0045572 A1 Feb. 18, 2016

Related U.S. Application Data

(60) Provisional application No. 61/801,635, filed on Mar. 15, 2013.

(51) Int. Cl.
*A61K 38/22* (2006.01)
*A61J 1/00* (2006.01)
*C07K 14/575* (2006.01)
*G01N 33/74* (2006.01)

(52) U.S. Cl.
CPC ............. *A61K 38/2278* (2013.01); *A61J 1/00* (2013.01); *C07K 14/57563* (2013.01); *G01N 33/74* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 3,989,816 A | 11/1976 | Rajadhyaksha | |
| 4,316,893 A | 2/1982 | Rajadhyaksha | |
| 4,405,616 A | 9/1983 | Rajadhyaksha | |
| 4,414,148 A | 11/1983 | Jansen et al. | |
| 4,557,934 A | 12/1985 | Cooper | |
| 4,568,343 A | 2/1986 | Leeper et al. | |
| 4,569,789 A | 2/1986 | Blattler et al. | |
| 4,589,071 A | 5/1986 | Yamamuro et al. | |
| 4,659,839 A | 4/1987 | Nicolotti et al. | |
| 4,671,958 A | 6/1987 | Rodwell et al. | |
| 4,680,338 A | 7/1987 | Sundoro | |
| 4,699,784 A | 10/1987 | Shih et al. | |
| 4,783,450 A | 11/1988 | Fawzi et al. | |
| 4,904,584 A | 2/1990 | Shaw | |
| 5,120,712 A | 6/1992 | Habener | |
| 5,188,835 A | 2/1993 | Lindskog et al. | |
| 5,218,092 A | 6/1993 | Sasaki et al. | |
| 5,464,933 A | 11/1995 | Bolognesi et al. | |
| 5,565,486 A | 10/1996 | Renno et al. | |
| 5,595,760 A | 1/1997 | Cherif-Cheikh | |
| 5,656,480 A | 8/1997 | Wild et al. | |
| 5,672,659 A | 9/1997 | Shalaby et al. | |
| 5,677,419 A | 10/1997 | Bolin et al. | |
| 5,686,511 A | 11/1997 | Bobo | |
| 5,739,106 A | 4/1998 | Rink et al. | |
| 5,990,077 A | 11/1999 | Drucker | |
| 5,998,367 A | 12/1999 | Gaeta et al. | |
| 6,007,792 A | 12/1999 | Dean et al. | |
| 6,051,555 A | 4/2000 | Hadley | |
| 6,051,557 A | 4/2000 | Drucker | |
| 6,060,585 A | 5/2000 | Gellman et al. | |

(Continued)

FOREIGN PATENT DOCUMENTS

| EP | 0188256 A2 | 7/1986 |
|---|---|---|
| EP | 0699686 A2 | 3/1996 |

(Continued)

OTHER PUBLICATIONS

The University of Maryland Medical Center (retrieved from http://umm.edu/health/medical/altmed/condition/parkinsons-disease on Jan. 10, 2017, 9 pages).*
The Mayo Clinic (retrieved from http://www.mayoclinic.org/diseases-conditions/parkinsons-disease/basics/prevention/con-20028488 on Jan. 10, 2017, 3 pages).*
WebMD (retrieved from http://www.webmd.com/parkinsons-disease/guide/parkinsons-disease-prevention on Jan. 10, 2017, 2 pages).*

(Continued)

*Primary Examiner* — Karlheinz R Skowronek
*Assistant Examiner* — Ronald Niebauer
(74) *Attorney, Agent, or Firm* — Pepper Hamilton LLP

(57) ABSTRACT

This invention relates to novel compositions comprising analogs of naturally occurring polypeptides, wherein the analog comprises an α-amino acid and at least one β-amino acid. Administration of the compositions may be used for effecting treatment or prevention of a plurality of disease states caused by dysfunctional biochemical or biological pathways. The compositions and methods of this invention are particularly useful to identify novel therapeutic modulators of in-vivo receptor activity with extended half-lives and relevant bioactivity as compared to the naturally translated polypeptides upon which the analogs are derived.

9 Claims, 14 Drawing Sheets

(56) References Cited

U.S. PATENT DOCUMENTS

| | | | |
|---|---|---|---|
| 6,133,418 | A | 10/2000 | Bolognesi et al. |
| 6,136,828 | A | 10/2000 | Elliott |
| 6,184,201 | B1 | 2/2001 | Drucker et al. |
| 6,218,410 | B1 | 4/2001 | Uehata et al. |
| 6,258,782 | B1 | 7/2001 | Barney et al. |
| 6,348,568 | B1 | 2/2002 | Barney et al. |
| 6,462,016 | B1 | 10/2002 | Wakita et al. |
| 6,562,787 | B1 | 5/2003 | Barney et al. |
| 6,608,174 | B1 | 8/2003 | Burman et al. |
| 6,656,906 | B1 | 12/2003 | Barney et al. |
| 6,683,154 | B1 | 1/2004 | Gellman et al. |
| 6,710,186 | B2 | 3/2004 | Gellman et al. |
| 6,727,368 | B1 | 4/2004 | Gellman et al. |
| 6,750,008 | B1 | 6/2004 | Jeffs et al. |
| 6,824,783 | B1 | 11/2004 | Bolognesi et al. |
| 6,849,714 | B1 | 2/2005 | Bridon et al. |
| 6,858,580 | B2 | 2/2005 | Ekwuribe et al. |
| 6,861,059 | B2 | 3/2005 | Johnson et al. |
| 6,958,384 | B2 | 10/2005 | Gellman et al. |
| 7,186,692 | B2 | 3/2007 | Quay et al. |
| 7,504,409 | B2 | 3/2009 | Zhou et al. |
| 7,723,288 | B2 | 5/2010 | During et al. |
| 8,273,713 | B2 | 9/2012 | Pittner et al. |
| 2002/0037997 | A1 | 3/2002 | Gellman et al. |
| 2002/0132766 | A1 | 9/2002 | DeGrado et al. |
| 2005/0288228 | A1 | 12/2005 | Cundy et al. |
| 2007/0224273 | A1 | 9/2007 | Xu et al. |
| 2009/0143283 | A1 | 6/2009 | Clairmont et al. |
| 2010/0048871 | A1 | 2/2010 | Cho et al. |

FOREIGN PATENT DOCUMENTS

| | | | |
|---|---|---|---|
| EP | 0708179 | A2 | 4/1996 |
| WO | 87/06941 | A1 | 11/1987 |
| WO | 90/11296 | A1 | 10/1990 |
| WO | 91/11457 | A1 | 8/1991 |
| WO | 97/39031 | A1 | 10/1997 |
| WO | 99/03887 | A1 | 1/1999 |
| WO | 99/07404 | A1 | 2/1999 |
| WO | 99/25727 | A2 | 5/1999 |
| WO | 99/25728 | A1 | 5/1999 |
| WO | 99/67291 | A2 | 12/1999 |
| WO | 00/26354 | A1 | 5/2000 |
| WO | 01/00224 | A1 | 1/2001 |
| WO | 02/47712 | A2 | 6/2002 |
| WO | 2011/133948 | A2 | 10/2011 |

OTHER PUBLICATIONS

Tams et al., Creation of a selective antagonist and agonist of the rat VPAC 1 receptor using a combinatorial approach with vasoactive intestinal peptide 6-23 as template, Molecular Pharmacology 2000 58:1035-1041.

Batterham et al., Gut hormone PYY(3-36) physiologically inhibits food intake, Nature 2002 418(6898):650-654.

Brenneman, Neuroprotection: a comparative view of vasoactive intestinal peptide and pituitary adenylate cyclase-activating polypeptide, Peptides 2007 28(9):1720-1726.

Deacon et al., Both subcutaneously and intravenously . . . from the NH2-terminus in type II diabetic patients and in healthy subjects, Diabetes 1995 44(9):1126-1131.

Deacon et al., Degradation of glucagon-like peptide-1 by . . . N-terminally truncated peptide that is a major endogenous metabolite in vivo, J Clin Endocrinol Metab 1995 80(3):952-957.

Delgado el. al., Anti-inflammatory neuropeptides: a new class of endogenous immunoregulatory agents, Brain Behav Immun 2008 22(8):1146-1151.

Dickson et al., VPAC and PAC receptors: From ligands to function, Pharmacology & Therapeutics 2009 121(3):294-316.

Eberlein et al., A new molecular form of PYY: structural characterization of human PYY(3-36) and PYY(1-36), Peptides 1989 10(4):797-803.

Gaudin et al, The human vasoactive intestinal Peptide/Pituitary adenylate cyclase activating peptide receptor 1 (VPAC1):constitutive activation by mutations at threonine 343, Biochem Biophys Res Commun 1999 254(1):15-20.

Gonzalez-Rey el. al., Anti-inflammatory neuropeptide receptors: new therapeutic targets for immune disorders?, TRENDS Pharmacal Sci 2007 28(9):482-491.

Gozes el. al., VIP and drug design, Current Pharmaceutical Design 2003 9(6):483-494.

Grandt et al., Two molecular forms of peptide YY (PYY) are abundant in human blood: characterization . recognizing PYY 1-36 and PYY 3-36, Regul Pept 1994 51(2):151-159.

Higuchi and Stella, Pro-Drugs as Novel Delivery Systems, Am Chem Soc 1975.

Knudsen et al., Potent derivatives of glucagon-like peptide-1 with pharmacokinetic properties suitable for once daily administration, J Med Chem 2000 43(9):1664-1669.

Lesma et al, An efficient enantioselective approach to cyclic b-amino acid derivatives via olefin metathesis reactions, J Org Chem 2006 71:3317-3320.

Miller, The Enantioselective Synthesis of Conformationally Constrained Cyclic beta-amino Acids, Mini Reviews in Organic Chemistry, vol. 2, No. 1, Jan. 2005.

Onoue et al., Structure-activity relationship . . . (VIP): potent agonists and potential clinical applications, Naunyn Schmiedebergs Arch Pharmacal 2008 377(4-6):579-590.

Rampelbergh et al., Characterization of a novel VPAC1 selective agonist and identifacation of the receptor domains Implicated in the carboxyl-terminal peptide recognition, British Journal of Pharmacology 2000 130:819-826.

Ritzel et al., Pharmacokinetic, insulinotropic, and glucagonostatic properties of . . in healthy volunteers. Dose-response-relationships, Diabetologia 1995 38(6):720-725.

Stark et al., Liposomal vasoactive intestinal peptide for lung application: Protection from proteolytic degradation, Eur J Pharm Biopharm 2008 70(1):153-64.

Varela el al., Tuning inflammation with anti-inflammatory neuropeptides, Expert Opin Biol Ther 2007 7(4):461-478.

de Serres et al., Immunogenicity of thrombopoietin mimetic peptide GW395058 in BALC/c mice and New Zealand white rabbits: evaluation of the potential for thrombopoietin neutralizing antibody production in man, Stem Cells 1999 17(4)203-209.

Dewit et al., The vasoactive intestinal peptide analogue RO25-1553 inhibits the production of TNF and IL-12 by LPS-activated monocytes, Immunol Lett 1998 60(1):57-60.

O'Donnell et al., RO25-1553: a novel long-acting vasoactive intestinal peptide agonist. Part 1: In vitro and in vivo bronchodilator studies, J Pharmacol Exp Ther 1994 270(3):1282-1288.

\* cited by examiner

Formula II

An APC residue within an undefined peptide chain, under neutral aqueous conditions (the ring N is protonated).

Formula III wherein X and Y combined, together with the carbon atoms to which they are bonded, define a substituted or unsubstituted $C_4$-$C_8$ cycloalkyl, cycloalkenyl or heterocyclic ring having one or more nitrogen atoms as the sole heteroatoms;

PEPTIDES COMPRISING NON-NATURAL AMINO ACIDS AND METHODS OF MAKING AND USING THE SAME

CROSS-REFERENCE TO RELATED APPLICATIONS

This application claims priority to and is a United States National Stage filing under 35 U.S.C. §371 of International PCT Application Serial No. PCT/US2014/030527, filed Mar. 17, 2014, which claims priority to U.S. Provisional Application No. 61/801,635, filed Mar. 15, 2013, which is incorporated herein by reference in its entirety.

FIELD OF THE INVENTION

The invention relates generally to compositions comprising modified polypeptide sequences with greater resistance to degradation and increased receptor selectivity as compared to naturally encoded, unmodified polypeptide sequences, and to methods of making the compositions and methods of using the compositions as pharmaceutically active agents to treat disease in animals, including humans.

BACKGROUND OF THE INVENTION

The q25 region of chromosome 6 on the human genome encodes a VIP family member that is 170 amino acids long which becomes post-translationally cleaved to form vasoactive intestinal peptide (VIP). The active form of the VIP polypeptide is a 28 amino acid protein that functions, among other ways, to reduce arterial blood pressure, to increase vasodilation of blood vessel walls, to relax smooth muscle in the respiratory system and gastrointestinal tissues, reduce inflammatory responses through both promotion of Th2 differentiation as well as the reduction of Th1 responses, modulate both the innate and adaptive immune response, and to stimulate secretion of electrolytes in the gut. VIP has also been shown to be active in the central nervous system as a neurotransmitter and in communication with lymphocytes.

VIP family members have short half-lives. For instance, VIP has a half-life of about two minutes in the blood stream. It is desirable to identify polypeptides that mimic the function of VIPs such as VIP, but have increased half-life and equivalent or more receptor selectivity than the naturally occurring VIP amino acid sequence.

Bioactivity of VIP is transmuted through three known receptor subtypes: $VIP_1R$, $VIP_2R$, and $PAC_1R$. These receptors are known to induce cAMP concentration as well as stimulate the production of intracellular calcium. Their affinities for VIPs such as VIP vary depending upon the subtype and the amino acid sequence of the ligand. VPAC1 has been implemented in cancer as well as inflammatory diseases such as multiple sclerosis, arthritis, parkinson's disease and alzheimers. VPAC2R dysfunction has been implemented in neurodegenerative disorders, diabetes, and pulmonary arterial hypertension (PAH), among other disorders. It desirable to identify a peptidomimetic of VIP to have selectively antagonize or affect one VIP receptor subtype over another VIP receptor subtype in order to treat a disease related to the biological affects of one receptor without disrupting or otherwise interfering with the normal biological affects of another receptor with the same ligand.

SUMMARY OF THE INVENTION

The selected pattern of synthetic amino acids along the helical polypeptide decreases the rate at which the polypeptide may degrade when administered to a subject or when reconstituted or placed in solution. Selected side chains of the amino acids increase the conformational rigidity of the polypeptide in order to constrain the polypeptide in its active state. The selected pattern of synthetic amino acids along the helical polypeptide increases the half-life of the polypeptide as compared to naturally encoded polypeptides with the same α-amino acid sequence. In some embodiments, the polypeptide comprises β-amino acids that spatially aligned along a longitudinal axis of the analog in order to confer degradation resistance to the composition while preserving the native binding interface. In some embodiments, the composition comprises a VIP analog. In some embodiments, the composition comprises a vasoactive intestinal peptide (VIP) analog based upon the sequences disclosed herein.

In some embodiments, the composition comprises a VIP analog wherein the total number of β-amino acids in the analog is from about 10 percent to about 60 percent of the total number of amino acids of the analog. In some embodiments, the composition comprises a VIP analog wherein the total number of β-amino acids in the analog is from about 12 percent to about 50 percent of the total number of amino acids of the analog. In some embodiments, the composition comprises a VIP analog wherein the total number of β-amino acids in the analog is from about 14 percent to about 50 percent of the total number of amino acids of the analog. In some embodiments, the composition comprises a VIP analog wherein the total number of β-amino acids in the analog is from about 16 percent to about 50 percent of the total number of amino acids of the analog. In some embodiments, the composition comprises a VIP analog wherein the total number of β-amino acids in the analog is from about 18 percent to about 50 percent of the total number of amino acids of the analog. In some embodiments, the composition comprises a VIP analog wherein the total number of β-amino acids in the analog is from about 20 percent to about 50 percent of the total number of amino acids of the analog. In some embodiments, the composition comprises a VIP analog wherein the total number of β-amino acids in the analog is from about 30 percent to about 50 percent of the total number of amino acids of the analog.

In some embodiments, the composition comprises a VIP analog wherein the total number of β-amino acids in the analog is from about 40 percent to about 50 percent of the total number of amino acids of the analog. In some embodiments, the composition comprises a VIP analog wherein the total number of β-amino acids in the analog is from about 45 percent to about 50 percent of the total number of amino acids of the analog. In some embodiments, the composition comprises a VIP analog wherein the total number of β-amino acids in the analog is from about 40 percent to about 45 percent of the total number of amino acids of the analog.

In some embodiments, the composition comprises a VIP analog wherein the total number of β-amino acids in the analog is from about 30 percent to about 40 percent of the total number of amino acids of the analog. In some embodiments, the composition comprises a VIP analog wherein the total number of β-amino acids in the analog is from about 35 percent to about 40 percent of the total number of amino acids of the analog. In some embodiments, the composition comprises a VIP analog wherein the total number of β-amino acids in the analog is from about 20 percent to about 30 percent of the total number of amino acids of the analog.

In some embodiments, the composition comprises a VIP analog wherein the total number of β-amino acids in the analog is from about 10 percent to about 20 percent of the total number of amino acids of the analog. In some embodiments, the composition comprises a VIP analog wherein the total number of β-amino acids in the analog is from about 15 percent to about 20 percent of the total number of amino acids of the analog. In some embodiments, the composition comprises a VIP analog wherein the total number of β-amino acids in the analog is from about 20 percent to about 25 percent of the total number of amino acids of the analog. In some embodiments, the composition comprises a VIP analog wherein the total number of β-amino acids in the analog is from about 25 percent to about 30 percent of the total number of amino acids of the analog. In some embodiments, the composition comprises a VIP analog wherein the total number of β-amino acids in the analog is from about 30 percent to about 35 percent of the total number of amino acids of the analog.

Those of skill in the art will appreciate that amino acid positions corresponding to positions in analogs can be readily identified in any other molecule such as analog fusions, variants, fragments, etc. For example, sequence alignment by visual means or computer programs such as BLAST can be used to align and identify a particular position in a protein that corresponds with a position in the analog of polypeptide sequences identified in this application or other GLP-1, VIP, PYY, IL-10, PACAP, Ghrelin, ANP/BNP/CNP, Maxadilan/M65, The term analog encompasses polypeptides comprising one or more amino acid substitutions, additions or deletions. Analogs of the present invention may be comprised of modifications with one or more natural amino acids in conjunction with one or more non-natural amino acid modification. Exemplary substitutions in a wide variety of amino acid positions in naturally-occurring analogs have been described, including but not limited to substitutions that modulate one or more of the biological activities of the analogs, such as but not limited to, increase agonist activity, increase solubility of the polypeptide, convert the polypeptide into an antagonist, decrease peptidase or protease susceptibility, etc. and are encompassed by the term analog.

In some embodiments, the analogs further comprise an addition, substitution or deletion that modulates biological activity of the analogs. For example, the additions, substitution or deletions may modulate one or more properties or activities of the analog. For example, the additions, substitutions or deletions may modulate affinity for the analog receptor or binding partner, modulate (including but not limited to, increases or decreases) receptor dimerization, stabilize receptor dimers, modulate the conformation or one or more biological activities of a binding partner, modulate circulating half-life, modulate therapeutic half-life, modulate stability of the polypeptide, modulate cleavage by peptidases or proteases, modulate dose, modulate release or bio-availability, facilitate purification, or improve or alter a particular route of administration. Similarly, analogs of the present invention may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

Vasoactive intestinal peptides (VIP/PHI) including, but not limited to, VIP, human, porcine, rat, ovine; VIP-Gly-Lys-Arg-NH$_2$; biotinyl-PHI (biotinyl-PHI-27), porcine; {Glp$^{16}$}VIP 16-28, porcine; PHI (PHI-27), porcine; PHI (PHI-27), rat; PHM-27 (PHI), human; prepro VIP 81-122, human; preproVIP/PHM 111-122; prepro VIP/PHM 156-170; biotinyl-PHM-27 (biotinyl-PHI), human; vasoactive intestinal contractor (endothelin-beta); vasoactive intestinal octacosa-peptide, chicken; vasoactive intestinal peptide, guinea pig; biotinyl-VIP, human, porcine, rat; vasoactive intestinal peptide 1-12, human, porcine, rat; vasoactive intestinal peptide 10-28, human, porcine, rat; vasoactive intestinal peptide 11-28, human, porcine, rat, ovine; vasoactive intestinal peptide (cod, Gadus morhua); vasoactive intestinal peptide 6-28; vasoactive intestinal peptide antagonist; vasoactive intestinal peptide antagonist ({Ac-Tyr$^1$, D-Phe$^2$}-GHRF 1-29 amide); vasoactive intestinal peptide receptor antagonist (4-Cl-D-Phe$^6$, Leu$^{17}$}-VIP); and vasoactive intestinal peptide receptor binding inhibitor, L-8-K. Additional constructs include but are not limited to, Ala{$^{11,22,28}$} VIP, Ala{$^{2,8,9,11,19,22,24,25,27,28}$} VIP, {K$^{15}$, R$^{16}$, L$^{27}$}-VIP(1-7)/GRF(8-27), Ro25-1553, Ro25-1392, BAY55-9837, R3P65, Maxadilan, PG97-269, PG99-465, Max.d.4., and M65 (Dickson & Finlayson, Pharmacology & Therapeutics, Volume 121, Issue 3, March 2009, Pages 294-316).

A very wide variety of non-naturally encoded amino acids are suitable for use in the present invention. Any number of non-naturally encoded amino acids can be introduced into an analog. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, an analog that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen {3+2} cycloaddition product.

In some embodiments, the composition or pharmaceutical compositions of the claimed invention comprises an analog of a polypeptide, wherein the analog amino acid sequence is based upon the fragments, polypeptides, polymers and functional deriviatives disclosed herein or combinations thereof and wherein the analog comprises at least one or a plurality of non-natural amino acids and at least one or a plurality of β-amino acid residues. A non-natural amino acid typically possesses an R group that is any substituent other than one component of the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-natural amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-natural amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. In some embodiments, the invention relates to a method of manufacturing a polypeptide analog wherein the polypeptide analog is manufactured using a synthesis technique disclosed in the following references, which are incorporated herein by reference: For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural (or non-natural) amino acids that contain novel side chains, unnatural amino acids that may be suitable for use in the present invention also optionally comprise modified backbone structures, including but not limited to, as illustrated by the structures of Formula II and III of U.S. Patent Application Publication 2010-0048871, wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids as well as hydrogen. For example, unnatural amino acids of the invention optionally comprise substitutions in the amino or carboxyl group as illustrated by Formulas II and III. Unnatural amino acids of this type include, but are not limited to, $\alpha$-hydroxy acids, $\alpha$-thioacids, $\alpha$-aminothiocarboxylates, including but not limited to, with side chains corresponding to the common twenty natural amino acids or unnatural side chains. In addition, substitutions at the $\alpha$-carbon optionally include, but are not limited to, L, D, or $\alpha$-$\alpha$-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, $\beta$ amino acids such as substituted $\beta$-alanine.

In some embodiments, the composition or pharmaceutical compositions of the claimed invention comprises an analog of a polypeptide, wherein the analog amino acid sequence is based upon the fragments, polypeptides, and functional deriviatives disclosed herein and wherein the analog comprises at least one or a plurality of unnatural amino acid or non-natural amino acid and at least one or a plurality of $\beta$-amino acid residues, wherein the unnatural amino acids based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, $\alpha$.-hydroxy derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an 0-4-allyl-L-tyrosine, a 4-propyl-L-tyrosine, a tri-O-acetyl-GlcNAc$\beta$-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002). Incorporation of azides into recombinant proteins for chemoselective modification by the Staudinger ligation, PNAS 99:19-24, for additional methionine analogs.

The chemical moieties via unnatural amino acids that can be incorporated into analogs offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. In some embodiments, the composition or pharmaceutical compositions of the claimed invention comprises an analog of a polypeptide, wherein the analog amino acid sequence is based upon the fragments, polypeptides, and functional deriviatives disclosed herein and wherein the analog comprises at least one or a plurality of unnatural amino acid or non-natural amino acid and at least one or a plurality of β-amino acid residues, wherein the unnatural amino is a photoreactive unnatural amino acid chosen from (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a {3+2} cycloaddition reaction.

A non-natural amino acid incorporated into a polypeptide at the amino terminus can be composed of an R group that is any substituent other than one used in the twenty natural amino acids and a second reactive group different from the $NH_2$ group normally present in α-amino acids. A similar non-natural amino acid can be incorporated at the carboxyl terminus with a second reactive group different from the COOH group normally present in α-amino acids.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chattenji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4{{4-(diethylamino)-}-methylbutyl}amino}quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 50:1239-1246; Barton et al., (1987) Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives. Tetrahedron 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Any of the compositions above may be used in the methods disclosed in this instant specification.

In another embodiment of the invention, the composition comprises a VIP analog, wherein the analog does not comprise a repetitive pattern of β-amino acids from the amino-terminus to the carboxy-terminus selected from the following: αααααβ, ααααβα, αααβαα, ααβααα, αβαααα, βααααα, ααααββ, αααββα, αααββαα, ααββαα, αββααα, ββαααα, βαααααβ, βααααβα, αβββαββ, βααβααα, βαβαααα, αβαααβ, αβαααβα, αβααβαα, αβαβααα, ααβαααβ, ααβααβα, ααβαβαα, αααβααβ, αααβαβα, and αααβααβ.

Some embodiments of the claimed invention include pharmaceutical compositions.

In some embodiments, the pharmaceutical composition comprises any of the aforementioned compositions in combination with a pharmaceutically acceptable carrier. In another embodiment of the invention, the pharmaceutical composition comprises a VIP analog and fused, covalently bound to or linked by chemical linkage to one other active agent. In some embodiments, the chemical linkage disclosed herein is used.

In another embodiment of the invention, the pharmaceutical composition comprises a VIP analog and one other active agent, wherein the VIP analog comprises at least one α-amino acid and at least one β-amino acid.

In some embodiments, the composition, pharmaceutical compositions, kit, or polypeptides of the invention comprise a VIP analog, wherein the analog is either: (a) an agonist of VPAC2 receptor; or (b) interferes with VPAC2 receptor signaling pathway and comprises the following repetitive pattern of β-amino acids from the amino-terminus to the carboxy-terminus: $β_1α_1α_2α_3β_2α_4α_5β_3$, wherein $β_1$, $β_2$ and $β_3$ are β-homo amino acids; wherein there is an optional β amino acid ($β_0$ or $β_4$) to one of the β-homo amino acids (e.g. $β_{1-3}$); wherein the composition, pharmaceutical compositions, kit, or polypeptides of the invention optionally comprise amino acids with a pattern selected from: αααααβ, αααααβα, αααβαα, αααβααα, ααβαααα, αβααααα, βααααααα, αααααββ, ααααββα, αααββαα, ααββααα, αββαααα, ββααααα, βααααααβ, βααααβα, βαααβαα, βααβααα, βαβαααα, αβααααβ, αβαααβα, αβααβαα, αβαβααα, ααβαααβ, αα immune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction comprising administrating any one of the compositions or pharmaceutical compositions comprising a VIP family analog, or a pharmaceutical salt derived therefrom, to a subject in need thereof.

The present invention also relates to methods of selectively targeting tumor cells which over-express the VPAC1 receptor. Specific analogs described herein are capable of high-affinity and high selectivity binding to the VPAC1 receptor in agonist mode. This selective binding enables a highly targeted approach to selective killing of tumor cells that over-express these receptors. By incorporating chemotherapeutic payloads to these compounds, these cells can be specifically targeted for chemotherapeutic delivery. This targeting ability greatly improves the side-effect profile of systemically available chemotherapeutics by delivering the toxic drug to tumor cells that express this receptor. The payloads cover a variety of biological mechanisms including tubulin inhibitors, DNA intercalators to name a few. These payload molecules can be covalently linked to the targeting parent molecules described herein for optional cleavage within the lysosomal endocytosis pathway as either a function of pH or enzymatic release. The internalization process is part of the endogenous molecular biology of this receptor upon activation. Payloads can be either a single molecule or a combination (linear or otherwise) of known chemotherapeutic candidates. Payload linkages can be achieved using either polymer or amino acid based approaches. Examples of cleavable linkers include di-peptides such as Pro-Pro or Cit-Val (Cit being citrulline). Linkages typically occur on either free amine or cysteine groups. Linkage chemistry is typically a result of click chemistry and can be conducted while the peptide analogs described herein are still attached to solid support by using orthogonal protecting groups resulting in site-specific protecting group removal thus enabling direct linkage at the desired position. It is also possible to link payloads on either the c or n termini of the peptide analogs described herein. Covalently attached payloads may also contain non-functional spacers in order to properly position the payload for its desired action. These non-functional spacers could be a combination of polyethylene glycol or amino acid derivatives ($\alpha$, $\beta$ or gamma amino acid in nature). The length of these spacers fulfills the required biophysical orientation between the targeting molecule and its toxic payload.

The present invention also relates to methods of inhibiting secretion of TNF-$\alpha$ in a subject comprising administering a composition comprising a vasoactive intestinal peptide (VIP) analog to a subject, wherein said analog comprises at least one of the sequences disclosed herein. In some embodiments, the method comprises administering the composition comprising any of the percentages of $\beta$-amino acids disclosed herein.

The present invention is also directed towards kits comprising any of the aforementioned compositions or pharmaceutical compositions comprising a VIP analog, wherein the VIP analog comprises an $\alpha$-amino acid and at least one $\beta$-amino. The present invention is directed toward kits comprising any of the aforementioned compositions or pharmaceutical compositions comprising a VIP analog, wherein the VIP analog comprises an a-amino acid and at least on $\beta$-amino acid. In some embodiments, the kit further comprises a vehicle for administration of the composition.

The present invention also relates to methods of identifying a modulator of VIP receptor activity comprising:

a) contacting a human receptor with a VIP analog, wherein the analog comprises an $\alpha$-amino acid and at least one $\beta$-amino acid;

b) measuring the association of the VIP analog to the human receptor in the presence and absence of an unknown compound; and c) comparing the rate of association of the VIP analog to the human receptor in the presence of an unknown compound to the rate of association of the VIP analog to the human receptor in the absence of an unknown compound.

The present invention also relates to methods of identifying a modulator of animal receptor activity comprising:

a) contacting an animal receptor with a VIP analog, wherein the analog comprises an $\alpha$-amino acid and at least one $\beta$-amino acid;

b) measuring the association of the VIP analog to the animal receptor in the presence and absence of an unknown compound; and c) comparing the rate of association of the VIP analog to the animal receptor in the presence of an unknown compound to the rate of association of the VIP analog to the animal receptor in the absence of an unknown compound.

In addition, imaging agents (Tc99 based or other well-known agents) may be covalently or non-covalently attached to either the C or N-termini or free-amine groups of the analogs described herein. These agents enable the molecular detection of cell-surface receptors using well-known technologies (e.g. PET and MRI). The ability to detect cells that overexpress the VPAC1 receptor is a valuable diagnostic tool for clinical medicine. In addition, these imaging agents may be used in combination with either the optional spacers described above and/or the cytotoxic payloads also described earlier, thus resulting in a therapeutic agent with reporting capabilities. In some embodiments, the invention relates to a method of imaging cellular receptors, comprising administering an analog described herein with a imaging agent. In some embodiments, the invention relates to a method of imaging cellular receptors, comprising administering an analog described herein covalently bound to an imaging agent. In some embodiments, the imagining agent can be read by CAT scan, PET scan, or MRI.

The present invention also relates to methods of identifying a modulator of human VIP receptor activity comprising:

a) contacting a human VIP receptor with a VIP analog, wherein the analog comprises an $\alpha$-amino acid and at least one $\beta$-amino acid;

b) measuring the association of the VIP analog to the human VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

The present invention also relates to methods of identifying a modulator of human VIP receptor activity comprising:

a) contacting a human VIP receptor with the VIP analog, wherein the analog comprises an $\alpha$-amino acid and at least one $\beta$-amino acid;

b) measuring the association of the VIP analog to the human VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

DETAILED DESCRIPTION OF ILLUSTRATIVE EMBODIMENTS

Figure 1:
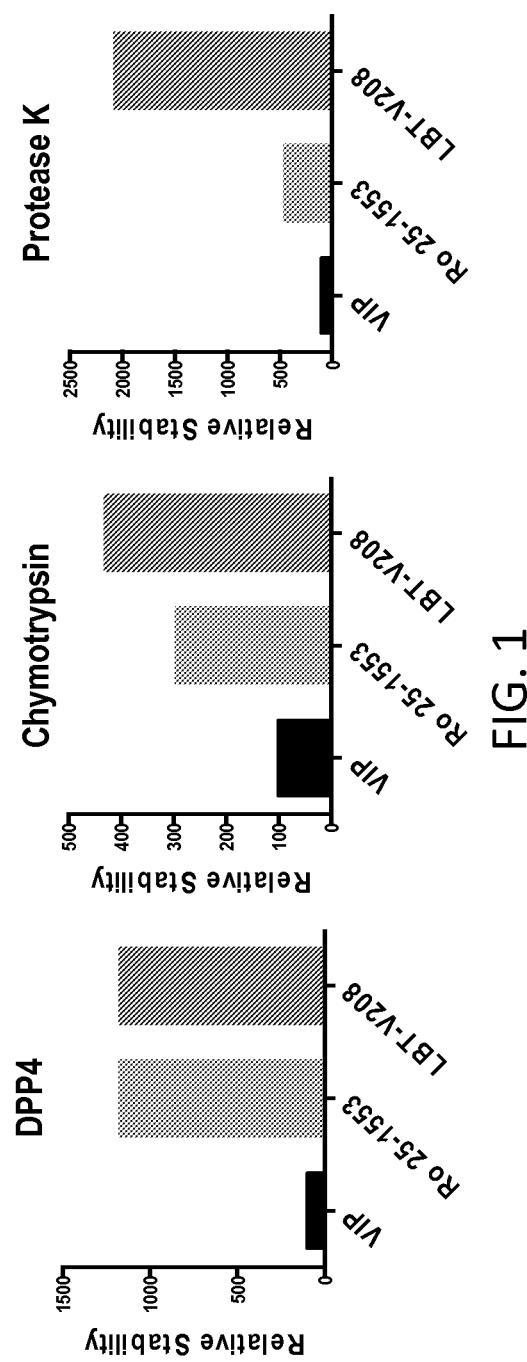
FIG. 1 depicts a representative in-vitro protease stability of VPAC-2 selective analog (LBT-V208, SEQ ID NO: 8) compared to the native VIP as well as the VPAC2 selective agonist Ro 25-1553. It is noteworthy that the stability is greater for the non-lactam containing LBT-V208 as compared to Ro 25-1553, which contains one lactam bridge between lysine and aspartic acid residues.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "active state" refers to the conformation or set of conformations of a polypeptide that allows functional domain or domains of the polypeptide to associate or disassociate with another compound, macromolecule, or ligand. In some embodiments, the association or disassociation of the polypeptide with another compound, macromolecule, or ligand may propagate or inhibit a biologic signal.

The terms "amino acid" refer to a molecule containing both an amino group and a carboxyl group bound to a carbon which is designated the α-carbon. Suitable amino acids include, without limitation, both the D- and L-isomers of the naturally-occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "analog" refers to any polypeptide comprising at least one α-amino acid and at least one β-amino acid residue, wherein the polypeptide is structurally similar to a naturally occurring full-length protein and shares the biochemical or biological activity of the naturally occurring full-length protein upon which the analog is based. In some embodiments, an analog is any polypeptide comprising at least two contiguous β-amino acid residues, wherein the polypeptide is structurally similar to a naturally occurring full-length protein and shares the biochemical or biological activity of the naturally occurring full-length protein upon which the analog is based and wherein the addition of one or more β-amino acid residues constrains an alpha helical structure in the polypeptide. In some embodiments, an analog is any polypeptide comprising at least three contiguous β-amino acid residues, wherein the polypeptide is structurally similar to a naturally occurring full-length protein and shares the biochemical or biological activity of the naturally occurring full-length protein upon which the analog is based.

Various references disclose modification of polypeptides by polymer conjugation or glycosylation. The term analog includes polypeptides conjugated to a polymer such as PEG and may be comprised of one or more additional derivatizations of cysteine, lysine, or other residues. In addition, analogs of the instant invention may comprise a linker or polymer, wherein the amino acid to which the linker or polymer is conjugated may be a non-natural amino acid, or may be conjugated to a naturally encoded amino acid utilizing techniques known in the art such as coupling to lysine or cysteine.

Polymer modification of polypeptides has been reported. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. Examples of PEGylated peptides include GW395058, a PEGylated peptide thrombopoietin receptor (TPOr) agonist (de Serres M., et al., Stem Cells. 1999; 17(4):203-9), and a PEGylated analogue of growth hormone releasing factor (PEG-GRP; D'Antonio M, et al. Growth Horm IGF Res. 2004 June; 14(3):226-34).

The term analog also includes glycosylated analogs, such as but not limited to, analogs glycosylated at any amino acid position, N-linked or O-linked glycosylated forms of the polypeptide. In addition, splice variants are also included. The term analog also includes heterodimers, homodimers, heteromultimers, or homomultimers of any one or more polypeptide, protein, carbohydrate, polymer, small molecule, linker, ligand, or other biologically active molecule of any type, linked by chemical means or expressed as a fusion protein, as well as polypeptide analogs containing, for example, specific deletions or other modifications yet maintain biological activity.

In some embodiments, the non-natural amino acid residue is a monomer of an aliphatic polypeptide. In some embodiments the aliphatic analogs are chosen from oligoureas, azapeptides, pyrrolinones, α-aminoxy-peptides, and sugar-based peptides. In some embodiments, the composition comprises a non-natural β-amino acid. In some embodiments, the analog or active agent couple thereto is a fragment of the full-length protein or macromolecule. In some embodiments, fragments are from about 5 to about 500 amino acids in length as compared to the naturally occurring, fully translated and fully processed protein sequences. In some embodiments, the analogs comprise a fragment of a naturally translated full-length protein that induces the biochemical or biological activity of a biological pathway of a subject at a level equivalent to or increased as compared to the activity induced by a naturally occurring full-length protein upon which the analog is derived. In some embodiments, the analog is a truncated polypeptide as compared to the full-length, naturally translated or naturally occurring polypeptide upon which the truncated polypeptide is derived. In some embodiments, the analog is a synthetic polypeptide, wherein at least one of the amino acid residues of the polypeptide comprises at least one non-natural side chain. In some embodiments, the analogs of the invention comprise at least one non-natural amino acid chosen from one of the following structures: aminoisobutyric acid, 3-Aminobutyric acid, and 2-hydroxy-4-(4-nitrophenyl)butyric acid. In some embodiments, the analog has a polypeptide backbone of identical length and similar homology to the polypeptides disclosed in Table 1. In some embodiments, the analog is about 70%, 75%, 80%, 85%, 90%, 95%, 98%, or 99% homolgous to at least one of the polypeptides disclosed in Table 1. In some embodiments, the analog is an agonist or antagonist of one or more of the following receptors: VPAC1, VPAC2, or PAC1. In some embodiments the analog of the present invention is modified by a bioactive lipid moiety on at least one amino acid residue of the analog. In such embodiments, 10 the lipid moieties may be chosen from the following lipid molecules: LPA, progesterone, prostanoids, SIP, LPA, cannabinoids, 2-arachidonylglycerol.

TABLE 1

| Identifier | Sequence | Seq ID |
|---|---|---|
| LBT-V201 | Ac-HSDAVFTENYTKLRKQLA<u>x</u>KKY<u>x</u>ND<u>l</u>KKG<u>g</u>T | (Seq ID NO: 1) |
| LBT-V202 | Ac-HSDAVFTENYTKLRKQLAA<u>z</u>KY<u>x</u>NDL<u>k</u>KG<u>g</u>T | (Seq ID NO: 2) |

TABLE 1-continued

| Identifier | Sequence | Seq ID |
|---|---|---|
| LBT-V203 | Ac-HSDAVFTENYTKLRKQxAAzKYLxDLkKGGT | (Seq ID NO: 3) |
| LBT-V204 | Ac-HBDAVFTENYTKLRKQLAAzKYxNDLkKGgT | (Seq ID NO: 4) |
| LBT-V205 | Ac-HBDAvFTENYTKLRKQLAAzKYxNDLkKGgT | (Seq ID NO: 5) |
| LBT-V206 | Ac-HBDAvFTEnYTKLRKQLAAzKYxNDLkKGgT | (Seq ID NO: 6) |
| LBT-V207 | Ac-HxDAVFTENYTKLRKQLAAzKYxNDLkKGgT | (Seq ID NO: 7) |
| LBT-V208 | Ac-HxDAxFTENYTKLRKQLAAzKYxNDLkKGgT | (Seq ID NO: 8) |
| LBT-V209 | Ac-HxDAxFTExYTKLRKQLAAzKYxNDLkKGgT | (Seq ID NO: 9) |
| LBT-V210 | Ac-HxDAvFTENYTKLRKQLAAzKYxNDLkKGgT | (Seq ID NO: 10) |
| LBT-V211 | Ac-HxDAvFTENYTKLRKQlAAzKYxNDLkKGgT | (Seq ID NO: 11) |
| LBT-V212 | Ac-HxDAvFTENYTKLRKqLAAzKYxNDLkKGgT | (Seq ID NO: 12) |
| LBT-V213 | Ac-HxDAvFTENYTKLRkQLAAzKYxNDLkKGgT | (Seq ID NO: 13) |
| LBT-V214 | Ac-HxDAvFTENYTKLrKQLAAzKYxNDLkKGgT | (Seq ID NO: 14) |
| LBT-V215 | Ac-HxDAvFTENYTKlRKQLAAzKYxNDLkKGgT | (Seq ID NO: 15) |
| LBT-V216 | Ac-HxDAxFTEnyTKLRKQLAAzKYxNDLkKGgT | (Seq ID NO: 16) |
| LBT-V217 | Ac-HxDAxFTExyTKLRKQlAAzKYxNDLkKGgT | (Seq ID NO: 17) |
| LBT-V218 | Ac-HxDAxFTExyTKLRKqLAAzKYxNDLkKGgT | (Seq ID NO: 18) |
| LBT-V219 | Ac-HxDAxFTExyTKLRkQLAAzKYxNDLkKGgT | (Seq ID NO: 19) |
| LBT-V220 | Ac-HSDAVFTENYTKLRKQxAAKzYLxDLkKGGT | (Seq ID NO: 20) |
| LBT-V221 | Ac-HSDAVFTDNYTRLRKQxAAKzYLxSIKnKRY | (Seq ID NO: 21) |
| LBT-V101 | HSDAVFTDNYtRLRkQLAvKKYlNAIlN | (Seq ID NO: 22) |
| LBT-V102 | HxDAVFTDNYtRLRkQLAvKKYlNAIlN | (Seq ID NO: 23) |
| LBT-V103 | HxDAxFTDNYtRLRkQLAvKKYlNAIlN | (Seq ID NO: 24) |
| LBT-V104 | HxDAvFTDNYtRLRkQLAvKKYlNAIlN | (Seq ID NO: 25) |
| LBT-V105 | HsDAvFTDNYtRLRkQLAvKKYlNAIlN | (Seq ID NO: 26) |
| LBT-V106 | HsDAvFTDnYtRLRkQLAvKKYlNAIlN | (Seq ID NO: 27) |
| LBT-V107 | HSdAVFtDNYtRLRkQLAvKKYlNAIlN | (Seq ID NO: 28) |
| LBT-V108 | HSdAVFTDNYtRLRkQLAvKKYlNAIlN | (Seq ID NO: 29) |
| LBT-V109 | HSDaVFTDNYtRLRkQLAvKKYlNAIlN | (Seq ID NO: 30) |
| LBT-V110 | HSDAVfTDNYtRLRkQLAvKKYlNAIlN | (Seq ID NO: 31) |
| LBT-V111 | HSDAVFtDNYtRLRkQLAvKKYlNAIlN | (Seq ID NO: 32) |
| LBT-V112 | HSDAVFTdNYtRLRkQLAvKKYlNAIlN | (Seq ID NO: 33) |
| LBT-V113 | HSDAVFTDnYtRLRkQLAvKKYlNAIlN | (Seq ID NO: 34) |
| LBT-V114 | HSDAVFTDNYtRLRkQLAvKKYlNAIlN | (Seq ID NO: 35) |
| LBT-V115 | HSDAVfTDNYytRLRkQLAvKKYlNAIlN | (Seq ID NO: 36) |
| LBT-V116 | HSDAVFtDNYtRLRkQLAvKKYlNAIlN | (Seq ID NO: 37) |
| LBT-V117 | HSDaVFtDNYtRLRkQLAvKKYlNAIlN | (Seq ID NO: 38) |
| LBT-V118 | HSDAVFTNSYrKVLkRLsaRKLlQDIl** | (Seq ID NO: 39) |
| LBT-V119 | HSDAVFTNSYRkVLkRrLSArKLLqDIL | (Seq ID NO: 40) |
| LBT-V120 | HSDAVFTNSyRKVlKRLsARKlLQDiL | (Seq ID NO: 41) |

TABLE 1-continued

| Identifier | Sequence | Seq ID |
|---|---|---|
| LBT-V121 | HxDAxFTNSYrKVLkRLSaRKLlQDIl | (Seq ID NO: 42) |
| LBT-V122 | HxDAxFTNxyRKVLKrLSAzKLxQDIl | (Seq ID NO: 43) |
| LBT-V123 | HSDAVFTNSYRKVLKrLSaRKLlQDIl | (Seq ID NO: 44) |
| LBT-V124 | HSDAVFTNSYRKVLKrLSaRKLlQDiL | (Seq ID NO: 45) |
| LBT-V125 | HSDAVFTNSYRKVLKRlSArKLLqDIl | (Seq ID NO: 46) |
| LBT-V126 | H*f*DAVFTDNYtRLRkQLAvKKYlNAIlN | (Seq ID NO: 47) |
| LBT-V127 | H*f*DAxFTDNYtRLRkQLAvKKYlNAIlN | (Seq ID NO: 48) |
| LBT-V128 | H*f*DAvFTDNYtRLRkQLAvKKYlNAIlN | (Seq ID NO: 49) |
| LBT-V129 | H*f*DAvFTDnYtRLRkQLAvKKYlNAIlN | (Seq ID NO: 50) |
| LBT-V130 | H*f*dAVFtDNYtRLRkQLAvKKYlNAIlN | (Seq ID NO: 51) |
| LBT-V131 | H*f*DAVFTNSYrKVLkRLSaRKLlQDIl | (Seq ID NO: 52) |
| LBT-V132 | H*f*DAVFTNSYRkVLKrLSArKLLqDIL | (Seq ID NO: 53) |
| LBT-V133 | H*f*DAVFTNSyRKVlKRLsARKlLQDiL | (Seq ID NO: 54) |
| LBT-V134 | H*f*DAxFTNSYrKVLkRLSaRKLlQDIl | (Seq ID NO: 55) |
| LBT-V135 | H*f*DAxFTNxyRKVLKrLSAzKLxQDIl | (Seq ID NO: 56) |
| LBT-V136 | H*f*DAVFTNSYRKVLKrLSaRKLlQDIl | (Seq ID NO: 57) |
| LBT-V137 | H*f*DAVFTNSYRKVLKrLSaRKLlQDiL | (Seq ID NO: 58) |
| LBT-V138 | H*f*DAVFTNSYRKVLKRlSArKLLqDIl | (Seq ID NO: 59) |
| LBT-V222 | Ac-HxDAxFTExyTKLRKqLAAzKYxNDLkKgGT | (Seq ID NO: 60) |
| LBT-V223 | Ac-HxDAxFTExyTKLRKqLAAzKYxNDLkKggT | (Seq ID NO: 61) |
| LBT-V224 | Ac-HxDAxFTExyTKLRKqLAAzKYxNDLkKGGt | (Seq ID NO: 62) |
| LBT-V225 | Ac-HxDAxFTExyTKLRKqLAAzKYxNDLkKgGt | (Seq ID NO: 63) |
| LBT-V226 | Ac-HxDAxFTExyTKLRKqLAAzKYxNDLkKGgt | (Seq ID NO: 64) |

LBT V201 through LBT-V226 (SEQ ID NOs: 1-21 and 60-64) are VPAC₂ selective
LBT V101 through LBT-138 (SEQ ID NOs: 22-59) are VPAC₁ selective
Lowercase, bold and underlined represent Homo-Beta3 amino acids
Italic, lowercase F represents d-Phenylalanine
Lowercase, bold and underlined x represents APCP (2-aminocyclopentane carboxylic acid)

The term "α-amino acid" refers to any and all natural and unnatural α-amino acids and their respective residues (i.e., the form of the amino acid when incorporated into a polypeptide molecule), without limitation. In some embodiments, "α-amino acid" explicitly encompasses the conventional and well-known naturally occurring amino acids, as well as all synthetic variations, derivatives, and analogs thereof. In some embodiments, "α-amino acid" means alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine. In some embodiments, α-amino acids also include analogs such as N-methylated α-amino acids, hydroxylated α-amino acids, and aminoxy acids. In some embodiments, α-amino refers to include N-alkyl α-amino acids (such as N-methyl glycine), hydroxylysine, 3-hydroxyproline, 4-hydroxyproline, nor-valine, nor-leucine, and ornithine.

The terms "β-amino acid" and "β-amino acid residue" refer to any and all β-amino acids and their respective residues (i.e., the form of the amino acid when incorporated into a polypeptide molecule), without limitation. In some embodiments, the terms "β-amino acid" refers to those β-amino acids described in U.S. Pat. No. 6,060,585, issued May 9, 2000, incorporated herein by reference, and those described in allowed U.S. Pat. No. 6,683,154, issued Jan. 27, 2004; U.S. Pat. No. 6,710,186, issued Mar. 23, 2004; and U.S. Pat. No. 6,727,368, issued Apr. 27, 2004, all of which are incorporated herein by reference. Further still, cyclic imino carboxylic acids and gem-di-substituted cyclic imino carboxylic acids (both of which are a type of cyclically-constrained β-amino acid) may also be used in the invention. In some embodiments, the term "β-amino acid" refers to residues disclosed in U.S. Pat. No. 6,958,384, issued Oct. 25, 2005, incorporated herein by reference. Further still, these β-residues may also take the form of the gem-di-substituted cyclic imino acids disclosed in U.S. Pat. No. 6,710,186, incorporated herein by reference. In some embodiments, the terms "β-amino acid" refers to β-homo amino acids. In some embodiments the β-amino acids refers to the selection of an amino acid chosen from the following:

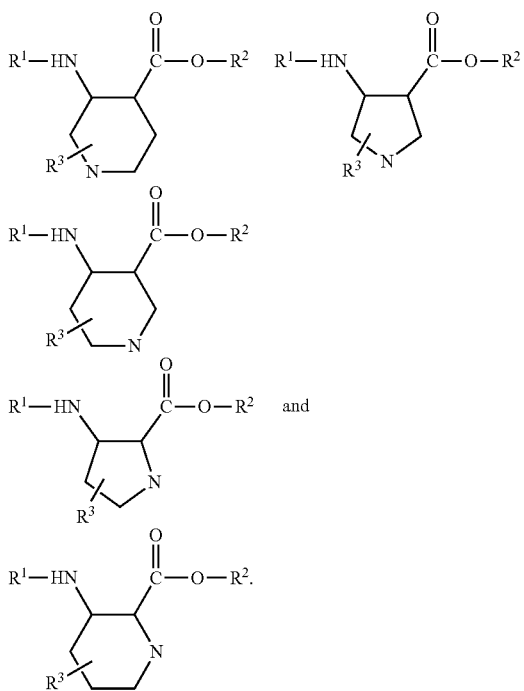

$R^1$ is selected from the group consisting hydrogen and an amino protecting group; $R^2$ is selected from the group consisting of hydrogen and a carboxy protecting group; and when $R^3$ is bonded to a carbon atom, $R^3$ is selected from the group consisting of hydrogen, hydroxy, linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —$(CH_2)_{n+1}$, —$OR^4$, —$(CH_2)_{n+1}$—$SR^4$, $(CH_2)_{n+1}$—$S(=O)$—$CH_2$—$R^4$, —$(CH_2)_{n+1}$—$S(=O)_2$—$CH_2$—$R^4$, —$(CH_2)+_1$—$NR^4R^4$, —$(CH_2)_{n+1}$—$NHC(=O)R^4$, —$(CH_2)_{n+1}$—$NHS(=O)_2$—$CH_2$—$R^4$, —$(CH_2)_{n+1}$—$O$—$(CH_2)_m$—$R^5$, —$(CH_2)_{n+1}$—$S$—$(CH_2)_mR^5$, —$(CH_2)_{n+1}$—$S(=O)$—$(CH_2)_m$ —$R^5$, —$(CH_2)_{n+1}$—$S(=O)_2$—$(CH_2)_m$—$R^5$, —$(CH_2)_{n+1}$—$NH$—$(CH_2)_m$—$R^5$, —$(CH_2)_{n+1}$—$N\{(CH_2)_m\ R^5\}_2$, —$(CH_2)_{n+1}$—$NHC(=O)$—$(CH_2)+_1$—$R^5$, and —$(CH_2)_{n+1}$—$NHS(=O)_2$—$(CH_2)_m$—$R^5$; wherein each $R^4$ is independently selected from the group consisting of hydrogen, $C_1$-$C_6$alkyl, alkenyl, or alkynyl; mono- or bicyclic aryl, mono- or bicyclic heteroaryl having up to S heteroatoms selected from N, O, and S; mono- or bicyclic aryl-$C_1$-$C_6$alkyl, mono- or bicyclic heteroaryl-$C_1$-$C_6$alkyl; and wherein $R^5$ is selected from the group consisting of hydroxy, $C_1$-$C_6$alkyloxy, aryloxy, heteroaryloxy, thio, $C_1$-$C_6$alkylthio, $C_1$-$C_6$alkylsulfinyl, $C_1$-$C_6$alkylsulfonyl, arylthio, arylsulfinyl, arylsulfonyl, heteroarylthio, heteroarylsulfinyl, heteroarylsulfonyl, amino, mono- or di-$C_1$-$C_6$alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$alkylamino, carboxylic acid, carboxamide, mono- or di-$C_1$-$C_6$alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$alkyl, aryl, heteroaryl; O-alkylurethane, O-arylurethane, and O-heteroarylurethane; and m is an integer of from 2-6 and n is an integer of from 0-6; and when $R^3$ is bonded to a nitrogen atom, $R^3$ is independently selected from the group consisting of those listed above for when $R^3$ is attached to a carbon atom, and further selected from the group consisting of —$S(=O)_2$—$CH_2$—$R^4$, —$C(=O)$—$R^4$—$S(=O)_2$—$(CH_2)_mR^5$, and —$C(=O)$—$(CH_2)_{n+1}$—$R^5$; wherein $R^4$ and $R^5$ are as defined hereinabove, and m is an integer of from 2-6 and n is an integer of from 0-6; provided that when the β-amino acid is of formula $R^3$ is not hydrogen; racemic mixtures thereof, isolated or enriched enantiomers thereof; isolated or enriched diastereomers thereof; and salts thereof. In some embodiments the β-amino acids refers to the selection of an amino acid chosen from the following:

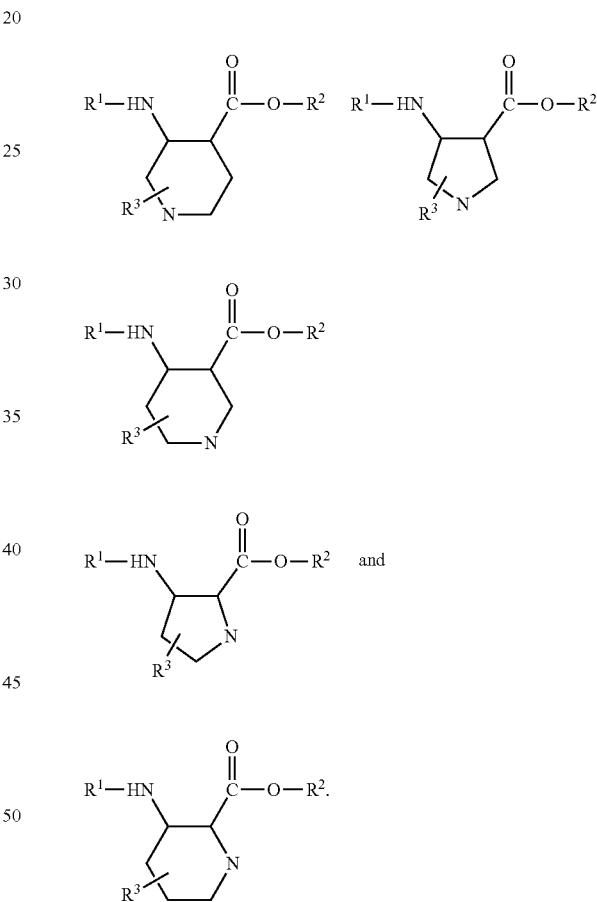

Figure 11:
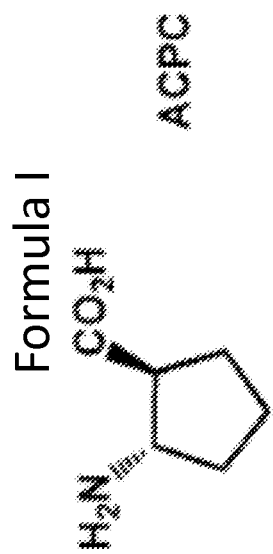
FIG. 11 depicts Formula I.

In some embodiments the β-amino acids refers to the following Formula I (FIG. 11):

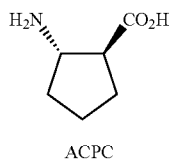

ACPC

Figure 12:
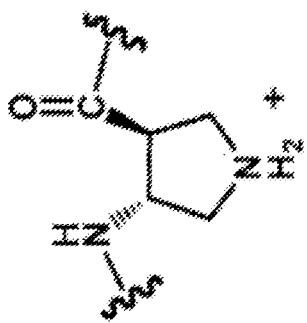
FIG. 12 depicts Formula II.

In some embodiments the β-amino acids refers to the following Formula II (FIG. 12):

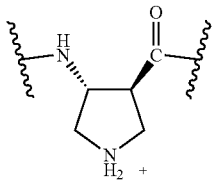

An APC residue within an undefined peptide chain, under neutral aqueous conditions (the ring N is protonated).

wherein the NH$_2$ and/or COOH groups are replaced with functional peptide bonds.

Figure 13:
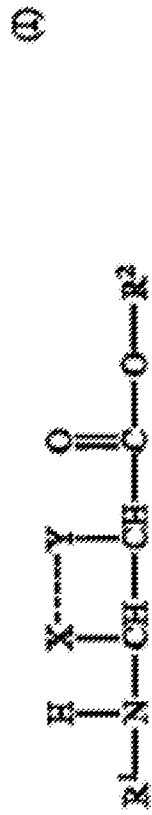
FIG. 13 depicts Formula III.

In some embodiments the term "β-amino acid" refers to the following Formula III (FIG. 13):

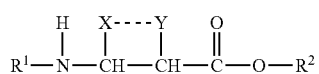

(I)

wherein X and Y combined, together with the carbon atoms to which they are bonded, define a substituted or unsubstituted C$_4$-C$_8$ cycloalkyl, cycloalkenyl or heterocyclic ring having one or more nitrogen atoms as the sole heteroatom;

the substituents on carbon atoms of the rings being independently selected from the group consisting of linear or branched C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl, —(CH$_2$)$_{n+1}$—OR$^4$, —(CH$_2$)$_{n+1}$—SR$^4$, —(CH$_2$)$_{n+1}$—S(=O)—CH$_2$—R$^4$, —(CH$_2$)$_{n+1}$—S(=O)$_2$—CH$_2$—R$^4$, —(CH$_2$)$_{n+1}$—NR$^4$R$^4$, —(CH$_2$)$_{n+1}$—NHC(=O)R$^4$, —(CH$_2$)$_{n+1}$—NHS(=O)$_2$—CH$_2$—R$^4$, —(CH$_2$)$_{n+1}$—O—(CH$_2$)$_m$—R$^5$, —(CH$_2$)$_{n+1}$—S—(CH$_2$)$_m$—R$^5$, —(CH$_2$)$_{n+1}$ S(=O)(CH$_2$)$_m$—R$^5$, —(CH$_2$)$_{n+1}$—S(=O)$_2$—(CH$_2$)$_m$—R$^5$, —(CH$_2$)$_{n+1}$—NH—(CH$_2$)$_m$—R$^5$, —(CH$_2$)$_{n+1}$—N—{(CH$_2$)$_m$—R$^5$}$_2$, (CH$_2$)$_{n+1}$—NHC(=O)—(CH$_2$)$_{n+1}$—R$^5$, and —(CH$_2$)$_{n+1}$—NHS(=O)$_2$—(CH$_2$)$_m$—R$^5$;

wherein R$^4$ is independently selected from the group consisting of hydrogen, C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl; and wherein R$^5$ is selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$-C$_6$-alkylamino, carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroaryl-sulfonamide, N-aryl-N-heteroarylsulfonamide, urea; mono- di- or tri-substituted urea, wherein the subsitutent(s) is selected from the group consisting of C$_1$-C$_6$-alkyl, aryl, heteroaryl; O-alkylurethane, O-arylurethane, and O-heteroarylurethane; and m is an integer of from 2-6 and n is an integer of from 0-6;

the substituents on heteroatoms of the ring being independently selected from the group consisting of —S(=O)$^2$—CH$_2$—R$^4$—C(=O)—R$^4$—S(=O)$_2$—(CH$_2$)$_m$—R$^5$, and —C(=O)—(CH$_2$)$_{n+1}$—R$^5$; wherein R$^4$ and R$^5$ are as defined hereinabove, and m is an integer of from 2-6 and n is an integer of from 0-6;

provided that when X & Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted;

R$^1$ is selected from the group consisting hydrogen and an amino protecting group;

R$^2$ is selected from the group consisting of hydrogen and a carboxy protecting group;

racemic mixtures thereof; isolated or enriched enantiomers thereof; isolated or enriched diastereomers thereof; and salts thereof.

Figure 14:
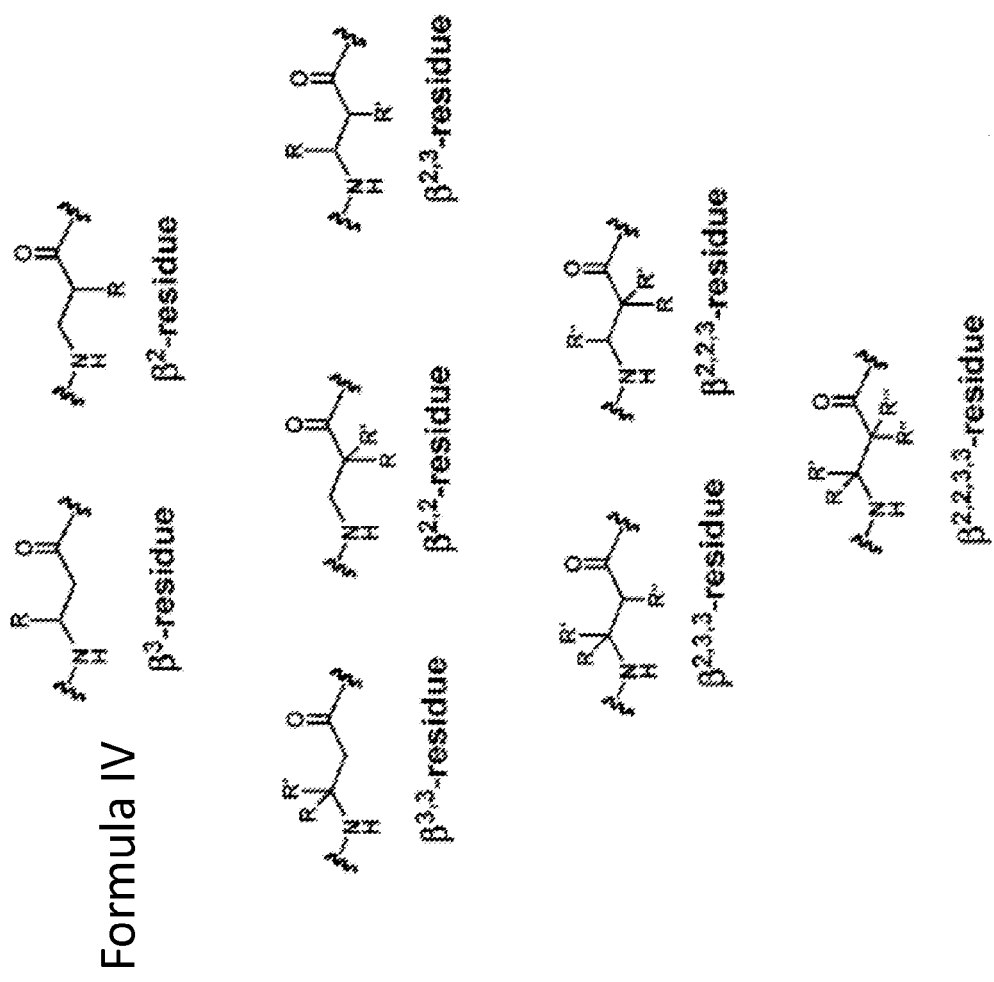
FIG. 14 depicts Formula IV.

In some embodiments the term "β-amino acid" refers to selection of an amino acid chosen from the following: β$^3$ or β$^2$. In some embodiments the term "β-amino acid" refers to selection of an amino acid chosen from the following Formula IV (FIG. 14):

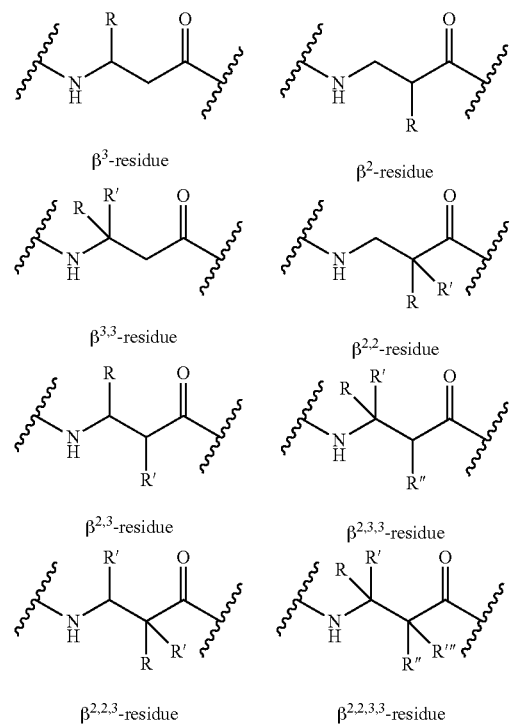

β$^3$-residue        β$^2$-residue

β$^{3,3}$-residue     β$^{2,2}$-residue

β$^{2,3}$-residue     β$^{2,3,3}$-residue

β$^{2,2,3}$-residue   β$^{2,2,3,3}$-residue wherein R, R', R", and R'" are any substituent.

In some embodiments the term "β-amino acid" refers to selection of an amino acid chosen from the following Formula IV (FIG. 14):

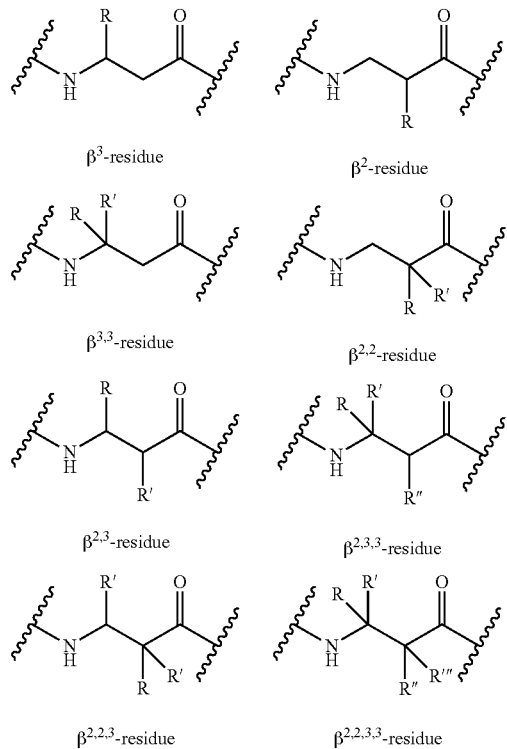

wherein R, R', R", and R'" is an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl; wherein X is any substituent.

In some embodiments the term "β-amino acid" refers to selection of an amino acid chosen from the following Formula IV (FIG. 14):

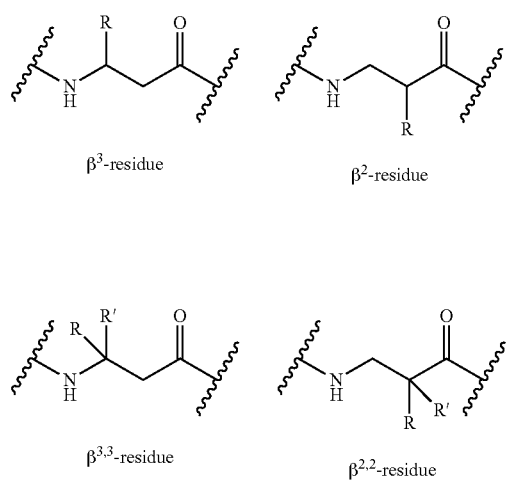

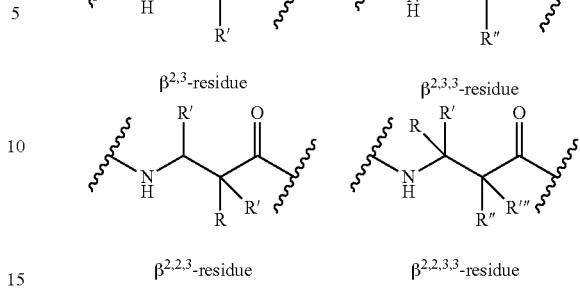

wherein R, R', R", and R'" are any substituent, provided that: (i) R is not O, N, or halo when the R is in a β$^3$-residue, (ii) R and R' are not O, N, or halo when the R and R' are in a β$^{3,3}$-residue; (iii) R is not O, N, or halo when the R is in a β$^{2,3}$-residue; (iv) R and R' are not O, N, or halo when the R and R' are in a β$^{2,3,3}$-residue; (v) R" is not O, N, or halo when the R" is in β$^{2,2,3}$-residue; (vi) R and R' are not O, N, or halo when the R and R' are in a β$^{2,2,3,3}$-residue.

In some embodiments the term "β-amino acid" refers to selection of an amino acid chosen from the following:
wherein R, R', R", and R'" is an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cycloalkyl, heteroaryl, heteroarylalkyl, heteroarylalkoxy, or heterocyclyl; wherein X is any substituent; provided that: (i) R is not O, N, or halo when the R is in a β$^3$-residue, (ii) R and R' are not O, N, or halo when the R and R' are in a β$^{3,3}$-residue; (iii) R is not O, N, or halo when the R is in a β$^{2,3}$-residue; (iv) R and R' are not O, N, or halo when the R and R' are in a β$^{2,3,3}$-residue; (v) R" is not O, N, or halo when the R" is in a β$^{2,2,3}$-residue; (vi) R and R' are not O, N, or halo when the R and R' are in a β$^{2,2,3,3}$-residue.

A "cyclic" beta-amino acid is acid is an amino acid of the following formula I:

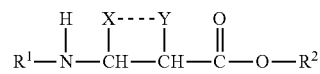

wherein X and Y combined, together with the carbon atoms to which they are bonded, define a substituted or unsubstituted C$_4$-C$_8$ cycloalkyl or cycloalkenyl group; wherein substituents on carbon atoms of the rings being independently selected from the group consisting of linear or branched C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl, —(CH2)$_{n+1}$—OR$_4$, —(CH2)$_{n+1}$—SR$_4$, —(CH$_2$)$_{n+1}$—S(=O)—CH$_2$—R$_4$, —(CH$_2$)$_{n+1}$—S(=O)$_2$—CH$_2$—R$_4$, —(CH$_2$)$_{n+1}$—NR$_4$R$_4$, —(CH$_2$)$_{n+1}$—NHC(=O)R$_4$, —(CH$_2$)n+$_1$—NHS(=O)$_2$—CH$_2$—R$_4$, —(CH$_2$)$_{n+1}$—O—(CH$_2$)$_m$R$_5$, —(CH$_2$)$_{n+1}$—S—(CH$_2$)$_m$—R$_5$, —(CH$_2$)$_{n+1}$—S(=O)—(CH$_2$)$_m$R$_5$, —(CH$_2$)$_{n+1}$—S(=O)$_2$—(CH$_2$)$_m$—R$_5$, —(CH$_2$)$_{n+1}$—NH—(CH$_2$)$_m$—R$_5$, —(CH$_2$)$_{n+1}$—N—{(CH$_2$)$_m$—R$_5$}$_2$, —(CH$_2$)$_{n+1}$—NHC(=O)—(CH$_2$)$_{n+1}$—R$_5$, and —(CH$_2$)$_{n+1}$—NHS(=O)$_2$—(CH$_2$)$_m$—R$_5$; wherein R$_4$ is independently selected from the group consisting of hydrogen, C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—CH$_2$—R$_4$—C(=O)—R$_4$—S(=O)$_2$—(CH$_2$)$_m$—R$_5$, and —C(=O)—(CH$_2$)$_{n+1}$—R$_5$; wherein R$_4$ and R$_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; R$_1$ is selected from the group consisting hydrogen and an amino protecting group; R$_2$ is selected from the group consisting of hydrogen and a carboxy protecting group; racemic mixtures thereof, isolated or enriched enantiomers thereof; isolated or enriched diastereomers thereof; and salts thereof.

A "heterocyclic" beta-amino acid is an amino acid of formula I, wherein X and Y combined, together with the carbon atoms to which they are bonded, define a substituted or unsubstituted $C_4$-$C_8$ cyclically or cycloalkenyl group having one or more nitrogen, oxygen or sulfur atoms as a heteroatom(s) within the cycloakyl or cycloalkenyl group; wherein substituents on carbon atoms of the cycloakyl or cycloalkenyl rings being independently selected from the group consisting of linear or branched $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, —(CH$_2$)$_{n+1}$—OR$_4$, —(CH$_2$)$_{n+1}$—SR$_4$, —(CH$_2$)$_{n+1}$—S(=O)—CH$_2$—R$_4$, —(CH$_2$)$_{n+1}$—S(=O)$_2$—CH$_2$—R$_4$, —(CH$_2$)$_{n+1}$—NR$_4$R$_4$, —(CH$_2$)$_{n+1}$—NHC(=O)R$_4$, —(CH$_2$)$_{n+1}$—NHS(=O)$_2$—CH$_2$—R$_4$, —(CH$_2$)$_{n+1}$—O—(CH$_2$)$_m$R$_5$, —(CH$_2$)$_{n+1}$—S—(CH$_2$)$_m$—R$_5$, —(CH$_2$)$_{n+1}$—S(=O)—(CH$_2$)$_m$R$_5$, —(CH$_2$)$_{n+1}$—S(=O)$_2$—(CH$_2$)$_m$—R$_5$, —(CH$_2$)$_{n+1}$—NH—(CH$_2$)$_m$—R$_5$, —(CH$_2$)$_{n+1}$—N—{(CH$_2$)$_m$—R$_5$}$_2$, —(CH$_2$)$_{n+1}$—NHC(=O)—(CH$_2$)$_{n+1}$—R$_5$, and —(CH$_2$)$_{n+1}$—NHS(=O)$_2$—(CH$_2$)$_m$—R$_5$; wherein R$_4$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein R$_5$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane; and m is an integer of from 2-6 and n is an integer of from 0-6; the substituents on heteroatoms of the ring being independently selected from the group consisting of —S(=O)$_2$—CH$_2$—R$_4$—C(=O)—R$_4$—S(=O)$_2$—(CH$_2$)$_m$—R$_5$, and —C(=O)—(CH$_2$)$_{n+1}$—R$_5$; wherein R$_4$ and R$_5$ are as defined hereinabove, and m is an integer of from 2-6 and n is an integer between 0 and 6; provided that when X and Y together with the carbons to which they are bonded define a five- or six-membered cycloalkyl or a five-membered heterocyclic ring having one nitrogen as the sole heteroatom, and the nitrogen is bonded to a carbon atom adjacent to the carboxy carbon of Formula I, the cycloalkyl or heterocyclic ring is substituted; R$_1$ is selected from the group consisting hydrogen and an amino protecting group; R$_2$ is selected from the group consisting of hydrogen and a carboxy protecting group; racemic mixtures thereof, isolated or enriched enantiomers thereof; isolated or enriched diastereomers thereof; and salts thereof.

In some embodiments, at least one of the β-amino acid residues in the analog is replaced with at least one β-amino acid residue that is cyclically constrained via a ring encompassing its $β^2$ and $β^3$ carbon atoms. In another embodiment of the invention, most or all of the inserted β-amino acid residues are cyclically constrained. In another version of the invention, at least one of the β-amino acid residues is unsubstituted at its $β^2$ and $β^3$ carbon atoms. Alternatively, all of the β-amino acid residues may be substituted at their $β^2$ and $β^3$ carbon atoms (with linear, branched or cyclic substituents). In some embodiments, the cyclic substituents of the claimed invention comprise side chains that are covalently bonded to the side chains of other contiguous amino acids. In some embodiments, the cyclic substituents of the claimed invention comprise side chains that are covalently bonded to the side chains of other non-contiguous amino acids. In some embodiments the cyclic substituents of the claimed invention do not include side chains that are covalently bonded to the side chains of other contiguous or non-contiguous amino acids. In some embodiments the terms beta-3 or beta-2 amino acid refers to β3-homo β2-homo amino acids.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C, H), nonpolar side chains (e.g., G, A, V, L, I, P, F, M, W), beta-branched side chains (e.g., T, V, I) and aromatic side chains (e.g., Y, F, W, H). Thus, a predicted nonessential amino acid residue in a VIP analog, for example, replaced with another amino acid residue from the same side chain family. Other examples of acceptable substitutions are substitutions based on isosteric considerations (e.g. norleucine for methionine) or other properties (e.g. 2-thienylalanine for phenylalanine).

As used herein, the term "derived from" in the context of the relationship between a chemical structure or amino acid sequence and a related chemical structure or related amino acid sequence describes a chemical structure or amino acid sequence that may be homologous to or structurally similar to the related chemical structure or related amino acid sequence.

As used herein, the term "inflammatory disease" refers to any disease, condition, or ailment that results from an immune response or a pathogen infection, which in some instances may be characterized by one or more of pain, swelling, and redness of a tissue types. In some embodiments, inflammatory disease refers to rheumatoid arthritis, Crohn's disease, sepsis, ulcerative colitis, irritable bowel disease, chronic irritable bowel syndrome, and allergies such as allergic rhinitis.

A "non-essential" amino acid residue is a residue that can be altered from the wild-type sequence of a polypeptide (e.g., a short domain of VIP) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "non-natural side chain" is a modified or synthetic chain of atoms joined by covalent bond to the α-carbon atom, β-carbon atom, or γ-carbon atom which does not make up the backbone of the polypeptide chain of amino acids. The natural side chain, or R group, of of alanine is a methyl group. In some embodiments, the non-natural side chain of the composition is a methyl group in which on e or more of the hydrogen atoms is replaced by a deuterium atom.

The term "polypeptide" encompasses two or more naturally or non-naturally-occurring amino acids joined by a covalent bond (e.g., an amide bond). Polypeptides as described herein include full-length proteins (e.g., fully processed pro-proteins or full-length synthetic polypeptides) as well as shorter amino acid sequences (e.g., fragments of naturally-occurring proteins or synthetic polypeptide fragments).

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising either a VIP or VIP analog may be formed by reacting the free base, or a salt, enantiomer or racemate thereof, with one or more equivalents of the appropriate acid. In some embodiments, pharmaceutical acceptable salts of the present invention refer to analogs having at least one basic group or at least one basic radical. In some embodiments, pharmaceutical acceptable salts of the present invention comprise a free amino group, a free guanidino group, a pyrazinyl radical, or a pyridyl radical that forms acid addition salts. In some embodiments, the pharmaceutical acceptable salts of the present invention refer to analogs that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present invention may be found in their anhydrous form or as in hydrated crystalline form (i.e., complexed or crystallized with one or more molecules of water).

The term "subject" is used throughout the specification to describe an animal to whom treatment with the compositions according to the present invention is provided or administered. For treatment of those conditions which are specific for a specific subject, such as a human being, the term "patient" may be interchangeably used. In some instances in the description of the present invention, the term "patient" will refer to human patients. In some embodiments, the subject may be a mammal to whom the present invention is provided or administered. In some embodiments, the subject may be a non-human animal to whom the present invention is provided or administered.

The term "soluble" or "water soluble" refers to solubility that is higher than $1/100,000$ (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is $1/10,000$ (mg/ml) or less. Water soluble or soluble substances include, for example, polyethylene glycol. In some embodiments, the polypeptide of the claimed invention may be bound by polyethylene glycol to better solubilize the composition comprising the peptide.

The terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with any condition. The treatment may be a pre-treatment as well as a treatment at the onset of symptoms.

"Effective amount" refers to an amount of a compound, material, or composition, as described herein effective to achieve a particular biological result such as, but not limited to, biological results disclosed, described, or exemplified herein. Such results may include, but are not limited to, the effective reduction of symptoms associated with any of the disease states mentioned herein, as determined by any means suitable in the art. The effective amount of the composition may be dependent on any number of variables, including without limitation, the species, breed, size, height, weight, age, overall health of the subject, the type of formulation, the mode or manner or administration, the type and/or severity of the particular condition being treated, or the need to modulate the activity of the molecular pathway induced by association of the analog to its receptor. The appropriate effective amount can be routinely determined by those of skill in the art using routine optimization techniques and the skilled and informed judgment of the practitioner and other factors evident to those skilled in the art. A therapeutically effective dose of the analogs described herein may provide partial or complete biological activity as compared to the biological activity induced by the wild-type or naturally occurring polypeptides upon which the analogs are derived. A therapeutically effective dose of the analogs described herein may provide a sustained biochemical or biological affect and/or an increased resistance to degradation when placed in solution as compared with the normal affect observed when the naturally occurring and fully processed translated protein is administered to the same subject.

The term "fragment" refers to any analog of a naturally occurring polypeptide disclosed herein that comprises at least 4 amino acids identical to the naturally occurring polypeptide upon which the analog is based. The term "functional fragment" refers to any fragment of any analog of a naturally occurring polypeptide disclosed herein that comprises at least 4 amino acids identical to the naturally occurring polypeptide upon which the analog is based and shares the function of the naturally occurring polypeptide upon which the analog is based. In some embodiments, the compositions or pharmaceutical composition comprises an analog comprising at least one β-amino acid, wherein the analog is a fragment of VIP, a VIP family member, an interleukin, or any of the polypeptides disclosed in the instant application. In some embodiments, the compositions or pharmaceutical composition comprises an analog comprising at least one β-amino acid, wherein the analog is a fragment of VIP, a VIP family member, an interleukin, or any of the polypeptides disclosed in the instant application and wherein the fragment shares at least 4 contiguous amino acid residues with the naturally occurring polypeptide upon which the analog is based and wherein the fragment retains the biological activity of the naturally occurring polypeptide upon which the analog is based. In some embodiments, the VIP analog is a fragment that comprises between about 1 to about 26 amino acids of the naturally occurring VIP sequence. In some embodiments, the VIP analog is a fragment that comprises between about 1 to about 25 amino acids of the naturally occurring VIP sequence. In some embodiments, the VIP analog is a fragment that comprises between about 1 to about 24 amino acids of the naturally occurring VIP sequence. In some embodiments, the VIP analog is a fragment that comprises between about 1 to about 23 amino acids of the naturally occurring VIP sequence. In some embodiments, the VIP analog is a fragment that comprises between about 1 to about 22 amino acids of the naturally occurring VIP sequence. In some embodiments, the VIP analog is a fragment that comprises between about 1 to about 21 amino acids of the naturally occurring VIP sequence. In some embodiments, the VIP analog is a frag-ment that comprises between about 1 to about 20 amino acids of the naturally occurring VIP sequence. In some embodiments, the VIP analog is a fragment that comprises between about 1 to about 19 amino acids of the naturally occurring VIP sequence. In some embodiments, the VIP analog is a fragment that comprises between about 1 to about 18 amino acids of the naturally occurring VIP sequence. In some embodiments, the VIP analog is a fragment that comprises between about 1 to about 19 amino acids of the naturally occurring VIP sequence. In some embodiments, the VIP analog is a fragment that comprises between about 1 to about 17 amino acids of the naturally occurring VIP sequence. In some embodiments, the VIP analog is a fragment that comprises between about 1 to about 16 amino acids of the naturally occurring VIP sequence. In some embodiments, the VIP analog is a fragment that comprises between about 1 to about 15 amino acids of the naturally occurring VIP sequence. In some embodiments, the VIP analog is a fragment that comprises between about 1 to about 14 amino acids of the naturally occurring VIP sequence. In some embodiments, the VIP analog is a fragment that comprises between about 1 to about 13 amino acids of the naturally occurring VIP sequence. In some embodiments, the VIP analog is a fragment that comprises between about 1 to about 12 amino acids of the naturally occurring VIP sequence. In some embodiments, the VIP analog is a fragment that comprises between about 1 to about 11 amino acids of the naturally occurring VIP sequence. In some embodiments, the VIP analog is a fragment that comprises between about 1 to about 10 amino acids of the naturally occurring VIP sequence. In some embodiments, the VIP analog is a fragment that comprises between about 1 to about 9 amino acids of the naturally occurring VIP sequence. In some embodiments, the VIP analog is a fragment of VIP that comprises between about 1 to about 8 amino acids of the naturally occurring VIP sequence. In some embodiments, the VIP analog is a fragment that comprises between about 1 to about 7 amino acids of the naturally occurring VIP sequence. In some embodiments, the VIP analog is a fragment that comprises between about 1 to about 6 amino acids of the naturally occurring VIP sequence. In some embodiments, the VIP analog is a fragment that comprises between about 1 to about 5 amino acids of the naturally occurring VIP sequence. In some embodiments, the VIP analog is a fragment that comprises between about 1 to about 4 amino acids of the naturally occurring VIP sequence. In some embodiments, the analog is modified with at least one PEG molecule on at least one of the non-natural amino acids.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it. In some embodiments the alkyl group is chosen from: $C_1$-$C_{10}$, $C_2$-$C_{10}$, $C_3$-$C_{10}$, $C_4$-$C_{10}$, $C_5$-$C_{10}$, $C_6$-$C_{10}$, $C_7$-$C_{10}$, $C_8$-$C_{10}$, $C_9$-$C_{10}$, $C_1$-$C_{10}$, $C_1$-$C_2$, $C_1$-$C_3$, $C_1$-$C_4$, $C_1$-$C_5$, $C_1$-$C_6$, $C_1$-$C_7$, $C_1$-$C_8$, or $C_1$-$C_9$, The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having about 2 to about 20 (inclusive) carbon atoms in it.

The term "aryl" refers to an aromatic ring system. In some embodiments, the aryl group of the analog include substituents, wherein 0, 1, 2, 3, 4, 5, 6, 7, 8, 9, or 10 atoms of each ring are substituted by a substituent. In some embodiments, the aryl group refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl. "Arylalkyl" refers to an aryl group, as defined above, wherein one of the aryl group's hydrogen atoms has been replaced with an alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl.

"Alkylheterocycle" refers to an alkyl group, as defined above, wherein one of the alkyl group's hydrogen atoms has been replaced with a heterocycle. Representative examples of an alkylheterocyclo group include, but are not limited to, —CH$_2$CH$_2$-morpholine, —CH$_2$CH$_2$piperidine, —CH$_2$CH$_2$CH$_2$-morpholine, and —CH$_2$CH$_2$CH$_2$-imidazole.

"Alkylamido" refers to an alkyl group, as defined above, wherein one of the alkyl group's hydrogen atoms has been replaced with a —C(O)NH$_2$ group. Representative examples of an alkylamido group include, but are not limited to, —CH$_2$C(O)NH$_2$, —CH$_2$CH$_2$C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$CH$_2$NHC(O)CH$_3$, —CH$_2$CH$_2$NHC(O)CH$_2$CH$_3$, and —CH$_2$CH$_2$NHC(O)CH=CH$_2$.

"Alkylamino" refers to an alkyl group, as defined above, wherein one of the alkyl group's hydrogen atoms has been replaced with a —NH$_2$ group. Representative examples of an alkylamido group include, but are not limited to —CH$_2$NH$_2$, CH$_2$CH$_2$NH$_2$, CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$.

"Alkylguanidino" refers to an alkyl group, as defined above, wherein one of the alkyl group's hydrogen atoms has been replaced with a —NH$_2$(C=NH)NH$_2$ group. Representative examples of an alkylamido group include, but are not limited to —CH$_2$NH$_2$(C=NH)NH$_2$, CH$_2$CH$_2$NH$_2$(C=NH) NH$_2$, CH$_2$CH$_2$CH$_2$NH$_2$(C=NH)NH$_2$, —CH$_2$CH$_2$CH$_2$CH$_2$NH$_2$(C=NH)NH$_2$, —CH$_2$CH$_2$CH$_2$CH$_2$CH$_2$NH$_2$(C=NH)NH$_2$. In some embodiments alkyl units can be found on the N atom(s) of the alkylamino or alkylguanidino groups (for example, —CH$_2$NH(CH$_3$), CH$_2$N(CH$_3$)$_2$).

"Alkanol" refers to an alkyl group, as defined above, wherein one of the alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to an alkyl group, as defined above, wherein one of the alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH) CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, 3 to 8 carbons, or 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include, but are not limited to, pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include, but are not limited to, piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thio-alkoxy, aryloxy, amino, alkoxycarbonyl, amido, carboxy, alkanesulfonyl, alkylcarbonyl, and cyano groups.

In some embodiments, the composition comprises an analog comprises one or more asymmetric centers and thus occur as racemates and racemic mixtures, single enantiomers, individual diastereomers and diastereomeric mixtures. Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

All tautomeric forms and isomeric forms and mixtures, whether individual geometric isomers or stereoisomers or racemic or non-racemic mixtures, of a chemical structure or entire analog is intended, unless the specific stereochemistry or isomeric form is specifically indicated in the analog name, chemical name or structure. All such isomeric forms of these compositions are included in the present invention unless expressly provided otherwise. In some embodiments, the analogs of this invention are also represented in multiple tautomeric forms, in such instances, the invention includes all tautomeric forms of the analogs described herein (e.g., if alkylation of a ring system results in alkylation at multiple sites, the invention includes all such reaction products). All such isomeric forms of such analogs are included in the present invention unless expressly provided otherwise. All crystal forms of the analogs described herein are included in the present invention unless expressly provided otherwise. All deuterated form of the analogs described herein are included in the present invention. In some embodiments as least one hydrogen atom of the analog is replace with a deuterium atom. In some embodiments at least one hydrogen atom that is involved with a hydrogen-bond is replaced with a deuterium atom. In some embodiments at least one solvent exchangeable hydrogen atom is replaced with a deuterium atom. In some embodiments, the compositions, pharmaceutical compositions, and analogs contained therein comprise from about 1% to about 100% of their hydrogen replaced with deuterium atoms. In some embodiments, the compositions, pharmaceutical compositions, and analogs contained therein comprise from about 90% to about 100% of their hydrogen replaced with deuterium atoms. In some embodiments, the compositions, pharmaceutical compositions, and analogs contained therein comprise from about 80% to about 90% of their hydrogen replaced with deuterium atoms. In some embodiments, the compositions, pharmaceutical compositions, and analogs contained therein comprise from about 70% to about 80% of their hydrogen replaced with deuterium atoms. In some embodiments, the compositions, pharmaceutical compositions, and analogs contained therein comprise from about 60% to about 70% of their hydrogen replaced with deuterium atoms. In some embodiments, the compositions, pharmaceutical compositions, and analogs contained therein comprise from about 50% to about 60% of their hydrogen replaced with deuterium atoms. In some embodiments, the compositions, pharmaceutical compositions, and analogs contained therein comprise from about 40% to about 50% of their hydrogen replaced with deuterium atoms. In some embodiments, the compositions, pharmaceutical compositions, and analogs contained therein comprise from about 30% to about 40% of their hydrogen replaced with deuterium atoms. In some embodiments, the compositions, pharmaceutical compositions, and analogs contained therein comprise from about 20% to about 30% of their hydrogen replaced with deuterium atoms. In some embodiments, the compositions, pharmaceutical compositions, and analogs contained therein comprise from about 10% to about 20% of their hydrogen replaced with deuterium atoms. In some embodiments, the compositions, pharmaceutical compositions, and analogs contained therein comprise from about 5% to about 10% of their hydrogen replaced with deuterium atoms. If the analog of the claimed invention includes a methyl group, a deuterated analog may have one, two, or three of the hydrogens replaced by deuterium atoms. In some embodiments, the analog may contain one or more radioisotopes. In some embodiments, as least one hydrogen atom of the analog is replace with a tritium atom. In some embodiments, the compositions, pharmaceutical compositions, and analogs contained therein comprise from about 1% to about 5% of their hydrogens are replaced with tritium atoms.

As used herein, the terms "increase" and "decrease" mean, respectively, to cause a statistically significantly (i.e., $p<0.15$) increase or decrease of at least 1%, 2%, or 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, $10^{-12}$, $10^{-11}$, $10^{-10}$, $10^{-9}$, $10^{-8}$, $10^{-7}$, $10^{-6}$, $10^{-5}$, $10^{-4}$ or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

The term "biological activity" encompasses structural and functional properties of a macrocycle of the invention. Biological activity is, for example, structural stability, alpha-helicity, affinity for a target (for example as measured by $EC_{50}$ or $IC_{50}$ values), resistance to proteolytic degradation, cell penetrability, intracellular stability, in vivo stability, or any combination thereof.

The terms "prodrug" or "prodrug derivative" mean a covalently-bonded derivative or carrier of the analog of the claimed invention or active drug substance which undergoes at least some biotransformation prior to exhibiting its pharmacological effect(s). In general, such prodrugs have metabolically cleavable groups and are rapidly transformed in vivo to yield the analog of the claimed invention, for example, by hydrolysis in blood, and generally include esters and amide analogs of the analogs. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the analogs using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987, each of which is incorporated herein by reference in their entireties. In some embodiments, the analog may be a prodrug that, when administered to the subject becomes biologically active.

In some embodiments, the invention relates to a composition or pharmaceutical composition comprising a pharmaceutically acceptable prodrug that, when administered to the subject becomes biologically active. The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

In some embodiments, the analog of the claimed invention is a pharmaceutically-acceptable acid addition salt. The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like. In some embodiments, the analog of the claimed invention is a pharmaceutically-acceptable base addition salt. The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Suitable salts include the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. In some embodiments, the composition of the claimed invention comprises at least one organic nontoxic bases chosen from isopropylamine, diethylamine, ethanolamine, trimethylamine, dicyclohexylamine, choline, and caffeine.

The term "solvate" means a physical association of a compound with one or more solvent molecules or a complex of variable stoichiometry formed by a solute (the analog of the claimed invention) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, and methanolates.

The invention relates to compositions comprising an analog of a naturally occurring polypeptide sequence. In some embodiments the invention relates to a composition comprising an analog of a naturally occurring polypeptide sequence wherein the analog is from about 80% to 99% homologous to a naturally occurring polypeptide sequence. In some embodiments the invention relates to a composition comprising an analog of a naturally occurring polypeptide sequence wherein the analog is from about 80% to 85% homologous to a naturally occurring polypeptide sequence. In some embodiments the invention relates to a composition comprising an analog of a naturally occurring polypeptide sequence wherein the analog is from about 85% to 90% homologous to a naturally occurring polypeptide sequence. In some embodiments the invention relates to a composition comprising an analog of a naturally occurring polypeptide sequence wherein the analog is from about 90% to 95% homologous to a naturally occurring polypeptide sequence. In some embodiments the invention relates to a composition comprising an analog of a naturally occurring polypeptide sequence wherein the analog is from about 95% to 99% homologous to a naturally occurring polypeptide sequence. In some embodiments the invention relates to a composition comprising an analog of a naturally occurring polypeptide sequence wherein the analog is about 95%, 96%, 97%, 98%, or 99% homologous to a naturally occurring polypeptide sequence. In some embodiments the analog is derived from the naturally occurring polypeptide of the VIP family. In some embodiments, the analog is derived from the naturally occurring polypeptide of the VIP family and has at least one β-amino acid residue and/or at least one modified amino acid residue comprising APC or ACPC. VIP is

```
                                          (SEQ ID NO: 65)
       HSDGTFTSELSRLREGARLQRLLQGLV (SEQ ID NO: 66)
       HSDAVFTDNYTRLRKQMAVKKYLNSILN
```

In some embodiments, the VIP analog is selective for one particular receptor versus another. In some embodiments, the composition comprises a VIP analog wherein the VIP analog is selective for, or preferentially binds to, VPAC1, VPAC2, PAC1, VIPR1, or VIPR2. In some embodiments, the composition comprises a VIP analog wherein the VIP analog is selective for, or preferentially binds, VPAC1. In some embodiments, the composition comprises a VIP analog wherein the VIP analog is selective for, or preferentially binds, VPAC2. In some embodiments, the composition comprises a VIP analog wherein the VIP analog is selective for, or preferentially binds, PAC1. In some embodiments, the composition comprises a VIP analog wherein the VIP analog is selective for, or preferentially binds, VIPR1. In some embodiments, the composition comprises a VIP analog wherein the VIP analog is selective for, or preferentially binds, VIPR2. In some embodiments, the VIP analog is an agonist of at least one of the following: VPAC1, VPAC2, PAC1, VIPR1, or VIPR2. In some embodiments, the the VIP analog is an antagonist of at least one of the following: VPAC1, PAC1, VIPR1, or VIPR2.

The invention relates to the manufacturing of a synthetic polypeptide which is an amino acid sequence that corresponds to the sequence of the polypeptides disclosed herein or fragment thereof. In some embodiments, the synthetic polypeptides comprises a repeated pattern of αααβ but does not comprise any other repeated pattern of any alpha or beta amino acids. In some embodiments, the invention relates to an animal cell comprising any of the polypeptides disclosed herein. In some embodiments, animal cells can be contacted with the synthetic polypeptide to induce the biochemical pathway or biological activity ordinarily induced by the naturally occurring polypeptide upon which the analog is based.

The compositions of the invention may be prepared by the synthetic chemical procedures described herein, as well as other procedures similar to those which may be used for making β-amino acid peptides. Such procedures include both solution and solid phase procedures, e.g., using either Boc and Fmoc methodologies. The compounds of the invention may be synthesized using solid phase synthesis techniques. Fmoc-N-Protected β-amino acids can be used to synthesize poly-α/βP-peptides by conventional manual solid-phase synthesis procedures under standard conditions on any number of solid supports, including ortho-chloro-trityl chloride resin. Esterification of Fmoc-β-amino acids with the ortho-chloro-trityl resin can be performed according to the method of Barlos et. al., Tetrahedron Lett., 1989, 30, 3943. The resin (150 mg, 1.05 mmol Cl) is swelled in 2 ml CH$_2$Cl$_2$ for 10 min. A solution of the Fmoc-protected β-amino acid in CH$_2$Cl$_2$ and iPr$_2$EtN are then added successively and the suspension is mixed under argon for 4 h. Subsequently, the resin is filtered and washed with CH$_2$Cl$_2$/MeOH/iPr$_2$EtN (17:2:1, 3×3 min), CH$_2$Cl$_2$ (3×3 min), DMF (2×3 min), CH$_2$Cl$_2$ (3×3 min), and MeOH (2×3 min). The substitution of the resin is determined on a 3 mg sample by measuring the absorbance of the dibenzofulvene adduct at 300 nm. The Fmoc group is removed using 20% piperidine in DMF (4 ml, 2×20 min) under Ar bubbling. The resin is then filtered and washed with DMF (6×3 min). For each coupling step, a solution of the β-amino acid (3 equiv.), BOP (3 equiv.) and HOBT (3 equiv.) in DMF (2 ml) and iPr$_2$EtN (9 eq) are added successively to the resin and the suspension is mixed for 1 h under Ar. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for a further 1 h. The resin is then filtered and washed with DMF (3×3 min) prior to the following Fmoc deprotection step. After the removal of the last Fmoc protecting group, the resin is washed with DMF (6×3 min), CH$_2$Cl$_2$ (3×3 min), Et$_2$O (3×3 min) and dried under vacuum for 3 h. Finally the peptides are cleaved from the resin using 2% TFA in CH$_2$Cl$_2$ (2 ml, 5×15 min) under Ar. The solvent is removed and the oily residues are triturated in ether to give the crude α-/β-polypeptides. The compounds are further purified by HPLC.

The compositions of the invention may be prepared by the synthetic chemical procedures described herein, as well as other procedures similar to those which may be used for making β-amino acid peptides. Such procedures include both solution and solid phase procedures, e.g., using either Boc or Fmoc methodologies. The compounds of the invention may be synthesized using solid phase synthesis techniques. Fmoc-N-Protected β-amino acids can be used to synthesize poly-α/β-peptides by conventional manual solid-phase synthesis procedures under standard conditions on any number of solid supports, including ortho-chloro-trityl chloride resin, Wang resin (NovaBiochem 0.75 mmol substitution) and Rink amid resin (NovaBiochem 0.55 mmol substitution). Resin is typically swelled in 100% DMF for 30 minutes then deprotected using 20% piperidine in DMF for 2 minutes at 800 (3×). Fmoc protected amino acids (natural or non-natural) can then be coupled to the resin using a cocktail of AA:HATU:DIEA:Resin (3:2.5:4:1, LiCL 0.8M final concentration) in DMF for 2 minutes at 700 (3×). The resin is then washed (3×) with DMF, DCM (dichloromethane) (3×) and again with DMF (3×) between deprotection and coupling steps. Monitoring of the coupling reaction is performed with 2,4,6-trinitrobenzene-sulfonic acid (TNBS) (W. S. Hancock and J. E. Battersby, Anal. Biochem. (1976), 71, 260). In the case of a positive TNBS test (indicating incomplete coupling), the suspension is allowed to react for another three times. This process is repeated until the desired product has been achieved. After the removal of the last Fmoc protecting group, the resin is washed with DMF (3×), CH$_2$Cl$_2$ (3×) and DMF again (3×). The remaining free-amine group is then acetylated using a cocktail of DIEA:Ac$_2$O (1:1) for 5 minutes at room temperature. Full-length peptides were then cleaved from solid support using TFA:TIS:H$_2$O (95:2.5:2.5) for 150 minutes, precipitated in cold ethyl ether and lyophilized. The polymer was reconstituted in a 1:1 solution of A:B (A: H$_2$O, 0.1% TFA) (B: 90:10:0.1 acetonitrile/H$_2$O/TFA).

The compositions described herein may be prepared by successive amide bond-forming procedures in which amide bonds are formed between the β-amino group of a first β-amino acid residue or a precursor thereof and the α-carboxyl group of a second β-amino acid residue or α-amino acid residue or a precursor thereof. The amide bond-forming step may be repeated as many times, and with specific α-amino acid residues and/or β-amino acid residues and/or precursors thereof, as required to give the desired α/β-polypeptide. Also analogs comprising two, three, or more amino acid residues (α- or β-) may be joined together to yield larger analogs comprising any combination of α-, or β-amino acids. Cyclic compounds may be prepared by forming peptide bonds between the N-terminal and C-terminal ends of a previously synthesized linear polypeptide or through the disulfide crosslinking of sidechains of non-adjacent residues. $β^3$-amino acids may be produced enantioselectively from corresponding β-amino acids. For instance, by Arndt-Eisert homologation of N-protected α-amino acids. Homologation may be followed by coupling of the reactive diazoketone intermediate of the Wolff rearrangement with a β-amino acid residue.

In some embodiments, the invention relates to All unique patterns of α- or β-amino acids residues from about two to about seven residues in length are explicitly within the scope of the invention. In some embodiments, the composition comprises an analog, wherein the analog wherein the analog comprises a repetitive pattern of sequential β-amino acids from the amino-terminus to the carboxy-terminus, and wherein the analog is an agonist or antagonist of the receptor to which it selectively binds or associates. For instance, in some embodiments, the analog is a VIP analog or a functional fragment thereof that selectivity binds to VPAC1, VPAC2, or PAC1 and wherein the VIP analog of functional fragment thereof is an agonist or antagonist of at least one receptor chosen from: VPAC1, VPAC2, and PAC1. In some embodiments, the methods of treatment or prevention include administration of VIP analogs, wherein the VIP analog is an an agonist or antagonist of at least one receptor chosen from: VPAC1, VPAC2, and PAC1. In some embodiments, the composition comprises an analog, wherein the analog wherein the analog does not comprise a repetitive pattern of sequential β-amino acids from the amino-terminus to the carboxy-terminus chosen from the following: ααααααβ, αααααβα, ααααβαα, αααβααα, ααβαααα, αβααααα, βαααααα, αααααββ, ααααββα, αααββαα, ααββααα, αββαααα, ββαααααα, βααααβ, βαααβα, βααβαα, βαβααα, βαβααα, αβααααβ, αβαααβα, αβααβαα, ααβααβ, αααβααβ, αααβαβα, and αααβαβα. In some embodiments, the composition comprises an analog, wherein the analog does not comprises a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ. In some embodiments, the composition comprises an analog, wherein the analog that does not comprise a repetitive pattern of sequential β-amino acids from the amino-terminus to the carboxy-terminus chosen from the following: ββαβαααβααβααααβαβ; βαββαααβααβααααβαβ; βααββααβααβααααβαβ; βααβαβαβααβααααβαβ; βααβααββααβααααβαβ; βααβαααββαβααααβαβ; βααβαααβαββααααβαβ; βααβαααβααββαααβαβ; βααβαααβαααβββαααβαβ; βααβαααβααββααβαβ; βααβαααβααβαβαβαβ; βααβαααβααβααββαβ; βααβαααβααβαααβββ; and βααβαααβααβαααβαβα.

In some embodiments, the composition comprises an analog, wherein the analog does not comprises a repetitive pattern of sequential β-amino acids from the amino-terminus to the carboxy-terminus chosen from the following: ββααβαααβααβαααα; βαβαβαααβααβαααα; βααβαααβααβαααβααα; βααβαβαβααβαααβααα; βαααββαβαααβαααβααα; βαααβααββαβααααβααα; βααβαααβαβαβααααβααα; βααβαααβααββααααβααα; βααβαααβααααβββααα; βααβαααβααααβαβα; and βααβαααβααααβααβ.

In some embodiments, the composition comprises an analog, wherein the analog doe not comprise a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ, wherein any α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ, wherein at least one α-amino acid residue may be a non-natural amino acid. In some embodiments, the composition comprises an analog, wherein the analog comprises a repetitive pattern of sequential β-amino acids from the amino-terminus to the carboxy-terminus chosen from the following: βααβαααβααβαααβααα, βααβαααβααβαααββαα, βααβαααβααβαααβββα, and βααβαααβααβαααββββ, wherein from about 1 to about 10 α-amino acid residues may be a non-natural amino acid. In any of the above-mentioned patterns one or more of the β-amino acid residues may be replaced or modified with cyclic β-amino acid (cyclically-constrained beta amino acid), such as APC or ACPC.

In some embodiments, the composition, pharmaceutical compositions, kit, or polypeptides of the invention comprise a VIP analog, wherein the analog is either: (a) an agonist of VPAC2 receptor; or (b) interferes with VPAC2 receptor signaling pathway and comprises the following repetitive pattern of β-amino acids from the amino-terminus to the carboxy-terminus: $β_1α_1α_2β_2α_3α_4α_5β_3$, wherein $β_1$, $β_2$ and $β_3$ are β-homo amino acids; wherein there is an optional β amino acid ($β_0$ or $β_4$) to one of the β-homo amino acids (e.g. $β_{1-3}$); wherein the composition, pharmaceutical compositions, kit, or polypeptides of the invention optionally comprise amino acids with a pattern selected from: ααααααβ, αααααβα, ααααβαα, αααβααα, ααβαααα, αβααααα, βαααααα, αααααββ, ααααββα, αααββαα, ααββααα, αββαααα, ββαααααα, βααααβ, βαααβα, βααβαα, βαβααα, αβααααα, αβαααβ, αβααβα, αβαααα, αβαβααα, αβααααβ, ααβαααβ, ααβααβα, ααβαβαα, αααβααβ, αααβαβα, and αααβαβ.

In some embodiments, the composition, pharmaceutical compositions, kit, or polypeptides of the invention comprise a VIP analog, wherein the analog does not comprises a repetitive pattern of sequential β-amino acids from the amino-terminus to the carboxy-terminus chosen from the following: β ααβαααβααβαααβααα; βααβαααβααβαααββαα; βααβαααβααβαααβββα; and βααβαααβααβαααββββ.

In some embodiments, the composition, pharmaceutical compositions, kit, or polypeptides of the invention comprise a VIP analog, wherein the analog that does not comprise a pattern of sequential α or β-amino acids from the amino-terminus to the carboxy-terminus chosen from the following: ββαβαααβααβαααβααβ; βαββαααβααβαααβααβ; βαβαβαααβααβαααβααβ; βααββααβααβαααβααβ; βααβαβαβααβαααβααβ; βααβααββααβαααβααβ;

βααβαααβααββααβααβ; βααβαααβααβαβαααβ; βααβαααβααββααβ; βααβαααβααβαααββαβ; and βααβαααβααβαααβαββ;

In some embodiments, the composition, pharmaceutical compositions, kit, or polypeptides of the invention comprise a VIP analog, wherein the analog does not comprise a repetitive pattern of sequential β-amino acids from the amino-terminus to the carboxy-terminus chosen from the following: ββααβααβαααβααβααα; βαβαβααβαααβααβααα; βααββααβαααβααβααα; βαααββαβαααβααβααα; βαααβααββαααβααβααα; βαααβααβαβαβααβααα; βαααβααβααββααβααα; βαααβααβαααββαβααα; βαααβααβαααβββααα; βαααβααβαααβααββαα; βαααβααβαααβαβαβα; and βαααβααβαααβααβααβ.

In some embodiments, the composition, pharmaceutical compositions, kit, or polypeptides of the invention comprise a VIP analog, wherein the analog doe not comprise a repetitive pattern of sequential β-amino acids from the amino-terminus to the carboxy-terminus chosen from the following: β ααβαααβααβαααβααα; βααβαααβααβαααββαα; βααβαααβααβαααββββα; and βααβαααβααβαααββββ; wherein any α-amino acid residue may be a non-natural amino acid.

In some embodiments, the composition, pharmaceutical compositions, kit, or polypeptides of the invention comprise a VIP analog, wherein the analog comprises a repetitive pattern of sequential β-amino acids from the amino-terminus to the carboxy-terminus chosen from the following: βααβαααβααβαααβαα; βααβαααβααβαααββαα; βααβαααβααβαααβββα; and βααβαααβααβαααβββββ; wherein at least one α-amino acid residue may be a non-natural amino acid.

In some embodiments, the composition, pharmaceutical compositions, kit, or polypeptides of the invention comprise a VIP analog, wherein the analog comprises a repetitive pattern of sequential β-amino acids from the amino-terminus to the carboxy-terminus chosen from the following: βααβαααβααβαααβααα; βααβαααβααβαααββαα; βααβαααβααβαααβββα; and βααβαααβααβαααββββ; wherein from about 1 to about 10 α-amino acid residues may be a non-natural amino acid.

In any of the above-mentioned patterns one or more of the β-amino acid residues may be replaced or modified with cyclic β-amino acid (cyclically-constrained beta amino acid), such as APC or ACPC;
wherein the C-terminus is, optionally, amidated; and
wherein the N-terminus is, optionally, acylated;
or functional fragments thereof.

In some embodiments, the composition, pharmaceutical compositions, kit, or polypeptides of the invention comprises a VIP analog, comprising FTENYTKLRK (Seq ID No. 138) wherein at least two adjacent amino acids are replaced by two sequential β-amino acids. In some embodiments, the composition, pharmaceutical compositions, kits, or polypeptides of the invention comprise a VIP analog, wherein the at least two adjacent β-amino acids are x and y.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\beta_6$, wherein $\beta_1$=a beta-3 threonine or ACPC; $\alpha_1$=an alpha arginine; $\alpha_2$=an alpha leucine; $\beta_2$=a beta-3 arginine or APC; $\alpha_3$=an alpha lysine; $\alpha_4$=an alpha glutamine; $\alpha_5$=an alpha leucine; $\beta_3$=a beta-3 alanine or ACPC; $\alpha_6$=an alpha valine; $\alpha_7$=an alpha lysine; $\beta_4$=a beta-3 lysine or APC; $\alpha_5$=an alpha tyrosine; $\alpha_6$=an alpha leucine; $\alpha_{10}$=an alpha asparagine; $\beta_5$=a beta-3 alanine or ACPC; $\alpha_{11}$=an alpha isoleucine; $\alpha_{12}$=an alpha leucine; $\beta_6$=a beta-3 asparagine; wherein the repetitive pattern is, optionally, preceded by: HSDAVFTDNY (SEQ ID NO: 68) if the composition comprises; and
wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=any beta amino acid; $\alpha_1$=any alpha amino acid; $\alpha_2$=any alpha amino acid; $\alpha_3$=any alpha amino acid; $\beta_2$=any beta amino acid; $\alpha_4$=any alpha amino acid; $\alpha_5$=any alpha amino acid; $\beta_3$=any beta amino acid; α6=any alpha amino acid; α7=any alpha amino acid; α8=any alpha amino acid; $\beta_4$=any beta amino acid; $\alpha_9$=any alpha amino acid; $\alpha_{10}$=any alpha amino acid; $\beta_5$=any beta amino acid; $\alpha_{11}$=any alpha amino acid; $\alpha_{12}$=any alpha amino acid; $\alpha_{13}$=any alpha amino acid; wherein the repetitive pattern is, optionally, preceded by: HSDAVFTDNY (SEQ ID NO: 68) if the composition comprises; and
wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$, wherein $\beta_1$=a beta-3 threonine; $\alpha_1$=any alpha amino acid; $\alpha_2$=any alpha amino acid; $\alpha_3$=any alpha amino acid; $\beta_2$=a beta-3 lysine; $\alpha_4$=any alpha amino acid; $\alpha_5$=any alpha amino acid; $\beta_3$=a beta-3 alanine; α6=any alpha amino acid; α7=any alpha amino acid; α8=any alpha amino acid; $\beta_4$=a beta-3 tyrosine; $\alpha_9$=any alpha amino acid; $\alpha_{10}$=any alpha amino acid; $\beta_5$=a beta-3 alanine; $\alpha_{11}$=any alpha amino acid; $\alpha_{12}$=any alpha amino acid; $\alpha_{13}$=any alpha amino acid; wherein the repetitive pattern is, optionally, preceded by: HSDAVFTDNY (SEQ ID NO: 68) if the composition comprises; and
wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}$; wherein $\beta_1$=any beta amino acid; $\alpha_1$=an alpha arginine; $\alpha_2$=an alpha leucine; $\alpha_3$=an alpha arginine; $\beta_2$=any beta amino acid; $\alpha_4$=an alpha glutamine; $\alpha_5$=an alpha leucine; $\beta_3$=any beta amino acid; $\alpha_6$=an alpha valine acid; $\alpha_7$=an alpha lysine; $\alpha_8$=an alpha lysine; $\beta_4$=any beta amino acid; $\alpha_9$=an alpha leucine; $\alpha_{10}$=an alpha asparagine; $\beta_5$=any beta amino acid; $\alpha_{11}$=an alpha isoleucine; $\alpha_{12}$=an alpha leucine; $\alpha_{13}$=an alpha asparagine; wherein the repetitive pattern is, optionally, preceded by: HSDAVFTDNY (SEQ ID NO: 68) if the composition comprises; and
wherein the C-terminus is, optionally, amidated; and
wherein the N-terminus is, optionally, acylated;
or functional fragments thereof.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=any alpha amino acid; $\alpha_2$=any alpha amino acid; $\alpha_3$=an alpha amino acid; $\beta_2$=a beta-3 arginine; $\alpha_4$=an alpha alpha amino acid; $\alpha_5$=any alpha amino acid; $\beta_3$=a beta-3 leucine; $\alpha$=any alpha amino acid; $\alpha_7$=any alpha amino acid; $\alpha_8$=any alpha amino acid; $\beta_4$=a beta-3 lysine; $\alpha_9$=any alpha amino acid; $\alpha_{10}$=any alpha amino acid; $\beta_5$=a beta-3 asparagine; $\alpha_{11}$=any alpha amino acid; $\alpha_{12}$=any alpha amino acid; $\alpha_{13}$=any alpha amino acid; and $\beta_6$=a beta-3 asparagine; wherein the repetitive pattern is, optionally, preceded by: HSDAVFTDN (SEQ ID NO: 67); and
  wherein the C-terminus is, optionally, amidated; and
  wherein the N-terminus is, optionally, acylated;
  or functional fragments thereof.

In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=an alpha threonine; $\alpha_2$=an alpha arginine; $\alpha_3$=an alpha leucine; $\beta_2$=a beta-3 arginine or APC; $\alpha_4$=an alpha lysine; $\alpha_5$=an alpha glutamine; $\beta_3$=a beta-3 leucine or ACPC; $\alpha_6$=an alpha alanine; $\alpha_7$=an alpha valine; $\alpha_8$=an alpha lysine; $\beta_4$=a beta-3 lysine or APC; $\alpha_9$=an alpha tyrosine; $\alpha_{10}$=an alpha leucine; $\gamma_5$=a beta-3 asparagine or ACPC; $\alpha_{11}$=an alpha alanine; $\alpha_{12}$=an alpha isoleucine; $\alpha_{13}$=an alpha leucine; and $\beta_6$=a beta-3 asparagine; wherein the repetitive pattern is, optionally, preceded by: HSDAVFTDN (SEQ ID NO: 67); and
  wherein the C-terminus is, optionally, amidated; and
  wherein the N-terminus is, optionally, acylated;
  or functional fragments thereof In some embodiments, the composition comprises a VIP analog, wherein the analog comprises the following repetitive pattern of sequential β-amino acids from the amino-terminus:
$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;
wherein $\beta_1$=a beta-3 tyrosine; $\alpha_1$=an alpha threonine; $\alpha_2$=an alpha arginine; $\alpha_3$=an alpha leucine; $\beta_2$=a beta-3 arginine or APC; $\alpha_4$=an alpha lysine; $\alpha_5$=an alpha glutamine; $\beta_3$=a beta-3 leucine or ACPC; $\alpha_6$=an alpha alanine; $\alpha_7$=an alpha valine; $\alpha_8$=an alpha lysine; $\beta_4$=a beta-3 lysine or APC; $\alpha_9$=an alpha tyrosine; $\alpha_{10}$=an alpha leucine; $\beta_5$=a beta-3 asparagine or ACPC; $\alpha_{11}$=an alpha alanine; $\alpha_{12}$=an alpha isoleucine; $\alpha_{13}$=an alpha leucine; and $\beta_6$=a beta-3 asparagine; wherein the repetitive pattern is, optionally, preceded by: HSDAVFTDN (SEQ ID NO: 67); and
  wherein the C-terminus is, optionally, amidated; and
  wherein the N-terminus is, optionally, acylated;
  or functional fragments thereof In some embodiments, the composition comprises HSDAVFTDN (SEQ ID NO: 67) or HSDAVFTDNY (SEQ ID NO: 68), wherein at least one of the amino acids from HSDAVFTDN (SEQ ID NO: 67) or HSDAVFTDNY (SEQ ID NO: 68) are non-natural or beta amino acids. In some embodiments, the composition comprises HSDAVFTDN (SEQ ID NO: 67) or HSDAVFTDNY (SEQ ID NO: 68), wherein at least one of the amino acids from HSDAVFTDN (SEQ ID NO: 67) or HSDAVFTDNY (SEQ ID NO: 68) is a beta-3, beta-2, cyclic, or heterocyclic beta amino acids. In some embodiments, the C-terminus is not amidated. In some embodiments, the N-terminus is not acylated. In some embodiments, the composition comprises HSDAVFTDN (SEQ ID NO: 67) or HSDAVFTDNY (SEQ ID NO: 68), wherein the the amino acids from HSDAVFTDN (SEQ ID NO: 67) or HSDAVFTDNY (SEQ ID NO: 68) are alpha amino acids. In some embodiments, the composition comprises HSDAVFTDN (SEQ ID NO: 67) or HSDAVFTDNY (SEQ ID NO: 68), wherein the the amino acids from HSDAVFTDN (SEQ ID NO: 67) or HSDAVFTDNY (SEQ ID NO: 68) are not alpha amino acids. In some embodiments, the composition comprises HSDAVFTDN (SEQ ID NO: 67) or HSDAVFTDNY (SEQ ID NO: 68), wherein none of the amino acids from HSDAVFTDN (SEQ ID NO: 67) or HSDAVFTDNY (SEQ ID NO: 68) are beta-3 amino acids. In some embodiments, the composition comprises HSDAVFTDN (SEQ ID NO: 67) or HSDAVFTDNY (SEQ ID NO: 68), wherein none of the amino acids from HSDAVFTDN (SEQ ID NO: 67) or HSDAVFTDNY (SEQ ID NO: 68) are beta-2 amino acids. In some embodiments, the composition comprises HSDAVFTDN (SEQ ID NO: 67) or HSDAVFTDNY (SEQ ID NO: 68), wherein none of the amino acids from HSDAVFTDN (SEQ ID NO: 67) or HSDAVFTDNY (SEQ ID NO: 68) are ACPC or APC. In some embodiments, the composition comprises HSDAVFTDN (SEQ ID NO: 67) or HSDAVFTDNY (SEQ ID NO: 68), wherein none of the amino acids from HSDAVFTDN (SEQ ID NO: 67) or HSDAVFTDNY (SEQ ID NO: 68) are cyclic. In some embodiments, the composition comprises HSDAVFTDN (SEQ ID NO: 67) or HSDAVFTDNY (SEQ ID NO: 68), wherein none of the amino acids from HSDAVFTDN (SEQ ID NO: 67) or HSDAVFTDNY (SEQ ID NO: 68) are heterocyclic.

"Selective" or "Selectivity" means that the analog of the present invention has a binding preference for one protein as compared to another protein. In some embodiments, the binding preference may be measured as an affinity for a protein in terms of half maximal inhibitory concentration (IC50). In some embodiments, the binding preference may be measured as an affinity for a protein in terms of half maximal effective concentration (EC50). For example, an analog selective to VPAC2 receptor with a selectivity to VPAC2 means that the analog may bind to VPAC1 receptor but has a higher binding affinity for a domain of the VPAC2 receptor if the analog is exposed to both VPAC1 and VPAC2 at similar or equivalent concentrations. As used herein, an analog that selectively binds to VPAC2 refers to an analog with increased selectivity for the VPAC2 receptor compared to other known receptors or proteins to which the peptide may bind. In some embodiments, the analog selective for VPAC2 may be an agonist of the VPAC2 receptor peptide. In some embodiments, the analog selective for VPAC2 may be an antagonist of VPAC2 receptor. In some embodiments, an analog selective to VPAC2 receptor means that the analog may bind to VPAC1 receptor but has a higher binding affinity for a domain of the VPAC2 receptor if the analog is exposed to PAC1, VPAC1 receptor and VPAC2 receptors at similar or equivalent concentrations. In some embodiments, an analog selective to VPAC1 receptor means that the analog may bind to a domain of VPAC2 or PAC1 receptor but has a higher binding affinity for a domain of the VPAC1 receptor if the analog is exposed to to PAC1, VPAC1 receptor and VPAC2 receptors at similar or equivalent concentrations. As used herein, an analog that selectively binds to VPAC1 refers to an analog with increased selectivity for the VPAC1 receptor compared to other known receptors or proteins to which the peptide may bind. In some embodiments, the analog selective for VPAC1 may be an agonist of the VPAC1 receptor peptide. In some embodiments, the analog selective for VPAC1 may be an antagonist of VPAC1 receptor. In some embodiments, an analog selective to VPAC1 receptor means that the analog may bind to VPAC2 receptor but has a higher binding affinity for a domain of the VPAC1 receptor if the analog is exposed to both VPAC1 receptor and VPAC2 receptor at similar or equivalent concentrations. As used herein, an analog that selectively binds to PAC1 refers to an analog with increased selectivity for the PAC1 receptor as compared to other known receptors or proteins to which the peptide may bind. In some embodiments, the analog selective for PAC1 may be an agonist of the PAC1 receptor peptide. In some embodiments, the analog selective for PAC1 may be an antagonist of PAC1 receptor. In some embodiments, an analog selective to PAC1 receptor means that the analog may bind to VPAC2 or VPAC1 receptors but has a higher binding affinity for a domain of the PAC1 receptor if the analog is exposed to to PAC1, VPAC1 receptor and VPAC2 receptors at similar or equivalent concentrations. The degree of selectivity may be determined by a ratio of VPAC2 receptor binding affinity to VPAC1 receptor binding affinity or by a ratio of VPAC2 receptor binding affinity to PAC1 receptor binding affinity. Binding affinity is determined as described below in Example 1.

In any of the embodiments described below wherein the polypeptide comprises a residue designated f, the residue designated f is D-Phe or L-Phe or S. In some embodiments, the invention relates to compositions or pharmaceutical compositions comprising a VIP analog, wherein the analog comprises an α-amino acid and at least one β-amino acid, and wherein the analog is between 75% and 99% homologous to HfDAVFTNSYRKVLKRLSARKLLQDIL (SEQ ID NO: 69); where residue designated f (position 2) is D-Phe, and wherein the analog interferes with the VPAC1 receptor signaling pathway. In some embodiments, the invention relates to compositions or pharmaceutical compositions comprising a VIP analog, wherein the analog comprises an α-amino acid and at least one β-amino acid, and wherein the analog is between 75% and 99% homologous to HfDAVFTNSYRKVLKRLSARKLLQDIL (SEQ ID NO: 69), where residue designated f (position 2) is D-Phe, and wherein the analog is an antagonist of the VPAC1 receptor. In some embodiments, the composition comprises a VIP analog is from about 80% to about 99% homologous to HfDAVFTNSYRKVLKRLSARKLLQDIL (SEQ ID NO: 69), where residue designated f (position 2) is D-Phe. In some embodiments the VIP analog is from about 80% to about 85% homologous to HfDAVFTNSYRKVLKRLSARKLLQDIL (SEQ ID NO: 69), where residue designated f (position 2) is D-Phe. In some embodiments the VIP analog is from about 85% to about 90% homologous to HfDAVFTNSYRKVLKRLSARKLLQDIL (SEQ ID NO: 69), where residue designated f (position 2) is D-Phe. In some embodiments the VIP analog is from about 90% to about 95% homologous to HfDAVFTNSYRKVLKRL-SARKLLQDIL (SEQ ID NO: 69), where residue designated f (position 2) is D-Phe. In some embodiments the VIP analog is from about 95% to about 99% homologous to HfDAVFTNSYRKVLKRLSARKLLQDIL (SEQ ID NO: 69), where residue designated f (position 2) is D-Phe. In some embodiments the VIP analog is about 95%, 96%, 97%, 98%, or 99% homologous to HfDAVFTNSYRKVLKRL-SARKLLQDIL (SEQ ID NO: 69), where residue designated f (position 2) is D-Phe. In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$, wherein $\beta_1$=any beta amino acid; $\alpha_1$=any alpha amino acid; $\alpha_2$=any alpha amino acid; $\beta_2$=any beta amino acid; $\alpha_3$=any alpha amino acid; $\alpha_4$=any alpha amino acid; as =any alpha amino acid; $\beta_3$=any beta amino acid; $\alpha_6$=any alpha amino acid; $\alpha_7$=any alpha amino acid; $\beta_4$=any beta amino acid; $\alpha_8$=any alpha amino acid; $\alpha_9$=any alpha amino acid; $\alpha_{10}$=any alpha amino acid; $\beta_5$=any beta amino acid; wherein the repetitive pattern is, optionally, preceded by: HfDAV FTNSY (SEQ ID NO: 70); and wherein residue designated f (position 2) is D-Phe
wherein the C-terminus is, optionally, amidated; and
wherein the N-terminus is, optionally, acylated;
or functional fragments thereof.

In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$, wherein $\beta_1$=any beta 3 amino acid; $\alpha_1$=any alpha amino acid; $\alpha_2$=any alpha amino acid; $\beta_2$=any beta 3 amino acid; $\alpha_3$=any alpha amino acid; $\alpha_4$=any alpha amino acid; $\alpha_5$=any alpha amino acid; $\beta_3$=any beta 3 amino acid; $\alpha_6$=any alpha amino acid; $\alpha_7$=any alpha amino acid; $\beta_4$=any beta 3 amino acid; $\alpha_8$=any alpha amino acid; $\alpha_9$=any alpha amino acid; $\alpha_{10}$=any alpha amino acid; $\beta_5$=any beta 3 amino acid; wherein the repetitive pattern is, optionally, preceded by: HfDAV FTNSY (SEQ ID NO: 70); and wherein residue designated f (position 2) is D-Phe
wherein the C-terminus is, optionally, amidated; and
wherein the N-terminus is, optionally, acylated;
or functional fragments thereof.

In some embodiments, the composition or pharmaceutical compositions comprise a VIP analog, wherein the analog is either: (a) an antagonist of VPAC1 receptor; or (b) interferes with VPAC1 receptor signaling pathway and comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$, wherein $\beta_1$=a beta-3 arginine; $\alpha_1$=any alpha amino acid; $\alpha_2$=any alpha amino acid; $\beta_2$=a beta-3 leucine; $\alpha_3$=any alpha amino acid; $\alpha_4$=any alpha amino acid; as =any alpha amino acid; 13=a beta-3 serine; $\alpha_6$=any alpha amino acid; $\alpha_7$=any alpha amino acid; $\beta_4$=a beta-3 lysine; $\alpha_8$=any alpha amino acid; $\alpha_9$=any alpha amino acid; $\alpha_{10}$=any alpha amino acid; $\beta_5$=a beta-3 aspartic acid; wherein the repetitive pattern is, optionally, preceded by: HfDAV FTNSY (SEQ ID NO: 70); and wherein residue designated f (position 2) is D-Phe
wherein the C-terminus is, optionally, amidated; and
wherein the N-terminus is, optionally, acylated;
or functional fragments thereof.

In some embodiments, the composition comprises HfDAVFTDN (SEQ ID NO: 71) or HfDAVFTDNY (SEQ ID NO:72), wherein at least one of the amino acids from HfDAVFTDN (SEQ ID NO: 71) or HfDAVFTDNY (SEQ ID NO:72) are non-natural or beta amino acids, wherein residue designated f (position 2) is D-Phe. In some embodiments, the composition comprises HfDAVFTDN (SEQ ID NO: 71) or HfDAVFTDNY (SEQ ID NO:72), wherein at least one of the amino acids from HfDAVFTDN (SEQ ID NO: 71) or HfDAVFTDNY (SEQ ID NO:72) is a beta-3, beta-2, cyclic, or heterocyclic beta amino acids, and wherein residue designated f (position 2) is D-Phe. In some embodiments, the C-terminus is not amidated. In some embodiments, the N-terminus is not acylated. In some embodiments, the composition comprises HfDAVFTDN (SEQ ID NO: 71) or HfDAVFTDNY (SEQ ID NO:72), wherein the the amino acids from HfDAVFTDN (SEQ ID NO: 71) or HfDAVFTDNY (SEQ ID NO:72) are alpha amino acids, and wherein residue designated f (position 2) is D-Phe. In some embodiments, the composition comprises HfDAVFTDN (SEQ ID NO: 71) or HfDAVFTDNY (SEQ ID NO:72), wherein the the amino acids from HfDAVFTDN (SEQ ID NO: 71) or HfDAVFTDNY (SEQ ID NO:72) are not alpha amino acids, and wherein residue designated f (position 2) is D-Phe. In some embodiments, the composition comprises HfDAVFTDN (SEQ ID NO: 71) or HfDAVFTDNY (SEQ ID NO:72), wherein none of the amino acids from HfDAVFTDN (SEQ ID NO: 71) or HfDAVFTDNY (SEQ ID NO:72) are beta-3 amino acids, and wherein residue designated f (position 2) is D-Phe. In some embodiments, the composition comprises HfDAVFTDN (SEQ ID NO: 71) or HfDAVFTDNY (SEQ ID NO:72), wherein none of the amino acids from HfDAVFTDN (SEQ ID NO: 71) or HfDAVFTDNY (SEQ ID NO:72) are beta-2 amino acids, and wherein residue designated f (position 2) is D-Phe. In some embodiments, the composition comprises HfDAVFTDN (SEQ ID NO: 71) or HfDAVFTDNY (SEQ ID NO:72), wherein none of the amino acids from HfDAVFTDN (SEQ ID NO: 71) or HfDAVFTDNY (SEQ ID NO:72) are ACPC or APC, and wherein residue designated f (position 2) is D-Phe. In some embodiments, the composition comprises HfDAVFTDN (SEQ ID NO: 71) or HfDAVFTDNY (SEQ ID NO:72), wherein none of the amino acids from HfDAVFTDN (SEQ ID NO: 71) or HfDAVFTDNY (SEQ ID NO:72) are cyclic, wherein residue designated f (position 2) is D-Phe. In some embodiments, the composition comprises HfDAVFTDN (SEQ ID NO: 71) or HfDAVFTDNY (SEQ ID NO:72), wherein none of the amino acids from HfDAVFTDN (SEQ ID NO: 71) or HfDAVFTDNY (SEQ ID NO:72) are heterocyclic, and wherein residue designated f (position 2) is D-Phe.

In some embodiments, the composition comprises a VIP analog, wherein the analog comprises the following repetitive pattern of sequential β-amino acids from the amino-terminus: $(\beta_1\alpha_1\alpha_2\alpha_3\beta_2\alpha_4\alpha_5\beta_3\alpha_6\alpha_7\alpha_8\beta_4\alpha_9\alpha_{10}\beta_5)$; wherein $\beta_1$=any beta amino acid; $\alpha_1$=any alpha amino acid; $\alpha_2$=any alpha amino acid; $\alpha_3$=an alpha amino acid; $\beta_2$=any beta amino acid; $\alpha_4$=an alpha alpha amino acid; $\alpha_5$=any alpha amino acid; $\beta_3$=any beta amino acid; $\alpha_6$=any alpha amino acid; $\alpha_7$=any alpha amino acid; $\alpha_8$=any alpha amino acid; $\beta_4$=any beta amino acid; $\alpha_9$=any alpha amino acid; $\alpha_{10}$=any alpha amino acid; $\beta_5$=any beta amino acid; wherein the repetitive pattern is, optionally, preceded by: HfDAV FTNSY (SEQ ID NO: 70) or HfDAV FTNS (SEQ ID NO: 73); and wherein the C-terminus is, optionally, amidated; and
wherein the N-terminus is, optionally, acylated;
or functional fragments thereof; and wherein residue designated f (position 2) is D-Phe.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=a beta-3 arginine or beta-3 tyrosine; $\alpha_1$=any alpha amino acid; $\alpha_2$=any alpha amino acid; $\alpha_3$=an alpha amino acid; $\beta_2$=a beta-3 lysine or beta-3 leucine; $\alpha_4$=an alpha alpha amino acid; $\alpha_5$=any alpha amino acid; $\beta_3$=a beta-3 serine or a beta-3 leucine; $\alpha_6$=any alpha amino acid; $\alpha_7$=any alpha amino acid; $\alpha_8$=any alpha amino acid; $\beta_4$=a beta-3 leucine or beta-3 lysine; $\alpha_9$=any alpha amino acid; $\alpha_{10}$=any alpha amino acid; $\beta_5$=a beta-3 aspartic acid or beta-3 glutamine; wherein the repetitive pattern is, optionally, preceded by: HfDAV FTNSY (SEQ ID NO: 70) or HfDAV FTNS (SEQ ID NO: 73); and wherein the C-terminus is, optionally, amidated; and
wherein the N-terminus is, optionally, acylated;
or functional fragments thereof, and wherein residue designated f (position 2) is D-Phe.

In some embodiments, the composition comprises a VIP analog, wherein the analog comprises the following repetitive pattern of sequential β-amino acids from the amino-terminus: $\beta_1\alpha_1\alpha_2\alpha_3\beta_2\alpha_4\alpha_5\beta_3\alpha_6\alpha_7\alpha_8\beta_4\alpha_9\alpha_{10}\beta_5$; wherein $\beta_1$=a beta-3 arginine, beta-3 tyrosine, or APC; $\alpha_1$=any alpha amino acid; $\alpha_2$=any alpha amino acid; $\alpha_3$=an alpha amino acid; $\beta_2$=ACPC or APC; $\alpha_4$=an alpha alpha amino acid; $\alpha_5$=any alpha amino acid; $\beta_3$=ACPC or a beta-3 leucine; $\alpha_6$=any alpha amino acid; $\alpha_7$=any alpha amino acid; $\alpha_8$=any alpha amino acid; $\beta_4$=a beta-3 leucine, beta-3 lysine, or APC; $\alpha_9$=any alpha amino acid; $\alpha_{10}$=any alpha amino acid; $\beta_5$=a beta-3 aspartic acid or ACPC; wherein the repetitive pattern is, optionally, preceded by: HfDAV FTNSY (SEQ ID NO: 70) or HfDAV FTNS (SEQ ID NO: 73); and wherein the C-terminus is, optionally, amidated; and
wherein the N-terminus is, optionally, acylated;
or functional fragments thereof, and wherein residue designated f (position 2) is D-Phe.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HfDAV FTNSY Z̲KVX̲K RLX̲AR KLLQD̲ IL    (SEQ ID NO: 74)
HfDAV FTNSY R̲KVX̲K RLX̲AR Z̲LLQD̲ IL    (SEQ ID NO: 75)
HfDAV FTNSY R̲KVX̲K RLX̲AR KLLQX̲ IL    (SEQ ID NO: 76)
HfDAV FTNSY Z̲KVX̲K RLX̲AR Z̲LLQX̲ IL    (SEQ ID NO: 77)
HfDAV FTNSY R̲KVLZ̲ RLX̲AR KL̲LQX̲ IL    (SEQ ID NO: 78)
HfDAV FTNSY Z̲KVLZ̲ RLX̲AR KL̲LQX̲ IL    (SEQ ID NO: 79)
HfDAV FTNSY̲ RKVX̲K RLSAR Z̲LLX̲D IL    (SEQ ID NO: 80)
HfDAV FTNSY̲ RKVX̲K RX̲SAR KLLX̲D IL    (SEQ ID NO: 81)
HfDAV FTNSY̲ RKVX̲K RX̲SAR Z̲LLX̲D IL    (SEQ ID NO: 82)

wherein residue designated f (position 2) is D-Phe, wherein each underlined residue is a beta amino acid, wherein X is a ACPC, wherein Z is APC, and wherein the analog interferes with the VPAC1 receptor signaling pathway. In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

HfDAV FTNSY Z̲KVX̲K RLX̲AR KLLQD̲ IL    (SEQ ID NO: 74)
HfDAV FTNSY R̲KVX̲K RLX̲AR Z̲LLQD̲ IL    (SEQ ID NO: 75)
HfDAV FTNSY R̲KVX̲K RLX̲AR KLLQX̲ IL    (SEQ ID NO: 76)
HfDAV FTNSY Z̲KVX̲K RLX̲AR Z̲LLQX̲ IL    (SEQ ID NO: 77)
HfDAV FTNSY R̲KVLZ̲ RLX̲AR KL̲LQX̲ IL    (SEQ ID NO: 78)
HfDAV FTNSY Z̲KVLZ̲ RLX̲AR KL̲LQX̲ IL    (SEQ ID NO: 79)

```
HfDAV FTNSY RKVXK RLSAR ZLLXD IL        (SEQ ID NO: 80)

HfDAV FTNSY RKVXK RXSAR KLLXD IL        (SEQ ID NO: 81)

HfDAV FTNSY RKVXK RXSAR ZLLXD IL        (SEQ ID NO: 82)
``` wherein residue designated f (position 2) is D-Phe, wherein each underlined residue is a beta amino acid, wherein X is a ACPC, wherein Z is APC, and wherein the analog is an antagonist of the VPAC1 receptor; or functional fragments thereof.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HSDAV FTDNY TRLRK QIAVK KYLNa ILN       (SEQ ID NO: 83)

HSDAV FTDNY tRLrK QLaVK kYLNa Iln       (SEQ ID NO: 84)

HSDAV FTDNY tRLRk QLaVK KyLNa ILN       (SEQ ID NO: 85)

HSDAV FTDNy TRLrK QIAVK kYLnA Iln       (SEQ ID NO: 86)

HSDAV FTDNY tRLzK QLxVK kYLNx ILn       (SEQ ID NO: 87)

HSDAV FTDNY tRLzK QLxVK zYLNx Iln       (SEQ ID NO: 88)

HSDAV FTDNY xRLzK QLxVK kYLNx Iln       (SEQ ID NO: 89)

HSDAV FTDNY xRLzK QLxVK zYLNx Iln       (SEQ ID NO: 90)

HSDAV FTDNY tRLRz QLxVK KyLNx ILN       (SEQ ID NO: 91)

HSDAV FTDNY xRLRz QLxVK KyLNx ILN       (SEQ ID NO: 92)

HSDAV FTDNy TRLzK QIAVK zYLxA Iln       (SEQ ID NO: 93)

HSDAV FTDNy TRLzK QxAVK kYLxA Iln       (SEQ ID NO: 94)

HSDAV FTDNy TRLzK QxAVK zYLxA Iln       (SEQ ID NO: 95)
``` wherein each underlined residue is a beta amino acid corresponding to the single code amino acid upon which it is based, wherein X is a ACPC, and wherein Z is APC; or functional fragments thereof.

In some embodiments, the invention relates to compositions or pharmaceutical compositions comprising a VIP analog, wherein the analog comprises an α-amino acid and at least one β-amino acid, and wherein the analog is between 75% and 99% homologous to HSDAVFTDNYTRLRKQVAAKKYLQSIKNKRY (SEQ ID NO: 96), and wherein the analog stimulates the VPAC2 receptor signaling pathway. In some embodiments, the invention relates to compositions or pharmaceutical compositions comprising a VIP analog, wherein the analog comprises an α-amino acid and at least one β-amino acid, and wherein the analog is between 75% and 99% homologous to HSDAVFTDNYTRLRKQVAAKKYLQSIKNKRY (SEQ ID NO: 96), wherein the analog is an agonist of the VPAC2 receptor. In some embodiments, the composition comprises a VIP analog is from about 80% to about 99% homologous to HSDAVFTDNYTRLRKQVAAKKYLQSIKNKRY (SEQ ID NO: 96). In some embodiments the VIP analog is from about 80% to about 85% homologous to HSDAVFTDNYTRLRKQVAAKKYLQSIKNKRY (SEQ ID NO: 96). In some embodiments the VIP analog is from about 85% to about 90% homologous to HSDAVFTDNYTRLRKQVAAKKYLQSIKNKRY (SEQ ID NO: 96). In some embodiments the VIP analog is from about 90% to about 95% homologous to HSDAVFTDNYTRLRKQVAAKKYLQSIKNKRY (SEQ ID NO: 96). In some embodiments the VIP analog is from about 95% to about 99% homologous to HSDAVFTDNYTRLRKQVAAKKYLQSIKNKRY (SEQ ID NO: 96). In some embodiments the VIP analog is about 95%, 96%, 97%, 98%, or 99% homologous to HSDAVFTDNYTRLRKQVAAKKYLQSIKNKRY (SEQ ID NO: 96). In some embodiments the VIP analog is HSDAVFTDNYTRLRKQVAAKKYLQSIKNKRY (SEQ ID NO: 96).

wherein the C-terminus is, optionally, amidated; and wherein the N-terminus is unmodified or modified; or functional fragments thereof.

In some embodiments, the composition comprises a VIP analog, wherein the analog comprises the following repetitive pattern of sequential β-amino acids from the amino-terminus:

$\beta_1\alpha_1\alpha_2\alpha_3\beta_2\alpha_4\alpha_5\beta_3\alpha_6\alpha_7\alpha_8\beta_4\alpha_9\alpha_{10}\beta_5\alpha_{11}\alpha_{12}\alpha_{13}\beta_6$;

wherein $\beta_1$=a beta-3 threonine or a beta-3 tyrosine; $\alpha_1$=any alpha amino acid; $\alpha_2$=any alpha amino acid; $\alpha_3$=an alpha amino acid; $\beta_2$=a beta-3 lysine or a beta-3 arginine; $\alpha_4$=an alpha alpha amino acid; $\alpha_5$=any alpha amino acid; $\beta_3$=a beta-3 alanine or a beta-3 valine; $\alpha_6$=any alpha amino acid; $\alpha_7$=any alpha amino acid; $\alpha_8$=any alpha amino acid; $\beta_4$=a beta-3 tyrosine or a beta-3 lysine; $\alpha_9$=any alpha amino acid; $\alpha_{10}$=any alpha amino acid; $\beta_5$=a beta-3 serine or a beta-3 glutamine; $\alpha_{11}$=any alpha amino acid; $\alpha_{12}$=any alpha amino acid; $\alpha_{13}$=any alpha amino acid; and $\beta_6$=a beta-3 lysine or a beta-3 asparagine; and wherein the repetitive pattern is, optionally, preceded by: HSDAV FTDNY (SEQ ID NO: 68) or HSDAV FTDN (SEQ ID NO: 67); and wherein the repetitive pattern is, optionally, succeeded by: K, KR, or KRY.

wherein the C-terminus is, optionally, amidated; and wherein the N-terminus is unmodified or modified; or functional fragments thereof;

and wherein the analog or functional fragment thereof is a VPAC2 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HSDAVFTDNYXRLZKQVXAKKYLQSIKNKRY     (SEQ ID NO: 97)

HSDAVFTDNYTRLZKQVXAKZYLQSIKNKRY     (SEQ ID NO: 98)

HSDAVFTDNYTRLZKQVXAKKYLQXIKNKRY     (SEQ ID NO: 99)

HSDAVFTDNYXRLZKQVXAKZYLQXIKXKRY     (SEQ ID NO: 100)

HSDAVFTDNYTRLRZQVXAKKYLQXIKNKRY     (SEQ ID NO: 101)

HSDAVFTDNYXRLRZQVXAKKYLQXIKNKRY     (SEQ ID NO: 102)

HSDAVFTDNYTRLZKQVSAKZYLXSIKNKRY     (SEQ ID NO: 103)

HSDAVFTDNYTRLZKQXSAKKYLXSIKNKRY     (SEQ ID NO: 104)

HSDAVFTDNYTRLZKQXSAKZYLXSIKNKRY     (SEQ ID NO: 105)
``` wherein each underlined residue is a beta amino acid corresponding to the single code amino acid upon which it is based, wherein X is a ACPC, and wherein Z is APC; or functional fragments thereof; wherein the C-terminus is, optionally, amidated; and wherein the N-terminus is unmodified.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HSDAVFTDNYXRLZKQVXAKKYLQSIKNKRY    (SEQ ID NO: 97)
HSDAVFTDNYTRLZKQVXAKZYLQSIKNKRY    (SEQ ID NO: 98)
HSDAVFTDNYTRLZKQVXAKKYLQXIKNKRY    (SEQ ID NO: 99)
HSDAVFTDNYXRLZKQVXAKZYLQXIKXKRY    (SEQ ID NO: 100)
HSDAVFTDNYTRLRZQVXAKKYLQXIKNKRY    (SEQ ID NO: 101)
HSDAVFTDNYXRLRZQVXAKKYLQXIKNKRY    (SEQ ID NO: 102)
HSDAVFTDNYTRLZKQVSAKZYLXSIKNKRY    (SEQ ID NO: 103)
HSDAVFTDNYTRLZKQXSAKKYLXSIKNKRY    (SEQ ID NO: 104)
HSDAVFTDNYTRLZKQXSAKZYLXSIKNKRY    (SEQ ID NO: 105)
``` wherein each underlined residue is a beta amino acid corresponding to the single code amino acid upon which it is based, wherein X is a ACPC, and wherein Z is APC; or functional fragments thereof; wherein the C-terminus is, optionally, amidated; and wherein the N-terminus is, optionally, modified.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
HSDAVFTDNYXRLZKQVXAKKYLQSIKNKRY    (SEQ ID NO: 97)
HSDAVFTDNYTRLZKQVXAKZYLQSIKNKRY    (SEQ ID NO: 98)
HSDAVFTDNYTRLZKQVXAKKYLQXIKNKRY    (SEQ ID NO: 99)
HSDAVFTDNYXRLZKQVXAKZYLQXIKXKRY    (SEQ ID NO: 100)
HSDAVFTDNYTRLRZQVXAKKYLQXIKNKRY    (SEQ ID NO: 101)
HSDAVFTDNYXRLRZQVXAKKYLQXIKNKRY    (SEQ ID NO: 102)
HSDAVFTDNYTRLZKQVSAKZYLXSIKNKRY    (SEQ ID NO: 103)
HSDAVFTDNYTRLZKQXSAKKYLXSIKNKRY    (SEQ ID NO: 104)
HSDAVFTDNYTRLZKQXSAKZYLXSIKNKRY    (SEQ ID NO: 105)
``` wherein each underlined residue is a beta amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC2 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
                                   (SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 97)
HSDAV FTDNY XRLZK QVXAK KYLQS IKNKR Y (SEQ ID NO: 98)
HSDAV FTDNY TRLZK QVXAK ZYLQS IKNKR Y (SEQ ID NO: 99)
HSDAV FTDNY TRLZK QVXAK KYLQX IKNKR Y (SEQ ID NO: 100)
HSDAV FTDNY XRLZK QVXAK ZYLQX IKXKR Y (SEQ ID NO: 101)
HSDAV FTDNY TRLRZ QVXAK KYLQX IKNKR Y (SEQ ID NO: 102)
HSDAV FTDNY XRLRZ QVXAK KYLQX IKNKR Y (SEQ ID NO: 106)
HSDAV FTDNY TRLZK QVAAK ZYLXS IKNKR Y (SEQ ID NO: 107)
HSDAV FTDNY TRLZK QXAAK KYLXS IKNKR Y (SEQ ID NO: 108)
HSDAV FTDNY TRLZK QXAAK ZYLXS IKNKR Y
``` wherein each underlined residue is an unnatural amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

```
                                   (SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 97)
HSDAV FTDNY XRLZK QVXAK KYLQS IKNKR Y (SEQ ID NO: 98)
HSDAV FTDNY TRLZK QVXAK ZYLQS IKNKR Y (SEQ ID NO: 99)
HSDAV FTDNY TRLZK QVXAK KYLQX IKNKR Y (SEQ ID NO: 100)
HSDAV FTDNY XRLZK QVXAK ZYLQX IKXKR Y (SEQ ID NO: 101)
HSDAV FTDNY TRLRZ QVXAK KYLQX IKNKR Y (SEQ ID NO: 102)
HSDAV FTDNY XRLRZ QVXAK KYLQX IKNKR Y
```

```
                        (SEQ ID NO: 106)
HSDAV FTDNY TRLZK QVAAK ZYLXS IKNKR Y (SEQ ID NO: 107)
HSDAV FTDNY TRLZK QXAAK KYLXS IKNKR Y (SEQ ID NO: 108)
HSDAV FTDNY TRLZK QXAAK ZYLXS IKNKR Y
``` wherein each underlined residue is a beta amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one β-amino acid, and wherein the analog is between 75% and 100% homologous to one or more of the following sequences:

(SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 96)
HSDAV FTDNY TRLRK QVAAK KYLQS IKNKR Y (SEQ ID NO: 97)
HSDAV FTDNY XRLZK QVXAK KYLQS IKNKR Y (SEQ ID NO: 98)
HSDAV FTDNY TRLZK QVXAK ZYLQS IKNKR Y (SEQ ID NO: 99)
HSDAV FTDNY TRLZK QVXAK KYLQX IKNKR Y (SEQ ID NO: 100)
HSDAV FTDNY XRLZK QVXAK ZYLQX IKXKR Y (SEQ ID NO: 101)
HSDAV FTDNY TRLRZ QVXAK KYLQX IKNKR Y (SEQ ID NO: 102)
HSDAV FTDNY XRLRZ QVXAK KYLQX IKNKR Y (SEQ ID NO: 106)
HSDAV FTDNY TRLZK QVAAK ZYLXS IKNKR Y (SEQ ID NO: 107)
HSDAV FTDNY TRLZK QXAAK KYLXS IKNKR Y (SEQ ID NO: 108)
HSDAV FTDNY TRLZK QXAAK ZYLXS IKNKR Y wherein each underlined residue is a beta-3 homo amino acid corresponding to the single code amino acid upon which it is based, wherein X is a ACPC, and wherein Z is APC; or functional fragments thereof; wherein the C-terminus is, optionally, amidated; wherein the N-terminus is, optionally, modified; and wherein the VIP analog or functional fragment thereof is a VPAC1 agonist.

In some embodiments, the invention relates to compositions or pharmaceutical compositions comprising a VIP analog, wherein the analog comprises an α-amino acid and at least one β-amino acid, and wherein the analog comprises an amino acid sequence that is between 75% and 100% homologous to one or more of the following sequences:

HSDAVFTENYTKLRKQLAxKKYxNDlKKGgT (SEQ ID NO: 109)

HSDAVFTENYTKLRKQLAAzKYxNDLkKGgT (SEQ ID NO: 110)

HSDAVFTENYTKLRKQxAAzKYLxDLkKGGT (SEQ ID NO: 111)

HBDAVFTENYTKLRKQLAAzKYxNDLkKGgT (SEQ ID NO: 112)

HBDAvFTENYTKLRKQLAAzKYxNDLkKGgT (SEQ ID NO: 113)

HBDAvFTEnYTKLRKQLAAzKYxNDLkKGgT (SEQ ID NO: 114)

HxDAVFTENYTKLRKQLAAzKYxNDLkKGgT (SEQ ID NO: 115)

HxDAxFTENYTKLRKQLAAzKYxNDLkKGgT (SEQ ID NO: 116)

HxDAxFTExYTKLRKQLAAzKYxNDLkKGgT (SEQ ID NO: 117)

HxDAVFTDNYtRLRkQLAvKKYlNAIlN (SEQ ID NO: 118)

HxDAxFTDNYtRLRkQLAvKKYlNAIlN (SEQ ID NO: 119)

HFDAVFTDNYtRLRkQLAvKKYlNAIlN (SEQ ID NO: 139)

HFDAxFTDNYtRLRkQLAvKKYlNAIlN (SEQ ID NO: 140)

HxDAvFTDNYtRLRkQLAvKKYlNAIlN (SEQ ID NO: 120)

HFDAvFTDNYtRLRkQLAvKKYlNAIlN (SEQ ID NO: 141)

HsDAvFTDNYtRLRkQLAvKKYlNAIlN (SEQ ID NO: 142)

HsDAvFTDnYtRLRkQLAvKKYlNAIlN (SEQ ID NO: 143)

HFDAvFTDnYtRLRkQLAvKKYlNAIlN (SEQ ID NO: 121)

HFdAVFtDNYtRLRkQLAvKKYlNAIlN (SEQ ID NO: 144)

HSdAVFtDNYtRLRkQLAvKKYlNAIlN (SEQ ID NO: 122)

HxDAvFTENYTKLRKQLAAzKYxNDLkKGgT (SEQ ID NO: 123)

HxDAvFTENYTKLRKQIAAzKYxNDLkKGgT (SEQ ID NO: 124)

HxDAvFTENYTKLRKgLAAzKYxNDLkKGgT (SEQ ID NO: 125)

HxDAvFTENYTKLRkQLAAzKYxNDLkKGgT (SEQ ID NO: 126)

HxDAvFTENYTKLrKQLAAzKYxNDLkKGgT (SEQ ID NO: 127)

HxDAvFTENYTKlRKQLAAzKYxNDLkKGgT (SEQ ID NO: 128)

HxDAxFTEnyTKLRKQLAAzKYxNDLkKGgT (SEQ ID NO: 129)

HxDAxFTExyTKLRKQlAAzKYxNDLkKGgT (SEQ ID NO: 130)

HxDAxFTExyTKLRKgLAAzKYxNDLkKGgT (SEQ ID NO: 131)

HxDAxFTExyTKLRkQLAAzKYxNDLkKGgT (SEQ ID NO: 132)

wherein each underlined residue is any unnatural amino acid; or any beta-2 amino acid; any beta-3 amino acid; or a beta-3 homo amino acid corresponding to the single code amino acid upon which it is based; wherein X is a ACPC, and wherein Z is APC; or functional fragments thereof; wherein the C-terminus is, optionally, amidated; wherein the N-terminus is, optionally, modified; and wherein the VIP analog or functional fragment thereof is a $VPAC_2R$ agonist. In some embodiments, the VIP analog is a VPAC1 agonist that selectivity binds $VPAC_1R$ at least one order of magnitude greater than its selectivity for $VPAC_2R$. In some embodiments, the VIP analog is a $VPAC_2R$ agonist that selectivity binds $VPAC_2R$ at least one order of magnitude greater than its selectivity for $VPAC_1R$. In some embodiments the EC50 of the disclosed analogs herein results in greater selectivity for the specifically targeted receptor than for any of the disclosed receptors herein. In some embodiments, this selectivity is significantly greater than that of the natural receptor ligand.

In some embodiments, the invention relates to compositions or pharmaceutical compositions comprising a VIP analog or pharmaceutical salts thereof, wherein the analog comprises an α-amino acid and at least one β-amino acid, and wherein the analog comprises an amino acid sequence that is between 75% and 100% homologous to any of the amino acid sequences provided in this application.

The invention relates to methods of manufacturing a composition comprising an analog, wherein the analog comprises any of the compositions disclosed herein. In some embodiments, the invention relates to methods of manufacturing a composition comprising an analog, wherein the analog comprises an α-amino acid, at least one β-amino acid, and at least one modified amino acid residue comprising ACPC or APC. The invention relates to methods of manufacturing a composition comprising a VIP family analog, wherein the VIP family analog comprises an α-amino acid and at least one β-amino acid. The invention relates to methods of manufacturing a composition comprising a VIP analog, wherein the VIP analog comprises an α-amino acid and at least one β-amino acid. The method used to fabricate polypeptide compounds may be any means of polypeptide synthesis. Using methods of peptide synthesis, polypeptides fabricated according to the present method are generally less than about 100 residues long. In some embodiments, the invention relates to a method of manufacturing an analog (or fragments herein) comprising non-natural amino acids from from about 5 total residues to about 50 total residues, from about 10 total residues to about 20 total residues, from about 20 total residues to about 30 total residues, from about 30 total residues to about 40 total residues, from about 40 total residues to about 50 total residues, from about 50 to about 60 total residues, from about 60 to about 70 total residues from about 70 to about 80 total residues, from about 80 to about 90 total residues, and from about 90 to about 100 total residues. Ranges above and below these stated ranges are within the scope of the invention. Many commercial services, such as Abgent (San Diego, Calif., USA) offer peptide synthesis services up to about 100 residues. In some embodiments, the invention relates to a method of manufacturing an analog comprising no more than 100 non-natural amino acids. In some embodiments, the invention relates to a method of manufacturing an analog comprising no more than 90 non-natural amino acids. In some embodiments, the invention relates to a method of manufacturing an analog comprising no more than 80 non-natural amino acids. In some embodiments, the invention relates to a method of manufacturing an analog comprising no more than 70 non-natural amino acids. In some embodiments, the invention relates to a method of manufacturing an analog comprising no more than 60 non-natural amino acids. In some embodiments, the invention relates to a method of manufacturing an analog comprising no more than 50 non-natural amino acids. In some embodiments, the invention relates to a method of manufacturing an analog comprising no more than 40 non-natural amino acids. In some embodiments, the invention relates to a method of manufacturing an analog comprising no more than 30 non-natural amino acids. In some embodiments, the invention relates to a method of manufacturing an analog comprising no more than 20 non-natural amino acids. In some embodiments, the invention relates to a method of manufacturing an analog comprising no more than 10 non-natural amino acids. In some embodiments, the method of manufacturing the analog comprises synthesizing the analog using at least one, and, in some embodiments, a plurality of the following non-naturally occurring amino acid residues: (2S,3R)-3-(amino)-2-hydroxy-4-(4-nitrophenyl)butyric acid, (2R,3R)-3-(amino)-2-hydroxy-4-phenylbutyric acid, (R)-3-(amino)-5-phenylpentanoic acid, (R)-3-(amino)-4-(2-naphthyl)butyric acid, (R)-2-methyl-β-Phe-OH, (R)-3,4-dimethoxy-β-Phe-OH, (R)-(3-pyridyl)-β-Ala-OH, (R)-3-(trifluoromethyl)-β-Phe-OH, (R)-3-cyano-β-Phe-OH, (R)-3-methoxy-β-Phe-OH, (R)-3-methyl-β-Phe-OH, (R)-4-(4-pyridyl)-β-HomoAla-OH, (R)-4-(trifluoromethyl)-β-HomoPhe-OH, (R)-4-(trifluoromethyl)-β-Phe-OH, (R)-4-bromo-β-Phe-OH, (R)-4-chloro-β-HomoPhe-OH, (R)-4-chloro-β-Phe-OH, (R)-4-cyano-β-HomoPhe-OH, (R)-4-cyano-β-Phe-OH, (R)-4-fluoro-β-Phe-OH, (R)-4-methoxy-β-Phe-OH, (R)-4-methyl-β-Phe-OH, (R)-3-Tyr-OH, (R)-4β-pyridyl)-β-HomoAla-OH, (R)-4-fluoro-β-HomoPhe-OH, (S)-5-phenylpentanoic acid, (S)-5-hexenoic acid, (S)-5-phenyl-pentanoic acid, (S)-6-phenyl-5-hexenoic acid, (S)-2-(trifluoromethyl)-β-HomoPhe-OH, (S)-2-(trifluoromethyl)-β-Phe-OH, (S)-2-cyano-β-HomoPhe-OH, (S)-2-methyl-β-Phe-OH, (S)-3,4-dimethoxy-β-Phe-OH, (S)-3-(trifluoromethyl)-β-HomoPhe-OH, (S)-3-(trifluoromethyl)-β-Phe-OH, (S)-3-cyano-β-Phe-OH, (S)-3-methoxy-β-Phe-OH, (S)-3-methyl-β-Phe-OH, (S)-4-(4-pyridyl)-β-HomoAla-OH, (S)-4-(trifluoromethyl)-β-Phe-OH, (S)-4-bromo-β-Phe-OH, (S)-4-chloro-β-HomoPhe-OH, (S)-4-chloro-β-Phe-OH, (S)-4-cyano-β-HomoPhe-OH, (S)-4-cyano-β-Phe-OH, (S)-4-fluoro-β-Phe-OH, (S)-4-iodo-β-HomoPhe-OH, (S)-4-methyl-β-HomoPhe-OH, (S)-4-methyl-β-Phe-OH, (S)-β-Tyr-OH, (S)-γ,γ-diphenyl-β-HomoAla-OH, (S)-2-methyl-β-Homophe-OH, (S)-3,4-difluoro-β-HomoPhe-OH, (S)-3-(trifluoromethyl)-β-HomoPhe-OH, (S)-3-cyano-β-HomoPhe-OH, (S)-3-methyl-β-HomoPhe-OH, (S)-γ,γ-diphenyl-β-HomoAla-OH, 3-Amino-3-(3-bromophenyl)propionic acid, and 3-Amino-4,4,4-trifluorobutyric acid.

In some embodiments, the fragment comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 30, 31, 32, 33, 34, 35, 36, 37, 38, 39, or 40 amino acids of the wild type protein sequence. In some embodiments, the fragment comprises any of the above-mentioned numbers of amino acids located anywhere within the peptide. Thus, one skilled in the art understands that a fragment of any of these lengths can be walked along the length of the peptide, thus providing any fragment of the peptide with the same or similar function as the native or wild-type amino acid sequence.

One of ordinary skill in the art would readily appreciate that the protecting groups would be removed from the final chemical structure of the analog which becomes administered to a subject. One of ordinary skill would be able to predict the final chemical structure of the analog by using the protecting groups selectively to create a polypeptide with a desirable chirality or secondary structure. For instance, if the analog of the composition is manufactured using (S)-Fmoc-3-methyl-β-HomoPhe-OH, the final yielded product should comprise at least one β-amino acid residue of a 3-methyl-β-homophenylalanine.

In some embodiments, the method of manufacturing the analog comprises synthesizing the analog using at least one, and in some embodiments, a plurality of cyclic amino acid residues. In some embodiments, the VIP analog of the claimed invention comprises the cyclic amino acid residues. In some embodiments, the VIP analog of the claimed invention comprises at least one disulfide bridge that forms a cyclic chain of atoms along a side chain of two amino acid residues.

In some embodiments, the VIP analog of the claimed invention comprises at least 17% β-amino acid residues. In some embodiments, the VIP analog of the claimed invention comprises from about 15% to about 30% β-amino acid residues. In some embodiments, the VIP analog of the claimed invention comprises from about 15% to about 30% β-amino acid residues wherein the first ten amino acids of the amino acid sequence are alpha amino acids. In some embodiments, the VIP analog of the claimed invention comprises from about 16% to about 29% β-amino acid residues. In some embodiments, the VIP analog of the claimed invention comprises from about 17% to about 29% β-amino acid residues. In some embodiments, the VIP analog of the claimed invention comprises from about 18% to about 29% β-amino acid residues. In some embodiments, the VIP analog of the claimed invention comprises from about 19% to about 29% β-amino acid residues. In some embodiments, the VIP analog of the claimed invention comprises from about 20% to about 29% β-amino acid residues.

In some embodiments, at least one of the β³-amino acid residues is substituted with a residue chosen from the following: (S,S)-trans-2-aminocyclopentanecarboxylic acid ((S,S)-ACPC), (S,R)-trans-2-aminocyclopentanecarboxylic acid ((S,R)-ACPC), (R,S)-trans-2-aminocyclopentanecarboxylic acid ((R,S)-ACPC), or (R,R)-trans-2-aminocyclopentanecarboxylic acid ((R,R)-ACPC) if the amino acid is non-polar; or pyrrolidine analogue of (S,S)-ACPC, (R,S)-ACPC, (S,R)-ACPC, (R,R)-ACPC), which is designated APC, if the amino acid is basic. In some embodiments, at least one of the β³-amino acid residues is substituted with a residue chosen from the following: (S,S)-trans-2-aminocyclopentanecarboxylic acid ((S,S)-ACPC) if the amino acid is non-polar; or pyrrolidine analogue of (S,S)-ACPC if the residue is basic.

In some embodiments, the VIP analog of the claimed invention comprises the following sequence:

In some embodiments, the VIP analog comprises a cyclic amino acid residue covalently bonded to one or more contiguous or non-contiguous amino acid sidechain residues via the following synthetic linking structures:

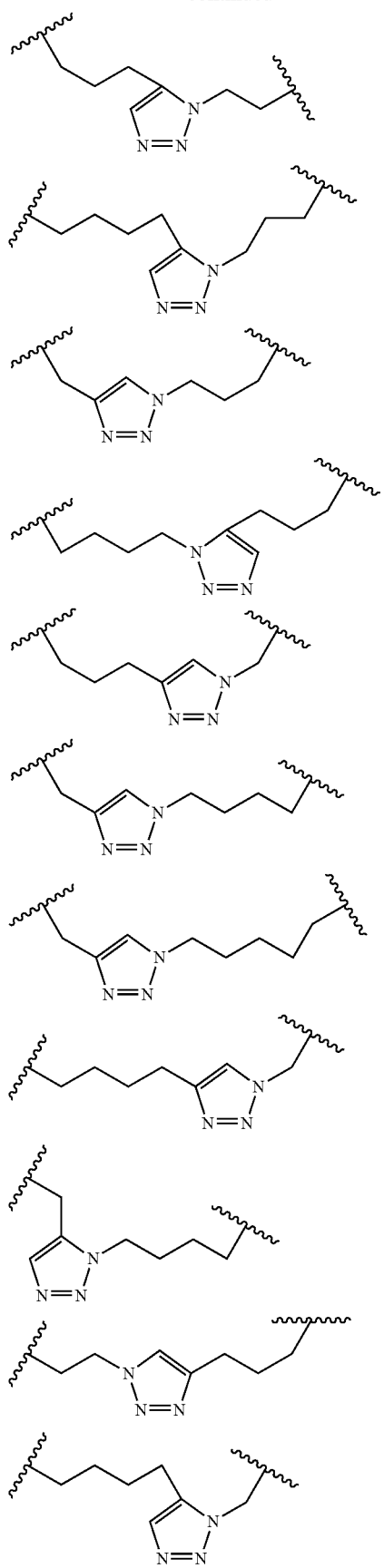

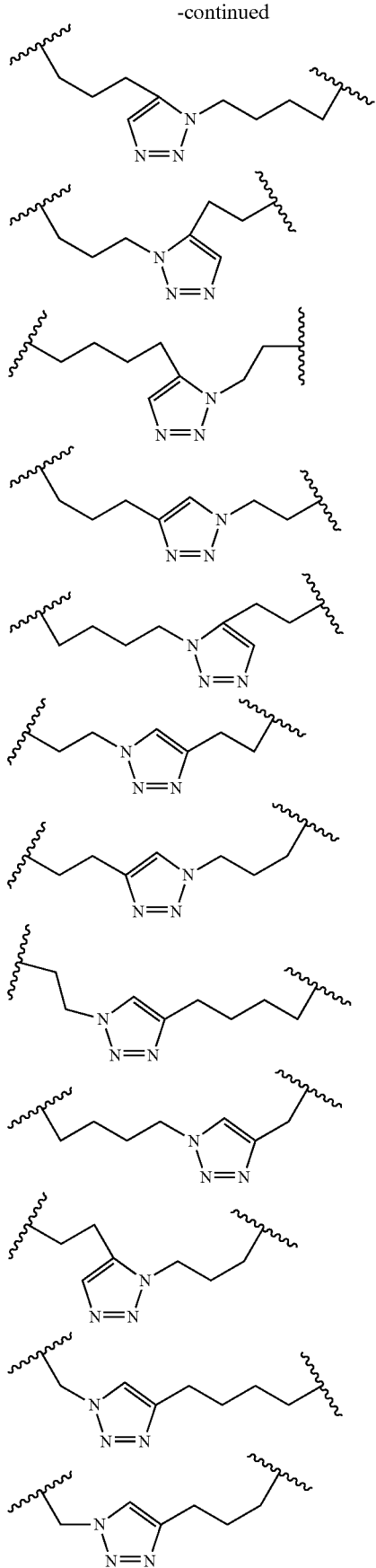
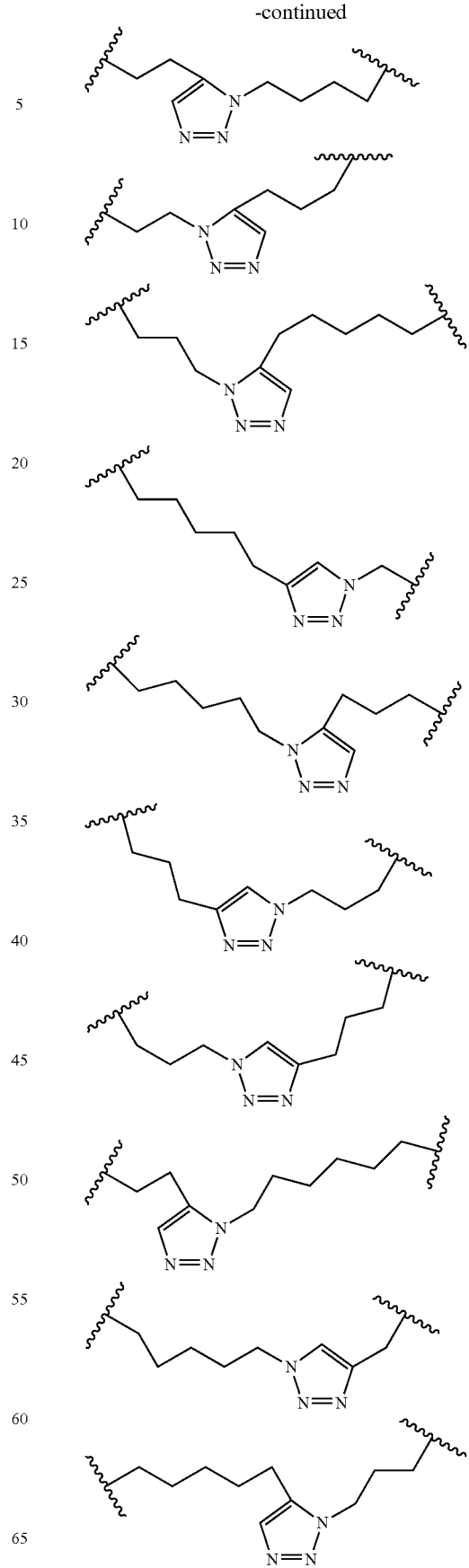

63
-continued
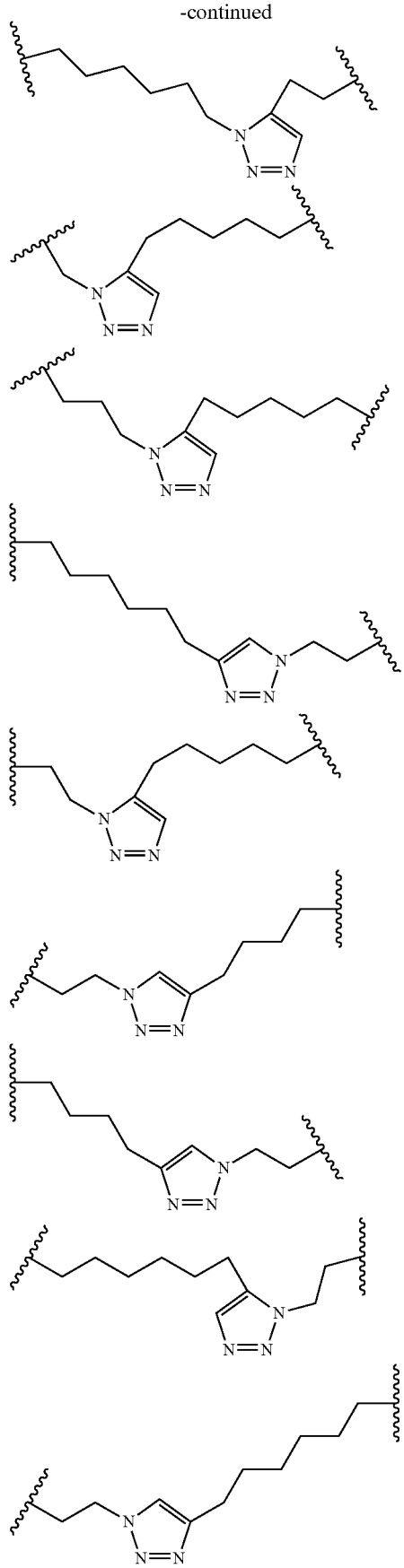
64
-continued
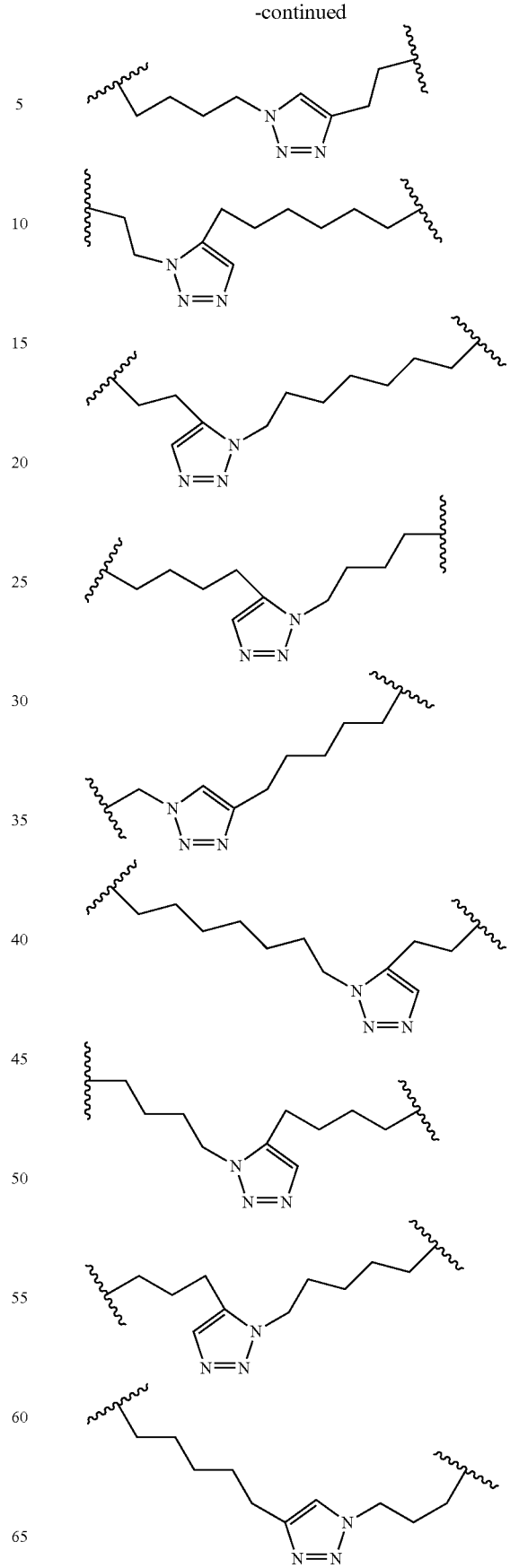

65
-continued
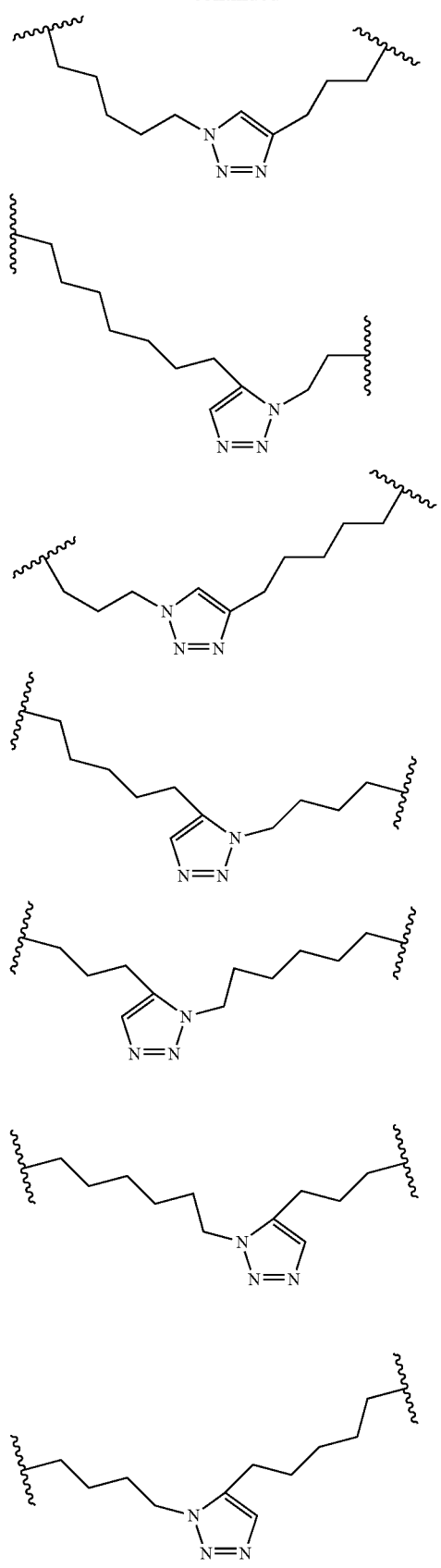
66
-continued
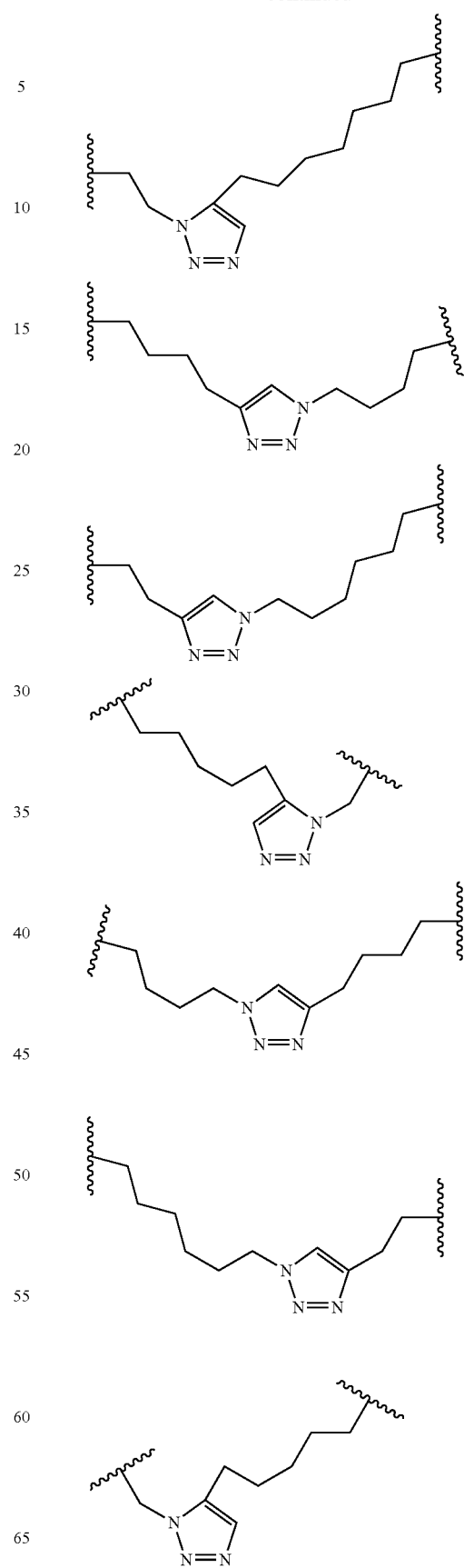

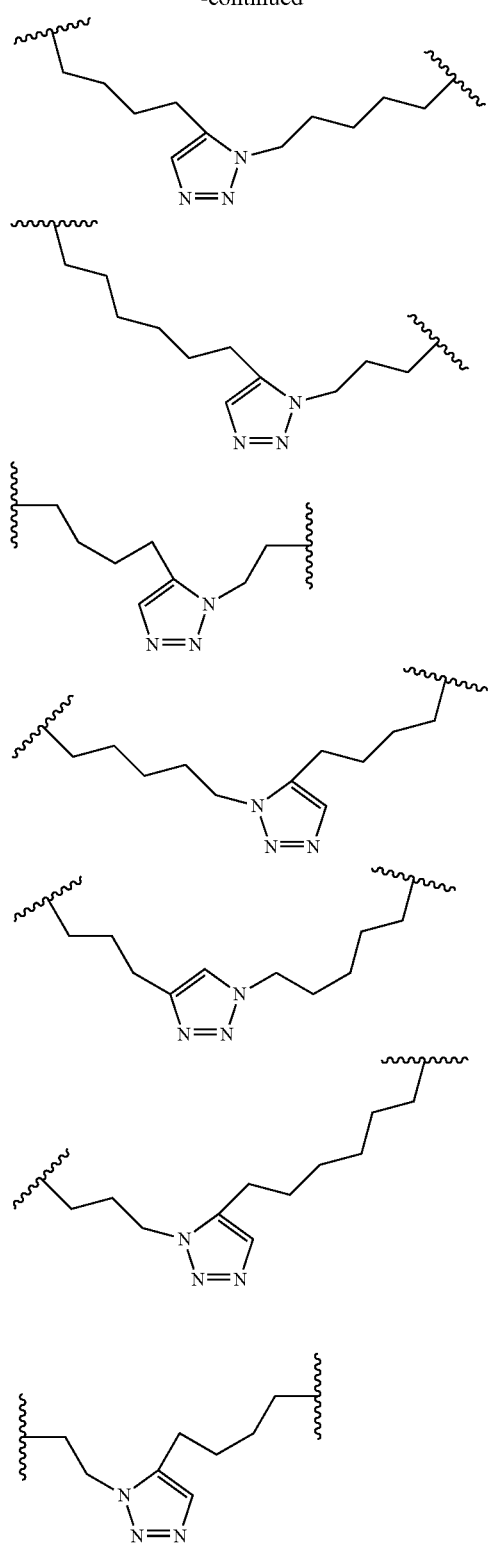
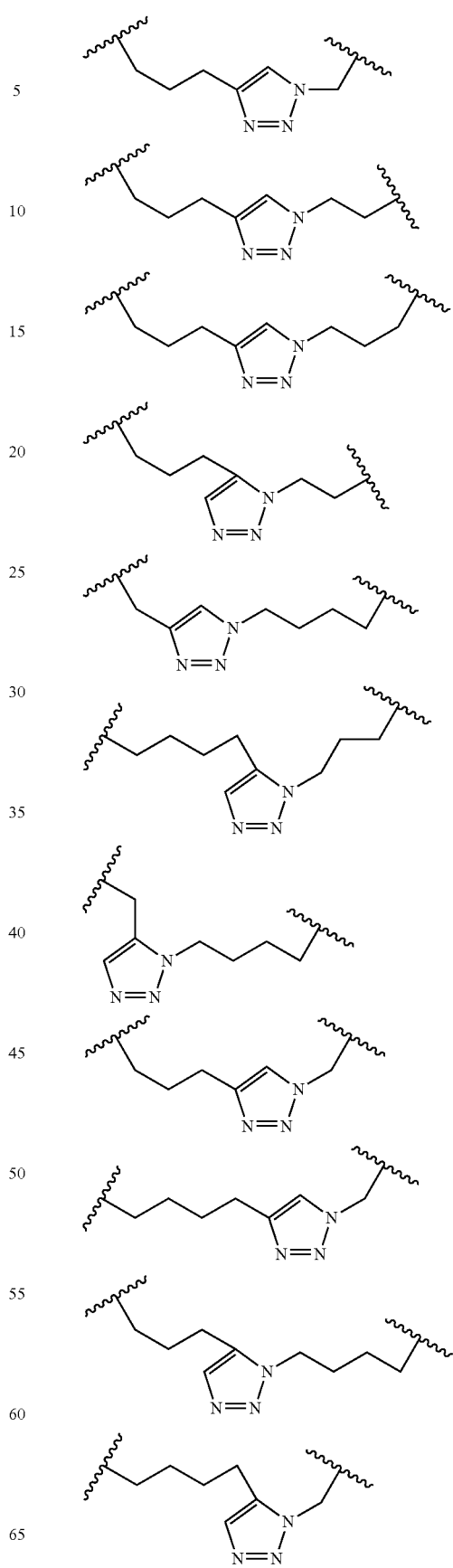
In some embodiments, the analog does not comprise a cyclic substituent in its side chain. In some embodiments, the cyclic amino acid residues are not covalently bonded to one or more contiguous or non-contiguous amino acid sidechain residues via the following synthetic linking structures:

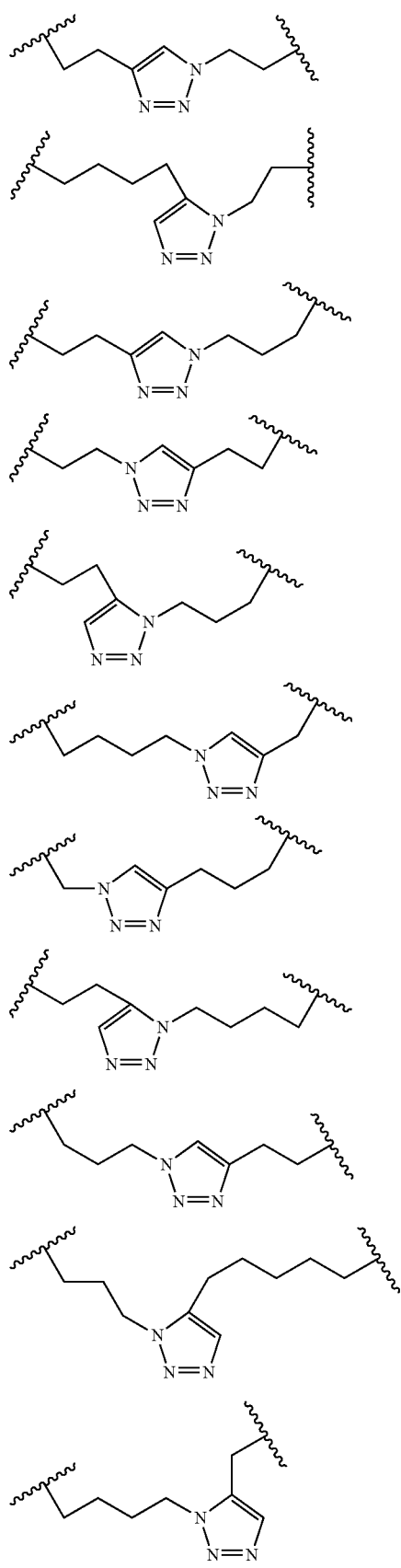
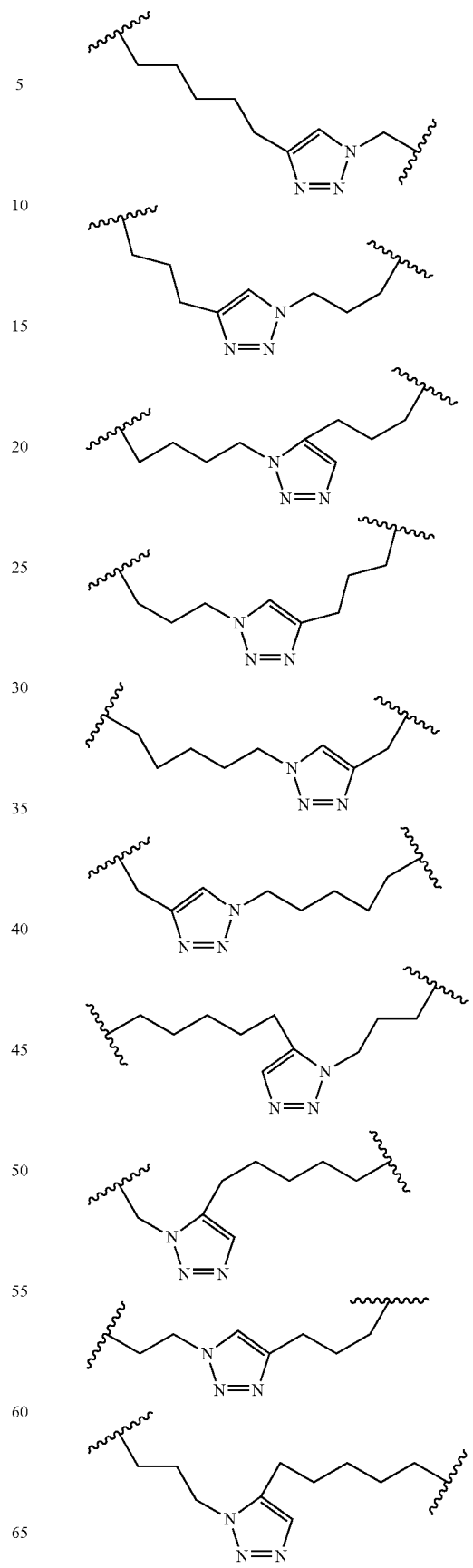

71
-continued
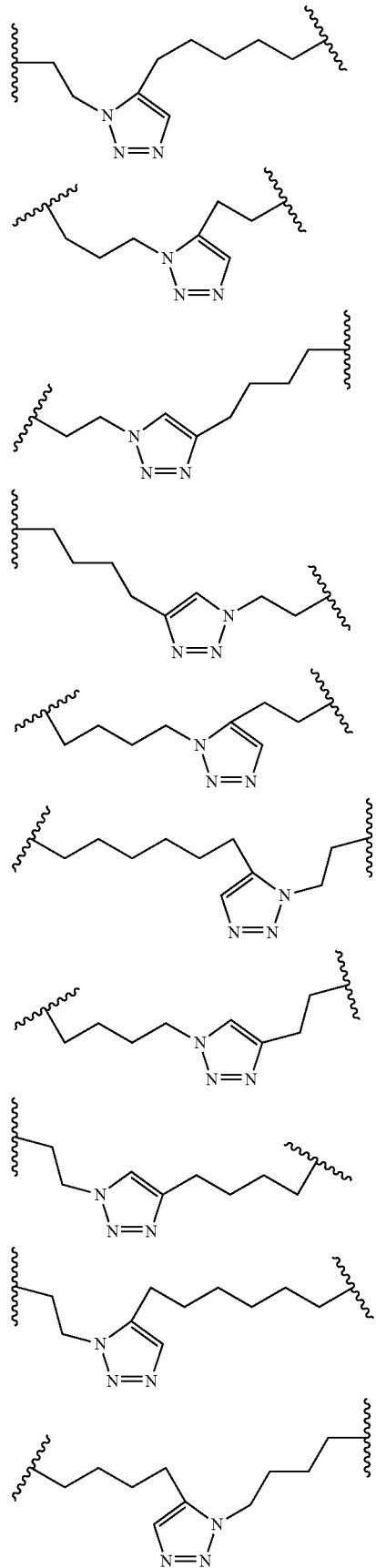
72
-continued
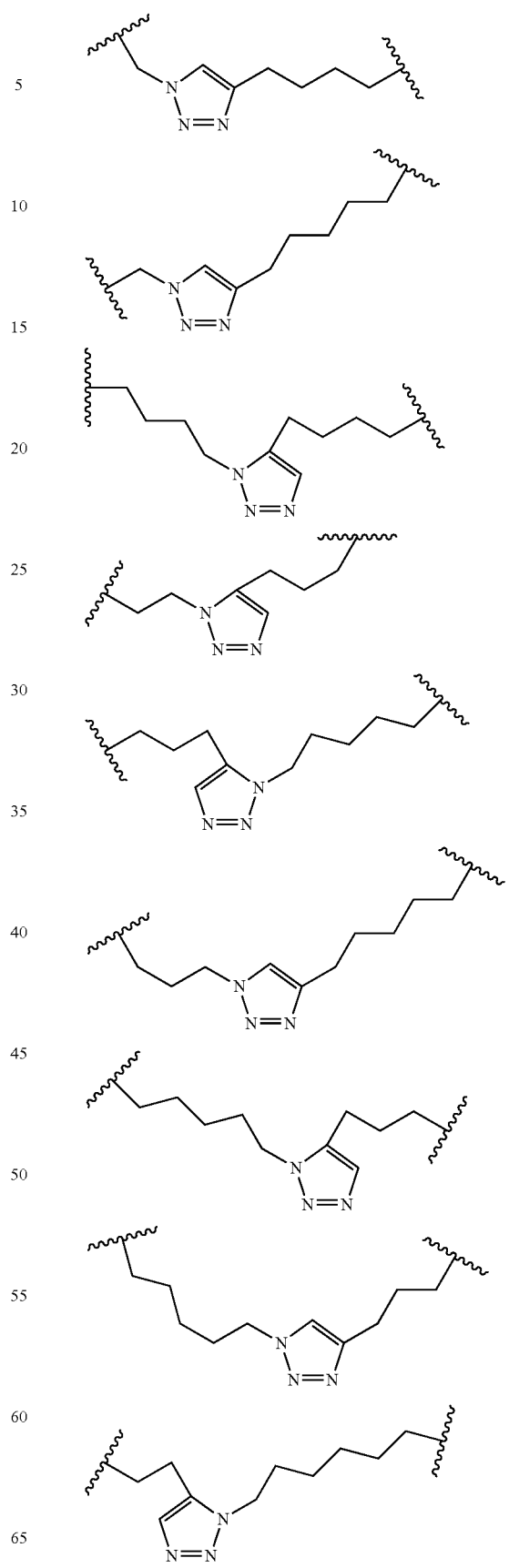

73
-continued
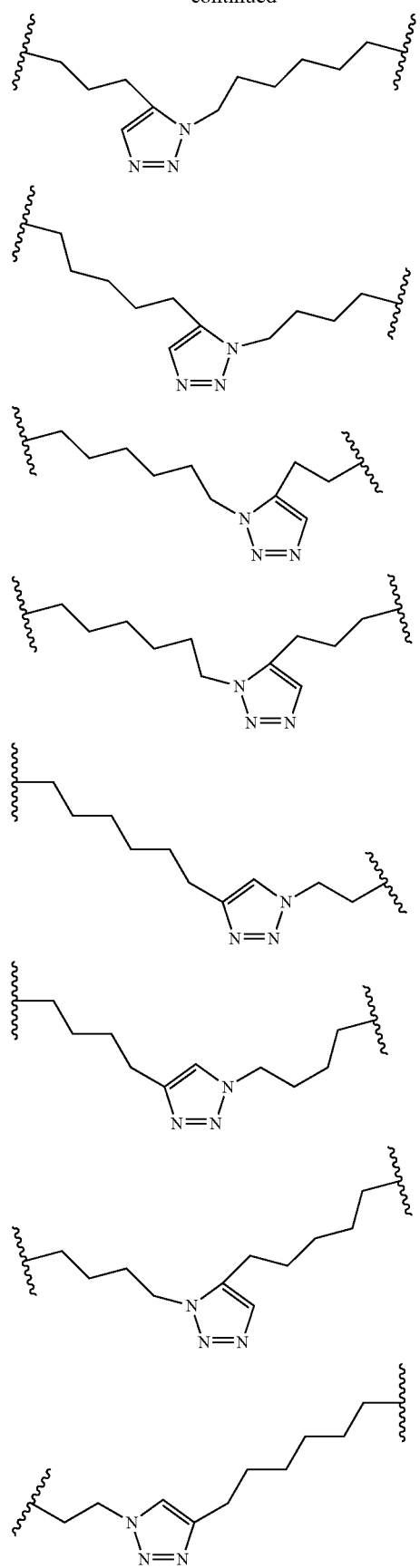
74
-continued
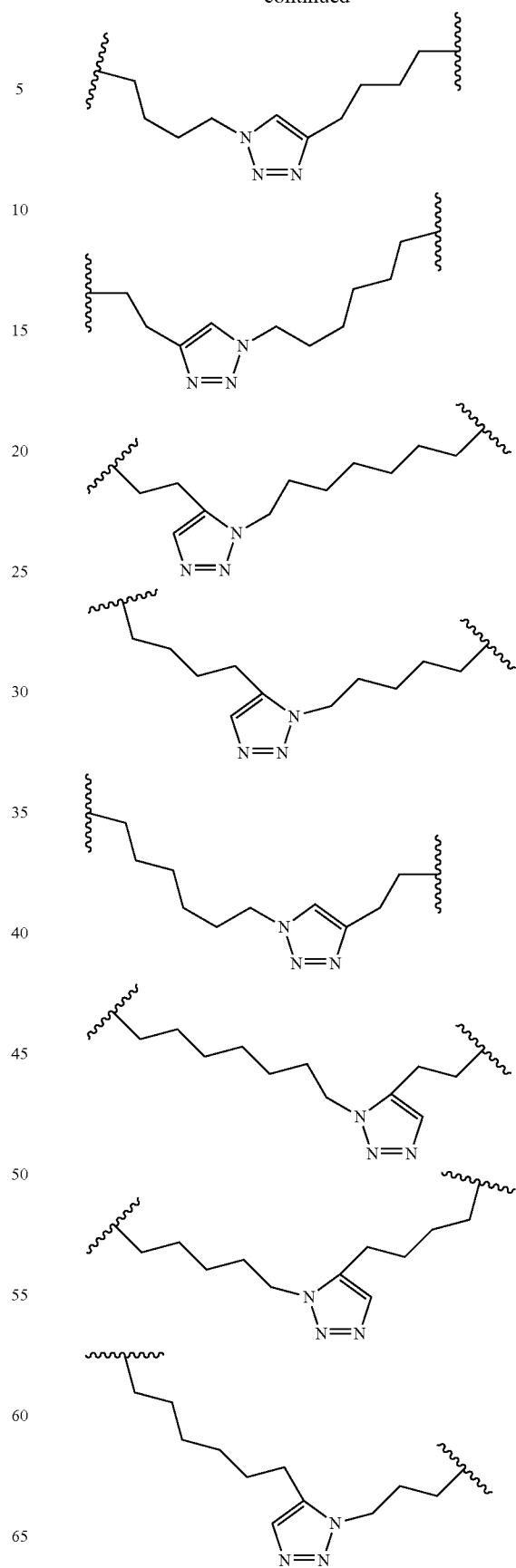

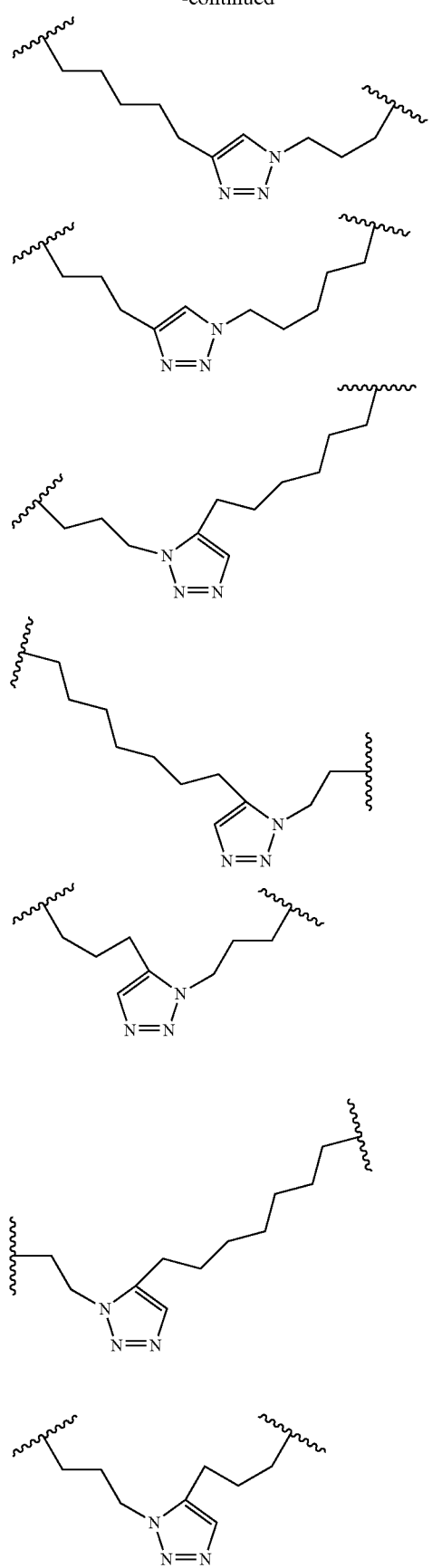
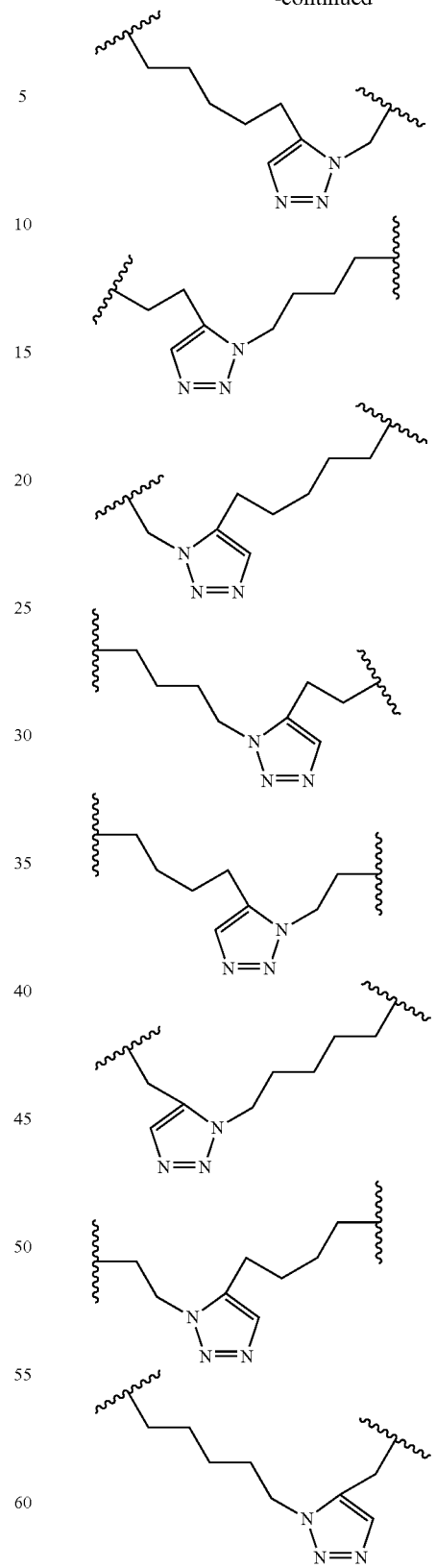
In some embodiments, the analogs of the present invention comprise at least one or a plurality of the following cyclic amino acid residues, some of which being described with a protecting group that becomes eliminated from the analog either during synthesis or when the analog is purified after synthesis:

L-β-HomohydroxyProline hydrochloride
(1R,2R)-Boc-2-aminocyclohexane carboxylic acid {(1R, 2R)-ACHC}
(1R,2R)-Fmoc-2-aminocyclohexane carboxylic acid {(1R, 2R)-ACHC}
(1R,2S)-Boc-2-aminocyclohexane carboxylic acid {(1R, 2S)-ACHC}
(1R,2S)-Fmoc-2-aminocyclohexane carboxylic acid {(1R, 2S)-ACHC}
(1S,2R)-Boc-2-aminocyclohexane carboxylic acid {(1S, 2R)-ACHC}
(1S,2R)-Fmoc-2-aminocyclohexane carboxylic acid (1S, 2R)-ACHC}
(1S,2S)-Boc-2-aminocyclohexane carboxylic acid {(1S,2S)-ACHC}
(1S,2S)-Fmoc-2-aminocyclohexane carboxylic acid {(1S, 2S)-ACHC}
(1R,2R)-Boc-2-aminocyclopentane carboxylic acid {(1R, 2R)-ACPC}
(1R,2R)-Fmoc-2-aminocyclopentane carboxylic acid {(1R, 2R)-ACPC}
(1S,2S)-Boc-2-aminocyclopentane carboxylic acid {(1S, 2S)-ACPC}
(1S,2S)-Fmoc-2-aminocyclopentane carboxylic acid {(1S, 2S)-ACPC}
Boc-cis-2-aminocyclopentane carboxylic acid, cis-Acpc
Fmoc-cis-2-aminocyclopentane carboxylic acid, cis-Acpc
(R)-Boc-(2-carboxymethyl)-piperidine, (R)-(1-piperidin-2-yl)-acetic acid
(R)-Fmoc-(2-carboxymethyl)-piperidine, (R)-(1-Fmoc-piperidin-2-yl)-acetic acid
(S)-Boc-(2-carboxymethyl)-piperidine (S)-(1-Boc-piperidin-2-yl)-acetic acid
(S)-Fmoc-(2-carboxymethyl)-piperidine (S)-(1-Fmoc-piperidin-2-yl)-acetic acid
(R,S)-Boc-2-carboxymorpholine Boc-Cop
(R,S)-Boc-2-carboxymorpholine Fmoc-Cop
(R,S)-Boc-nipecotic acid Boc-Nip
(R,S)-Boc-nipecotic acid Fmoc-Nip
(R)-Fmoc-nipecotic acid (R)-Fmoc-Nip
(R)-Fmoc-nipecotic acid (R)-Boc-Nip
(3S)-Boc-1-pyrrolidine-3-carboxylic acid (3S)-Boc-beta-Pro-OH
(3S)-Fmoc-1-pyrrolidine-3-carboxylic acid (3S)-Fmoc-beta-Pro-OH In some embodiments, the analogs of the present invention comprise at least one or a plurality of non-natural amino acid residues that can modified by PEGylation. In some embodiments the analogs or fragments of the polypeptides related to this invention comprise PEG molecules which are covalently bound to the side chain of the α, or β amino acids in the polypeptide. In some embodiments, the polypeptides of this invention comprise the PEGylated cyclic amino acid residues or cyclic amino acid side chains. PEG molecule(s) may be covalently attached to any Lys, Cys, K(W) or K(CO(CH$_2$)$_2$SH) residue at any position in the analog or fragment of analog. In some embodiments, the analog or a fragment thereof comprises a C-terminal extension may comprise one or more Cys residues which may be PEGylated. In some embodiment of the invention the polypeptides or fragments thereof may comprise one or more PEGylated residues in either or both sequences.

In some embodiments, the analog or fragment thereof comprises a PEG molecule covalently attached to one or all of the β-residue within the analog. In some embodiments, the analog is at least one PEG molecule covalently attached to a residue in the C-terminal extension of the analog or fragment thereof. In some embodiments, the analog comprises more than one PEG molecule, there may be a combination of Lys, Cys, K(CO(CH$_2$)$_2$SH), K(W) and carboxy-terminal amino acid PEGylation. For example, if there are two PEG molecules, one may be attached to a Lys residue and one may be attached to a Cys residue. In some embodiments, the polypeptide comprises one or more covalently bound PEG molecules, wherein at least one of the PEG molecules is branched. In some embodiments, one or more of the PEG molecules are linear. In some embodiments, the composition comprises one or more PEG molecule, wherein the PEG molecule is between about 200 daltons and about 100,000 daltons in molecular weight. In some embodiments, the PEG molecule is chosen from 10,000, 20,000, 30,000, 40,000, 50,000 and 60,000 daltons. In some embodiments, it is chosen from 20,000, 30,000, 40,000, or 60,000 daltons. Where there are two PEG molecules covalently attached to the analog or fragment thereof, each is 1,000 to 40,000 daltons and, they have molecular weights of 20,000 and 20,000 daltons, 10,000 and 30,000 daltons, 30,000 and 30,000 daltons, or 20,000 and 40,000 daltons. In some embodiments mini-PEG s™ are covalently bound to at least one residue or side chain of an α, or β-amino acid. In some embodiments, the mini-PEG™ is chosen from the following list of products: 8-Amino-3,6-Dioxaoctanoic Acid, 11-Amino-3,6,9-Trioxaundecanoic Acid, 8-Amino-3,6-Dioxaoctanoic Acid.DCHA, 11-Amino-3,6,9-Trioxaundecanoic Acid.DCHA.

In some embodiments the method of treatment or prevention of a human disorder depends upon the analog being synthesized. For instance: Peptides for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, WE; Schuler, M; Peschel, C.; Huber, C.; Interleukins. Clinical pharmacology and therapeutic use. Drugs. 48(5):667-77, November 1994) and cytokines (referenced in Peters, M.; Actions of cytokines on the immune response and viral interactions: an overview. Hepatology. 23(4):909-16, April 1996).

Peptides and peptidomimetics that target crucial enzymes, oncogenes or oncogene products, tumor-suppressor genes and their products, growth factors and their corresponding receptors can be used to treat cancer. Examples of these peptides are described in Unger, C. Current concepts of treatment in medical oncology: new anticancer drugs. Journal of Cancer Research & Clinical Oncology. 122(4):189-98, 1996.

VIP analogs, agonist analogs and antagonist analogs can be used to treat allergic respiratory diseases, PAH, asthma and allergic rhinitis, and nervous control of reproductive functions.

In some embodiments, the analog is a "bifunctional polymer," which refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component.

Many procedures and linker molecules for attachment of various compounds to peptides are known. See, e.g., European Patent Application No 188,256; U.S. Pat. Nos. 4,671,958, 4,659,839, 4,414,148, 4,699,784; 4,680,338; 4,569,789; and 4,589,071 which are incorporated by reference herein. In some embodiments, the analog is a "functional polymer" which refers to a polymer comprising two or more discrete functional groups that are functionally identical and capable of reacting specifically with other moieties (including but not limited to, amino acid side groups) to form covalent or non-covalent linkages. A functional polymer or multi-functional polymer may be any desired molecular length or molecular weight, and may be selected to provide a particular desired spacing or conformation between one or more molecules linked to the analog and its binding partner or the analog.

The present invention provides for the use of an antibody or binding composition which specifically binds to a specified analog. in some embodiments the antibody specifically binds the analog derived from a mammalian polypeptide, e.g., a polypeptide derived from a primate, human, cat, dog, rat, or mouse. Antibodies can be raised to various analogs, including individual, polymorphic, allelic, strain, or species variants, and fragments thereof, both in their naturally occurring (full-length) forms or in their synthetic forms. Additionally, antibodies can be raised to the analogs in their inactive state or active state. Anti-idiotypic antibodies may also be used.

A number of immunogens may be selected to produce antibodies specifically reactive with ligand or receptor proteins. Synthetic analogs may serve as an immunogen for the production of monoclonal or polyclonal antibodies. Such antibodies may be used as antagonists or agonists for their targets modulating the disease state associated with the naturally occurring proteins and analogs listed above. Synthetic polypeptides of the claimed invention may also be used either in pure or impure form. Synthetic peptides, made using the appropriate protein sequences, may also be used as an immunogen for the production of antibodies. Naturally folded or denatured material can be used, as appropriate, for producing antibodies. Either monoclonal or polyclonal antibodies may be generated, e.g., for subsequent use in immunoassays to measure the protein, or for immunopurification methods. Methods of producing polyclonal antibodies are well known to those of skill in the art.

Typically, an immunogen, such as a purified analog of the invention, is mixed with an adjuvant and animals are immunized with the mixture. The animal's immune response to the immunogen preparation is monitored by taking test bleeds and determining the titer of reactivity to the protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed if desired. See, e.g., Harlow and Lane; or Coligan. Immunization can also be performed through other methods, e.g., DNA vector immunization. See, e.g., Wang, et al. (1997) Virology 228:278-284.

Monoclonal antibodies may be obtained by various techniques familiar to researchers skilled in the art. Typically, spleen cells from an animal immunized with a desired analog are immortalized, commonly by fusion with a myeloma cell. See, Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, et al. (eds. 1994 and periodic supplements) Cell and Tissue Culture: Laboratory Procedures, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281.

Antibodies or binding compositions, including binding fragments, single chain antibodies, $F_v$, $F_{ab}$, single domain $V_H$, disulfide-bridged $F_v$, single-chain $F_v$ or $F(_{ab}')_2$ fragments of antibodies, diabodies, and triabodies against predetermined fragments of the analogs can be raised by immunization of animals with analogs or conjugates of analogs or receptor proteins with carrier proteins. Monoclonal antibodies are prepared from cells VIPg the desired antibody. These antibodies can be screened for binding to analogs described herein. These monoclonal antibodies will usually bind with at least a $K_D$ of about 1 mM, usually at least about 300 µM, typically at least about 10 µM, at least about 30 µM, at least about 10 µM, and at least about 3 µM or more. These antibodies can be screened for binding to the naturally occurring polypeptides upon which the analogs are derived.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) Basic and Clinical Immunology, 4th ed., Lange Medical Publications, Los Altos, Calif., and references cited therein; Harlow and Lane (1988) Antibodies: A Laboratory Manual CSH Press; Goding (1986) Monoclonal Antibodies: Principles and Practice, 2nd ed., Academic Press, New York, N.Y.; and particularly in Kohler and Milstein (1975) Nature 256:495-497, which discusses one method of generating monoclonal antibodies. Summarized briefly, this method involves injecting an animal with an analog described herein. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the analog. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) Science 246:1275-1281; and Ward, et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) Proc. Nat'l Acad. Sci. USA 86:10029-10033; or made in transgenic mice, see Mendez, et al. (1997) Nature Genetics 15:146-156; also see Abgenix and Medarex technologies.

The instant invention is related to pharmaceutical compositions of the instant invention or the pharmaceutical acceptable salts derived therefrom that comprise analogs that comprise isotopes. In some embodiments, the compositions of the claimed invention may contain any isotope described in Cyr and Pearson (Stabilization of radiopharmaceutical compositions using hydrophilic thioethers and hydrophilic 6-hydroxy chromans. Cyr, John E.; Pearson, Daniel A. (Diatide, Inc., USA). PCT Int. Appl. (2002), WO 200260491 A2 20020808), which is herein incorporated by reference. In some embodiments the compositions of the invention comprise analog that comprise one or more of the following isotopes: $^{125}$I, $^{131}$I, $^{211}$At, $^{47}$Sc, $^{67}$Cu, $^{72}$Ga, $^{90}$Y, $^{153}$Sm, $^{159}$Gd, $^{165}$Dy, $^{166}$Ho, $^{175}$Yb, $^{177}$Lu, $^{212}$Bi, $^{213}$Bi, $^{68}$Ga, $^{99}$Tc, $^{111}$In, $^{123}$I, and $^{3}$H.

The pharmaceutical compositions of the instant invention or the pharmaceutical acceptable salts derived therefrom may be in a liquid or solid dosage form. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, *Remington: The Science and Practice of Pharmacy*, 19th Edition, 1995; British Pharmacopoeia 2000, each of which is incorporated herein by reference. The compositions of the present invention may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin and sugars such as lactose, fructose, glucose and the like. Natural and synthetic gums are also convenient, including, but not limited to, acacia, alginates, methylcellulose, polyvinylpyrrolidone and the like. Polyethylene glycol, ethylcellulose and waxes can also serve as binders.

A lubricant can be used in a tablet formulation to prevent the tablet and punches from sticking in the die. The lubricant include, but are not limited to, such slippery solids as talc, magnesium and calcium stearate, stearic acid and hydrogenated vegetable oils. Tablets can be coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

Also contemplated are liquid formulations and solid form preparations which are intended to be converted, shortly before use, to liquid form preparations. Such liquid forms include, but are not limited to, solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle such as sterile water, saline solution, or alcohol, before use. Preparations may also contain mucosal enhancers.

In some embodiments, the oral transmucosal solid dosage further comprises a permeation enhancer. In some embodiments, the permeation enhancer is chosen from: a bile salt, sodium dodecyl sulfate, dimethyl sulfoxide, sodium lauryl sulfate, a derivative of a saturated or a unsaturated fatty acid, a surfactant, a bile salt analog, and a derivative of a bile salt. In some embodiments the oral transmucosal dosage form is chosen from: a chewing gum, a patch, a lozenge, a lozenge-on-a-handle, a tablet, a troche, a pastille, a sachet, a sublingual tablet, and a rapid disintegrating tablet. In some embodiments, the oral transmucosal solid dosage form of wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. The invention is directed to an oral transmucosal solid dosage form comprising from wherein the concentration of analog is from about 0.01% to about 90% of the dry matter weight of the composition.

Solid dosage forms such as lozenges and tablets may also be used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes which allows extended dissolution of the lozenge and absorption of the drug.

Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation.

A lozenge-on-a-handle (similar to a lollipop) is another dosage form suitable for transmucosal drug delivery. In addition to being non-invasive and providing a particularly easy method of delivery, the lozenge-on-a-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain symptoms, such as pain, nausea, motion sickness, and premedication prior to anesthesia because each patient needs a different amount of medication to treat these symptoms. For these types of treatments, the patient is the only one who knows how much medication is enough. Once the appropriate amount of drug is delivered, the patient or caregiver can remove the lozenge-on-a-handle, thus, stopping delivery of the drug. This feature is especially important for particularly potent drugs, which may present a significant advantage of terminating drug administration once the desired effect is achieved.

As used herein, the term "oral transmucosal delivery" (OTD) refers to the delivery of a pharmaceutical agent across a mucous membrane in the oral cavity, pharyngeal cavity, or esophagus, and may be contrasted, for example, with traditional oral delivery, in which absorption of the drug occurs in the intestines. Accordingly, routes of administration in which the pharmaceutical agent is absorbed through the buccal, sublingual, gingival, pharyngeal, and/or esophageal mucosa are all encompassed within "oral transmucosal delivery," as that term is used herein. Oral transmucosal delivery involves the administration of an oral transmucosal solid dosage form to the oral cavity of a patient, which is held in the oral cavity and dissolved, thereby releasing the pharmaceutical agent for oral transmucosal delivery. Of course, as the solid dosage form dissolves in the oral cavity, some of the saliva containing the pharmaceutical agent may be swallowed, and a portion of the drug may ultimately be absorbed from the intestines.

The compositions of the invention can be administered in a sustained release composition, such as those described in, for example, U.S. Pat. No. 5,672,659 and U.S. Pat. No. 5,595,760, and herein incorporate by reference. The use of immediate or sustained release compositions depends on the type of condition being treated.

The pharmaceutical compositions of the instant invention or the pharmaceutical acceptable salts derived therefrom may be in a dosage amount in an effective amount for inducing or increasing the naturally occurring biological activity of the wild-type polypeptide upon which the analog is derived. The pharmaceutical compositions of the instant invention or the pharmaceutical acceptable salts derived therefrom may be in a dosage amount in an effective amount for inducing or increasing the naturally occurring biological activity of the wild-type VIP polypeptide upon which the analog is derived. The pharmaceutical compositions of the instant invention or the pharmaceutical acceptable salts derived therefrom may be in a dosage amount in an effective amount for increasing the half-life of the composition when administered to a human being or other subject. In some embodiments the VIP analog is VIP.

The present invention also encompasses methods of using the compositions comprising a VIP analog. Any of these methods may involve the administration of a pharmaceutical composition comprising a VIP analog wherein the VIP analog is in a therapeutically effective dose. Any of these methods may involve the administration of a pharmaceutical composition comprising a VIP analog wherein the VIP analog is selective for VPAC1, VPAC2, PAC1, VIPR1, or VIPR2 at a magnitude between 1-100 time greater than the other VIP receptors disclosed herein. The composition comprising an analog of the invention produces a broad range of activities, depending on the dosage administered. The present invention encompasses methods of treating or preventing pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, exocrine pancreatic tumors, colorectal carcinoma, gastric carcinoma, hepatocellular carcinoma, esophageal carcinoma, renal cell carcinoma, prostate carcinoma, urinary bladder carcinoma, liver carcinoma, ductal pancreatic cancer, breast carcinoma, ovarian carcinoma, non-hodgkin's lymphoma, meningioma, GEP tumors (differentiated and undifferentiated), pituitary adenoma, endometrial cancer, astrocytoma, giloblastoma, non-small cell lung cancer, pancreatic cancer, melanoma, renal cancer, neuroblastoma, leukemia, prostate cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction comprising administering to at least one patient in need thereof, mammal in need thereof or human in need thereof a composition or pharmaceutical composition comprising a VIP family analog in a therapeutically effective amount. The compositions of the invention may also be used at lower doses in order to prevent pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. The compositions of the invention may also be used to prevent pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject susceptible to those indications. In some embodiments, the method of prevention comprising administering the composition or pharmaceutical compositions of the invention after the subject is tested for susceptibility or genetic propensity for developing the disease, indication or disorder.

The pharmaceutical composition comprising a pharmaceutically acceptable carrier/diluent and an analog comprising an α-amino acid and at least one β-amino acid may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field, which is incorporated herein in its entirety.

For parenteral administration, analog can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of analog in 0.9% sodium chloride solution.

The present invention relates to routes of administration include intramuscular, sublingual, intravenous, intraperitoneal, intrathecal, intravaginal, intraurethral, intradermal, intrabuccal, via inhalation, via nebulizer and via subcutaneous injection. Alternatively, the pharmaceutical composition may be introduced by various means into cells that are removed from the individual. Such means include, for example, microprojectile bombardment and liposome or other nanoparticle device.

Solid dosage forms for oral administration include capsules, tablets, pills, powders and granules. In solid dosage forms, the analogs are generally admixed with at least one inert pharmaceutically acceptable carrier such as sucrose, lactose, starch, or other generally regarded as safe (GRAS) additives. Such dosage forms can also comprise, as is normal practice, an additional substance other than an inert diluent, e.g., lubricating agent such as magnesium state. With capsules, tablets, and pills, the dosage forms may also comprise a buffering agent. Tablets and pills can additionally be prepared with enteric coatings, or in a controlled release form, using techniques know in the art.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as wetting agent, an emulsifying agent, a suspending agent, a sweetening agent, a flavoring agent or a perfuming agent.

In another embodiment of the invention the composition of the invention is used to treat a patient suffering from, or susceptible to, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject. In some embodiments, the invention relates to compositions comprising a VIP family analog for treatment or prevention of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof, wherein said analog comprises an α-amino acid and at least one β-amino acid. In some embodiments, the VIP family analog of the invention comprises an analog of VIP.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular analog chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods. In some embodiments, the period can be an hour, a day, a month, a year, a week, or a two-week period. In an additional embodiment of the invention, the total dosage is administered in two or more separate application periods, or separate doses.

In some embodiments, subjects can be administered the composition in which the composition is provided in a daily dose range of about 0.0001 mg/kg to about 5000 mg/kg of the weight of the subject. The dose administered to the subject can also be measured in terms of total amount of analog administered per day. In some embodiments, a subject is administered from about 0.001 to about 3000 milligrams of analog per day. In some embodiments, a subject is administered up to about 2000 milligrams of analog per day. In some embodiments, a subject is administered up to about 1800 milligrams of analog per day. In some embodiments, a subject is administered up to about 1600 milligrams of analog per day. In some embodiments, a subject is administered up to about 1400 milligrams of analog per day. In some embodiments, a subject is administered up to about 1200 milligrams of analog per day. In some embodiments, a subject is administered up to about 1000 milligrams of analog per day. In some embodiments, a subject is administered up to about 800 milligrams of analog per day. In some embodiments, a subject is administered from about 0.001 milligrams to about 700 milligrams of analog per dose. In some embodiments, a subject is administered up to about 700 milligrams of analog per dose. In some embodiments, a subject is administered up to about 600 milligrams of analog per dose. In some embodiments, a subject is administered up to about 500 milligrams of analog per dose. In some embodiments, a subject is administered up to about 400 milligrams of analog per dose. In some embodiments, a subject is administered up to about 300 milligrams of VIP analog per dose. In some embodiments, a subject is administered up to about 200 milligrams of analog per dose. In some embodiments, a subject is administered up to about 100 milligrams of analog per dose. In some embodiments, a subject is administered up to about 50 milligrams of analog per dose.

In some embodiments, subjects can be administered the composition in which the composition comprising a VIP analog or pharmaceutically acceptable salt thereof is administered in a daily dose range of about 0.0001 mg/kg to about 5000 mg/kg of the weight of the subject. In some embodiments, the composition comprising a VIP analog or pharmaceutically acceptable salt thereof is administered in a daily dosage of up about 450 mg/kg of the weight of the subject. In some embodiments, the composition comprising a VIP analog or pharmaceutically acceptable salt thereof is administered in a daily dosage of up about 400 mg/kg of the weight of the subject. In some embodiments, the composition comprising a VIP analog or pharmaceutically acceptable salt thereof is administered in a daily dosage of up about 350 mg/kg of the weight of the subject. In some embodiments, the composition comprising a VIP analog or pharmaceutically acceptable salt thereof is administered in a daily dosage of up about 300 mg/kg of the weight of the subject. In some embodiments, the composition comprising a VIP analog or pharmaceutically acceptable salt thereof is administered in a daily dosage of up about 250 mg/kg of the weight of the subject. In some embodiments, the composition comprising a VIP analog or pharmaceutically acceptable salt thereof is administered in a daily dosage of up about 200 mg/kg of the weight of the subject. In some embodiments, the composition comprising a VIP analog or pharmaceutically acceptable salt thereof is administered in a daily dosage of up about 150 mg/kg of the weight of the subject. In some embodiments, the composition comprising a VIP analog or pharmaceutically acceptable salt thereof is administered in a daily dosage of up about 100 mg/kg of the weight of the subject. In some embodiments, the composition comprising a VIP analog or pharmaceutically acceptable salt thereof is administered in a daily dosage of up about 50 mg/kg of the weight of the subject. In some embodiments, the composition comprising a VIP analog or pharmaceutically acceptable salt thereof is administered in a daily dosage of up about 25 mg/kg of the weight of the subject.

In some embodiments, the composition comprising a VIP analog or pharmaceutically acceptable salt thereof is administered in a daily dosage of up about 10 mg/kg of the weight of the subject. In some embodiments, the composition comprising a VIP analog or pharmaceutically acceptable salt thereof is administered in a daily dosage of up about 5 mg/kg of the weight of the subject. In some embodiments, the composition comprising a VIP analog or pharmaceutically acceptable salt thereof is administered in a daily dosage of up about 1 mg/kg of the weight of the subject. In some embodiments, the composition comprising a VIP analog or pharmaceutically acceptable salt thereof is administered in a daily dosage of up about 0.1 mg/kg of the weight of the subject. In some embodiments, the composition comprising a VIP analog or pharmaceutically acceptable salt thereof is administered in a daily dosage of up about 0.01 mg/kg of the weight of the subject. In some embodiments, the composition comprising a VIP analog or pharmaceutically acceptable salt thereof is administered in a daily dosage of up about 0.001 mg/kg of the weight of the subject. The dose administered to the subject can also be measured in terms of total amount of VIP analog administered per day.

In some embodiments, a subject in need thereof is administered from about 1 ng to about 500 μg of analog or pharmaceutically salt thereof per day. In some embodiments, a subject in need thereof is administered from about 1 ng to about 10 ng of analog or pharmaceutically salt thereof per day. In some embodiments, a subject in need thereof is administered from about 10 ng to about 20 ng of analog or pharmaceutically salt thereof per day. In some embodiments, a subject in need thereof is administered from about 10 ng to about 100 ng of analog or pharmaceutically salt thereof per day. In some embodiments, a subject in need thereof is administered from about 100 ng to about 200 ng of analog or pharmaceutically salt thereof per day. In some embodiments, a subject in need thereof is administered from about 200 ng to about 300 ng of analog or pharmaceutically salt thereof per day. In some embodiments, a subject in need thereof is administered from about 300 ng to about 400 ng of analog or pharmaceutically salt thereof per day. In some embodiments, a subject in need thereof is administered from about 400 ng to about 500 ng of analog or pharmaceutically salt thereof per day. In some embodiments, a subject in need thereof is administered from about 500 ng to about 600 ng of analog or pharmaceutically salt thereof per day. In some embodiments, a subject in need thereof is administered from about 600 ng to about 700 ng of analog or pharmaceutically salt thereof per day. In some embodiments, a subject in need thereof is administered from about 800 ng to about 900 ng of analog or pharmaceutically salt thereof per day. In some embodiments, a subject in need thereof is administered from about 900 ng to about 1 µg of analog or pharmaceutically salt thereof per day. In some embodiments, a subject in need thereof is administered from about 1 µg to about 100 µg of analog or pharmaceutically salt thereof per day. In some embodiments, a subject in need thereof is administered from about 100 µg to about 200 µg of analog or pharmaceutically salt thereof per day. In some embodiments, a subject in need thereof is administered from about 200 µg to about 300 µg of analog or pharmaceutically salt thereof per day. In some embodiments, a subject in need thereof is administered from about 300 µg to about 400 µg of analog or pharmaceutically salt thereof per day. In some embodiments, a subject in need thereof is administered from about 400 µg to about 500 µg of analog or pharmaceutically salt thereof per day. In some embodiments, a subject in need thereof is administered from about 500 µg to about 600 µg of analog or pharmaceutically salt thereof per day. In some embodiments, a subject in need thereof is administered from about 600 µg to about 700 µg of analog or pharmaceutically salt thereof per day. In some embodiments, a subject in need thereof is administered from about 800 µg to about 900 µg of analog or pharmaceutically salt thereof per day. In some embodiments, a subject in need thereof is administered from about 900 µg to about 1 mg of analog or pharmaceutically salt thereof per day.

In some embodiments, a subject in need thereof is administered from about 0.0001 to about 3000 milligrams of VIP analog or pharmaceutically salt thereof per day. In some embodiments, a subject is administered up to about 2000 milligrams of VIP analog or pharmaceutically salt thereof day. In some embodiments, a subject is administered up to about 1800 milligrams of VIP analog or pharmaceutically salt thereof per day. In some embodiments, a subject is administered up to about 1600 milligrams of VIP analog or pharmaceutically salt thereof per day. In some embodiments, a subject is administered up to about 1400 milligrams of VIP analog or pharmaceutically salt thereof per day. In some embodiments, a subject is administered up to about 1200 milligrams of VIP analog or pharmaceutically salt thereof per day. In some embodiments, a subject is administered up to about 1000 milligrams of VIP analog or pharmaceutically salt thereof per day. In some embodiments, a subject is administered up to about 800 milligrams of VIP analog or pharmaceutically salt thereof per day. In some embodiments, a subject is administered from about 0.0001 milligrams to about 700 milligrams of VIP analog or pharmaceutically salt thereof per dose. In some embodiments, a subject is administered up to about 700 milligrams of VIP analog or pharmaceutically salt thereof per dose. In some embodiments, a subject is administered up to about 600 milligrams of VIP analog or pharmaceutically salt thereof per dose. In some embodiments, a subject is administered up to about 500 milligrams of VIP analog or pharmaceutically salt thereof per dose. In some embodiments, a subject is administered up to about 400 milligrams of VIP analog or pharmaceutically salt thereof per dose. In some embodiments, a subject is administered up to about 300 milligrams of VIP analog or pharmaceutically salt thereof per dose. In some embodiments, a subject is administered up to about 200 milligrams of VIP analog or pharmaceutically salt thereof per dose. In some embodiments, a subject is administered up to about 100 milligrams of VIP analog or pharmaceutically salt thereof per dose. In some embodiments, a subject is administered up to about 50 milligrams of VIP analog or pharmaceutically salt thereof per dose. In some embodiments, a subject is administered up to about 25 milligrams of VIP analog or pharmaceutically salt thereof per dose. In some embodiments, a subject is administered up to about 15 milligrams of VIP analog or pharmaceutically salt thereof per dose.

In some embodiments, a subject is administered up to about 10 milligrams of VIP analog or pharmaceutically salt thereof per dose. In some embodiments, a subject is administered up to about 5 milligrams of VIP analog or pharmaceutically salt thereof per dose. In some embodiments, a subject is administered up to about 1 milligram of VIP analog or pharmaceutically salt thereof per dose. In some embodiments, a subject is administered up to about 0.1 milligrams of VIP analog or pharmaceutically salt thereof per dose. In some embodiments, a subject is administered up to about 0.001 milligrams of VIP analog or pharmaceutically salt thereof per dose.

The dose administered to the subject can also be measured in terms of total amount of VIP analog or pharmaceutically salt thereof administered per ounce of liquid prepared. In some embodiments, the VIP analog or pharmaceutically salt thereof is at a concentration of about 2.5 grams per ounce of solution. In some embodiments, the VIP analog or pharmaceutically salt thereof is at a concentration of about 2.25 grams per ounce of solution. In some embodiments, the VIP analog or pharmaceutically salt thereof is at a concentration of about 2.25 grams per ounce of solution. In some embodiments, the VIP analog or pharmaceutically salt thereof is at a concentration of about 2.0 grams per ounce of solution. In some embodiments, the VIP analog or pharmaceutically salt thereof is at a concentration of about 1.9 grams per ounce of solution. In some embodiments, the VIP analog or pharmaceutically salt thereof is at a concentration of about 1.8 grams per ounce of solution. In some embodiments, the VIP analog or pharmaceutically salt thereof is at a concentration of about 1.7 grams per ounce of solution. In some embodiments, the VIP analog or pharmaceutically salt thereof is at a concentration of about 1.6 grams per ounce of solution. In some embodiments, the VIP analog or pharmaceutically salt thereof is at a concentration of about 1.5 grams per ounce of solution. In some embodiments, the VIP analog or pharmaceutically salt thereof is at a concentration of about 1.4 grams per ounce of solution. In some embodiments, the VIP analog or pharmaceutically salt thereof is at a concentration of about 1.3 grams per ounce of solution. In some embodiments, the VIP analog or pharmaceutically salt thereof is at a concentration of about 1.2 grams per ounce of solution. In some embodiments, the VIP analog or pharmaceutically salt thereof is at a concentration of about 1.1 grams per ounce of solution. In some embodiments, the VIP analog or pharmaceutically salt thereof is at a concentration of about 1.0 grams per ounce of solution. In some embodiments, the VIP analog or pharmaceutically salt thereof is at a concentration of about 0.9 grams per ounce of solution. In some embodiments, the VIP analog or pharmaceutically salt thereof is at a concentration of about 0.8 grams per ounce of solution. In some embodiments, the VIP analog or pharmaceutically salt thereof is at a concentration of about 0.7 grams per ounce of solution. In some embodiments, the VIP analog or pharmaceutically salt thereof is at a concentration of about 0.6 grams per ounce of solution. In some embodiments, the VIP analog or pharmaceutically salt thereof is at a concentration of about 0.5 grams per ounce of solution. In some embodiments, the VIP analog or pharmaceutically salt thereof is at a concentration of about 0.4 grams per ounce of solution. In some embodiments, the VIP analog or pharmaceutically salt thereof is at a concentration of about 0.3 grams per ounce of solution. In some embodiments, the VIP analog or pharmaceutically salt thereof is at a concentration of about 0.2 grams per ounce of solution. In some embodiments, the VIP analog or pharmaceutically salt thereof is at a concentration of about 0.1 grams per ounce of solution. In some embodiments, the VIP analog or pharmaceutically salt thereof is at a concentration of about 0.01 grams per ounce of solution. In some embodiments, the VIP analog or pharmaceutically salt thereof is at a concentration of about 0.001 grams per ounce of solution prepared. In some embodiments, the VIP analog or pharmaceutically salt thereof is at a concentration of about 0.0001 grams per ounce of solution prepared. In some embodiments, the VIP analog or pharmaceutically salt thereof is at a concentration of about 0.00001 grams per ounce of solution prepared. In some embodiments, the VIP analog or pharmaceutically salt thereof is at a concentration of about 0.000001 grams per ounce of solution prepared.

Dosage may be measured in terms of mass amount of analog per liter of liquid formulation prepared. One skilled in the art can increase or decrease the concentration of the analog in the dose depending upon the strength of biological activity desired to treat or prevent any above-mentioned disorders associated with the treatment of subjects in need thereof. For instance, one embodiment of the invention can include up to 0.00001 grams of analog per 5 mL of liquid formulation and up to about 10 grams of analog per 5 mL of liquid formulation.

In some embodiments the pharmaceutical compositions of the claimed invention comprise at least one other active agent. In some embodiments the active agent is covalently linked to the VIP analog disclosed herein optionally by a protease cleavable linker (including by not limited to Pro-Pro or Citruline-Valine di-α-amino acid linkers). In some embodiments, at least one active agent is a chemotherapeutic agent. In some embodiments, the at least one chemotherapeutic agent is chosen from: Mitotic inhibitors, including Dolastatin and auristatin based compounds such as Dola-10 or Dola-15 or MMAE, Taxanes including paclitaxel, Maytansinoid including Maytansine like based compounds, Alkaloids including vincristine like compounds; Antibiotic based compounds including enediyne antibiotics such as calicheamicins and antharcyclines such as Doxorubicin; Alkylating agents including agents that modify DNA such as cisplatin or carboplatin; Antimetabolites, such as methotrexate based compounds and Topoisomerase Inhibitor based compounds including Camptothecin and Etoposide or a combination thereof.

In some embodiments, the active agent is a vasoactive agent. In some embodiments the vasoactive agent is chosen from the naturally occurring prostaglandins prostaglandin E0 (PGE0, also referred to 13,14-dihydro-PGE1; hereinafter, the abbreviation "PG" is used for "prostaglandin"), PGE1, 19-hydroxy-PGE1, PGE2, 19-hydroxy-PGE2, PGA1, 19-hydroxy-PGA1, PGA2, 19-hydroxy-PGA2, PGB1, 19-hydroxy-PGB1, PGB2, 19-hydroxy-PGB2, PGB3, PGD2, PGF1α, PGF2α(dinoprost), PGE3, PGF3α, PGI2 (prostacyclin), and combinations thereof. PGE0, PGE1, PGE2, and the hydrolyzable lower alkyl esters thereof (e.g., the methyl, ethyl and isopropyl esters) are, however, particularly suitable. Other suitable prostaglandins are exemplified, without limitation, by arboprostil, carbaprostacyclin, carboprost tromethamine, dinoprost tromethamine, dinoprostone, enprostil, iloprost, lipoprost, gemeprost, metenoprost, sulprostone, tiaprost, viprostil (CL 115,347), viprostil methyl ester, 16,16-dimethyl-Δ2-PGE1 methyl ester, 15-deoxy-16-hydroxy-16-methyl-PGE1 methyl ester (misoprostol), 16,16-dimethyl-PGE1, 11-deoxy-15-methyl-PGE1, 16-methyl-18,18,19,19-tetrahydrocarbacyclin, 16(RS)-15-deoxy-16-hydroxy-16-methyl-PGE1 methyl ester, (+)-4,5-didehydro-16-phenoxy-α-tetranor-PGE2 methyl ester, 11-deoxy-11α,16,16-trimethyl-PGE2, (+)-11α,16α,16β-dihydroxy-1-(hydroxymethyl)-16-methyl-trans-prostene, 9-chloro-16,16-dimethyl-PGE2, 16,16-dimethyl-PGE2, 15(S)-15-methyl-PGE2, 9-deoxy-9-methylene-16,16-dimethyl-PGE2, potassium salt, 19(R)-hydroxy-PGE2, and 11-deoxy-16,16-dimethyl-PGE2. Additional vasoactive agents useful as secondary active agents herein include endothelin-derived relaxation factors ("EDRFs") such as nitric oxide releasing agents, e.g., sodium nitroprusside and diazenium diolates, or "NONOates." NONOates include, but are not limited to, (Z)-1-{N-methyl-N-{6-(N-methyl-ammoniohexyl)amino}}diazen-1-ium-1,2-diolate ("MAHMA/NO"), (Z)-1-{N-β-ammoniopropyl)-N-(n-propyl)amino}-diazen-1-ium-1,2-diolate ("PAPA/NO"), (Z)-1-{N-{3-aminopropyl}-N-{4-(β-aminopropylammonio)butyl}amino}diazen-1-ium-1,2-diolate (spermine NONOate or "SPER/NO") and sodium (Z)-1-(N,N-diethylamino)-diazen-1-ium-1,2-diolate (diethylamine NONOate or "DEA/NO") and derivatives thereof). Still other vasoactive agents include vasoactive intestinal polypeptide analogs and derivatives thereof (particularly derivatives in the form of hydrolyzable lower alkyl esters), smooth muscle relaxants, leukotriene inhibitors, calcium channel blockers, P2-adrenergic agonists, angiotensin-converting enzyme ("ACE") inhibitors, angiotensin II receptor antagonists, and phosphodiesterase inhibitors. Still other suitable vasoactive agents include, but are not limited to: nitrates and like compounds such as nitroglycerin, isosorbide dinitrate, erythrityl tetranitrate, amyl nitrate, molsidomine, linsidomine chlorhydrate ("SIN-1"), S-nitroso-N-acetyl-d,l-penicillamine ("SNAP") and S-nitroso-N-glutathione ("SNO-GLU"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; nimodepine; pinacidil; cyclandelate; dipyridamole; isoxsuprine; chlorpromazine; haloperidol; yohimbine; and trazodone.

In some embodiments, the pharmaceutical compositions of the invention comprise an active agent that is an inhibitor of rho kinase, an enzyme belonging to the rhoA/rho associated kinase pathway, which regulates the state of phosphorylation of myosin phosphatase, in turn leading to the control of smooth muscle contraction. One example of a suitable rho kinase inhibitor has the following structural formula and is identified as Y-27632. Other suitable rho kinase inhibitors are disclosed, for example, in U.S. Pat. No. 6,218,410, which is herein incorporated by reference.

In some embodiments, the pharmaceutical compositions of the invention comprise an active agent that are peptide analogs of α-melanocyte-stimulating hormone (α-MSH), also referred to as "melanocortin peptides." Such peptides include the sequence His-Phe-Arg-Trp, His-D-Phe-Arg-Trp, or are homologs thereof, and can be cyclic. A suitable melanocortin peptide is Ac-Nle-cyclo-(-Asp-His-D-Phe-Arg-Trp-Lys)-OH. See U.S. Pat. No. 6,051,555 to Hadley and International Patent Publication No. WO 01/00224 to Blood et al., assigned to Palatin Technologies, Inc. The aforementioned amino acid residues have their conventional meaning as given in Chapter 2422 of the Manual of Patent Examining Procedure (2000). Thus, "Arg" is arginine, "Nle" is norleucine, "His" is histamine, "Phe" is phenylalanine, "D-Phe" is D-phenylalanine, "Trp" is tryptophan, and "Ac" refers to an acetyl moiety, i.e., an acetyl moiety present in a peptide or amino acid sequence that is acetylated.

In some embodiments, the pharmaceutical compositions of the invention comprise an active agent that is an endothelin antagonists, including antagonists of any or all of the three isoforms of endothelin, i.e., ET-1, ET-2, and ET-3, and are exemplified by: phenoxyphenylacetic acids and derivatives thereof, such as N-(4-isopropylbenzene-sulfonyl)-α-(4-carboxy-2-n-propylphenoxy)-3,4-methylenedioxyphenyl acetamide dipotassium salt, 2-{(2,6-dipropyl-4-hydroxymethyl)-phenoxy}-2-(4-phenoxyphenyl)-acetic acid, 2-{(2,6-dipropyl-4-hydroxymethyl)phenoxy}-2-(4-phenylphenyl) acetic acid, 2-{(2,6-dipropyl-4-hydroxymethyl)phenoxy}-2-(3-carboxyphenyl)-acetic acid, 2-{(2,6-dipropyl-4-hydroxymethyl)phenoxy}-2-(3,4-ethylenedioxyphenyl) acetic acid, 2-{(2,6-dipropyl-4-hydroxymethyl)phenoxy}-2-(3,4,5-trimethoxyphenyl)acetic acid, 2-{(2,6-dipropyl-4-hydroxymethyl)phenoxy}-2-(3,4-methylenedioxyphenyl) acetic acid, N-(4-dimethylaminobenzenesulfonyl)-2-(4-methoxycarbonyl-2-propylphenoxy)-2-(3,4-methylenedioxyphenyl) acetamide, N-(2-methylbenzenesulfonyl)-2-(4-methoxycarbonyl-2-propylphenoxy)-2-(3,4-methylenedioxyphenyl)acetamide, N-(2-methoxycarbonyl-benzenesulfonyl)-2-(4-methoxycarbonyl-2-propylphenoxy)-2-(3,4-methylenedioxy-phenyl)acetamide, N-(2-chlorobenzene-sulfonyl)-2-(4-methoxycarbonyl-2-propylphenoxy)-2-(3,4-methylenedioxyphenyl) acetamide, and others, as described in U.S. Pat. No. 5,565,485; and certain isooxazoles, oxazoles, thiazoles, isothiazoles and imidazoles, as described, for example, in U.S. Pat. No. 6,136,828.

In some embodiments, the pharmaceutical compositions of the invention comprise an active agent that is a peptidyl drug including the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), VIP, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin.

In some embodiments, the pharmaceutical compositions of the invention comprise an active agent that is a selective androgen receptor modulators (SARMs) include LGD2226 and/or LGD1331, both available from Ligand Pharmaceuticals (San Diego, Calif.). See Negro-Villar et al. J. Clin. Endocrinol. & Metabol. 84(10):3459-62 (1999).

In some embodiments, the pharmaceutical compositions of the invention comprise an active agent that is a suitable neuropeptide including bradykinin, kallidin, des-Arg9-bradykinin, des-Arg10-kallidin, des-Arg9-{Leu8}-bradykinin, {D-Phe7}-bradykinin, HOE 140, neuropeptide Y, calcitonin gene-related peptide (cGRP), enkaphalins and related opioid peptides such as MetS-enkaphalin, LeuS-enkephalin, α-, β- and γ-endorphin, α- and β-neo-endorphin, and dynorphin, as well as the neurotransmitters GABA (γ-aminobutyric acid), glycine, glutamate, acetylcholine, dopamine, epinephrine, 5-hydroxytryptamine, substance P, serotonin, and catecholamines.

In some embodiments, the pharmaceutical compositions of the invention comprise an active agent that is a suitable serotonin agonists include, but are not limited to 2-methyl serotonin, buspirone, ipsaperone, tiaspirone, gepirone, ergot alkaloids, 8-hydroxy-(2-N,N-dipropyl-amino)-tetraline, 1-(4-bromo-2,5-dimethoxyphenyl)-2-aminopropane, cisapride, sumatriptan, m-chlorophenylpiperazine, trazodone, zacopride, mezacopride, and combinations thereof. Suitable serotonin antagonists include, for example, ondansetron, granisetron, metoclopramide, tropisetron, dolasetron, palonosetron, trimethobenzamide, methysergide, risperidone, ketanserin, ritanserin, clozapine, amitriptyline, MDL 100,907 (R(+)-α-(2,3-dimethoxyphenyl)-1-{2-(4-fluorophenyl)ethyl}-4-piperidine-methanol) (Marion Merrell Dow), azatadine, cyproheptadine, fenclonine, chlorpromazine, mianserin and combinations thereof.

In some embodiments, the pharmaceutical compositions of the invention comprise an active agent that is an ergot alkaloids include ergotamine and ergotamine analogs, e.g., acetergamine, brazergoline, bromerguride, cianergoline, delorgotrile, dihydroergotamine, disulergine, ergonovine, ergonovine maleate, ergotamine tartrate, etisulergine, lergotrile, lysergide, mesulergine, metergoline, metergotamine, nicergoline, pergolide, propisergide, proterguride and terguride.

In some embodiments, the pharmaceutical compositions of the invention comprise an active agent that is a calcium channel blockers that are suitable for use according to the present invention include, without limitation, amlodipine, felodipine, isradipine, nicardipine, nifedipine, nimodipine, nisoldipine, nitrendipine, bepridil, diltiazem, verapamil, and combinations thereof. In some embodiments, the pharmaceutical compositions of the invention comprise an active agent that is a potassium channel openers include, but are not limited to, pinacidil, diazoxide, cromakalim, nicorandil, minoxidil, (N-cyano-N'-(1,1-dimethylpropyl)-N"-3-pyridyl-guanidine (P-1075), and N-cyano-N'-(2-nitroxyethyl)-3-pridinecarboximidamide monomethanesulfonate (KRN 2391).

In some embodiments, the pharmaceutical compositions of the invention comprise an active agent that is a potassium channel blockers include tedisamil, agitoxin-2, apamin, BDS-I, BDS-II, charybdotoxin, α-dendrotoxin, β-dendrotoxin, γ-dendrotoxin, 8-dendrotoxin, dendrotoxin-I, dendrotoxin-K, E-4031, iberiotoxin, kaliotoxin, MCD-peptide, margatoxin, noxiustoxin, paxilline, penitrem A, stichodactyla, tertiapin, tityustoxin K alpha, verruculogen, and combinations thereof. Although all of the active agents are available commercially, most of the listed potassium channel blockers are available from Alomone Labs (Jerusalem, Israel).

In some embodiments, the pharmaceutical compositions of the invention comprise an active agent that is a dopamine agonist including, for example, levodopa, bromocriptine, pergolide, apomorphine, piribedil, pramipexole, ropinirole, and combinations thereof. Dopamine antagonists include, without limitation, spiroperidol, benperidol, trifluperidol, pimozide, fluphenazine, droperidol, haloperidol, thiothixene, trifluperazine, moperone, prochlorperazine, molindone, thioridazine, clozapine, chlorpromazine, promazine, sulpiride, clebopride, chlorpromazine, spiperone, flupenthixol, and combinations thereof.

In some embodiments, the pharmaceutical compositions of the invention comprise an active agent that is a non-androgenic steroid including progestins and estrogens. Suitable estrogens include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Suitable progestins include acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. It is generally desirable to co-administer a progestin along with an estrogen so that the estrogen is not "unopposed." As is well known in the art, estrogen-based therapies are known to increase the risk of endometrial hyperplasia and cancer, as well as the risk of breast cancer, in treated individuals. Co-administration of estrogenic agents with a progestin has been found to decrease the aforementioned risks.

The pharmaceutical compositions of the present invention may also include one or more chemotherapeutic agents. Suitable chemotherapeutic agents include, but are not limited to, platinum coordination compounds, topoisomerase inhibitors, antibiotics, antimitotic alkaloids and difluoronucleosides.

In one embodiment of the present invention, the chemotherapeutic agent is a platinum coordination compound. The term "platinum coordination compound" refers to any tumor cell growth inhibiting platinum coordination compound that provides the platinum in the form of an ion. Suitable platinum coordination compounds include, but are not limited to, cis-diamminediaquoplatinum (II)-ion; chloro (diethylenetriamine)-platinum (II) chloride; dichloro (ethylenediamine)-platinum (II); diammine (1,1-cyclobutanedicarboxylato) platinum (II) (carboplatin); spiroplatin; iproplatin; diammine (2-ethylmalonato)-platinum (II); ethylenediaminemalonatoplatinum (II); aqua (1,2-diaminodyclohexane)-sulfatoplatinum (II); (1,2-diaminocyclohexane) malonatoplatinum (II); (4-caroxyphthalato) (1,2-diaminocyclohexane) platinum (II); (1,2-diaminocyclohexane)-(isocitrato) platinum (II); (1,2-diaminocyclohexane) cis (pyruvato) platinum (II); (1,2-diaminocyclohexane) oxalatoplatinum (II); ormaplatin; and tetraplatin In some embodiments, the VIP analog and the additional active agent or agents may be incorporated into a single formulation, or they may be administered separately, either simultaneously or sequentially. In one embodiment, an androgenic agent is administered prior to administration of VIP or a VIP agonist, i.e., the androgenic agent is administered as a pretreatment. In some embodiments, such a method involves administration of an androgenic agent, e.g., via oral or topical (vulvar and/or vaginal) administration, followed by topical (again, vulvar and/or vaginal) administration of VIP or a VIP agonist.

In some embodiments, the formulations herein are administered by topical application to the vulvar region and/or by vaginal drug administration. These pharmaceutical formulations may typically contain one or more pharmaceutically acceptable carriers suited to the particular type of formulation, i.e., gel, ointment, suppository, or the like. The vehicles are comprised of materials of naturally occurring or synthetic origin that do not adversely affect the active agent or other components of the formulation. Suitable carriers for use herein include water, silicone, waxes, petroleum jelly, polyethylene glycol, propylene glycol, liposomes, sugars such as mannitol and lactose, and a variety of other materials, again depending, on the specific type of formulation used. As described in Section IV, infra, dosage forms used for administration to the vulvar region and/or vagina may be used to deliver drug on an as-needed, on-demand basis, and/or throughout an extended, sustained release profile.

The pharmaceutical compositions may also include a chemical compound to enhance permeation of the active agent through the mucosal tissue, i.e., a "permeation enhancer." Suitable permeation enhancers include those generally useful in conjunction with topical, transdermal or transmucosal drug delivery. Examples of suitable permeation enhancers include the following: sulfoxides such as dimethylsulfoxide (DMSO) and decylmethylsulfoxide (C10MSO); ethers such as diethylene glycol monoethyl ether (available commercially as TRANSCUTOL® (Gattefosse S. A., Saint-Priest, France) and diethylene glycol monomethyl ether; surfactants such as sodium laurate, sodium lauryl sulfate, cetyltrimethylammonium bromide, benzalkonium chloride, Poloxamer (231, 182, 184), TWEEN® (20, 40, 60, 80) (ICI Chemicals, Bridgewater, N.J.), and lecithin (U.S. Pat. No. 4,783,450); the 1-substituted azacycloheptan-2-ones, particularly 1-n-dodecylcyclaza-cycloheptan-2-one (available under the trademark AZONE® (Durham Pharmaceuticals, LLC, Durham, N.C.); see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

In some embodiments, the pharmaceutical compositions may include an enzyme inhibitor, i.e., a compound effective to inhibit enzymes present in the vagina or vulvar area that could degrade or metabolize the active agent. That is, inhibitors of enzymes that decrease or eliminate the activity of the active agent may be included in the formulation so as to effectively inhibit the action of those enzymes. Such compounds include, for example, fatty acids, fatty acid esters, and NAD inhibitors.

In some embodiments, the pharmaceutical composition may be in the form of an ointment, cream, emulsion, lotion, gel, solid, solution, suspension, foam or liposomal formulation. Alternatively, the formulations may be contained within avaginal ring (e.g., as disclosed in U.S. Pat. No. 5,188,835 to Lindskog et al., assigned to Kabi Pharmacia AB), or within a tampon, suppository, sponge, pillow, puff, or osmotic pump system; these platforms are useful solely for vaginal delivery. Ointments are semisolid preparations that are typically based on petrolatum or other petroleum derivatives. The specific ointment base to be used, as will be appreciated by those skilled in the art, is one that will provide for optimum drug delivery. As with other carriers or vehicles, an ointment base should be inert, stable, non irritating and nonsensitizing. As explained in *Remington: The Science and Practice of Pharmacy*, supra, at pages 1034-1038, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Suitable water-soluble ointment bases are prepared from polyethylene glycols of varying molecular weight; again, reference may be had to *Remington: The Science and Practice of Pharmacy* for further information.

In one aspect of the invention, a method is provided for treating or preventing cancer comprising administering any of the disclosed compositions disclosed herein in a therapeutically or prophylactically effective amount. In some embodiments, a method is provided for treating or preventing one or a combination of the following cancer types: small lung cell cancer, exocrine pancreatic tumors, colorectal carcinoma, gastric carcinoma, hepatocellular carcinoma, esophageal carcinoma, renal cell carcinoma, prostate carcinoma, urinary bladder carcinoma, liver carcinoma, ductal pancreatic cancer, breast carcinoma, ovarian carcinoma, non-hodgkin's lymphoma, meningioma, GEP tumors (differentiated and undifferentiated), pituitary adenoma, endometrial cancer, astrocytoma, giloblastoma, non-small cell lung cancer, pancreatic cancer, melanoma, renal cancer, neuroblastoma, leukemia, prostate cancer In one aspect of the invention, a method is provided for treating sexual dysfunction in a female individual comprising administering to the vagina and/or vulvar area a pharmaceutical formulation comprising a VIP family analog. In some embodiments, the VIP family analog is a vasodilator, with vasodilators selected from the group consisting of VIP and vasoactive intestinal polypeptide analogs and combinations of any of the foregoing. Any number of drug delivery platforms may be used, e.g., suppositories, ointments, creams, gels, solutions and the like. Also, one or more additional types of drugs, i.e., pharmacologically active agents may be incorporated into the pharmaceutical formulations. In other aspects of the invention, vaginal administration of a vasoactive agent as just described is used to improve vaginal muscle tone and tissue health, to enhance vaginal lubrication, or to minimize collagen misdeposition resulting from hypoxia as well as the associated lack of elasticity resulting from the collagen misdeposition.

In another embodiment of the invention, a method is provided for improving memory by administering a VIP family analog.

In another aspect of the invention, pharmaceutical compositions and dosage forms are provided for carrying out the aforementioned methods. The compositions and dosage forms contain a vasoactive agent as described above, a pharmaceutically acceptable vehicle, and, optionally, one or more additional pharmacologically active agents. The formulations contain a therapeutically effective amount of the active agent, or a therapeutically effective concentration of the active agent, i.e., a concentration that provides a therapeutically effective amount of active agent upon administration of a selected volume of composition.

The subject can be any animal, including but not necessarily limited to mammals such as a human, mouse, rat, hamster, guinea pig, rabbit, cat, dog, monkey, cow, horse, pig, and the like. In some embodiments, the subject is a human.

According to some embodiments of the invention, the formulation may be supplied as part of a kit. The kit comprise comprising an analog, wherein the analog comprises an $\alpha$-amino acid and at least one $\beta$-amino acid. In another embodiment, the kit comprises a pharmaceutically acceptable salt of an analog with a rehydration mixture. In another embodiment, the pharmaceutically acceptable salt of an analog are in one container while the rehydration mixture is in a second container. The rehydration mixture may be supplied in dry form, to which water or other liquid solvent may be added to form a suspension or solution prior to administration. Rehydration mixtures are mixtures designed to solubilize a lyophilized, insoluble salt of the invention prior to administration of the composition to a subject takes at least one dose of a purgative. In another embodiment, the kit comprises a pharmaceutically acceptable salt in orally available pill form.

The kit may contain two or more containers, packs, or dispensers together with instructions for preparation and administration. In some embodiments, the kit comprises at least one container comprising the pharmaceutical composition or compositions described herein and a second container comprising a means for delivery of the compositions such as a syringe. In some embodiments, the kit comprises a composition comprising an analog in solution or lyophilized or dried and accompanied by a rehydration mixture. In some embodiments, the analog and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

In another embodiment, a packaged kit is provided that contains the pharmaceutical formulation to be administered, i.e., a pharmaceutical formulation containing VIP analog or a for enhancing female sexual desire and responsiveness, a container (e.g., a vial, a bottle, a pouch, an envelope, a can, a tube, an atomizer, an aerosol can, etc.), optionally sealed, for housing the formulation during storage and prior to use, and instructions for carrying out drug administration in a manner effective to enhance sexual desire and responsiveness. The instructions will typically be written instructions on a package insert, a label, and/or on other components of the kit.

Depending on the type of formulation and the intended mode of administration, the kit may also include a device for administering the formulation (e.g., a transdermal delivery device). The administration device may be a dropper, a swab, a stick, or the nozzle or outlet of an atomizer or aerosol can. The formulation may be any suitable formulation as described herein. For example, the formulation may be an oral dosage form containing a unit dosage of the active agent, or a gel or ointment contained within a tube. The kit may contain multiple formulations of different dosages of the same agent. The kit may also contain multiple formulations of different active agents.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

The invention relates to the use of an analog in the preparation of a medicament for treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. In some embodiments, the invention relates to compositions comprising a VIP family analog for treatment or prevention of chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof.

The present invention relates to inhibiting secretion of TNF-α in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to inhibiting binding of VIP to a VIP receptor in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to inhibiting biological effect of GHRH in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to inhibiting chemotaxis of T cells in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to inhibiting expression of LPS in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to modulating the amount of cyclic cAMP in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to increasing the activity or expression of adenylate cyclase in a subject comprising administering a composition comprising an analog to a subject, wherein said analog comprises an α-amino acid and at least one β-amino acid. In some embodiments the analog is a VIP family analog. In some embodiments the analog is a VIP family analog and a VPAC1 antagonist. In some embodiments the analog is a VIP family analog. and a VPAC2 agonist. In some embodiments the analog is a VIP analog. In some embodiments, the composition or pharmaceutical composition of the claimed invention comprises a VIP analog, wherein the VIP analog is a VIPR1 agonist, and has substantially reduced selectivity or no selectivity for VIPR2 or PAC1 receptors. In some embodiments, the composition or pharmaceutical composition of the claimed invention comprises a VIP analog, wherein the VIP analog is a PAC1 agonist, and has substantially reduced selectivity or no selectivity for VIPR2 or VIPR1 receptors. In some embodiments, the composition or pharmaceutical composition of the claimed invention comprises a VIP analog, wherein the VIP analog is a VIPR2 agonist, and has substantially reduced selectivity or no selectivity for VIPR1 or PAC1 receptors. In some embodiments, the composition or pharmaceutical composition of the claimed invention comprises a VIP analog, wherein the VIP analog is a VIPR2 antagonist, but does not antagonize VIPR1 or PAC1 receptors. In some embodiments, the composition or pharmaceutical composition of the claimed invention comprises a VIP analog, wherein the VIP analog is a VIPR1 antagonist, but does not antagonize VIPR2 or PAC1 receptors. In some embodiments, the composition or pharmaceutical composition of the claimed invention comprises a VIP analog, wherein the VIP analog is a PAC1 antagonist, but does not antagonize VIPR2 or VIPR1 receptors. Any of the above-mentioned selective agonist or antagonists may be used in any of the method claims provided herein.

The present invention relates to modulating the amount of PLD in the nervous system of a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to modulating the amount of antibody production of a B cell in a subject comprising administering a composition comprising an analog to a subject, wherein said analog comprises an α-amino acid and at least one β-amino acid. In some embodiments the analog is a VIP family analog. In some embodiments the analog is a VIP analog.

The present invention relates to modulating the amount of antibody production of a B cell or a B cell hybridoma cell in vitro comprising treating a culture containing B cells or a hyvridoma with a composition comprising an analog to a subject, wherein said analog comprises an α-amino acid and at least one β-amino acid. In some embodiments the analog is a VIP family analog. In some embodiments the analog is a VIP analog.

The present invention relates to modulating the immune response of a subject comprising administering a subject with a composition comprising an analog to a subject, wherein said analog comprises an α-amino acid and at least one β-amino acid. In some embodiments the analog is a VIP family analog. In some embodiments the analog is a VIP analog.

The present invention relates to modulating the activation of cystic fibrosis transmembrane conductance regulator (CFTR) in a subject comprising administering a subject with a composition comprising an analog to a subject, wherein said analog comprises an α-amino acid and at least one β-amino acid. In some embodiments the analog is a VIP family analog. In some embodiments the analog is a VIP analog.

The present invention also relates measuring the modulation of activity of a VIP receptor molecule by measuring receptor activity comprising:

a) contacting a human VIP family receptor with a VIP family analog, wherein the analog comprises an α-amino acid and at least one β-amino acid;

b) measuring the association of the VIP family analog to the VIP receptor in the presence and absence of an unknown compound; and c) comparing the rate of association of the VIP family analog to the human VIP receptor in the presence of an unknown compound to the rate of association of the VIP analog to the human VIP receptor in the absence of an unknown compound.

The present invention also relates identifying a modulator of activity of a VIP receptor molecule by measuring receptor activity comprising:

a) contacting a human VIP family receptor with a VIP family analog, wherein said analog comprises an α-amino acid and at least one β-amino acid;

b) measuring the association of the VIP family analog to the VIP receptor in the presence and absence of an unknown compound; and c) comparing the rate of association of the VIP family analog to the human VIP receptor in the presence of an unknown compound to the rate of association of the VIP analog to the human VIP receptor in the absence of an unknown compound.

The present invention also relates to a method of measuring the modulation of activity of a human VIP receptor molecule by measuring receptor activity comprising:

a) contacting a human VIP family receptor with a VIP analog, wherein the analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

The present invention also relates identifying a modulator of activity of a VIP family receptor molecule by measuring receptor activity comprising:

a) contacting a human VIP family receptor with a VIP analog, wherein said analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound. In some embodiments, the VIP family receptor is chosen from VIPR1, VIPR2, VPAC$_1$, VPAC$_2$ or PAC$_1$.

The present invention also relates identifying a modulator of activity of a VIP family receptor molecule by measuring receptor activity comprising:

a) contacting a VIP family receptor with a VIP analog in a known concentration, wherein said analog comprises an α-amino acid and at least one β-amino acid;

b) measuring the binding affinity of the VIP analog to the VIP family receptor in the presence and absence of a compound that binds to the VIP family receptor; and c) comparing the binding affinity of the VIP analog to the VIP receptor in the presence of a compound that binds to the VIP family receptor to the binding affinity of the VIP analog to the VIP receptor in the absence of a compound that binds to the VIP family receptor. In some embodiments, the VIP family receptor is chosen from VIPR1, VIPR2, VPAC$_1$, VPAC$_2$ or PAC$_1$.

The invention also relates to the use of an analog with selectivity for VPAC1, PAC1, or VPAC2 in the preparation of a medicament for treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood glucose levels, elevated blood pressure, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction due to administration of a medication that causes onset of or exacerbates symptoms of pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof. In some embodiments, the invention relates to compositions comprising a VIP family analog with selectivity for VPAC1, PAC1, or VPAC2 for treatment or prevention of chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small cell lung carcinoma, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction in a subject in need thereof.

The present invention also relates to a method of treating or preventing cancer in a subject in need thereof comprising administering a VIP analog to the subject, wherein said analog comprises an α-amino acid and at least one β-amino acid and wherein said analog is a VPAC1, VPAC2, or PAC1 receptor antagonist or agonist with increased selectivity for the VPAC1, VPAC2, or PAC1 receptor as compared to the other receptors. In some embodiments, the cancer is chosen from the following: non-small cell lung carcinoma, small cell lung carcinoma, colorectal carcinoma, breast carcinoma, gastric carcinoma, prostate carcinoma, liver carcinoma, ductal pancreatic carcinoma, bladder carcinoma, Non-Hodgkin's lymphoma, maningioma, leiomyoma, endometrial carcinoma, pheochromocytoma, paraganglioma. The present invention also relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for the VPAC1, VPAC2, or PAC1 receptor as compared to the other receptors. In some embodiments the inflammatory disease is rheumatoid arthritis. In some embodiments, the VIP analog is administered at a therapeutically effective dose.

The present invention also relates to a method of treating or preventing cancer in a subject in need thereof comprising administering a VIP analog to the subject, wherein said analog comprises an α-amino acid and at least one β-amino acid and wherein said analog is a VPAC1 receptor antagonist with increased selectivity for the VPAC1 receptor. The present invention also relates to a method of treating or preventing inflammatory disease comprising administering a VIP analog to a subject in need thereof, wherein said analog comprises an α-amino acid and at least one β-amino acid and wherein said analog is a VPAC1 receptor antagonist with increased selectivity for the VPAC1 receptor. In some embodiments the inflammatory disease is rheumatoid arthritis. In some embodiments, the VIP analog is administered at a therapeutically effective dose.

The present invention also relates to a method of treating or preventing small cell lung carcinoma comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one VPAC1, VPAC2, or PAC1 receptor. The present invention also relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one of the following: VPAC1, VPAC2, or PAC1 receptors. In some embodiments, the VIP analog is administered at a therapeutically effective dose.

The present invention also relates to a method of treating or preventing primary arterial hypertension (PAH) comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one VPAC1, VPAC2, or PAC1 receptor. The present invention relates to a method of treating or preventing inflammatory disease comprising administering a VIP analog to a subject in need thereof, wherein said analog comprises an α-amino acid and at least one β-amino acid and wherein said analog is a VPAC1, VPAC2, or PAC1 receptor antagonist or agonist with increased selectivity for at least one of the following: VPAC1, VPAC2, or PAC1 receptors as compared to its selectivity for the other receptors. In some embodiments, the VIP analog is administered at a therapeutically effective dose.

The present invention also relates to a method of treating or preventing inflammatory disease comprising administering a VIP analog to a subject in need thereof, wherein said analog comprises an α-amino acid and at least one β-amino acid and wherein said analog is a VPAC1 receptor agonist with increased selectivity for the VPAC1 receptor. The present invention relates to a method of treating or preventing inflammatory disease comprising administering a VIP analog to a subject in need thereof, wherein said analog comprises an α-amino acid and at least one β-amino acid and wherein said analog is a VPAC1 receptor agonist with increased selectivity for the VPAC1 receptor. In some embodiments the inflammatory disease is rheumatoid arthritis. In some embodiments, the VIP analog is administered at a therapeutically effective dose.

The present invention also relates to a method of treating or preventing inflammatory disease comprising administering a VIP analog to a subject in need thereof, wherein said analog comprises an α-amino acid and at least one β-amino acid and wherein said analog is a VPAC2 receptor agonist with increased selectivity for the VPAC2 receptor. The present invention relates to a method of treating or preventing inflammatory disease comprising administering a VIP analog to a subject in need thereof, wherein said analog comprises an α-amino acid and at least one β-amino acid and wherein said analog is a VPAC2 receptor agonist with increased selectivity for the VPAC2 receptor. In some embodiments the inflammatory disease is rheumatoid arthritis. In some embodiments, the VIP analog is administered at a therapeutically effective dose.

The present invention also relates to a method of treating or preventing chronic obstructive pulmonary disease, pulmonary hypertension, primary arterial hypertension, pulmonary hypertension associated to post-ventricular septal defect, idiopathic pulmonary fibrosis, idiopathic pulmonary arterial hypertension comprising administering a VIP analog with selectivity for VPAC2 to a subject in need thereof, wherein said analog comprises an α-amino acid and at least one β-amino acid and wherein said analog is a VPAC2 receptor agonist with increased selectivity to VPAC2 receptor. In all methods of treatment or prevention, analogs of the present invention may be administered in therapeutically effective doses.

The present invention relates to a method of treating or preventing chronic obstructive pulmonary disease (COPD) comprising administering a VIP analog to a subject in need thereof, wherein said analog comprises an α-amino acid and at least one β-amino acid and wherein said analog is a VPAC1 receptor antagonist or agonist with increased selectivity for the VPAC1 receptor. The present invention relates to a method of treating or preventing COPD comprising administering a VIP analog to a subject in need thereof, wherein said analog comprises an α-amino acid and at least one β-amino acid and wherein said analog is a VPAC1 receptor antagonist or agonist with increased selectivity for the VPAC1 receptor. In some embodiments, the VIP analog is administered at a therapeutically effective dose via nebulizer or inhaler.

The invention also relates to a method of preventing or inhibiting activation of alveolar macrophages comprising administering a VIP analog to a subject, wherein said analog comprises an α-amino acid and at least one β-amino acid and wherein said analog is a VPAC1 receptor antagonist or agonist with increased selectivity for the VPAC1 receptor. In some embodiments, the VIP analog is administered at a therapeutically effective dose via nebulizer or inhaler.

The present invention relates to a method of treating or preventing chronic obstructive pulmonary disease (COPD) comprising administering a VIP analog to a subject in need thereof, wherein said analog comprises an α-amino acid and at least one β-amino acid and wherein said analog is a VPAC2 receptor agonist with increased selectivity for the VPAC2 receptor. The present invention relates to a method of treating or preventing COPD comprising administering a VIP analog to a subject in need thereof, wherein said analog comprises an α-amino acid and at least one β-amino acid and wherein said analog is a VPAC2 receptor agonist with increased selectivity for the VPAC2 receptor. In some embodiments, the VIP analog is administered at a therapeutically effective dose via nebulizer or inhaler. The invention relates to a method of preventing or inhibiting activation of alveolar macrophages comprising administering a VIP analog to a subject, wherein said analog comprises an α-amino acid and at least one β-amino acid and wherein said analog is a VPAC2 receptor agonist with increased selectivity for the VPAC2 receptor. In some embodiments, the VIP analog is administered at a therapeutically effective dose via nebulizer or inhaler.

The present invention also relates to methods of identifying a selective modulator of activity of a VIP family receptor molecule by measuring receptor activity comprising:

a) contacting a human VIP family receptor with a VIP analog, wherein said analog comprises an α-amino acid and at least one β-amino acid;

b) measuring the association of the VIP analog to the VIP receptor in the presence and absence of an unknown compound; and c) comparing the rate of association of the VIP analog to the human VIP receptor in the presence of an unknown compound to the rate of association of the VIP analog to the human VIP receptor in the absence of an unknown compound.

The present invention also relates to methods of identifying a selective modulator of activity of a VIP family receptor molecule by measuring receptor activity comprising:

a) contacting a first and a second VIP family receptor with a VIP analog in a known concentration, wherein said analog comprises an α-amino acid and at least one β-amino acid;

b) measuring the rate association of the VIP analog to the first and second VIP receptors in the presence and absence of an unknown compound; and c) comparing the rate of association of the VIP analog to the first VIP receptor in the presence of an unknown compound to the rate of association of the VIP analog to the the second VIP receptor in the absence of an unknown compound.

The present invention also relates to methods of identifying a selective modulator of activity of a VIP family receptor molecule by measuring receptor activity comprising:

a) contacting a first and a second VIP family receptor with a VIP analog in a known concentration, wherein said analog comprises an α-amino acid and at least one β-amino acid;

b) measuring the binding affinity of the VIP analog to the first and second VIP receptors in the presence and absence of an unknown compound; and c) comparing the binding affinity of the VIP analog to the first VIP receptor in the presence of an unknown compound to the binding affinity of the VIP analog to the the second VIP receptor in the absence of an unknown compound. In some embodiments, the VIP family receptor is chosen from VIPR1, VIPR2, VPAC$_1$, VPAC$_2$ or PAC$_1$.

The present invention also relates to methods of inhibiting the immune response against a transplanted organ in a subject, wherein the subject is an organ donor recipient. in some embodiments, the subject is a mammal. In some embodiments, the subject is a human. In some embodiments, the subject is a human experiencing organ rejection after transplantation.

In another embodiment, the present invention also relates to a method for inhibiting the growth of a tumor cell, the method comprising: contacting the tumor cell with an effective amount of a VIP family analog, wherein the VIP family analog or functional fragment thereof comprises at least one β-amino acid. In some embodiments, the method comprises contacting the tumor cell with an effective amount of a combination of a chemotherapeutic agent and a VIP family analog. In some embodiments, the VIP analog is a VIP analog. Suitable chemotherapeutic agents include, but are not limited to, platinum coordination compounds, topoisomerase inhibitors, antibiotics, antimitotic alkaloids and difluoronucleosides. In some embodiments, the VIP analog is a VPAC1 antagonist with selectivity for VPAC1. In some embodiments, the tumor cell is a tumor cell derived from a breast cancer, a lung cancer, a colon cancer, a prostate cancer, or a pancreatic cancer.

In another embodiment, the present invention also relates to a method of inhibiting the growth of a tumor cell in a mammalian subject in need thereof, the method comprising: administering to the subject an effective amount of a VIP family analog or functional fragment thereof, wherein the VIP family analog or functional fragment thereof comprises at least one β-amino acid. In some embodiments, the method comprises administering to the subject an effective amount of a combination of a chemotherapeutic agent and a VIP family analog. In some embodiments, the VIP analog is a VIP analog. In some embodiments, the tumor cell is a tumor cell derived from a breast cancer, a lung cancer, a colon cancer, a prostate cancer, hepatic cancer (HCC) or a pancreatic cancer. Suitable chemotherapeutic agents include, but are not limited to, platinum coordination compounds, topoisomerase inhibitors, antibiotics, antimitotic alkaloids and difluoronucleosides.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to VPAC$_1$; wherein the VIP analog is a VPAC$_1$ antagonist; and wherein the cancer cell is a bladder, breast, colon, liver, lung, prostate, stomach, thyroid or uterine cancer cell. The present invention relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to VPAC$_1$; wherein the VIP analog is a VPAC$_1$ antagonist; and wherein the cancer is a bladder, breast, colon, liver, lung, prostate, stomach, thyroid, hepatocellular, or uterine cancer. In some embodiments, the cancer has been diagnosed as being malignant. In some embodiments, the subject may have an increased risk or increased susceptibility to contracting a malignant cancer.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to VPAC$_2$; wherein the VIP analog is a VPAC$_2$ antagonist; and wherein the cancer cell is a lung, breast, stomach cancer cell. In some embodiments the cancer cell is derived from a stomach leiomyoma.

The present invention also relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to VPAC$_2$; wherein the VIP analog is a VPAC$_2$ antagonist; and wherein the cancer a lung, breast, stomach, or hepatocellular cancer. In some embodiments, the cancer has been diagnosed as being malignant. In some embodiments, the subject may have an increased risk or increased susceptibility to contracting a malignant cancer.

The present invention also relates to a method of treating or preventing airway constriction comprising administering a VIP analog or functional fragment thereof to a subject in need thereof, wherein said analog comprises an α-amino acid and at least one P-amino acid and wherein said analog is a VPAC2 receptor agonist. In some embodiments, the VIP analog or functional fragment thereof has increased selectivity to VPAC2 receptor. In all methods of treatment or prevention, analogs of the present invention may be administered in therapeutically effective doses.

The present invention also relates to a method of treating or preventing asthma, comprising administering a VIP analog or functional fragment thereof to a subject in need thereof, wherein said analog comprises an α-amino acid and at least one β-amino acid and wherein said analog is a VPAC2 receptor agonist. In some embodiments, the VIP analog or functional fragment thereof has increased selectivity to VPAC2 receptor. In all methods of treatment or prevention, analogs of the present invention may be administered in therapeutically effective doses. In some embodiments, the VIP analog or functional fragment thereof may be administered via an inhaler or nebulizer.

The present invention also relates to a method of treating or preventing cancer cell growth in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $PAC_1$; wherein the VIP analog is a $PAC_1$ antagonist; and wherein the cancer cell is a nerve cell, adrenal cell, pituitary cell, or breast cell. The present invention also relates to a method of treating or preventing cancer in a subject in need thereof comprising the steps of: administering a VIP analog or functional fragment thereof the subject, wherein the VIP analog or functional fragment comprises at least one β-amino acid, wherein the VIP analog or functional fragment thereof is selective or has increased selectivity to $PAC_1$; wherein the VIP analog is a $PAC_1$ antagonist; and wherein the cancer is a glioblastoma, neuroblastoma, adrenal, pituitary, catecholamine-VIPg tumors, pheochromocytomas, paragangliomas, endometrial cancers, or breast cancer. In some embodiments, the cancer has been diagnosed as being malignant. In some embodiments, the subject may have an increased risk or increased susceptibility to contracting a malignant cancer.

The invention also relates to methods of treating or preventing the aforementioned diseases using the analogs of the present invention. Any analog described in the present invention may or may not have preferred selectivity of one of its receptors versus another.

The invention relates to analogs based upon the polypeptide sequences identified in Tables 1, 2, and 3.

For purposes of interpreting polypeptide modifications throughout the application, please refer to the following legend:

Ac—Acylation
p-Cl-dF=para-Chlorine, D-Phenylalanine
4cl=Chlorinated Phenylalaine
$_dF$=para-Chlorine, D-Phenylalanine
$_dR$=D-Arginine
$_dY$=D-Tyrosine
$_dA$=D-Alanine
$_hR$=homoarginine
pY=Phosphoroylated Tyrosine
pS=Phosphoroylated Serine
pE=Pyroglutamic acid
PEG=Polyetheythlene Glycol
PEG{number kD}=Polyetheythlene Glycol with a molecular weight near {number} in kilodaltons.
Nle=Noraleucine
$N_{le}$=Noraleucine
$Y_m$=methoxy-tyrosine.
$Y_M$=methoxy-tyrosine.
$K_m$=methalyated-lysine.
Aib=α-aminoisobutyric acid
Abu=ALPHA-AMINOBUTYRIC ACID
Gab=γ-aminobutyric acid;
Dip=β,β-diphenyl-L-alanine;
*=indicates cyclization between residues (lactam ring)
dHis=D-His
w=D-Tryptophan
Dnp=di-nitro-phenol
Mca=methoxycoumarin 4 acetic acid
Sar=sarcosine
Sta=statine
Ste=Stearyl
Pyr=pyroglutamic acid
Fam=carboxyfluoresceine
LC=—($NH_2$—($CH_2$)$_5$—C=O)—
TAMRA=carboxytetramethylrhodamine
T*=N-acetyl galactosamine labeled Thr
$NH_2$=amidation of carboxy terminus
Orn=ornithine
K(W)=Trp residue which is coupled to the side chain of a Lys
Y(OMe)=methylated Tyrosine
Cit=citrulline
C6=hexanoyl
Nva=Norvaline In some embodiments, analogs of the present invention (including any polypeptide sequence identified in Tables 1, 2, or 3) are either be N-terminal acylated or an N-terminal free-amine. In some embodiments, analogs of the present invention are either either a c-terminal amine or a c-terminal acid. These terminal groups do not preclude additional solubilization and/or stabilization attachments such a polyethylene glycol.

In some embodiments, the invention relates to any composition, kit, or pharmaceutical composition comprising of SEQ ID NO: 1.

In some embodiments, the invention relates to any composition, kit, or pharmaceutical composition consisting of SEQ ID NO: 1.

In some embodiments, the invention relates to any composition, kit, or pharmaceutical composition comprising of SEQ ID NO: 2.

In some embodiments, the invention relates to any composition, kit, or pharmaceutical composition consisting of SEQ ID NO: 2.

In some embodiments, the invention relates to any composition, kit, or pharmaceutical composition comprising of SEQ ID NO: 3.

In some embodiments, the invention relates to any composition, kit, or pharmaceutical composition consisting of SEQ ID NO: 3.

In some embodiments, the invention relates to any composition, kit, or pharmaceutical composition comprising of SEQ ID NO: 4.

In some embodiments, the invention relates to any composition, kit, or pharmaceutical composition consisting of SEQ ID NO: 4.

In some embodiments, the invention relates to any composition, kit, or pharmaceutical composition comprising of SEQ ID NO: 5.

In some embodiments, the invention relates to any composition, kit, or pharmaceutical composition consisting of SEQ ID NO: 5.

In some embodiments, the invention relates to any composition, kit, or pharmaceutical composition comprising of SEQ ID NO: 6.

In some embodiments, the invention relates to any composition, kit, or pharmaceutical composition consisting of SEQ ID NO: 6.

In some embodiments, the invention relates to any composition, kit, or pharmaceutical composition comprising of SEQ ID NO: 7.

In some embodiments, the invention relates to any composition, kit, or pharmaceutical composition consisting of SEQ ID NO: 7.

In some embodiments, the invention relates to any composition, kit, or pharmaceutical composition comprising of SEQ ID NO: 8.

In some embodiments, the invention relates to any composition, kit, or pharmaceutical composition consisting of SEQ ID NO: 8.

In some embodiments, the invention relates to any composition, kit, or pharmaceutical composition comprising of SEQ ID NO: 9.

In some embodiments, the invention relates to any composition, kit, or pharmaceutical composition consisting of SEQ ID NO: 9.

In some embodiments, the invention relates to any composition, kit, or pharmaceutical composition comprising of SEQ ID NO: 10.

In some embodiments, the invention relates to any composition, kit, or pharmaceutical composition consisting of SEQ ID NO: 10.

In some embodiments, the invention relates to any composition, kit, or pharmaceutical composition comprising of SEQ ID NO: 11.

In some embodiments, the invention relates to any composition, kit, or pharmaceutical composition consisting of SEQ ID NO: 11.

In some embodiments, the invention relates to any composition, kit, or pharmaceutical composition comprising of SEQ ID NO: 12.

In some embodiments, the invention relates to any composition, kit, or pharmaceutical composition consisting of SEQ ID NO: 12.

In some embodiments, the invention relates to any composition, kit, or pharmaceutical composition comprising of SEQ ID NO: 13.

In some embodiments, the invention relates to any composition, kit, or pharmaceutical composition consisting of SEQ ID NO: 13.

In some embodiments, the invention relates to any composition, kit, or pharmaceutical composition comprising of SEQ ID NO: 14.

In some embodiments, the invention relates to any composition, kit, or pharmaceutical composition consisting of SEQ ID NO: 14.

In some embodiments, the invention relates to any composition, kit, or pharmaceutical composition comprising of SEQ ID NO: 15.

In some embodiments, the invention relates to any composition, kit, or pharmaceutical composition consisting of SEQ ID NO: 15.

In some embodiments, the invention relates to any composition, kit, or pharmaceutical composition comprising of SEQ ID NO: 16.

In some embodiments, the invention relates to any composition, kit, or pharmaceutical composition consisting of SEQ ID NO: 16.

In some embodiments, the invention relates to any composition, kit, or pharmaceutical composition comprising of SEQ ID NO: 17.

In some embodiments, the invention relates to any composition, kit, or pharmaceutical composition consisting of SEQ ID NO: 17.

In some embodiments, the invention relates to any composition, kit, or pharmaceutical composition comprising of SEQ ID NO: 18.

In some embodiments, the invention relates to any composition, kit, or pharmaceutical composition consisting of SEQ ID NO: 18.

In some embodiments, the invention relates to any composition, kit, or pharmaceutical composition comprising of SEQ ID NO: 19.

In some embodiments, the invention relates to any composition, kit, or pharmaceutical composition consisting of SEQ ID NO: 19.

In some embodiments, the invention relates to any composition, kit, or pharmaceutical composition comprising of SEQ ID NO: 20.

In some embodiments, the invention relates to any composition, kit, or pharmaceutical composition consisting of SEQ ID NO: 20.

In some embodiments, the invention relates to any composition, kit, or pharmaceutical composition comprising of SEQ ID NO: 21.

In some embodiments, the invention relates to any composition, kit, or pharmaceutical composition consisting of SEQ ID NO: 21.

In some embodiments, the invention relates to any composition, kit, or pharmaceutical composition comprising of SEQ ID NO: 22.

In some embodiments, the invention relates to any composition, kit, or pharmaceutical composition consisting of SEQ ID NO: 22.

In some embodiments, the invention relates to any composition, kit, or pharmaceutical composition comprising of SEQ ID NO: 23.

In some embodiments, the invention relates to any composition, kit, or pharmaceutical composition consisting of SEQ ID NO: 23.

In some embodiments, the invention relates to any composition, kit, or pharmaceutical composition comprising of SEQ ID NO: 24.

In some embodiments, the invention relates to any composition, kit, or pharmaceutical composition consisting of SEQ ID NO: 24.

In some embodiments, the invention relates to any composition, kit, or pharmaceutical composition comprising of SEQ ID NO: 25.

In some embodiments, the invention relates to any composition, kit, or pharmaceutical composition consisting of SEQ ID NO: 25.

In some embodiments, the invention relates to any composition, kit, or pharmaceutical composition comprising of SEQ ID NO: 26.

In some embodiments, the invention relates to any composition, kit, or pharmaceutical composition consisting of SEQ ID NO: 26.

In some embodiments, the invention relates to any composition, kit, or pharmaceutical composition comprising of SEQ ID NO: 27.

In some embodiments, the invention relates to any composition, kit, or pharmaceutical composition consisting of SEQ ID NO: 27.

In some embodiments, the invention relates to any composition, kit, or pharmaceutical composition comprising of SEQ ID NO: 28.

In some embodiments, the invention relates to any composition, kit, or pharmaceutical composition consisting of SEQ ID NO: 28.

In some embodiments, the invention relates to any composition, kit, or pharmaceutical composition comprising of SEQ ID NO: 29.

In some embodiments, the invention relates to any composition, kit, or pharmaceutical composition consisting of SEQ ID NO: 29.

In some embodiments, the invention relates to any composition, kit, or pharmaceutical composition comprising of SEQ ID NO: 30.

In some embodiments, the invention relates to any composition, kit, or pharmaceutical composition consisting of SEQ ID NO: 30.

In some embodiments, the invention relates to any composition, kit, or pharmaceutical composition comprising of SEQ ID NO: 31.

In some embodiments, the invention relates to any composition, kit, or pharmaceutical composition consisting of SEQ ID NO: 31.

In some embodiments, the invention relates to any composition, kit, or pharmaceutical composition comprising of SEQ ID NO: 32.

In some embodiments, the invention relates to any composition, kit, or pharmaceutical composition consisting of SEQ ID NO: 32.

In some embodiments, the invention relates to any composition, kit, or pharmaceutical composition comprising of any one or plurality of polypeptides chosen from: SEQ ID NO: 1 through SEQ ID NO: 64.

In some embodiments, the invention relates to any composition, kit, or pharmaceutical composition consisting of any one or plurality of polypeptides chosen from: SEQ ID NO: 1 through SEQ ID NO: 64.

The following examples are provided to describe the invention in greater detail. They are intended to illustrate, not to limit, the invention. Various publications, including patents, published applications, technical articles and scholarly articles are cited throughout the specification. Each of these cited publications is incorporated by reference herein, in its entirety.

EXAMPLES

Example 1: Chemical Scheme to Synthesize Polypeptides (not Prophetic)

This example describes how the polypeptide analogs are manufactured. The sequence of human vasoactive intestinal peptide (VIP) is given below, using the standard one-letter code for proteinogenic amino acid residues. For purposes of interpretation "position 1" of the sequence below is the N-terminal histidine. Each amino acid residue is numbered in sequence from the N-terminal end of the polypeptide to the C-terminal.

HSDAVFTDNYTRLRKQMAVKKYLNSILN  (SEQ ID NO: 66)

Design.

A family of analogues will be prepared, each containing multiple α to $\beta^3$ replacements. Each $\beta^3$-amino acid residue will bear the side chain of the α-amino acid indicated by the one-letter code. The analogues to be prepared are shown below; the positions indicated with lowercase letters are those at which α-to-$\beta^3$ replacement has occurred. In addition, the n-terminal of these analogues may be optionally acetylated.

TABLE 2

VPAC2 selective analogs. EC50 values are the results of cell-based cAMP assays. Values reported are in molar concentration.

| Identifier | Sequence | Seq ID | EC 50 vpac1 (Molar) | EC50 vpac2 (Molar) |
|---|---|---|---|---|
| LBT-V201 | Ac-HSDAVFTENYTKLRKQLAxKKYxNDlKKGgT | Seq ID NO: 1 | 9.088E-09 | 1.039E-07 |
| LBT-V202 | Ac-HSDAVFTENYTKLRKQLAAzKYxNDLkKGgT | Seq ID NO: 2 | >1E-6 | 9.629E-10 |
| LBT-V203 | Ac-HSDAVFTENYTKLRKQxAAzKYLxDLkKGGT | Seq ID NO: 3 | 2.177E-07 | 1.804E-10 |
| LBT-V204 | Ac-HBDAVFTENYTKLRKQLAAzKYxNDLkKGgT | Seq ID NO: 4 | 5.163E-07 | 5.286E-10 |
| LBT-V205 | Ac-HBDAvFTENYTKLRKQLAAzKYxNDLkKGgT | Seq ID NO: 5 | >1E-6 | 8.162E-10 |
| LBT-V206 | Ac-HBDAvFTEnYTKLRKQLAAzKYxNDLkKGgT | Seq ID NO: 6 | >1E-6 | 3.472E-09 |
| LBT-V207 | Ac-HxDAVFTENYTKLRKQLAAzKYxNDLkKGgT | Seq ID NO: 7 | >1E-6 | 5.928E-10 |
| LBT-V208 | Ac-HxDAxFTENYTKLRKQLAAzKYxNDLkKGgT | Seq ID NO: 8 | 1.33E-07 | 6.46E-10 |
| LBT-V209 | Ac-HxDAxFTExYTKLRKQLAAzKYxNDLkKGgT | Seq ID NO: 9 | >1E-6 | 5.579E-09 |
| LBT-V210 | Ac-HxDAvFTENYTKLRKQLAAzKYxNDLkKGgT | Seq ID NO: 10 | 1.42E-06 | 8.586E-10 |
| LBT-V211 | Ac-HxDAvFTENYTKLRKQIAAzKYxNDLkKGgT | Seq ID NO: 11 | >1E-6 | 1.258E-09 |
| LBT-V212 | Ac-HxDAvFTENYTKLRKqLAAzKYxNDLkKGgT | Seq ID NO: 12 | 1.53E-06 | 3.515E-09 |
| LBT-V213 | Ac-HxDAvFTENYTKLRkQLAAzKYxNDLkKGgT | Seq ID NO: 13 | 2.93E-07 | 1.266E-09 |
| LBT-V214 | Ac-HxDAvFTENYTKLrKQLAAzKYxNDLkKGgT | Seq ID NO: 14 | >1E-6 | 1.372E-09 |
| LBT-V215 | Ac-HxDAvFTENYTKlRKQLAAzKYxNDLkKGgT | Seq ID NO: 15 | 1.42E-06 | 1.334E-09 |
| LBT-V216 | Ac-HxDAxFTEnyTKLRKQLAAzKYxNDLkKGgT | Seq ID NO: 16 | 9.318E-07 | 9.559E-08 |
| LBT-V217 | Ac-HxDAxFTExyTKLRKQlAAzKYxNDLkKGgT | Seq ID NO: 17 | 7.853E-07 | 1.166E-09 |
| LBT-V218 | Ac-HxDAxFTExyTKLRKqLAAzKYxNDLkKGgT | Seq ID NO: 18 | >1E-6 | 1.018E-09 |
| LBT-V219 | Ac-HxDAxFTExyTKLRkQLAAzKYxNDLkKGgT | Seq ID NO: 19 | 4.614E-07 | >1E-6 |

TABLE 2-continued

VPAC2 selective analogs. EC50 values are the results of cell-based cAMP assays. Values reported are in molar concentration.

| Identifier | Sequence | Seq ID | EC 50 vpac1 (Molar) | EC50 vpac2 (Molar) |
|---|---|---|---|---|
| LBT-V220 | Ac-HSDAVFTENYTKLRKQ<u>x</u>AAK<u>z</u>YL<u>x</u>DLK<u>k</u>GGT | Seq ID NO: 20 | 9.515E-09 | 4.22E-10 |
| LBT-V221 | Ac-HSDAVFTDNYTRLRKQ<u>x</u>AAK<u>z</u>YL<u>x</u>SlK<u>n</u>KRY | Seq ID NO: 21 | 1.952E-10 | 7.845E-11 | wherein Ac = acetyl; B = AIB.

In each of sequences above, at least one residue has been replaced by a cyclic or heterocyclic β-amino acid residue. In some embodiments, based upon the above sequences, X=ACPC, Z=APC; uncharged side chains replaced by ACPC, basic side chains replaced by APC, Protected $\beta^3$-amino acids). Individual α/β amino acids (Fmoc on the backbone nitrogen and appropriate protecting groups on side chains, when necessary) will be obtained from commercial suppliers or prepared via reported methods. Each $\beta^3$-peptide will be prepared manually by microwave-assisted Fmoc solid phase peptide synthesis resulting in a c-terminal amide, for example Rink Amide resin. Coupling steps will be carried out with a three-fold excess of the appropriate protected α- or $\beta^3$-amino acid, using HATU to mediate amide bond formation. Piperidine will be used for Fmoc deprotection steps. Each peptide will be cleaved from resin by treatment with 94:2.5:2.5 TFA/H2O/triisopropylsilane, precipitated by addition of cold ethyl ether, and purified by reverse phase HPLC on a prep-C18 column using gradients between 0.1% TFA in water and 0.1% TFA in acetonitrile. The identity and purity of the final products will be determined by mass spectrometry and analytical HPLC, respectively.

One purpose of this study is to demonstrate that the analogs of the application may be designed to increase the half-life of the polypeptide as compared to the half-life of the naturally encoded protein by introducing non-natural amino acid analogs that are resistant to degradation and/or induce an equivalent or increased bioactivity as compared to the naturally encoded polypeptide sequence upon which the analog is based or derived through the possible incorporation of conformationally-constrained residues.

In-Vitro Cell Based Activity Assay

In Vitro Binding Assay 1: VIP analogues in table 1 were prepared in appropriate phosphate buffer was at pH of 7.5 was exposed to a functional assay in parallel with wild-type VIP proteins. Division arrested cAMP Hunter cell lines (purchased from DiscoveRx) expressing VIPR1 and VIPR2 were plated into 96 or 384-well microplates for compound profiling according to the manufactures directions. Cells were allowed to adhere and recover overnight prior to compound addition. cAMP modulation was determined using the DiscoveRx HitHunter cAMP XS+ assay.

For profiling compound in agonist mode, the cells were incubated in the presence of compound at room temperature for 60 minutes. Cells expressing both VIPR1 and VIPR2 were exposed to serial dilutions (3 fold or 10 fold as appropriate) of wild-type VIP and separate samples of the same type of cells were exposed to serial dilutions (3 fold or 10 fold as appropriate) of a VIP analogue to determine $EC_{50}$ values of the analogue as compared to wild-type VIP. All dilutions were within the range of millimolar to picomolar in final compound concentration in each well. After appropriate compound incubation, assay signal was generated through incubation with DiscoverX lysis cocktail according to the manufacturers standard protocol. Dose curves were plotted using GraphPad Prism. Percentage activity is calculated using the following formula:

% Activity=100%×(mean RLU of test sample−mean RLU of vehicle control)/(mean RLU of MAX control−mean RLU of vehicle control).

In Vitro Competitive Binding Assay (Prophetic)

Binding assays: Membranes prepared from a stable VPAC2 cell line (such as a CHO-S cell line stably expressing human VPAC2 receptor or from cells transiently transfected with human VPAC1 or PAC1) will be used. A filter binding assay will be performed using $^{125}$I-labeled VIP for VPAC1 and VPAC2 and $^{125}$I-labeled PACAP-27 for PAC as the tracers. For this assay, the solutions and equipment include:

Presoak solution: 0.5% Polyethyleneamine in Aqua dest

Buffer for flushing filter plates: 25 mM HEPES pH 7.4

Blocking buffer: 25 mM HEPES pH 7.4; 0.2% protease free BSA

Assay buffer: 25 mM HEPES pH 7.4; 0.5% protease free BSA

Dilution and assay plate: PS-Microplate, U form

Filtration Plate Multiscreen FB Opaque Plate; 1.0 mM Type B Glasfiber filter

In order to prepare the filter plates, the presoak solution will be aspirated by vacuum filtration. The plates will be flushed twice with 200 μL flush buffer. 200 μL blocking buffer will be added to the filter plate. The filter plate will then be incubated with 200 μL presoak solution for 1 hour at room temperature. The assay plate will be filled with 25 μL assay buffer, 25 μL membranes (2.5 g) suspended in assay buffer, 25 μL agonist in assay buffer, and 25 μL tracer (about 40000 cpm) in assay buffer. The filled plate will be incubated for 1 hour with shaking. The transfer from assay plate to filter plate will be conducted. The blocking buffer will be aspirated by vacuum filtration and washed two times with flush buffer. 90 μL will be transferred from the assay plate to the filter plate. The 90 μL transferred from assay plate will be aspirated and washed three times with 200 μL flush buffer. The plastic support is removed. It is dried for 1 hour at 60° C. 30 μL Microscint will beaded. The count will be performed based upon analog affinity to VPAC1, VPAC2, or PAC1 receptors. $IC_{50}$ and $EC_{50}$ calculations will be performed based upon affinity scoring.

Example 2: Structural Analysis of Helical Polypeptides (Prophetic)

This prophetic example describes how the polypeptide analogs of this invention may be characterized after manufacture through structural conformational assays such as circular dichrosim (CD) and Nuclear magnetic resonance (NMR).

Circular Dichroism Spectroscopy. Circular dichroism measurements will be carried out on an Aviv 202SF Circular Dichroism Spectrophotometer. Samples of each peptide will be prepared with a determined UV absorbance in the range of 0.1-1.0 at 280 nm in a pH buffered solution. Spectra will be recorded in a 1 mm cell with a step size of 1 nm and an averaging time of 5 sec. All spectra will be background corrected against buffer measured in the same cell. Thermal melts will be carried out in 1-degree increments with an equilibration time of 2 min between each temperature change. Thermal unfolding data will be fit to a simple two state folding model Shortle, D. Meeker, A. K. Freire, E. *Biochemistry* 1988, 27, 4761-4768) using GraphPad Prism.

Nuclear Magnetic Resonance: Structure elucidation of the proposed analogs can also be accomplished based on analyses of heteronuclear NMR experimental data. Global backbone structural information complementing the local structure information provided by backbone chemical-shift assignments can be obtained from nuclear Overhauser effect spectroscopy (NOESY) which yield atomic distance constraints together with residual dipolar coupling (RDC) experiments which provide orientation restraint information. Together, these techniques can be used to provide valuable structural information regarding the positioning and alignment of the amino acids within the polypeptide analog. Samples of each peptide or analog will be prepared with a determined UV absorbance in the range of 0.1-1.0 at 280 nm in an appropriate pH buffered solution. Each preparation will then be used to determine chemical shifts using the suite of multidimensional experiments, ie amide based backbone assignments HNCO and TOCSY, followed by conducting structure restraint experiments, ie NOESY and RDC, using standard NMR equipment (i.e. Bruker NMR) and data analysis software (i.e. Talos+, SPARKY and Al NMR). Further structural insight can be ascertained by comparing the results of NMR experiments in the presence and absence of the intended binding partner.

One purpose of this study is to evidence that the conformation of the analog is structurally constrained and that certain non-natural amino acids have been incorporated in the synthesized peptide in their predicted location along a longitudinal axis of the polypeptide.

Example 3: In-Vitro Stability Analysis of Helical Polypeptides in Solution (not Prophetic)

This example describes how the metabolic stability of the polypeptide analogs of this invention are characterized after manufacture through assays such as a protease resistance assay.

In Vitro Stability Assay: Stock solutions of the both the naturally occurring peptides as well as peptide analogs are prepared at a concentration of 250 µM (based on UV absorbance) in a 2% DMSO solution of appropriate buffering conditions. Standard solution of proteinase K in addition to other common animal proteases (i.e. Cathepsins, Trypsins, dipeptidyl peptidase IV and chymotrypsin) were prepared at the following concentrations in appropriate buffers separately: Protease K: 250 µg/ml, Chymotrypsin 25 µg/mL and DPP-IV 40 units/ml. For a Protease K assay, the following recipe was followed: 1 µL enzyme was added to 5 µL peptide analog in 44 µL PBS. For a Chymotrypsin assay, the following recipe was followed: 2 µL of enzyme was added to 5 µL of peptide analog in 43 µL PBS. For a DPP-IV assay, the following recipe was followed: 2 µL enzyme was added to 5 µL peptide analog in 18 µL PBS. All reactions (regardless of enzyme or analog) were then allowed to proceed at room temperature and quenched at the desired time point by addition of 10 µL of 1% TFA in 99% Acetonitrile. 50 µL of the resulting quenched reaction are then injected onto an analytical reverse phase HPLC, and the amount of starting peptide present quantified by integration of the appropriate chromatogram peak via absorbance at either 220 or 280 nm. Duplicate reactions are run for each time point. Half-lives are determined by fitting time dependent peptide concentration to an exponential decay using GraphPad Prism. Samples for some time points will be analyzed by mass spectrometery, and the products observed are used to identify amide bonds cleaved in the course of the reaction. The relative stability enhancement is determined through the comparison of the various analogs with its naturally occurring peptide counterpart. Percent degradation is be quantified by integration of peak areas related to undigested peptide peaks and corrected for degradation in the absence of enzyme.

Similar protocols were followed to examine the stability of the VIP analogs in simulated gastric fluid (SGF). SGF was prepared using the following recipe: 2 g NaCl, 64 mg Pepsin and 7 mL HCl were dissolved in 1 liter of deionized water. 45 µL of SGF were mixed with 5 uL of peptide solution (stock concentration of 250 uM) and incubated together. At timepoints, 0, 1, 2, 5, 10, 15, 20 minutes reactions were quenched with 10 uL 1M Tris pH 8.0 to stop the digestion. Final samples were injected onto an analytical reverse phase HPLC, and the amount of starting peptide present quantified by integration of the appropriate chromatogram peak via absorbance at either 220 or 280 nm. Duplicate reactions are run for each time point. Half-lives are determined by fitting time dependent peptide concentration to an exponential decay using GraphPad Prism. Samples for some time points were analyzed by mass spectrometery, and the products observed were used to identify amide bonds cleaved in the course of the reaction. The relative stability enhancement is determined through the comparison of the various analogs with its naturally occurring peptide counterpart. Percent degradation is be quantified by integration of peak areas related to undigested peptide peaks and corrected for degradation in the absence of enzyme.

FIG. 1: Representative in-vitro protease stability of VPAC-2 selective analog (LBT-V208, SEQ ID NO: 8) compared to the native VIP as well as the VPAC2 selective agonist Ro 25-1553. It is noteworthy that the stability is greater for the non-lactam containing LBT-V208 as compared to Ro 25-1553, which contains one lactam bridge between lysine and aspartic acid residues.

Figure 3:
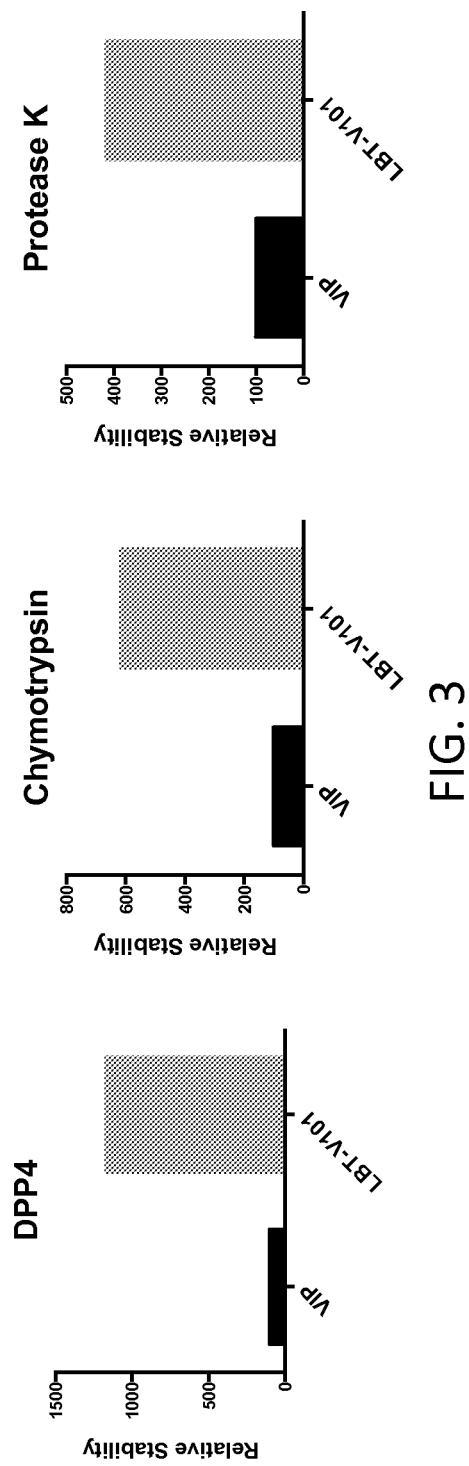
FIG. 3 depicts a representative in-vitro protease stability of VPAC-1 selective analog (LBT-V101, SEQ ID NO: 22) compared to the native VIP.

FIG. 3: Representative in-vitro protease stability of VPAC-1 selective analog (LBT-V101, SEQ ID NO: 22) compared to the native VIP.

Ex-vivo Stability Assay (prophetic): To investigate the plasma stability of the analogs, both the naturally occurring peptide as well as the analogs will be prepared at a concentration of 100 µM (based on UV absorbance) in appropriate buffer. 50 uL aliquots of animal plasma (i.e. rodent, canine, primate) are then spiked with the analog or the naturally occurring peptide. The reaction will be allowed to proceed at room temperature and quenched at the desired time point by addition of an equivalent volume of 1% TFA in Acetonitrile and diluted 1-10 fold with PBS. This solution is then passed over a C18 solid phase extraction column (eg. Sigma TPSC18) to further isolate the peptide or analog for subsequent LC/MS analysis by removal of unrelated lipids and plasma proteins. The analogs are then eluted from the C18 column by adding 1-3 column volumes of between 20 and 50% acetonitrile in 0.1% formic acid, collected and concentrated for subsequent analysis. Approximately 10 µL of the concentrated quenched reaction will be injected onto an analytical reverse phase HPLC, and the amount of starting peptide present quantified by integration of the appropriate chromatogram peak via absorbance at either 220 or 280 nm. Duplicate reactions will be run for each time point. Half-lives will be determined by fitting time dependent peptide concentration to an exponential decay using GraphPad Prism. Samples for some time points will be analyzed by mass spectrometery, and the products observed will be used to identify amide bonds cleaved in the course of the reaction. The relative stability enhancement will be determined through the comparison of the various analogs with its naturally occurring peptide counterpart.

Microsome Stability Analysis of Analogs Polypeptides in Solution (prophetic): A reaction mixture, minus NADPH, should be prepared as described below. Approximately 1 milligram of test compound originally in powdered form is suspended in DMSO prior to addition to a reaction mixture. The test compound was added into the reaction mixture (0.5 mg/mL human liver microsomes; 100 mM potassium phosphate; 5 mM Magnesium chloride) at a final concentration of 1 µM. An aliquot of the reaction mixture (without cofactor) was incubated in a shaking water bath at 37° C. for 3 minutes. The control compound, testosterone, should be run simultaneously with the test compound in a separate reaction. The reaction is initiated by the addition of NADPH cofactor (1 mM NADPH), and the mixture was then incubated in a shaking water bath at 37° C. Aliquots (100 µL) are withdrawn at 0, 10, 20, 30, and 60 minutes for the test compound and 0, 10, 30, and 60 minutes for testosterone. Test compound and testosterone samples are immediately combined with 400 µL of ice-cold 50/50 acetonitrile/dH$_2$O containing 0.1% formic acid and internal standard to terminate the reaction. The samples are then mixed and centrifuged to precipitate microsomal proteins. Testosterone samples are assayed via LC-MS/MS using electrospray ionization on an appropriate triple-quadropole mass spectrometer according to the manufacturer's instructions. A thermo BDS Hypersil C18 column (30×2.0 mm; 3 µm) can be used for chromatography at 300 µL/minute with an aqueous reservoir of 90% water and 10% buffer and an organic reservoir of 90% acetonitrile with 10% buffer (each 25 mM ammonium formate buffer at pH of 3.5). Test compound samples are also analyzed by using LC-MS/MS mass spectrometer. The peak area response ratio to internal standard (PARR) of the compounds at 10, 20, 30, and 60 minutes are then compared to the PARR at time 0 to determine the percent of test compound remaining at each timepoint. After the final time point, fluorimetry is used to confirm the addition of NADPH to the reaction mixture. Half-life was normalized of control using internal acceptance criteria. Half-life was calculated based upon a t1/2=0.693/k, where k is the elimination rate constant based upon the slope of the plot of natural logarithm percent remaining versus incubation time. Intrinsic clearance (CL$_{int}$) was calculated based upon CL$_{int}$=k/P, where k is the elimination rate constant and P is the protein concentration in the incubation.

In Vivo Stability Assay (not prophetic): To investigate the in vivo stability of the analogs, both the naturally occurring peptide as well as the analogs were administered to male C57BL/6 mice by IV, SC and PO routes at concentrations ranging from 0.001 to 50 mg/kg and blood specimens drawn at periodic time-points for up to 24 hours post-injection. Specific dose concentrations used include 50 nmol/kg, 100 nmol/kg 250 nmol/kg 500 nmol/kg and 1000 nm/kg. Specific time-points used to perform these studies include: 0.5, 1, 2, 5, 8 and 20 hours after initial delivery. Levels of intact compound in 10 µL of freshly collected plasma was determined by injection onto an analytical reverse phase HPLC after following the solid phase extraction procedure discussed previously. The amount of starting peptide present quantified by integration of the appropriate chromatogram peak via absorbance at either 220 or 280 nm or other means of measuring the presence or absence of fully intact analog as described herein. Samples were analyzed using Multiple Reaction Monitoring (MRM) mass spectrometry techniques wherein the amount of full-length (as judged by calculated molecular weight) analog was determined by integration of the data resulting from the MRM analysis and compared against a standard curve of known amounts of analog under the same conditions. This analysis technique also allows the examination of the in-vivo metabolites by determination of fragment molecular weights. Area-under-the-curve calculations were performed using Graphpad Prism on the MRM data resulting from LC/MS-MS analysis, thus resulting in a relative concentration value for each data point collected. The relative stability enhancement was determined through the comparison of the relative concentration values of the various analogs with its naturally occurring peptide counterpart.

Figure 4:
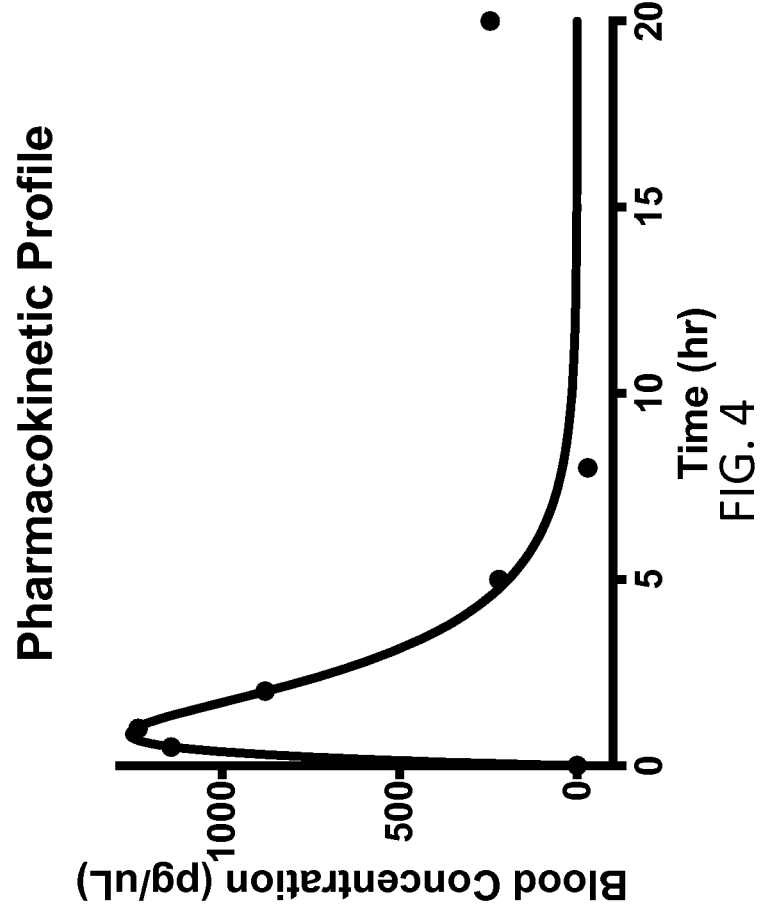
FIG. 4 depicts a pharmacokinetic study of LBT-V218 (SEQ ID NO: 18) via subcutaneous administration in C57 BL/6 male mice. Analysis conducted via LC/MS/MS techniques to confirm presence of target molecule. Points represent AUC for each time point described in the x axis

FIG. 4. Representative pharmacokinetic study of LBT-V218, SEQ ID NO: 18 via subcutaneous administration in C57 BL/6 male mice. Analysis conducted via LC/MS/MS techniques to confirm presence of target molecule. Points represent AUC values for each time point described in the x-axis.

Determination of Oral Bioavailability (not prophetic): The oral bioavailability was evaluated by comparative analysis between Intraduodenal and Intravenous administration of the analogs. Each compound/test article was first converted to an appropriate salt form and dissolved in a combination of biocompatible acids (e.g. citric acid, citrate, taurodeoxycholic acid, stearic acid, etc.) along with an optional permeation enhancer (e.g. DL-Lauroylcarnitine, sodium lauryl sulfate, Acetylated monoglycerides, sucrose, chitosan, tri-methyl chitosan, etc) or buffer (e.g. PBS, sodium bicarbonate, etc). Chitosan was purchased from TCI chemicals with a range of viscosities (5 mPa to 527 mPa) each with an average degree of deacetylation between (80-90%). Trimethyl chitosan (TMC) was prepared based on these chitosan samples according to the two-step synthesis protocol described by Sieval et. al. in Carbohydrate Polymers 36 (1998) 157-165. Specifically, A mixture of 2 g of sieved chitosan (~80-90% deacetylated), 4.8 g of sodium iodide, 11 ml of a 15% aqueous sodium hydroxide solution and 11.5 ml of methyl iodide in 80 ml of 1-methyl-2-pyrrolidinone was stirred on a water bath of 60° C. for 1 h (Le Dung et al., 1994). Special care was taken to keep the methyl iodide in the reaction mixture by using a Liebig condenser. The product was precipitated using ethanol and thereafter isolated by centrifugation. The N-trimethyl chitosan iodide obtained after this first step was washed twice with ether to remove the ethanol. It was dissolved in 80 ml of 1-methyl-2-pyrrolidinone and heated to 60° C., thus removing most of the absorbed ether. Subsequently, 4.8 g of NaI, 11 ml of 15% NaOH solution and 7 ml of methyl iodide were added with rapid stirring and the mixture was heated on a water bath at 60° C. for 30 min. An additional 2 ml of methyl iodide and 0.6 g of NaOH pellets were added and the stirring was continued for 1 h. The product, prepared as described above, was dissolved in 40 ml of a 10% NaCl aqueous solution, instead of HCl, to exchange the iodide. The polymer was precipitated with ethanol, isolated by centrifugation and thoroughly washed with ethanol and ether. In vacua drying yielded a white, water-soluble powder. Subsequently TMC solutions for each of the initial chitosan (varying viscosities ~5 to ~500 mPa) starting materials ranging in concentrations from 0.1%-20% TMC in biologically acceptable buffers (PBS, Sodium bicarbonate, etc) were prepared. Degree of tri-methylation was confirmed via NMR techniques.

Figure 10:
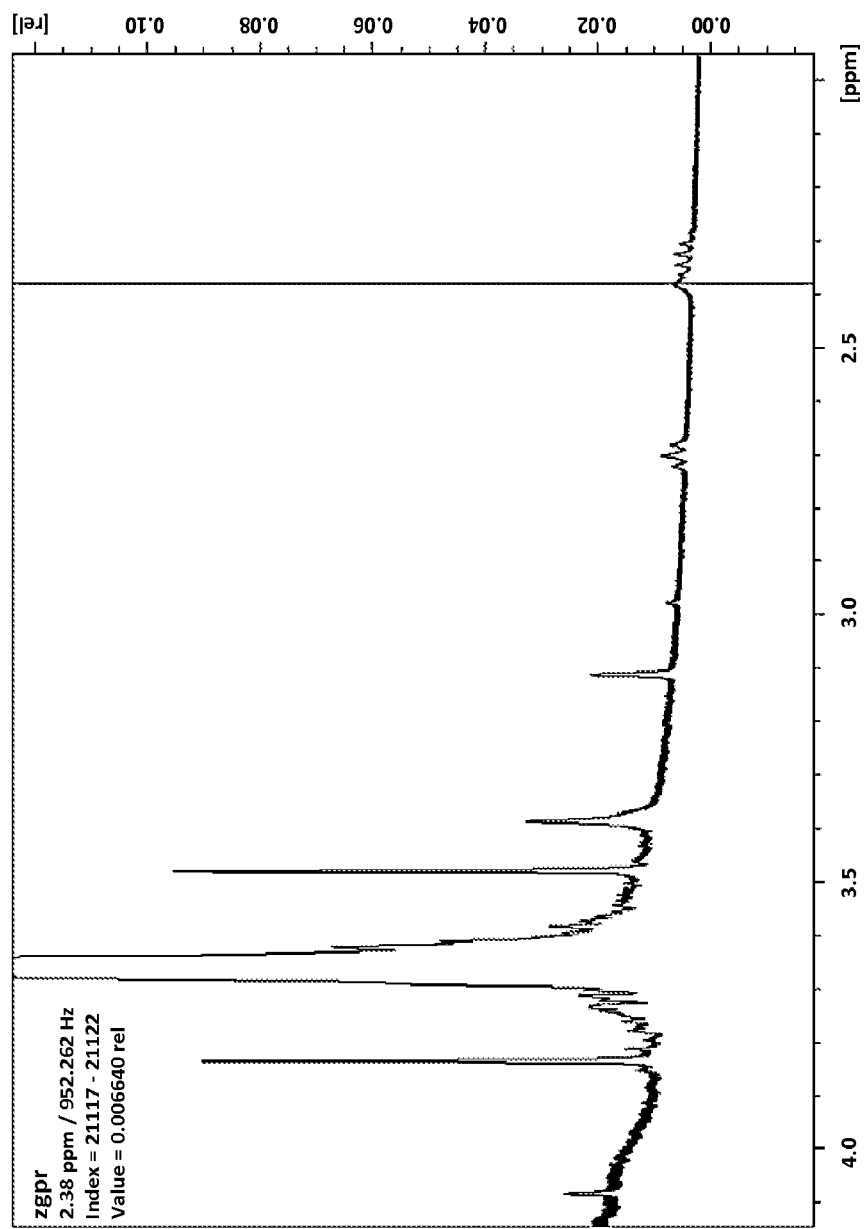
FIG. 10 depicts NMR spectra of TMC (in DCl) prepared from chitosan with viscosity of 5 mPa. The large peak observed at 3.65 is assigned to the tri-methylated state of chitosan.

FIG. 10: Representative NMR spectra of TMC (in DCl) prepared from chitosan with viscosity of 5 mPa. The large peak observed at 3.65 ppm is assigned to the tri-methylated state of chitosan, indicating complete tri-methylation.

Subsequently, intraduodenal (ID) catheterized male C57/BL6 mice, 8 weeks old (Charles River Labs) are quarantined for at least one day and have continuous access to food and water. A single dose of the appropriate formulated analog is then administered via catheter to each mouse. Single doses of 1000 nmol/kg (seq ids 208, 218 and 101) were dissolved in 5% TMC in PBS (pH 7.5) and delivered via intraduodenal catheter infusion.

Blood samples were collected via tail vein at the following time points: 0 h, 0.75 h, 1.5 h, 3 h. Samples were kept in EDTA containing (10 uL of 50 mM) microtainer tubes under subambient temperature (4° C.) before they are processed. Blood samples were centrifuged (10,000 rpm for 5 minutes) and plasma samples were flash frozen with liquid nitrogen and subsequently stored in a −20° C. freezer until analyzed for analog levels. Analog levels in the plasma will be analyzed using the following protocol for direct plasma precipitation.

The in vivo plasma samples are then prepared in 0.5 mL microfuge tube, by adding, 10 µL of test plasma to 50 µL of cold methanol with 0.1% formic acid followed by vortexing for 10 minutes at 4° C. Samples are then centrifuged for 3 minutes, when the supernatant is decanted into a new tube and lyophilized. The dried supernatant is then resuspended in 12 µL of 20% acetonitrile, 0.1% formic acid. 10 L of this final sample will then be injected into the LC/MS-MS for analysis. The prepared sample will be injected onto a reverse phase column (Phenomonex 3.0×50 mm) using a mobile phase of 20% $CH_3OH$, 0.1% formic-35% $CH_3OH$, 0.1% formic acid for LC/MS-MS analysis. The run time will be about 10 minutes at a flow rate of about 400 µL/minutes. The Area Under the Curve (AUC) will be calculated using the linear trapezoidal rule from t=0 to the last plasma concentration sampling time tx (see Handbook of Basic Pharmacokinetics, Wolfgang A. Ritschel and Gregory L. Kearns, 5th ed, 1999). $AUC^0\text{-}tx = \Sigma^0\text{-}n((C_n+C_n+1)/2))(t_n+1-t_n)$ {in (µg/mL)h}

One purpose of this study is to evidence that the analog is more resistant to peptidases as compared to the resistance of similarly-structured, naturally occurring polypeptides upon which the structure of the analog is based or derived. The results may show that, when treated with the same proteolytic enzymes or in vivo biological conditions, the analogs of the invention will resist degradation, become substantially more bioavailable and have longer half-lives than similarly-structured, naturally occurring polypeptides upon which the structure of the analog is based or derived.

Example 4: In-Vivo Functional Analysis of VPAC2 Selective Polypeptides (Prophetic)

This prophetic example describes the function of polypeptide analogs of this invention may be characterized after manufacture through assays that measure bioactivity of the analogs when exposed to tissue culture or when administered to an animal model of one of the following human disease states: COPD, pulmonary hypertension, primary arterial hypertension, pulmonary hypertension associated to post-ventricular septal defect, idiopathic pulmonary fibrosis, idiopathic pulmonary arterial hypertension, CREST syndrome—Calcinosis; Raynaud's disease; loss of muscle control of the Esophagus; Sclerodactyly; Telangiectasia, Acute respiratory distress, congestive heart failure, chronic obstructed pulmonary disorder, asthma, chronic obstructive pulmonary disease, sarcoidosis, small lung cell cancer, exocrine pancreatic tumors, colorectal carcinoma, gastric carcinoma, hepatocellular carcinoma, esophageal carcinoma, renal cell carcinoma, prostate carcinoma, urinary bladder carcinoma, liver carcinoma, ductal pancreatic cancer, breast carcinoma, ovarian carcinoma, non-hodgkin's lymphoma, meningioma, GEP tumors (differentiated and undifferentiated), pituitary adenoma, endometrial cancer, astrocytoma, giloblastoma, non-small cell lung cancer, pancreatic cancer, melanoma, renal cancer, neuroblastoma, leukemia and prostate cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood pressure levels, elevated blood glucose levels, elevated blood pressure levels, hyperglycemia, diabetes, insulin resistance, metabolic acidosis, obesity, Type I diabetes, Type II diabetes Multiple Sclerosis, osteoporosis, Sjogren's syndrome, pancreatitis, uveoretinitis, osteoporosis, female sexual dysfunction and diabetic nephropathy.

In Vivo Efficacy in Animal Models: To determine the activity of analogs of the invention in vivo as compared to the naturally occurring polypeptides upon which the analogs are derived, the analogs will be administered alone (IP, IV, SC, PO, by inhalation or nasal routes) or in combination with known active agent to monitor the above-mentioned disease states. Secretin family analogs alone or in combination with sub-optimal doses of relevant active agents for specific indications or disease states will be, for example, administered to an appropriate animal model mice (8-10 days after injection/day 1 of experiment) by tail vein or IP routes at doses ranging from 0.0001 mg/kg to 50 mg/kg for 1 to 21 days. Optionally, the mice will be assayed throughout the experiment with a selection marker relevant to the particular studies disease state every other day and survival monitored daily for the duration of the experiment. Expired mice will be optionally subjected to necropsy at the end of the experiment. These in vivo tests optionally generate preliminary pharmacokinetic, pharmacodynamic and toxicology data.

Adjuvant-Induced Arthritis in Rats: Adjuvant induced arthritis ("AIA") is an animal model useful in the study of rheumatoid arthritis ("RA"), which is induced by injecting *M. tuberculosis* in the base of the tail of Lewis rats. Between 10 and 15 days following injection, animals develop a severe, progressive arthritis.

Generally, analogs will be tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw.

Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

Collagen Induced Arthritis in Rats: To determine the efficacy of a representative analog of this invention administered by po, iv, sc or nasal dosing according to bid or qd schedules (Days (−1)-20) for inhibition of the inflammation, cartilage destruction and bone resorption that occurs in developing type II collagen arthritis in rats.

Animals: Female Lewis rats (Harlan), weighing 125-150 g on arrival. (inject subtotal of rats with collagen to get responders on days 10, 11, 12 for 6 groups of 10). The animals (a group for arthritis, a group for normal control), housed 4-5/cage, will be acclimated for 4-8 days. The animals will be dosed from about po1 mg/kg bid to po100 mg/kg bid.

Materials: Peptides or analogs in vehicle, Type II collagen, Freund's incomplete adjuvant, methotrexate (Sigma)

General Study Design: Dosing initiated on day minus 1. The acclimated animals will be anesthetized with isoflurane and given collagen injections (D0). On day 6 they will be anesthetized again for the second collagen injection. Collagen is prepared by making a 4 mg/mL solution in 0.01 N acetic acid. Equal volumes of collagen and Freund's incomplete adjuvant, will be emulsified by hand mixing until a bead of this material held its form when placed in water. Each animal will receive 300 uL of the mixture each time spread over 3 sites on back. Calipering of normal (pre-disease) right and left ankle joints are to be done approximately one ay prior to the expected days on onset of disease.

Rats will be weighed on days (−) 1, 6, 9, 10, 11, 12, 13, 14, 15, 16, 17, 18, 19, and 20 of the study and caliper measurements of ankles taken every day beginning on day 9. Final body weights will be taken on day 20. After final body weight measurement, animals are to be anesthetized for terminal plasma collection and then euthanization. Both hind paws and knees will be removed. Hind paws will be weighed, placed (with knees) in formalin and then processed for microscopy.

Processing of Joints: Following 1-2 days in fixative and then 4-5 days in decalcifier, the ankle joints will be cut in half longitudinally, knees will be cut in half in the frontal plane, processed, embedded, sectioned and stained with toluidine blue.

Induction of Colitis in HLA-B27 Rats: The efficacy of the analogs of the present invention in reversing colitis can be determined in HLA-B27 transgenic rats. HLA-B27 transgenic rats have been utilized as an animal model of Inflammatory Bowel Disease which mimics Crohn's Disease in humans. The rats overexpress the human MHC class I HLA-B27 heavy chain and beta-2 microglobulin proteins, which induces a variety of autoimmune diseases that include inflammation of the colon.

The therapeutic effect of the analogs described in this invention in terms of resolving colitis can be evaluated in HLA-B27 transgenic rats. Diseased rats will be dosed subcutaneously with 0.001-100 mg/kg of a single analog of this invention once or twice a day for 16 days or once per week for two weeks.

Disease Activity Index (DAI) scores will be used to determine the efficacy of each analog as compared to rats dosed with vehicle. In addition, fecal consistency and FOB scores for both rats dosed with analogs will be statistically compared to the vehicle group.

Induction of Colitis: 1-20 HLA-B27 (6-9 weeks old) transgenic rats will be acclimated in animal facility for 10 weeks. Animal bedding will be mixed from different cages once a week to control for a "dirty" environmental flora.

Treatments: Rats are to be enrolled and randomized into four groups (n=5) based on weight and DAI scores (FC.g-toreq.3, FOB.gtoreq.2). The experimental groups will be dosed subcutaneously with an analog 0.001-100 mg/kg once or twice a day for 16 days or once per week for two weeks and terminated at trough. The control groups include a vehicle-treated group and a GG5/3 (mouse anti-rat alpha-4 integrin antibody) positive control group dosed subcutaneously at 10 mg/kg (5 mL/kg) on d0, d3, and d6 and terminated at trough on d8. Fresh analog and vehicle treatments are to be formulated in advance of treatment.

Endpoint Read-outs: Disease Activity Index scores, Fecal Consistency test and Fecal Occult Blood test, are to be taken 4 times a week to generate in-life clinical scores. The primary read-out for the study is a histopathological analysis of cecum, proximal colon, mid-colon, and distal colon. An IBD scoring system was applied (Table H2). TABLE H2 IBD Scoring System Multiple Endpoints A Destruction of epithelium and glands B Dilatation of glandular crypts C Depletion and loss of goblet cells D Inflammatory cell infiltrates E Edema F Vascular congestion G Crypt Abscesses H Atrophia.

Primary Arterial Hypertension animal model: 36 adult male Sprague-Dawley rats (300-350 g in body weight are to be randomized for treatment 22 days after a s.c. injection of saline or 60 mg/kg monocrotaline (MCT)(Sigma-Aldrich) to induce pulmonary hypertension. In addition to a group of untreated rats, the experimental groups included rats that will receive daily, weekly or monthly delivery of a secretin analog at an appropriate dose of (0.001-50 mg/kg or the delivery vehicle alone. On Day 22 a carotid/femoral artery will be accessed for arterial blood gases (systemic blood pressure can be monitored as well). Thoracotomy would then be performed and right ventricle catheterized with a Millar catheter (or other appropriate catheter), which will be advanced to the pulmonary artery. Animals will have anesthesia induced and maintained on isoflurane throughout the experiment. Rats will be intubated prior to surgical procedures. Hemodynamic measurements such as Pulmonary arterial pressure, systemic blood pressure (SAP, DAP, MAP) and heart rate are to be collected continuously via a Gould-Ponemah physiograph. Statistical analysis will be performed on all hemodynamic data. Arterial blood samples will be collected at protocol specified time points (up to 8 time points) for analysis of drug concentration and/or arterial blood gases. Animals will euthanized after 30 minutes and lungs will be collected and snap frozen for subsequent analyzed of levels of drug. Animals are to be clinically observed once daily with body weight measured weekly.

Another model of PAH requires chronic exposure to a hypoxic environment (e.g. 10% $O_2$) and optionally a VEGF inhibitor to further exacerbate the condition. Mice will be housed in this environment for up to three weeks with ad lib access to food and water. In some cases, the mice will receive implantable telemetry devices (e.g. DSI-HD-S21)

capable of routinely monitoring both systemic and pulmonary arterial blood pressures along with body temperature and other relevant biometrics. The experimental protocol entails a 1-8 week preconditioning housing step where mice are housed in the hypoxic environment before drugs are administered. In some cases, the VEGF-inhibitor as well as the test articles are dosed on a regular schedule during the preconditioning step. Once begun, the study would last between 7-28 days wherein the mice will be evaluated between 2-14 times a week using the telemetry system to acquire real time in vivo data. Comparison between the untreated, analog treated and positive control (current approved or clinical stage PAH therapeutics) arms consist of the determination of relative percent change in arterial blood flow, arterial blood pressure, overall survival along with pathology and histology analysis. Pathology and histology studies will be conducted post-mortem, post perfusion and subsequent sectioning and staining (e.g. H&E) following standard biological sample preparation procedures known to those skilled in the art. Comparative analysis is to be performed based on the resulting slides, including average artery diameter and density of inflammatory markers near the blood vessels.

While some embodiments of the invention have been illustrated and described, it will be appreciated that various changes can be made therein without departing from the spirit and scope of the invention.

Parkinson's Disease (PD) Model (not prophetic): Male C57/BL6 mice, 8-12 w old, housed in the IACUC approved housing were administered an analog described herein as well as a pharmaceutically acceptable carrier for five days at a dose between (0.1 nM and 100 nM). Thereafter, SPC and Tregs from the mice are harvested and then transferred to another set of MPTP intoxicated mice using the following protocol.

Immediately following the final dose, mice were sacrificed, and single-cell suspensions were prepared from inguinal lymph nodes and spleens. CD4+ T cell populations from spleens and lymph nodes were enriched by negative selection with CD4-enrichment columns (R&D Systems, Minneapolis, Minn.), followed by CD25-PE positive selection with AutoMACS (Miltenyi Biotec, Auburn, Calif.). As determined by flow cytometric analysis, populations of Tregs and Teffs were consistently 0.95% pure using this method (12). T cells were cultured in complete RPMI 1640 (RPMI 1640 [Invitrogen, Carlsbad, Calif.] supplemented with 10% FBS, 2 mM L-glutamine, 25 mM HEPES, 1 mM sodium pyruvate, 13 nonessential amino acids, 55 nM 2-ME, 100 U/ml penicillin, and 100 mg/ml streptomycin [Mediatech, Manassas, Va.]) in the presence of anti-CD3 (145-2C11; BD Pharmingen, San Diego, Calif.), 4YSyn, or N-4YSyn. Proliferation and inhibition assays were performed, as described (3, 10). MPTP-intoxicated mice received an i.v. tail injection of $5.3 \times 10^7$ freshly isolated SPCs or $1.3 \times 10^6$ freshly enriched Tregs in 0.25 ml HBSS. Each Th subset was harvested, and $10^3$-$10^6$ T cells from each subset were transferred to separate recipient groups. For stimulation of cytokine production, Th subsets were stimulated with 20 ng/ml PMA and 1 mM ionomycin (Sigma-Aldrich) for 5 h, cells were washed, media were replaced, and supernatants were collected 24 h later for analysis. (J Immunol 2010; 184:2261-2271;). Recipient mice were then followed and sacrificed, their brains were excised and stained with appropriate markers for microglia cell identification according to the following protocol:

Mice were postmortem transcardially perfused with PBS, followed by 4% para-formaldehyde (Sigma-Aldrich). Frozen midbrain sections (30 mm) were immunostained for Mac-1 (CD11b, 1:1000; Serotec, Raleigh, N.C.). Fluorojade C (FJ-C) staining (Millipore, Billerica, Mass.) was performed on adjacent sections, according to the manufacturer's protocol, to assess de-generating neurons and was quantified using ImageJ. Overall, dopaminergic neuron survival was assessed 7 d following MPTP intoxication and resolution of cell death processes with polyclonal Abs to mouse tyrosine hydroxylase (TH; 1:1000; EMD Chemicals/Calbiochem, San Diego, Calif.) and were counterstained for Nissl substance by thionin staining. Total numbers of Mac-1+ cells, CD4+ T cells, and TH- and Nissl-stained neurons in the SN were estimated by stereo-logical analysis with Stereo Investigator software (MBF Bioscience, Williston, Vt.), using the optical fractionator module. Quantitation of striatal TH (1:500; EMD Chemicals/Calbiochem, Gibbstown, N.J.) was performed by densitometric analysis. Adjacent midbrain sections were immunostained for CD4 (clone RM4-5, 1:200, BD Pharmingen). Sections were incubated in streptavidin-HRP solution (ABC Elite vector kit, Vector Laboratories, Burlingame, Calif.) and color developed using a generation system consisting of diaminobenzidine (DAB) chromogen (Sigma-Aldrich). (J Immunol 2010; 184:2261-2271;). Comparisons between treated and untreated brain sections were conducted and evaluated for neuroprotection and neuroregeneration. Brain section images were analyzed for stain density and location to arrive at a statistical performance evaluation.

Figure 5:
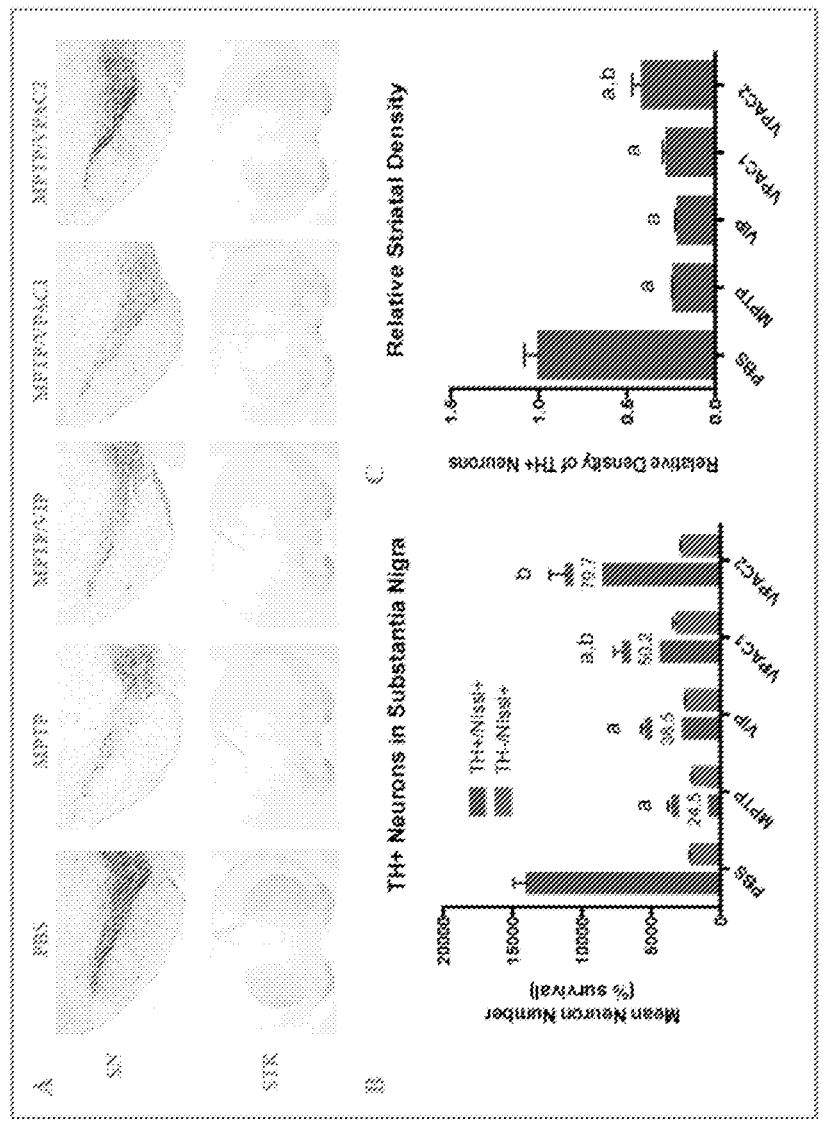
FIG. 5 depicts an adoptive transfer of splenocytes from drug-treated donors is neuroprotective in vivo. A. Photomicrographs of TH+/Nissl+ neurons in the SN and TH+ striatal termini in mice treated with PBS, MPTP, or MPTP followed by adoptive transfer of splenocytes from either VIP, VPAC1, or VPAC2-treated mice. Sections were immunostained with anti-TH and HRP-conjugated secondary Ab and visualized with DAB. SN sections were counterstained with thionin. B. Total number of surviving dopaminergic neurons (TH+/Nissl+) and nondopaminergic neurons (TH-/Nissl+) in the SN following MPTP treatment and adoptive transfer. Percentages of spared dopaminergic neurons are included for each treatment. C. Relative TH densitometry of total dopaminergic termini in the striatum. B and C. Differences in means (±SEM, n=8 mice per group) were determined where P<0.05 compared with groups treated with PBS (a) and MPTP (b). VIP, VPAC1 agonist (LBT-V101, SEQ ID NO: 22) and VPAC2 agonist (LBT-V218, SEQ ID NO: 18) arms received 15 ug/day/5 days.

FIG. 5. Adoptive transfer of splenocytes from drug-treated donors is neuroprotective in vivo. A. Photomicrographs of TH+/Nissl+ neurons in the SN and TH+ striatal termini in mice treated with PBS, MPTP, or MPTP followed by adoptive transfer of splenocytes from either VIP, VPAC1, or VPAC2-treated mice. Sections were immunostained with anti-TH and HRP-conjugated secondary Ab and visualized with DAB. SN sections were counterstained with thionin. B. Total number of surviving dopaminergic neurons (TH+/Nissl+) and nondopaminergic neurons (TH-/Nissl+) in the SN following MPTP treatment and adoptive transfer. Percentages of spared dopaminergic neurons are included for each treatment. C. Relative TH densitometry of total dopaminergic termini in the striatum. B and C. Differences in means (±SEM, n=8 mice per group) were determined where $P<0.05$ compared with groups treated with PBS (a) and MPTP (b). VIP, VPAC1 agonist (LBT-V101, SEQ ID NO: 22) and VPAC2 agonist (LBT-V218, SEQ ID NO: 18) arms received 15 ug/day/5 days Direct administration of analog performance in a PD model. 70 Male C57/BL6 mice, 8-12 w old, housed in the IACUC approved housing across 10 arms (n=7 per arm) were administered an analog described herein as well as a pharmaceutically acceptable carrier for five days at a dose between (0.1 nM and 100 nM) or are administered a control (PBS or VIP) dose. Thereafter, all mice were intoxicated by MPTP delivery mice and analyzed according to the following protocol. 1 day following the final dose, the same mice were administered MPTP (16 mg/kg) and followed for additional analysis. Two days after MPTP delivery a subset of mice (arms 1-5) were sacrificed according the procedures described above. These mice were then evaluated for Mac-1+ expression levels. Five days after that (total of 7 days post MPTP treatment), the remaining mice (arms 6-10) were also sacrificed according the procedures described above and evaluated for neurological damage. Immunological, pathological and other relative analysis were performed as described above. Comparisons between treated and untreated brain sections were conducted and evaluated for neuroprotection and neuroregeneration. Brain section images can be analyzed for stain density and location to arrive at a statistical performance evaluation.

Figure 6:
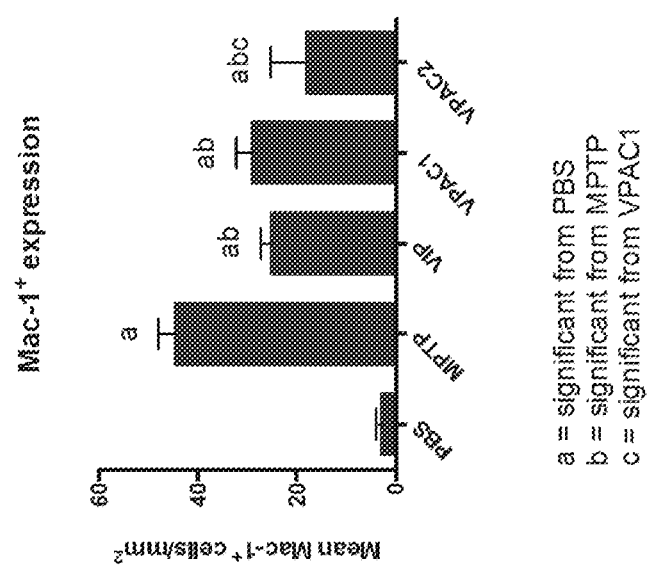
FIG. 6 depicts an average Mac-1+ expression for each of the arm of the study. Mice were administered 15 ug VIP, VPAC1 agonist (LBT-V101, SEQ ID NO: 22), VPAC2 agonist (LBT-V218, SEQ ID NO: 18) per day for 5 days prior to MPTP challenge. Mice were sacrificed and Mac-1+ levels were determined 2 days later.

FIG. 6. Average Mac-1+ expression for each of the arm of the direct administration study. Mice were administered 15 ug VIP, VPAC1 agonist (LBT-V101, SEQ ID NO: 22), VPAC2 agonist (LBT-V218, SEQ ID NO: 18) per day for 5 days prior to MPTP challenge. Mice were sacrificed and Mac-1+ levels were determined 2 days later.

Figure 7:
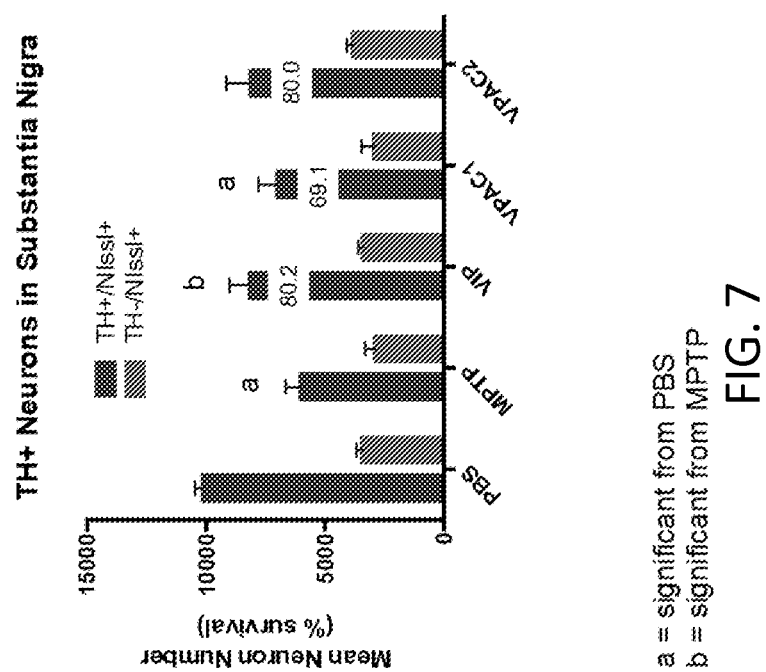
FIG. 7 depicts an adoptive transfer of splenocytes from drug-treated donors is neuroprotective in vivo. Total number of surviving dopaminergic neurons (TH+/Nissl+) and non-dopaminergic neurons (TH-/Nissl+) in the SN following direct administration and MPTP treatment. Percentages of spared dopaminergic neurons are included for each treatment. Differences in means (±SEM, n=8 mice per group) were determined where P<0.05 compared with groups treated with PBS (a) and MPTP (b). VIP, VPAC1 agonist (LBT-V101, SEQ ID NO: 22) and VPAC2 agonist (LBT-V218, SEQ ID NO: 18) arms received 15 ug/day/5 days.

FIG. 7. Adoptive transfer of splenocytes from drug-treated donors is neuroprotective in vivo. Total number of surviving dopaminergic neurons (TH+/Nissl+) and nondopaminergic neurons (TH-/Nissl+) in the SN following direct administration and MPTP treatment. Percentages of spared dopaminergic neurons are included for each treatment. Differences in means (±SEM, n=8 mice per group) were determined where P<0.05 compared with groups treated with PBS (a) and MPTP (b). VIP, VPAC1 agonist (LBT-V101, SEQ ID NO: 22) and VPAC2 agonist (LBT-V218, SEQ ID NO: 18) arms received 15 ug/day/5 days.

To assess whether VIP, LBT-V101 (SEQ ID NO: 22), LBT-V218 (SEQ ID NO: 18) and PBS treated splenocytes (SPC) suppress effector T cell proliferative responses, we evaluated SPC co-cultures from VIP-treated donors for their proliferative capacity in the presence of either anti-CD3. At a 1:1 ratio of SPC to VIP SPC, proliferation to anti-CD3 stimulation were suppressed and diminished in a dose dependent fashion with the diminution of VIP SPC number. We hypothesized that Treg function stimulated by VIP, LBT-V101 (SEQ ID NO: 22), LBT-V218 (SEQ ID NO: 18). To test this hypothesis, we evaluated CD4+CD25+CD62Llow Treg isolated from naïve and VIP-treated mice for their capacity to inhibit CD3-mediated proliferation of CD4+CD25-naïve T cells. VIP Treg showed increased functional capacity to suppress T cell proliferation compared with naïve Treg showing a consistent or greater inhibition of proliferation. VIP and LBT-V101 (SEQ ID NO: 22), LBT-V218 (SEQ ID NO: 18) Treg showed enhanced suppressive capacity compared to PBS Treg populations, with greater inhibition versus naïve Treg at a 1:1 Treg to responder ratio. These data suggested that LBT-V101 (SEQ ID NO: 22), LBT-V218 (SEQ ID NO: 18) enhances T cell regulatory function.

Figure 8:
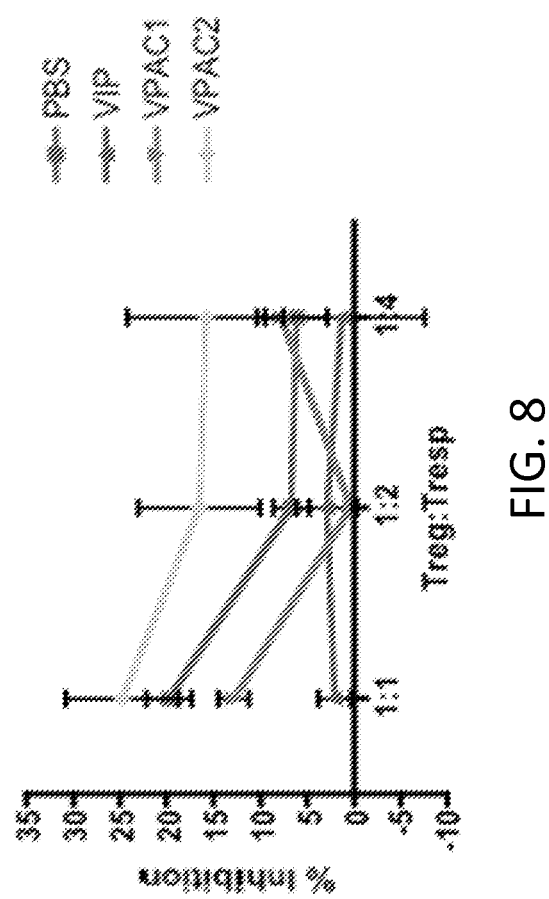
FIG. 8 depicts an inhibition assay to assess the suppressive function of Treg isolated from each donor group which includes VPAC1 agonist (LBT-V101, SEQ ID NO: 22), VPAC2 agonist (LBT-V218, SEQ ID NO: 18), VIP and PBS (no treatment) on proliferation of anti-CD3 stimulated naïve $CD4^+CD25^-$ T cells. injections given daily/5 days/i.p., VIP 15 ug, VPAC1 and VPAC2 300 ug. To assess whether VIP, VPAC1, 2 and PBS splenocytes (SPC) suppress effector T cell proliferative responses, we evaluated SPC co-cultures from VIP-treated donors for their proliferative capacity in the presence of either anti-CD3. At a 1:1 ratio of SPC to VIP SPC, proliferation to anti-CD3 stimulation were suppressed by xx % and yy %, respectively and diminished in a dose dependent fashion with the diminution of VIP SPC number. We hypothesized that Treg function stimulated by VIP, VPAC 1,2. To test this hypothesis, we evaluated $CD4^+CD25^+CD62L^{low}$ Treg isolated from naïve and VIP-treated mice for their capacity to inhibit CD3-mediated proliferation of $CD4^+CD25^-$ naïve T cells. VIP Treg showed increased functional capacity to suppress T cell proliferation compared with naïve Treg showing a consistent or greater inhibition of proliferation. VIP and VPAC 1,2 Treg showed enhanced suppressive capacity compared to PBS Treg populations, with YY % greater inhibition versus naïve Treg at a 1:1 Treg to responder ratio. These data suggested that VPAC 1, 2 enhances T cell regulatory function.

FIG. 8. Inhibition assay to assess the suppressive function of Treg isolated from each donor group which includes VPAC1 agonist (LBT-V101, SEQ ID NO: 22), VPAC2 agonist (LBT-V218, SEQ ID NO: 18), VIP and PBS (no treatment) on proliferation of anti-CD3 stimulated naïve CD4+CD25- T cells. injections given daily/5 days/i.p., VIP 15 ug, VPAC1 and VPAC2 300 ug.

In-vivo Cancer Model (prophetic): Female athymic BAL-Byc nude mice, 4-5 weeks old, will be housed in filter-top cages in a pathogen free, temperature-controlled, laminar-flow, filtered-air, isolated room and will be exposed to light from 7:00 a.m. to 7:00 p.m. Cells from the appropriate tumor type will be injected subcutaneously into the right flank of each mouse. Four experimental groups, of four mice each, three of which will receive VIP and/or an analog of VIP (1.0, 5.0, or 10 mg/day) in PBS; as a control, the fourth will receive only PBS. All solutions will be infused for 8 weeks, beginning 1 week after injection of the cells, and delivered by i.v., i.p., subc., i.m. injection or osmotic pumps placed aseptically under the skin of the back of the mice. The pump will release its contents at a rate of 0.5 ml/h for a duration of 2 weeks. The spent pumps will be removed every 2 weeks, and new pumps, containing fresh solutions, will be implanted with known techniques; this procedure will be repeated three times. After treatment, the tumors will be measured with calipers, and the mice will be weighed weekly for 8 weeks. Tumor volume will be calculated for an ellipsoid as (maximal length)×(maximal height)×(maximal width)×($\pi/6$). On the last day of the experiment, blood will be sampled from either the retroorbital plexus or tail vein into chilled heparin-containing tubes rinsed with 0.05% NaEDTA and containing three protease inhibitors, 10 mg/ml soybean trypsin inhibitor, 100 TIU/ml aprotinin, and 10 mg/ml phosphamidon), as well as 0.1 mM IBMX for measurement of plasma VIP and cAMP levels. The mice will then euthanized. The tumors will be excised, weighed, and frozen in liquid nitrogen for subsequent extraction (in methanol) and for measurement of protein content by known techniques; a portion of the tumor will be fixed in 10% neutral buffered formalin for morphologic examination.

One purpose of these studies is to evidence that the analogs are capable of producing the desired biological, biochemical, diagnostic, medicinal and/or therapeutic outcome in a living animal.

Example 5: Chemical Scheme to Synthesize Polypeptides (not Prophetic)

This example describes how the polypeptide analogs are manufactured. The sequence of human vasoactive intestinal peptide (VIP) is given below, using the standard one-letter code for proteinogenic amino acid residues. For purposes of interpretation "position 1" of the sequence below is the N-terminal histidine. Each amino acid residue is numbered in sequence from the N-terminal end of the polypeptide to the C-terminal.

HSDAVFTDNYTRLRKQMAVKKYLNSILN    (SEQ ID NO: 66)

Design.

A family of analogues will be prepared, each containing multiple $\alpha$ to $\beta^3$ replacements. Each $\beta^3$-amino acid residue will bear the side chain of the $\alpha$-amino acid indicated by the one-letter code. The analogues to be prepared are shown below; the positions indicated with lowercase letters are those at which $\alpha$-to-$\beta^3$ replacement has occurred. In addition, the n-terminal of these analogues may be optionally acetylated.

TABLE 3

VPAC1 selective analogs. EC50 values are the results of cell-based cAMP assays. Values reported are in molar concentration.

| Identifier | Sequence | Seq ID | EC50 vpac1 (Molar) | EC50 vpac2 (Molar) |
| --- | --- | --- | --- | --- |
| LBT-V101 | HSDAVFTDNYtRLRkQLAvKKYINAIIN | Seq ID NO: 22 | 2.17E-09 | 0.008262 |
| LBT-V102 | HxDAVFTDNYtRLRkQLAvKKYINAIIN | Seq ID NO: 23 | 5.658E-09 | 4.90E-06 |

TABLE 3-continued

VPAC1 selective analogs. EC50 values are the results of cell-based cAMP assays. Values reported are in molar concentration.

| Identifier | Sequence | Seq ID | EC50 vpac1 (Molar) | EC50 vpac2 (Molar) |
| --- | --- | --- | --- | --- |
| LBT-V103 | HxDAxFTDNYtRLRkQLAvKKYINAIIN | Seq ID NO: 24 | 3.575E-10 | 7.964E-08 |
| LBT-V104 | HxDAvFTDNYtRLRkQLAvKKYINAIIN | Seq ID NO: 25 | 4.426E-09 | 2.624E-07 |
| LBT-V105 | HsDAvFTDNYtRLRkQLAvKKYINAIIN | Seq ID NO: 26 | 6.44E-08 | 7.163E-07 |
| LBT-V106 | HsDAvFTDnYtRLRkQLAvKKYINAIIN | Seq ID NO: 27 | 2.98E-04 | 5.034E-07 |
| LBT-V107 | HSdAVFtDNYtRLRkQLAvKKYINAIIN | Seq ID NO: 28 | >1E-6 | >1E-6 |
| LBT-V108 | HSdAVFTDNYtRLRkQLAvKKYINAIIN | Seq ID NO: 29 | | |
| LBT-V109 | HSDaVFTDNYtRLRkQLAvKKYINAIIN | Seq ID NO: 30 | | |
| LBT-V110 | HSDAVfTDNYtRLRkQLAvKKYINAIIN | Seq ID NO: 31 | | |
| LBT-V111 | HSDAVFtDNYtRLRkQLAvKKYINAIIN | Seq ID NO: 32 | | |
| LBT-V112 | HSDAVFTdNYtRLRkQLAvKKYINAIIN | Seq ID NO: 33 | | |
| LBT-V113 | HSDAVFTDnYtRLRkQLAvKKYINAIIN | Seq ID NO: 34 | | |
| LBT-V114 | HSDAVFTDNytRLRkQLAvKKYINAIIN | Seq ID NO: 35 | | |
| LBT-V115 | HSDAVFtDNytRLRkQLAvKKYINAIIN | Seq ID NO: 36 | | |
| LBT-V116 | HSDAVFtDNYtRLRkQLAvKKYINAIIN | Seq ID NO: 37 | | |
| LBT-V117 | HSDaVFtDNYtRLRkQLAvKKYINAIIN | Seq ID NO: 38 | | |
| LBT-V118 | HSDAVFTNSYrKVLkRLSaRKLIQDII | Seq ID NO: 39 | | |
| LBT-V119 | HSDAVFTNSYRkVLKrLSArKLLqDIL | Seq ID NO: 40 | | |
| LBT-V120 | HSDAVFTNSyRKVIKRLsARKILQDiL | Seq ID NO: 41 | | |
| LBT-V121 | HxDAxFTNSYrKVLkRLSaRKLIQDII | Seq ID NO: 42 | | |
| LBT-V122 | HxDAxFTNxyRKVLKrLSAzKLxQDII | Seq ID NO: 43 | |

In each of sequences above, at least one residue has been optionally replaced by a cyclic or heterocyclic β-amino acid residue. In some embodiments, based upon the above sequences, X̲=ACPC, Z̲=APC; uncharged side chains replaced by ACPC, basic side chains replaced by APC, Protected β³-amino acids).α/β-Peptide synthesis (Fmoc on the backbone nitrogen and appropriate protecting groups on side chains, when necessary) will be obtained from commercial suppliers or prepared via reported methods. Each β³-peptide will be prepared manually by microwave-assisted Fmoc solid phase peptide synthesis resulting in a c-terminal amide, for example Rink Amide resin. Coupling steps will be carried out with a three-fold excess of the appropriate protected α- or β³-amino acid, using HATU to mediate amide bond formation. Piperidine will be used for Fmoc deprotection steps. Each peptide will be cleaved from resin by treatment with 94:2.5:2.5 TFA/H2O/triisopropylsilane, precipitated by addition of cold ethyl ether, and purified by reverse phase HPLC on a prep-C18 column using gradients between 0.1% TFA in water and 0.1% TFA in acetonitrile. The identity and purity of the final products will be determined by mass spectrometry and analytical HPLC, respectively.

One purpose of this study is to demonstrate that the analogs of the application may be designed to increase the half-life of the polypeptide as compared to the half-life of the naturally encoded protein by introducing non-natural amino acid analogs that are resistant to degradation and/or induce an equivalent or increased bioactivity as compared to the naturally encoded polypeptide sequence upon which the analog is based or derived through the possible incorporation of conformationally-constrained residues.

Example 6: In-Vitro Cell Based Activity Assay

In Vitro Binding Assay 1: VIP analogs in table 1 were prepared in appropriate phosphate buffer was at pH of 7.5 was exposed to a functional assay in parallel with wild-type VIP proteins. cAMP Hunter cell lines expressing VIPR1 and VIPR2 were expanded from freezer stocks in T25 flasks according to standard procedures and maintained in selective growth media prior to assay. Once it was established that the cells were healthy and growing normally, cells were passaged from flasks using cell dissociation reagent buffer and seeded into white walled clear bottom 384-well microplates for compound profiling. For profiling, cells were seeded at a density of 10,000 cells per well in a total volume of 20 µL and were allowed to adhere and recover overnight prior to compound addition. cAMP modulation was determined using the DiscoveRx HitHunter cAMP XS+ assay.

For profiling compound in agonist mode, the cells were incubated in the presence of compound at 37° C. for 30 minutes. Cells expressing both VIPR1 and VIPR2 were exposed to serial dilutions of wild-type VIP and separate samples of the same type of cells were exposed to serial dilutions of a VIP analogue to determine $EC_{50}$ values of the analogue as compared to wild-type VIP. After appropriate compound incubation, assay signal was generated through incubation with DiscoverX lysis cocktail according to the manufacturers standard protocol. Dose curves were plotted using GraphPad Prism or Activity Base. Percentage activity is calculated using the following formula:

% Activity=100%×(mean RLU of test sample−mean RLU of vehicle control)/(mean RLU of MAX control−mean RLU of vehicle control).

In Vitro Competitive Binding Assay (prophetic): Binding assays: Membranes prepared from a stable VPAC2 cell line (such as a CHO-S cell line stably expressing human VPAC2 receptor or from cells transiently transfected with human VPAC1 or PAC1) will be used. A filter binding assay will be performed using $^{125}$I-labeled VIP for VPAC1 and VPAC2 and $^{125}$I-labeled PACAP-27 for PAC as the tracers. For this assay, the solutions and equipment include:

Presoak solution: 0.5% Polyethyleneamine in Aqua dest
Buffer for flushing filter plates: 25 mM HEPES pH 7.4
Blocking buffer: 25 mM HEPES pH 7.4; 0.2% protease free BSA
Assay buffer: 25 mM HEPES pH 7.4; 0.5% protease free BSA
Dilution and assay plate: PS-Microplate, U form
Filtration Plate Multiscreen FB Opaque Plate; 1.0 mM Type B Glasfiber filter In order to prepare the filter plates, the presoak solution will be aspirated by vacuum filtration. The plates will be flushed twice with 200 µL flush buffer. 200 µL blocking buffer will be added to the filter plate. The filter plate will then be incubated with 200 µL presoak solution for 1 hour at room temperature. The assay plate will be filled with 25 µL assay buffer, 25 µL membranes (2.5 g) suspended in assay buffer, 25 µL agonist in assay buffer, and 25 µL tracer (about 40000 cpm) in assay buffer. The filled plate will be incubated for 1 hour with shaking. The transfer from assay plate to filter plate will be conducted. The blocking buffer will be aspirated by vacuum filtration and washed two times with flush buffer. 90 µL will be transferred from the assay plate to the filter plate. The 90 µL transferred from assay plate will be aspirated and washed three times with 200 µL flush buffer. The plastic support is removed. It is dried for 1 hour at 60° C. 30 µL Microscint will beaded. The count will be performed based upon analog affinity to VPAC1, VPAC2, or PAC1 receptors. $IC_{50}$ and $EC_{50}$ calculations will be performed based upon affinity scoring.

In-vitro Internalization Assay (not prophetic): The analogs of the present invention were serially diluted into aqueous solutions with appropriate buffer. The various concentrations of analogs were administered to a plurality of cells in culture that expresses relevant naturally occurring receptor family for the naturally occurring polypeptide upon which the analog is derived. The analogs were administered to the PathHunter® eXpress CHO-K1 VIPR1 (DiscoveRx) cells according to the manufacturers suggested protocol in a 96-well plate. PathHunter® Detection Reagents were used to detect the concentration of analog internalized via the endosomal pathway as a function of signal strength in the absence and presence of wild-type VIP provided as a control. Upon receptor internalization, a complete β-galactosidase enzyme was formed and then able to hydrolyze a DiscoveRx substrate, thus generating a chemiluminescent signal. Various $EC_{50}$ values for the VIP analogs were calculated per the manufacturer's recommended instructions using Graphpad Prism. Chemiluminescent signal were read on a Dynex Technology MLX or BIO-TEK ELx800 Universal Microplate Reader.

Figure 2:
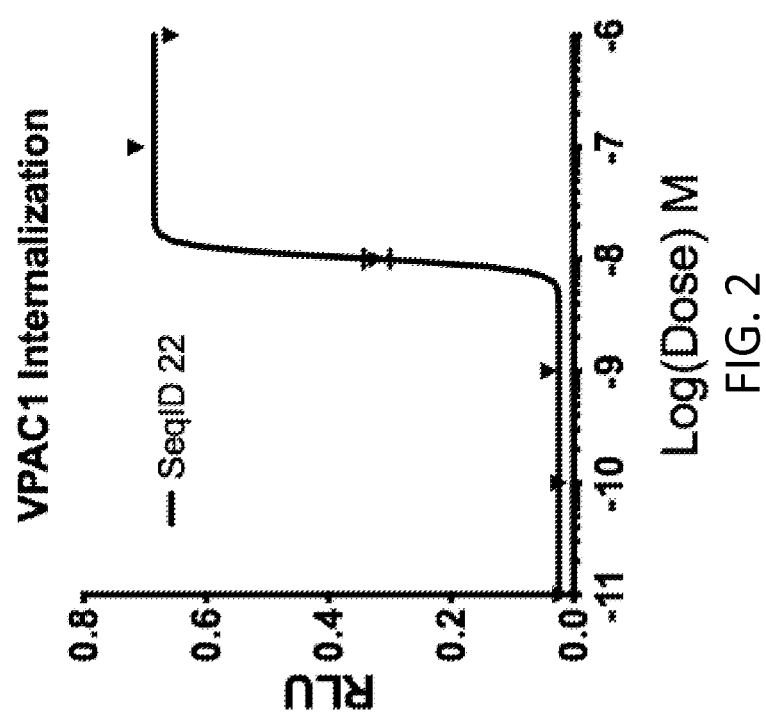
FIG. 2 depicts a representative dose response curve for ligand mediated receptor internalization, resulting in a relative chemiluminescent signal for LBT-V101 (SEQ ID NO: 22). EC50 value is 1.024e-008 Molar.

FIG. 2: Representative dose response curve for ligand mediated receptor internalization, resulting in a relative chemiluminescent signal for LBT-V208 (SEQ ID NO: 22). EC50 value is 1.024e-008 Molar.

Example 6b: Glucose Tolerance Test (not Prophetic)

The analogs described in this document were evaluated in a intraperitinal glucose tolerance test (IPGTT) to determine their ability to control glucose levels in vivo. 12 DIO mice were fasted overnight and subsequently received subcutaneous delivery (time point −60) of PBS (n=4), VPAC1 (LBT-V101 (SEQ ID NO: 22), 20 nm/kg, n=3) or VPAC2 (LBT-V218 (SEQ ID NO: 18), 10 nm/kg, n=4) agonist as described herein. Glucose levels were determined using a Aviv Accucheck one-touch glucose meter. One hour later, the mice received a bolus injection of glucose (time-point 0) 1 g/kg and were followed for the ensuing 2 hours. Glucose levels were monitored with the same glucose meter at the following time intervals: 15, 45, 60, 90 and 120 minutes after glucose delivery. The data was averaged and plotted using Graphpad Prism. The VPAC2 agonist evaluated demonstrated modest glucose control when compared to the vehicle arm.

Figure 9:
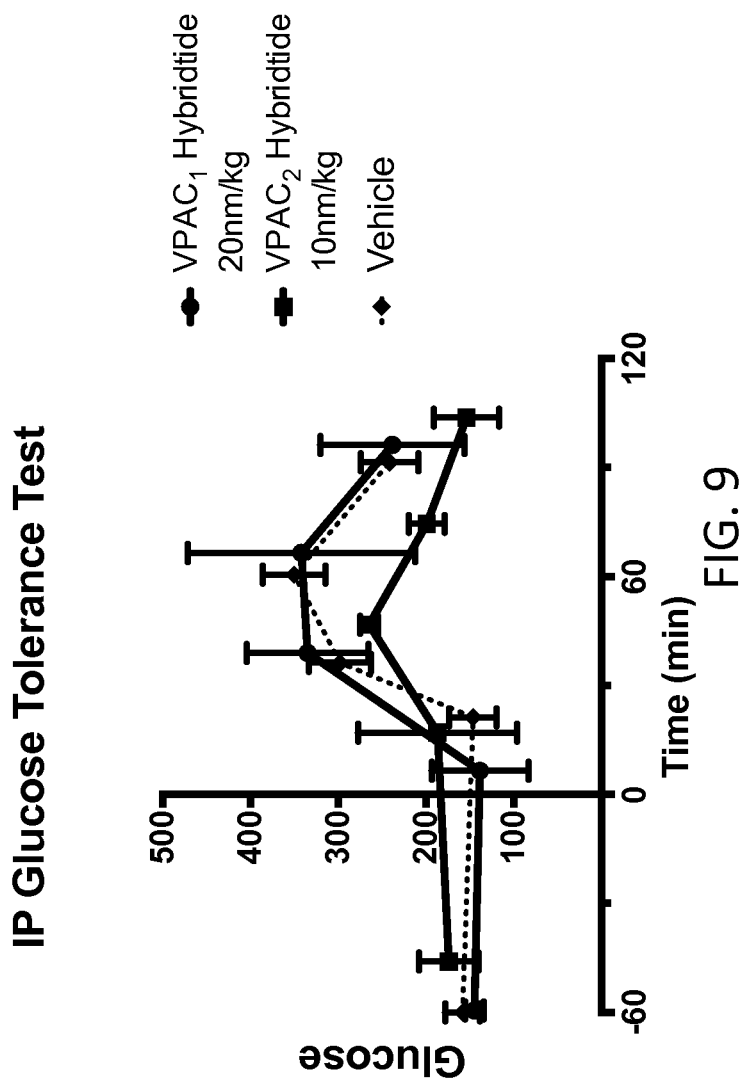
FIG. 9 depicts an IP Glucose Tolerance Test for VPAC1 agonist (LBT-V101, SEQ ID NO: 22) and VPAC2 agonist (LBT-V208, SEQ ID NO: 8). DIO mice were fasted overnight followed by subcutaneous delivery of the specific VIP agonist. 60 minutes later, a bolus injection of glucose was delivered intraperitoneally. Glucose reading were taken at the following timepoints -60, 0, 15, 45, 60, 90 and 120 minutes post glucose delivery.

FIG. 9. IP Glucose Tolerance Test for VPAC1 agonist (LBT-V101, SEQ ID NO: 22) and VPAC2 agonist (LBT-V208, SEQ ID NO: 8). DIO mice were fasted overnight followed by subcutaneous delivery of the specific VIP agonist. 60 minutes later, a bolus injection of glucose was delivered intraperitoneally. Glucose reading were taken at the following timepoints −60, 0, 15, 45, 60, 90 and 120 minutes post glucose delivery.

Example 7: Structural Analysis of Helical Polypeptides (Prophetic)

This prophetic example describes how the polypeptide analogs of this invention may be characterized after manufacture through structural conformational assays such as circular dichrosim (CD) and Nuclear magnetic resonance (NMR).

Circular Dichroism Spectroscopy. Circular dichroism measurements will be carried out on an Aviv 202SF Circular Dichroism Spectrophotometer. Samples of each peptide will be prepared with a determined UV absorbance in the range of 0.1-1.0 at 280 nm in a pH buffered solution. Spectra will be recorded in a 1 mm cell with a step size of 1 nm and an averaging time of 5 sec. All spectra will be background corrected against buffer measured in the same cell. Thermal melts will be carried out in 1-degree increments with an equilibration time of 2 min between each temperature change. Thermal unfolding data will be fit to a simple two state folding model Shortle, D. Meeker, A. K. Freire, E. *Biochemistry* 1988, 27, 4761-4768) using GraphPad Prism.

Nuclear Magnetic Resonance: Structure elucidation of the proposed analogs can also be accomplished based on analyses of heteronuclear NMR experimental data. Global backbone structural information complementing the local structure information provided by backbone chemical-shift assignments can be obtained from nuclear Overhauser effect spectroscopy (NOESY) which yield atomic distance constraints together with residual dipolar coupling (RDC) experiments which provide orientation restraint information. Together, these techniques can be used to provide valuable structural information regarding the positioning and alignment of the amino acids within the polypeptide analog. Samples of each peptide or analog will be prepared with a determined UV absorbance in the range of 0.1-1.0 at 280 nm in an appropriate pH buffered solution. Each preparation will then be used to determine chemical shifts using the suite of multidimensional experiments, ie amide based backbone assignments HNCO and TOCSY, followed by conducting structure restraint experiments, ie NOESY and RDC, using standard NMR equipment (i.e. Bruker NMR) and data analysis software (i.e. Talos+, SPARKY and Al NMR). Further structural insight can be ascertained by comparing the results of NMR experiments in the presence and absence of the intended binding partner.

One purpose of this study is to evidence that the conformation of the analog is structurally constrained and that certain non-natural amino acids have been incorporated in the synthesized peptide in their predicted location along a longitudinal axis of the polypeptide.

Example 8: In-Vitro Stability Analysis of Helical Polypeptides in Solution (not Prophetic)

This example describes how the metabolic stability of the polypeptide analogs of this invention were characterized after manufacture through assays such as a protease resistance assay.

In Vitro Stability Assay: Stock solutions of the both the naturally occurring peptides as well as peptide analogs are prepared at a concentration of 25 µM (based on UV absorbance) in appropriate buffer. A solution of proteinase K in addition to other common animal proteases (i.e. Cathepsins, Trypsins, dipeptidyl peptidase IV and chymotrypsin) will be prepared at an appropriate concentration of 50 µg/mL (based on weight to volume) in separate appropriate buffers. For each proteolysis evaluation, 40 µL of peptide stock will be mixed with 10 µL of the appropriate protease stock. The reaction is then allowed to proceed at room temperature and quenched at the desired time point by addition of 100 µL of 1% TFA in water. 125 µL of the resulting quenched reaction are then injected onto an analytical reverse phase HPLC, and the amount of starting peptide present quantified by integration of the appropriate chromatogram peak via absorbance at either 220 or 280 nm. Duplicate reactions are run for each time point. Half-lives are determined by fitting time dependent peptide concentration to an exponential decay using GraphPad Prism. Samples for some time points will be analyzed by mass spectrometery, and the products observed are used to identify amide bonds cleaved in the course of the reaction. The relative stability enhancement is determined through the comparison of the various analogs with its naturally occurring peptide counterpart. Percent degradation is be quantified by integration of peak areas related to undigested peptide peaks and corrected for degradation in the absence of enzyme.

FIG. 3: Representative in-vitro protease stability of VPAC-1 selective analog (LBT-V101, SEQ ID NO: 22) compared to the native VIP.

Ex-Vivo Stability Assay (Prophetic):

To investigate the plasma stability of the analogs, both the naturally occurring peptide as well as the analogs will be prepared at a concentration of 100 µM (based on UV absorbance) in appropriate buffer. 50 uL aliquots of animal plasma (i.e. rodent, canine, primate) are then spiked with the analog or the naturally occurring peptide. The reaction will be allowed to proceed at room temperature and quenched at the desired time point by addition of an equivalent volume of 1% TFA in Acetonitrile and diluted 1-10 fold with PBS. This solution is then passed over a C18 solid phase extraction column (eg. Sigma TPSC18) to further isolate the peptide or analog for subsequent LC/MS analysis by removal of unrelated lipids and plasma proteins. The analogs are then eluted from the C18 column by adding 1-3 column volumes of between 20 and 50% acetonitrile, collected and concentrated for subsequent analysis. Approximately 10 µL of the concentrated quenched reaction will be injected onto an analytical reverse phase HPLC, and the amount of starting peptide present quantified by integration of the appropriate chromatogram peak via absorbance at either 220 or 280 nm. Duplicate reactions will be run for each time point. Half-lives will be determined by fitting time dependent peptide concentration to an exponential decay using GraphPad Prism. Samples for some time points will be analyzed by mass spectrometery, and the products observed will be used to identify amide bonds cleaved in the course of the reaction. The relative stability enhancement will be determined through the comparison of the various analogs with its naturally occurring peptide counterpart.

Microsome Stability Analysis of Analogs Polypeptides in Solution (prophetic): Human liver microsomes were prepared by Absorption Systems. A reaction mixture, minus NADPH, was prepared as described below. About 1 milligram of the test compound originally in powdered form was suspended in DMSO prior to addition to a reaction mixture. The test compound was added into the reaction mixture (0.5 mg/mL human liver microsomes; 100 mM potassium phosphate; 5 mM Magnesium chloride) at a final concentration of 1 µM. An aliquot of the reaction mixture (without cofactor) was incubated in a shaking water bath at 37° C. for 3 minutes. The control compound, testosterone, was run simultaneously with the test compound in a separate reaction. The reaction was initiated by the addition of NADPH cofactor (1 mM NADPH), and the mixture was then incubated in a shaking water bath at 37° C. Aliquots (100 µL) were withdrawn at 0, 10, 20, 30, and 60 minutes for the test compound and 0, 10, 30, and 60 minutes for testosterone. Test compound and testosterone samples were immediately combined with 400 µL of ice-cold 50/50 acetonitrile/dH$_2$O containing 0.1% formic acid and internal standard to terminate the reaction. The samples were then mixed and centrifuged to precipitate microsomal proteins. Testosterone samples were assayed by LC-MS/MS using electrospray ionization on a PE SCIEX API 3000 according to the manufacturer's instructions. A thermo BDS Hypersil C18 column (30×2.0 mm; 3 µm) was used for chromatography at 300 µL/minute with an aqueous reservoir of 90% water and 10% buffer and an organic reservoir of 90% acetonitrile with 10% buffer (each 25 mM ammonium formate buffer at pH of 3.5). Test compound samples were analyzed by orbitrap. The peak area response ratio to internal standard (PARR) of the compounds at 10, 20, 30, and 60 minutes was compared to the PARR at time 0 to determine the percent of test compound remaining at each timepoint. After the final time point, fluorimetry is used to confirm the addition of NADPH to the reaction mixture. Half-life was normalized of control using internal acceptance criteria. Half-life was calculated based upon a $t1/2=0.693/k$, where k is the elimination rate constant based upon the slope of the plot of natural logarithm percent remaining versus incubation time. Intrinsic clearance ($CL_{int}$) was calculated based upon $CL_{int}=k/P$, where k is the elimination rate constant and P is the protein concentration in the incubation.

In Vivo Stability Assay (prophetic): To investigate the in vivo stability of the analogs, both the naturally occurring peptide as well as the analogs will be administered to mice and/or rats by IV, IP, SC, PO and/or inhalation routes at concentrations ranging from 0.001 to 50 mg/kg and blood specimens withdrawn at 0 minutes, 5 minutes, 15 minutes, 30 minutes, 1 hr, 4 hrs, 8 hrs, 12 hrs, 24 hrs and 48 hrs post-injection. Levels of intact compound in 10 µL of fresh plasma will be injected onto an analytical reverse phase HPLC after following the solid phase extraction procedure discussed previously, and the amount of starting peptide present quantified by integration of the appropriate chromatogram peak via absorbance at either 220 or 280 nm or other means of measuring the presence or absence of fully intact analog as described herein. The expected molecular weights will be determined using LC/MS analysis. This analysis technique also allows the examination of the in-vivo metabolites by determination of fragment molecular weights. The relative stability enhancement will be determined through the comparison of the various analogs with its naturally occurring peptide counterpart.

Determination of Oral Bioavailability (prophetic): The oral bioavailability will be evaluated by comparative analysis between Intraduodenal and Intrajugular administration of the analogs. Each compound/test article will be converted to an appropriate salt form and dissolved in a combination of biocompatible acids (e.g. citric acid, citrate, taurodeoxycholic acid, stearic acid, etc.) along with an optional permeation enhancer (e.g. DL-Lauroylcarnitine, sodium lauryl sulfate, Acetylated monoglycerides, sucrose, etc).

Intraduodenal and Intrajugular catheterized male C57/BL6 mice, 8 weeks old (Charles River Labs) are quarantined for at least one day and have continuous access to food and water. A single dose of the appropriate analog is then administered via catheter to each mouse. The dose (1-1000 nm/kg) and time will then be recorded.

Blood samples will be collected via tail vein at the following time points: 0 h, 0.5 h, 1 h, 3 h, 6 h and 12 h. Samples will be kept in EDTA containing (10 uL of 50 mM) microtainer tubes under subambient temperature (4° C.) before they are processed. Blood samples will be centrifuged (10,000 rpm for 5 minutes) and plasma samples should be removed and stored in a −20° C. freezer until analyzed for analog levels. Analog levels in the plasma will be analyzed using the following protocol for direct plasma precipitation.

The in vivo plasma samples will be prepared in a 1.5 mL 96-well plate, by adding, in order, 100 µL of the test plasma, 150 µl of methanol, followed by vortexing for 10-20 seconds. 150 µL of 0.05 ng/µL of an Internal Standard in acetonitrile shall be added and vortexed for 30 seconds.

The standard curve samples were prepared in a 1.5 mL 96-well plate, by adding, in order, 100 µL of control mouse plasma, followed by 150 µL of methanol and vortexing for 10-20 seconds. 150 µL of 0.05 ng/µL of an Internal Standard in acetonitrile shall be added and vortexed for 30 seconds. The samples will then be spiked with 0-200 ng (10 concentrations) of the compound of interest in 50% methanol to obtain a standard curve range of 0.5 ng/mL to 2,000 ng/mL. Again, the sample is vortexed for 30 seconds.

The samples should then be centrifuged for 20-30 minutes at 3,000 rpm in an Eppendorf microfuge before 80-90% of supernatant is transferred into a clean 96-well plate. The organic solvent will then be evaporated until the samples are dry (under $N_2$ at 40° C./30-60 min. (ZymarkTurbovap)).

The residue will then be dissolved in <100 uL mobile phase (40% $CH_3OH$/0.1% TFA). LC/MS/MS will then be run using a mass spectrometer with pump. Data analysis and quantification accomplished using Thermo LCQ ion trap mass spectrometer. A 5-50 µl sample volume will be injected onto a reverse phase column (Keystone 2.0×20 mm, 5 m, PN: 8823025-701) using a mobile phase of 40% $CH_3OH$, 0.1% TFA-100% $CH_3OH$, 0.1% TFA. The run time will be about 8 minutes at a flow rate of about 400 L/minutes. The Area Under the Curve (AUC) will be calculated using the linear trapezoidal rule from t=0 to the last plasma concentration sampling time tx (see Handbook of Basic Pharmacokinetics, Wolfgang A. Ritschel and Gregory L. Kearns, 5th ed, 1999). $AUC^0\text{-tx}=\Sigma^0\text{-n}((C_n+C_{n+1})/2))(t_n+1-t_n)$ {in (g/mL)h}

One purpose of this study is to evidence that the analog is more resistant to peptidases as compared to the resistance of similarly-structured, naturally occurring polypeptides upon which the structure of the analog is based or derived. The results may show that, when treated with the same proteolytic enzymes, the analogs of the invention will resist degradation and have longer half-lives than similarly-structured, naturally occurring polypeptides upon which the structure of the analog is based or derived.

Example 9: In-Vivo Functional Analysis of VPAC1 Selective Polypeptides (Prophetic)

This prophetic example describes the function of polypeptide analogs of this invention may be characterized after manufacture through assays that measure bioactivity of the analogs when exposed to tissue culture or when administered to an animal model of one of the following human disease states: Acute respiratory distress, chronic obstructed pulmonary disorder, asthma, chronic obstructive pulmonary disease, sarcoidosis, small lung cell cancer, exocrine pancreatic tumors, colorectal carcinoma, gastric carcinoma, hepatocellular carcinoma, esophageal carcinoma, renal cell carcinoma, prostate carcinoma, urinary bladder carcinoma, liver carcinoma, ductal pancreatic cancer, breast carcinoma, ovarian carcinoma, non-hodgkin's lymphoma, meningioma, GEP tumors (differentiated and undifferentiated), pituitary adenoma, endometrial cancer, astrocytoma, giloblastoma, non-small cell lung cancer, pancreatic cancer, melanoma, renal cancer, neuroblastoma, leukemia and prostate cancer, autoimmune disease, inflammatory disease, sepsis, Hirschsprung's Disease, sexual dysfunction, erectile dysfunction, Parkinson's disease, Alzheimer's disease, circadian rhythm dysfunction, pain, colorectal cancer, hepatocellular cancer, elevated blood glucose levels, hyperglycemia, diabetes, insulin resistance, metabolic acidosis, obesity, Type I diabetes, Type II diabetes, Multiple Sclerosis, osteoporosis, Sjogren's syndrome, pancreatitis, uveoretinitis, osteoporosis, female sexual dysfunction and diabetic nephropathy.

In Vivo Efficacy in Animal Models: To determine the activity of analogs of the invention in vivo as compared to the naturally occurring polypeptides upon which the analogs are derived, the analogs will be administered alone (IP, IV, SC, PO, by inhalation or nasal routes) or in combination with known active agent to monitor the above-mentioned disease states. Secretin family analogs alone or in combination with sub-optimal doses of relevant active agents for specific indications or disease states will be, for example, administered to an appropriate animal model mice (8-10 days after injection/day 1 of experiment) by tail vein or IP routes at doses ranging from 0.0001 mg/kg to 50 mg/kg for 1 to 21 days. Optionally, the mice will be assayed throughout the experiment with a selection marker relevant to the particular studies disease state every other day and survival monitored daily for the duration of the experiment. Expired mice will be optionally subjected to necropsy at the end of the experiment. These in vivo tests optionally generate preliminary pharmacokinetic, pharmacodynamic and toxicology data.

Adjuvant-Induced Arthritis in Rats: Adjuvant induced arthritis ("AIA") is an animal model useful in the study of rheumatoid arthritis ("RA"), which is induced by injecting M. tuberculosis in the base of the tail of Lewis rats. Between 10 and 15 days following injection, animals develop a severe, progressive arthritis.

Generally, analogs will be tested for their ability to alter hind paw swelling and bone damage resulting from adjuvant induced edema in rats. To quantitate the inhibition of hind paw swelling resulting from AIA, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, Arth. Rheum., 20, 1135-1141 (1977).

Using an animal model of RA, such as AIA, enables one to study the cellular events involved in the early stages of the disease. CD44 expression on macrophages and lymphocytes is up regulated during the early development of adjuvant arthritis, whereas LFA 1 expression is up regulated later in the development of the disease. Understanding the interactions between adhesion molecules and endothelium at the earliest stages of adjuvant arthritis could lead to significant advances in the methods used in the treatment of RA.

Collagen Induced Arthritis in Rats: To determine the efficacy of a representative analog of this invention administered by po bid dosing (Days (–1)-20) for inhibition of the inflammation, cartilage destruction and bone resorption that occurs in developing type II collagen arthritis in rats.

Animals: Female Lewis rats (Harlan), weighing 125-150 g on arrival. (inject subtotal of rats with collagen to get responders on days 10, 11, 12 for 6 groups of 10). The animals (a group for arthritis, a group for normal control), housed 4-5/cage, will be acclimated for 4-8 days. The animals will be dosed from about po1 mg/kg bid to po100 mg/kg bid.

Materials: Peptides or analogs in vehicle, Type II collagen, Freund's incomplete adjuvant, methotrexate (Sigma)

General Study Design: Dosing initiated on day minus 1. The acclimated animals will be anesthetized with isoflurane and given collagen injections (D0). On day 6 they will be anesthetized again for the second collagen injection. Collagen is prepared by making a 4 mg/mL solution in 0.01 N acetic acid. Equal volumes of collagen and Freund's incomplete adjuvant, will be emulsified by hand mixing until a bead of this material held its form when placed in water. Each animal will receive 300 uL of the mixture each time spread over 3 sites on back. Calipering of normal (pre-disease) right and left ankle joints are to be done approximately one ay prior to the expected days on onset of disease.

Rats will be weighed on days (–) 1, 6, 9, 10, 11, 12, 13, 14, 15, 16, 17, 18, 19, and 20 of the study and caliper measurements of ankles taken every day beginning on day 9. Final body weights will be taken on day 20. After final body weight measurement, animals are to be anesthetized for terminal plasma collection and then euthanization. Both hind paws and knees will be removed. Hind paws will be weighed, placed (with knees) in formalin and then processed for microscopy.

Processing of Joints: Following 1-2 days in fixative and then 4-5 days in decalcifier, the ankle joints will be cut in half longitudinally, knees will be cut in half in the frontal plane, processed, embedded, sectioned and stained with toluidine blue.

Induction of Colitis in HLA-B27 Rats: The efficacy of the analogs of the present invention in reversing colitis can be determined in HLA-B27 transgenic rats. HLA-B27 transgenic rats have been utilized as an animal model of Inflammatory Bowel Disease which mimics Crohn's Disease in humans. The rats overexpress the human MHC class I HLA-B27 heavy chain and beta-2 microglobulin proteins, which induces a variety of autoimmune diseases that include inflammation of the colon.

The therapeutic effect of the analogs described in this invention in terms of resolving colitis can be evaluated in HLA-B27 transgenic rats. Diseased rats will be dosed subcutaneously with 0.001-100 mg/kg of a single analog of this invention once or twice a day for 16 days or once per week for two weeks.

Disease Activity Index (DAI) scores will be used to determine the efficacy of each analog as compared to rats dosed with vehicle. In addition, fecal consistency and FOB scores for both rats dosed with analogs will be statistically compared to the vehicle group.

Induction of Colitis: 1-20 HLA-B27 (6-9 weeks old) transgenic rats will be acclimated in animal facility for 10 weeks. Animal bedding will be mixed from different cages once a week to control for a "dirty" environmental flora.

Treatments: Rats are to be enrolled and randomized into four groups (n=5) based on weight and DAI scores (FC.gtoreq.3, FOB.gtoreq.2). The experimental groups will be dosed subcutaneously with an analog 0.001-100 mg/kg once or twice a day for 16 days or once per week for two weeks and terminated at trough. The control groups include a vehicle-treated group and a GG5/3 (mouse anti-rat alpha-4 integrin antibody) positive control group dosed subcutaneously at 10 mg/kg (5 mL/kg) on d0, d3, and d6 and terminated at trough on d8. Fresh analog and vehicle treatments are to be formulated in advance of treatment.

Endpoint Read-outs: Disease Activity Index scores, Fecal Consistency test and Fecal Occult Blood test, are to be taken 4 times a week to generate in-life clinical scores. The primary read-out for the study is a histopathological analysis of cecum, proximal colon, mid-colon, and distal colon. An IBD scoring system was applied (Table H2).

Table H2: IBD Scoring System Multiple Endpoints
A Destruction of epithelium and glands
B Dilatation of glandular crypts
C Depletion and loss of goblet cells
D Inflammatory cell infiltrates
E Edema
F Vascular congestion
G Crypt Abscesses
H Atrophia Parkinson's Disease Model: Male C57/BL6 mice, 8-12 w old, housed in the IACUC approved housing are administered an analog described herein as well as a pharmaceutically acceptable carrier for five days at a dose between (0.1 nM and 100 nM). After five days, SPC and Tregs from the mice are harvested and then transferred to another set of MPTP intoxicated mice using the following protocol.

Five days following boost, mice were sacrificed, and single-cell suspensions were prepared from inguinal lymph nodes and spleens. CD4+ T cell populations from spleens and lymph nodes were enriched by negative selection with CD4-enrichment columns (R&D Systems, Minneapolis, Minn.), followed by CD25-PE positive selection with AutoMACS (Miltenyi Biotec, Auburn, Calif.). As determined by flow cytometric analysis, populations of Tregs and Teffs were consistently 0.95% pure using this method (12). T cells were cultured in complete RPMI 1640 (RPMI 1640 [Invitrogen, Carlsbad, Calif.] supplemented with 10% FBS, 2 mM L-glutamine, 25 mM HEPES, 1 mM sodium pyruvate, 13 nonessential amino acids, 55 nM 2-ME, 100 U/ml penicillin, and 100 mg/ml streptomycin [Mediatech, Manassas, Va.]) in the presence of anti-CD3 (145-2C11; BD Pharmingen, San Diego, Calif.), 4YSyn, or N-4YSyn. Proliferation and inhibition assays were performed, as described (3, 10). MPTP-intoxicated mice received an i.v. tail injection of 5 3 107 freshly isolated SPCs or 1 3 106 freshly enriched Tregs in 0.25 ml HBSS. Each Th subset was harvested, and 10 3 106 T cells from each subset were transferred to separate recipient groups. For stimulation of cytokine production, Th subsets were stimulated with 20 ng/ml PMA and 1 mM ionomycin (Sigma-Aldrich) for 5 h, cells were washed, media were replaced, and supernatants were collected 24 h later for analysis. (J Immunol 2010; 184:2261-2271;). Recipient mice are then followed and sacrificed, their brains are excised and stained with appropriate markers for microglia cell identification according to the following protocol:

Mice were postmortem transcardially perfused with PBS, followed by 4% para-formaldehyde (Sigma-Aldrich). Frozen midbrain sections (30 mm) were immunostained for Mac-1 (CD1 b, 1:1000; Serotec, Raleigh, N.C.). Fluorojade C (FJ-C) staining (Millipore, Billerica, Mass.) was performed on adjacent sections, according to the manufacturer's protocol, to assess de-generating neurons and was quantified using ImageJ. Overall, dopaminergic neuron survival was assessed 7 d following MPTP intoxication and resolution of cell death processes with polyclonal Abs to mouse tyrosine hydroxylase (TH; 1:1000; EMD Chemicals/ Calbiochem, San Diego, Calif.) and were counterstained for Nissl substance by thionin staining. Total numbers of Mac-1+ cells, CD4+ T cells, and TH- and Nissl-stained neurons in the SN were estimated by stereo-logical analysis with Stereo Investigator software (MBF Bioscience, Williston, Vt.), using the optical fractionator module. Quantitation of striatal TH (1:500; EMD Chemicals/Calbiochem, Gibbstown, N.J.) was performed by densitometric analysis. Adjacent midbrain sections were immunostained for CD4 (clone RM4-5, 1:200, BD Pharmingen). Sections were incubated in streptavidin-HRP solution (ABC Elite vector kit, Vector Laboratories, Burlingame, Calif.) and color developed using a generation system consisting of diaminobenzidine (DAB) chromogen (Sigma-Aldrich). (J Immunol 2010; 184:2261-2271;). Comparisons between treated and untreated brain sections are conducted and evaluated for neuroprotection and neuroregeneration. Brain section images can be analyzed for stain density and location to arrive at a statistical performance evaluation.

In-vivo Cancer Model: Female athymic BALByc nude mice, 4-5 weeks old, will be housed in filter-top cages in a pathogenfree, temperature-controlled, laminar-flow, filtered-air, isolated room and will be exposed to light from 7:00 a.m. to 7:00 p.m. Cells from the appropriate tumor type will be injected subcutaneously into the right flank of each mouse. There were four experimental groups, of four mice each, three of which will receive VIP and/or an analog of VIP (1.0, 5.0, or 10 mg/day) in PBS; as a control, the fourth will receive only PBS. All solutions will be infused for 8 weeks, beginning 1 week after injection of the cells, and delivered by i.v., i.p., subc., i.m. injection or osmotic pumps placed aseptically under the skin of the back of the mice. The pump will release its contents at a rate of 0.5 ml/h for a duration of 2 weeks. The spent pumps will be removed every 2 weeks, and new pumps, containing fresh solutions, will be implanted with known techniques; this procedure will be repeated three times. After treatment, the tumors will be measured with calipers, and the mice will be weighed weekly for 8 weeks. Tumor volume will be calculated for an ellipsoid as (maximal length)×(maximal height)×(maximal width)×($\pi/6$). On the last day of the experiment, blood will be sampled from the retroorbital plexus into chilled heparin-containing tubes rinsed with 0.05% NaEDTA and containing three protease inhibitors, 10 mg/ml soybean trypsin inhibitor, 100 TIU/ml aprotinin, and 10 mg/ml phosphamidon), as well as 0.1 mM IBMX for measurement of plasma VIP and cAMP levels. The mice will then euthanized. The tumors will be excised, weighed, and frozen in liquid nitrogen for subsequent extraction (in methanol) and for measurement of protein content by known techniques; a portion of the tumor will be fixed in 10% neutral buffered formalin for morphologic examination.

One purpose of these studies is to evidence that the analogs are capable of producing the desired biological, biochemical, diagnostic, medicinal and/or therapeutic outcome in a living animal.

Example 10 (Prophetic): In Vivo Functional Determination in Diabetic Nephropathy Models In order to determine if the analogs presented herein are capable of beneficial effects in animal models designed to mimic human diabetic nephropathy. An example of one of the appropriate protocols is described below and would be familiar to those skilled in the art. BTBR ob/ob mice treatment and analysis. BTBR ob/ob mice along with heterozygous BTBR ob/+ control mice will be purchased from Jackson Laboratories. Mice will be injected subcutaneously with 1 pM/kg to 1 mM/kg of VIP analog or saline as reported previously, daily, three times per week, once per week or less frequently for up to 5 months. Urine will be collected, and body weight and glycemia (OneTouch) will be determined weekly. Approximately six mice per group will be analyzed. All animal procedures will be approved by the Institutional Animal Care and Use Committee (IACUC). After isotonic saline perfusion, the right kidney will be removed for cholesterol content determination and mRNA extraction. One left kidney pole will be embedded in OCT, while a second pole will be fixed in 4% PFA and paraffin-embedded for histological analysis. Blood samples will be analyzed for CBC, lipid panel, AST, ALT, Alkaline Phosphatase, GGT, and BUN in a Laboratory Core Facility, such as the one located at University of Miami. Serum creatinine can be determined by tandem mass spectrometry at an appropriate facility, using the methods previously described. The urine albumin content can be measured by ELISA (Bethyl Laboratories). Urinary creatinine will be assessed by an assay based on the Jaffe method (Stanbio). Values will be expressed as ig albumin/mg creatinine. Fasting plasma insulin can be determined by ELISA (Mercodia, SW). Intraperitoneal glucose tolerance tests (IPGTT) will be performed up to 4 months after treatment onset; after an approximate 5-hr fasting, blood glucose will be recorded at baseline and then up to 180 minutes after a glucose bolus (1.5 g/kg). For insulin sensitivity, glycemia will be monitored at baseline and up to 150 minutes after intraperitoneal injection of 4 mU/g of short acting insulin. All studies will be conducted in a head-to-head manner to determine functional performance and the analogs described herein would be compared to standard ACE (angiotensin converting enzyme) inhibitors and ARBs (angiotensin receptor blockers) such as (Lotensin, Capoten, Vasotec, Monopril, Atacand, Teveten, Cozaar, Diovan, etc).

Histology, assessment of mesangial expansion and glomerular surface area. Periodic acid-Shiffs (PAS) staining of approximately 4 μm thick tissue sections will be performed. Approximately twenty glomeruli per section will be analyzed for mesangial expansion by serniquantitative analysis (scale 0-4) and would be performed by two blinded independent investigators. The glomerular surface will be delineated in each encountered glomerulus and the mean surface area will be calculated.

The following journal articles, which are herein incorporated by reference, disclose VIP family analogs contemplated to be a polypeptide backbone for the VIP family analogs of the invention. The journal articles also disclose a series of methods of administering VIP family analogs as part of pharmaceutical compositions:

1. Gozes, et. al., Current Pharmaceutical Design, 2003, Vol. 9, No. 6
2. Delgado, et. al., Brain Behav Immun. 2008 November; 22(8): 1146-1151. doi:10.1016/j.bbi.2008.06.001.
3. L. Dickson, K. Finlayson/Pharmacology & Therapeutics 121 (2009) 294-316.
4. Gonzales-Rey, et. al., TRENDS in Pharmacological Sciences Vol. 28 No. 9.
5. Varela, et. al., Expert Opin. Biol. Ther. (2007) 7(4): 461-478
6. Brenneman, Peptides 28 (2007) 1720-1726;
7. Onoue, et. al., Naunyn-Schmiedeberg's Arch Pharmacol (2008) 377:579-590

Any journal article, patent application, issued patent or other publication referenced in this application is herein incorporated by reference. The embodiments listed herein are not meant to be restrictive, but rather illustrative of the invention.

What is claimed is:

1. A peptide comprising SEQ ID NO:18.

2. The peptide of claim 1 wherein the peptide further comprises a primary amide at the C-terminus.

3. The peptide of claim 1, wherein the peptide further comprises an acetyl group at the N-terminus and a primary amide at the C-terminus.

4. A pharmaceutical composition, comprising: (i) the peptide of claim 1, or a pharmaceutical salt derived therefrom; and (ii) a pharmaceutically acceptable carrier.

5. The pharmaceutical composition of claim 4, wherein the composition further comprises one other active agent.

6. A method of treating Parkinson's Disease in a subject suffering from Parkinson's Disease comprising administrating the pharmaceutical composition of claim 4.

7. A method of inhibiting secretion of TNF-α in a subject comprising administering the pharmaceutical composition of claim 4 to a subject.

8. A kit comprising a first container comprising the pharmaceutical composition of claim 4.

9. The kit of claim 8, further comprising a second container comprising a vehicle for administration of the composition of claim 4.

* * * * *

SEQUENCE LISTING

```
<160> NUMBER OF SEQ ID NOS: 144

<210> SEQ ID NO 1
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
```

```
<220> FEATURE:
<221> NAME/KEY: MISC_FEATURE
<222> LOCATION: (26)..(26)
<223> OTHER INFORMATION: Xaa = Beta-3 homo- Leucine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 1

His Ser Asp Ala Val Phe Thr Glu Asn Tyr Thr Lys Leu Arg Lys Gln
1               5                   10                  15

Leu Ala Xaa Lys Lys Tyr Xaa Asn Asp Xaa Lys Lys Gly Xaa Thr
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 2

His Ser Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
```

-continued

<223> OTHER INFORMATION: Xaa = Beta-3 homo- Lysine

<400> SEQUENCE: 3

His Ser Asp Ala Val Phe Thr Glu Asn Tyr Thr Lys Leu Arg Lys Gln
1               5                   10                  15

Xaa Ala Ala Xaa Lys Tyr Leu Xaa Asp Leu Xaa Lys Gly Gly Thr
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 4

His Xaa Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE

```
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 5

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 6

His Xaa Asp Ala Xaa Phe Thr Glu Xaa Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
```

```
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 7

His Xaa Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 8

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 9

His Xaa Asp Ala Xaa Phe Thr Glu Xaa Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 10

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
```

<210> SEQ ID NO 11
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 11

His Xaa Asp Ala Xaa Phe Thr Glu Asn Tyr Thr Lys Leu Arg Lys Gln
1               5                   10                  15

Xaa Ala Ala Xaa Lys Tyr Xaa Asn Asp Leu Xaa Lys Gly Xaa Thr
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE

```
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 12

His Xaa Asp Ala Xaa Phe Thr Glu Asn Tyr Thr Lys Leu Arg Lys Xaa
1               5                   10                  15

Leu Ala Ala Xaa Lys Tyr Xaa Asn Asp Leu Xaa Lys Gly Xaa Thr
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 13

His Xaa Asp Ala Xaa Phe Thr Glu Asn Tyr Thr Lys Leu Arg Xaa Gln
1               5                   10                  15

Leu Ala Ala Xaa Lys Tyr Xaa Asn Asp Leu Xaa Lys Gly Xaa Thr
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (14)..(14)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 14

His Xaa Asp Ala Xaa Phe Thr Glu Asn Tyr Thr Lys Leu Xaa Lys Gln
1               5                   10                  15

Leu Ala Ala Xaa Lys Tyr Xaa Asn Asp Leu Xaa Lys Gly Xaa Thr
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (13)..(13)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 15

His Xaa Asp Ala Xaa Phe Thr Glu Asn Tyr Thr Lys Xaa Arg Lys Gln
```

```
                1               5                      10                      15
             Leu Ala Ala Xaa Lys Tyr Xaa Asn Asp Leu Xaa Lys Gly Xaa Thr
                            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 16

His Xaa Asp Ala Xaa Phe Thr Glu Xaa Xaa Thr Lys Leu Arg Lys Gln
1               5                      10                  15

Leu Ala Ala Xaa Lys Tyr Xaa Asn Asp Leu Xaa Lys Gly Xaa Thr
                20                  25                  30

<210> SEQ ID NO 17
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
```

```
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 17

His Xaa Asp Ala Xaa Phe Thr Glu Xaa Xaa Thr Lys Leu Arg Lys Gln
1               5                   10                  15

Xaa Ala Ala Xaa Lys Tyr Xaa Asn Asp Leu Xaa Lys Gly Xaa Thr
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
```

```
<222> LOCATION: (30)..(30)
<223> OTHER INFORMATION: Xaa = Beta-3 homo- Glycine

<400> SEQUENCE: 18

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Gly Xaa Thr
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 19

His Xaa Asp Ala Xaa Phe Thr Glu Xaa Xaa Thr Lys Leu Arg Xaa Gln
1               5                   10                  15

Leu Ala Ala Xaa Lys Tyr Xaa Asn Asp Leu Xaa Lys Gly Xaa Thr
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (28)..(28)
<223> OTHER INFORMATION: Xaa = Beta-3 homo- Lysine

<400> SEQUENCE: 20

His Ser Asp Ala Val Phe Thr Glu Asn Tyr Thr Lys Leu Arg Lys Gln
1               5                   10                  15

Xaa Ala Ala Lys Xaa Tyr Leu Xaa Asp Leu Lys Xaa Gly Gly Thr
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 21

His Ser Asp Ala Val Phe Thr Asp Asn Tyr Thr Arg Leu Arg Lys Gln
1               5                   10                  15

Xaa Ala Ala Lys Xaa Tyr Leu Xaa Ser Ile Lys Xaa Lys Arg Tyr
            20                  25                  30

<210> SEQ ID NO 22
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
```

```
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 22

His Ser Asp Ala Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 23

His Xaa Asp Ala Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 24
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
```

```
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 24

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 25

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Serine
<220> FEATURE:
<221> NAME/KEY: MISC_FEATURE
```

```
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 26

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 27
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Serine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 27

His Xaa Asp Ala Xaa Phe Thr Asp Xaa Tyr Xaa Arg Leu Arg Xaa Gln
1               5                   10                  15

Leu Ala Xaa Lys Lys Tyr Xaa Asn Ala Ile Xaa Asn
            20                  25
```

```
<210> SEQ ID NO 28
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (3)..(3)
<223> OTHER INFORMATION: Xaa = Beta-3 homo- Aspartic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 28

His Ser Xaa Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (3)..(3)
<223> OTHER INFORMATION: Xaa = Beta-3 homo- Aspartic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 29

His Ser Xaa Ala Val Phe Thr Asp Asn Tyr Xaa Arg Leu Arg Xaa Gln
```

```
1               5                   10                  15
Leu Ala Xaa Lys Lys Tyr Xaa Asn Ala Ile Xaa Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (4)..(4)
<223> OTHER INFORMATION: Xaa = Beta-3 homo- Alanine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 30

His Ser Asp Xaa Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (6)..(6)
<223> OTHER INFORMATION: Xaa = Beta-3 homo- Phenylalanine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 31
```

His Ser Asp Ala Val Xaa Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 32

His Ser Asp Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 33
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (8)..(8)
<223> OTHER INFORMATION: Xaa = Beta-3 homo- Aspartic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 33

```
His Ser Asp Ala Val Phe Thr Xaa Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 34

His Ser Asp Ala Val Phe Thr Asp Xaa Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 35
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine
```

```
<400> SEQUENCE: 35

His Ser Asp Ala Val Phe Thr Asp Asn Xaa Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (6)..(6)
<223> OTHER INFORMATION: Xaa = Beta-3 homo- Phenylalanine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 36

His Ser Asp Ala Val Xaa Thr Asp Asn Xaa Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 37
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
```

```
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 37

His Ser Asp Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 38
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (4)..(4)
<223> OTHER INFORMATION: Xaa = Beta-3 homo- Alanine
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 38

His Ser Asp Xaa Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 39
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Arginine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
```

```
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 39

His Ser Asp Ala Val Phe Thr Asn Ser Tyr Xaa Lys Val Leu Xaa Arg
1               5                   10                  15

Leu Ser Xaa Arg Lys Leu Xaa Gln Asp Ile Xaa
            20                  25

<210> SEQ ID NO 40
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (12)..(12)
<223> OTHER INFORMATION: Xaa = Beta-3 homo- Lysine
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (24)..(24)
<223> OTHER INFORMATION: Xaa = Beta-3 homo- Glutamine

<400> SEQUENCE: 40

His Ser Asp Ala Val Phe Thr Asn Ser Tyr Arg Xaa Val Leu Lys Xaa
1               5                   10                  15

Leu Ser Ala Xaa Lys Leu Leu Xaa Asp Ile Leu
            20                  25

<210> SEQ ID NO 41
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (18)..(18)
<223> OTHER INFORMATION: Xaa = Beta-3 homo- Serine
<220> FEATURE:
<221> NAME/KEY: MISC_FEATURE
<222> LOCATION: (22)..(22)
<223> OTHER INFORMATION: Xaa = Beta-3 homo- Leucine
<220> FEATURE:
<221> NAME/KEY: MISC_FEATURE
<222> LOCATION: (26)..(26)
<223> OTHER INFORMATION: Xaa = Beta-3 homo- Iso-leucine

<400> SEQUENCE: 41

His Ser Asp Ala Val Phe Thr Asn Ser Xaa Arg Lys Val Xaa Lys Arg
1               5                   10                  15
```

Leu Xaa Ala Arg Lys Xaa Leu Gln Asp Xaa Leu
            20                  25

<210> SEQ ID NO 42
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Arginine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 42

His Xaa Asp Ala Xaa Phe Thr Asn Ser Tyr Xaa Lys Val Leu Xaa Arg
1               5                   10                  15

Leu Ser Xaa Arg Lys Leu Xaa Gln Asp Ile Xaa
            20                  25

<210> SEQ ID NO 43
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:

<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 43

His Xaa Asp Ala Xaa Phe Thr Asn Xaa Xaa Arg Lys Val Leu Lys Xaa
1               5                   10                  15

Leu Ser Ala Xaa Lys Leu Xaa Gln Asp Ile Xaa
            20                  25

<210> SEQ ID NO 44
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 44

His Ser Asp Ala Val Phe Thr Asn Ser Tyr Arg Lys Val Leu Lys Xaa
1               5                   10                  15

Leu Ser Ala Xaa Lys Leu Xaa Gln Asp Ile Xaa
            20                  25

<210> SEQ ID NO 45
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (26)..(26)
<223> OTHER INFORMATION: Xaa = Beta-3 homo- Iso-leucine

<400> SEQUENCE: 45

His Ser Asp Ala Val Phe Thr Asn Ser Tyr Arg Lys Val Leu Lys Xaa
1               5                   10                  15

Leu Ser Xaa Arg Lys Leu Xaa Gln Asp Xaa Leu
            20                  25

<210> SEQ ID NO 46
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (24)..(24)
<223> OTHER INFORMATION: Xaa = Beta-3 homo- Glutamine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 46

His Ser Asp Ala Val Phe Thr Asn Ser Tyr Arg Lys Val Leu Lys Arg
1               5                   10                  15

Xaa Ser Ala Xaa Lys Leu Leu Xaa Asp Ile Xaa
            20                  25

<210> SEQ ID NO 47
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 47

His Xaa Asp Ala Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 48
<211> LENGTH: 28
<212> TYPE: PRT
<213> ORGANISM: Artificial Sequence
<220> FEATURE:

```
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 48

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 49
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 49

His Xaa Asp Ala Xaa Phe Thr Asp Asn Tyr Xaa Arg Leu Arg Xaa Gln
1               5                   10                  15
```

```
Leu Ala Xaa Lys Lys Tyr Xaa Asn Ala Ile Xaa Asn
            20                  25
```

<210> SEQ ID NO 50
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 50

```
His Xaa Asp Ala Xaa Phe Thr Asp Xaa Tyr Xaa Arg Leu Arg Xaa Gln
1               5                   10                  15

Leu Ala Xaa Lys Lys Tyr Xaa Asn Ala Ile Xaa Asn
            20                  25
```

<210> SEQ ID NO 51
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (3)..(3)
<223> OTHER INFORMATION: Xaa = Beta-3 homo- Aspartic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:

<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 51

His Xaa Xaa Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 52
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (11)..(11)
<223> OTHER INFORMATION: Xaa = Beta-3 homo- Arginine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 52

His Xaa Asp Ala Val Phe Thr Asn Ser Tyr Xaa Lys Val Leu Xaa Arg
1               5                   10                  15

Leu Ser Xaa Arg Lys Leu Xaa Gln Asp Ile Xaa
            20                  25

<210> SEQ ID NO 53
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (12)..(12)
<223> OTHER INFORMATION: Xaa = Beta-3 homo- Lysine
<220> FEATURE:
<221> NAME/KEY: MISC_FEATURE
<222> LOCATION: (16)..(16)
<223> OTHER INFORMATION: Xaa = Beta-3 homo- Arginine

```
<220> FEATURE:
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (24)..(24)
<223> OTHER INFORMATION: Xaa = Beta-3 homo- Glutamine

<400> SEQUENCE: 53

His Xaa Asp Ala Val Phe Thr Asn Ser Tyr Arg Xaa Val Leu Lys Xaa
1               5                   10                  15

Leu Ser Ala Xaa Lys Leu Leu Xaa Asp Ile Leu
            20                  25

<210> SEQ ID NO 54
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = Beta-3 homo- Leucine
<220> FEATURE:
<221> NAME/KEY: MISC_FEATURE
<222> LOCATION: (18)..(18)
<223> OTHER INFORMATION: Xaa = Beta-3 homo- Serine
<220> FEATURE:
<221> NAME/KEY: MISC_FEATURE
<222> LOCATION: (22)..(22)
<223> OTHER INFORMATION: Xaa = Beta-3 homo- Leucine
<220> FEATURE:
<221> NAME/KEY: MISC_FEATURE
<222> LOCATION: (26)..(26)
<223> OTHER INFORMATION: Xaa = Beta-3 homo- Iso-leucine

<400> SEQUENCE: 54

His Xaa Asp Ala Val Phe Thr Asn Ser Xaa Arg Lys Val Xaa Lys Arg
1               5                   10                  15

Leu Xaa Ala Arg Lys Xaa Leu Gln Asp Xaa Leu
            20                  25

<210> SEQ ID NO 55
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Arginine
<220> FEATURE:
<221> NAME/KEY: MISC_FEATURE
<222> LOCATION: (15)..(15)
```

-continued

```
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 55

His Xaa Asp Ala Xaa Phe Thr Asn Ser Tyr Xaa Lys Val Leu Xaa Arg
1               5                   10                  15

Leu Ser Xaa Arg Lys Leu Xaa Gln Asp Ile Xaa
            20                  25

<210> SEQ ID NO 56
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 56

His Xaa Asp Ala Xaa Phe Thr Asn Xaa Xaa Arg Lys Val Leu Lys Xaa
1               5                   10                  15

Leu Ser Ala Xaa Lys Leu Xaa Gln Asp Ile Xaa
            20                  25

<210> SEQ ID NO 57
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
```

<222> LOCATION: (2)..(2)
<223> OTHER INFORMATION: Xaa = d-Phenylalanine
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 57

His Xaa Asp Ala Val Phe Thr Asn Ser Tyr Arg Lys Val Leu Lys Xaa
1               5                   10                  15
Leu Ser Ala Xaa Lys Leu Xaa Gln Asp Ile Xaa
            20                  25

<210> SEQ ID NO 58
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (16)..(16)
<223> OTHER INFORMATION: Xaa = Beta-3 homo- Arginine
<220> FEATURE:
<221> NAME/KEY: MISC_FEATURE
<222> LOCATION: (19)..(19)
<223> OTHER INFORMATION: Xaa = Beta-3 homo- Alanine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (26)..(26)
<223> OTHER INFORMATION: Xaa = Beta-3 homo- Iso-leucine

<400> SEQUENCE: 58

His Xaa Asp Ala Val Phe Thr Asn Ser Tyr Arg Lys Val Leu Lys Xaa
1               5                   10                  15
Leu Ser Xaa Arg Lys Leu Xaa Gln Asp Xaa Leu
            20                  25

<210> SEQ ID NO 59
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:

```
<221> NAME/KEY: MISC_FEATURE
<222> LOCATION: (20)..(20)
<223> OTHER INFORMATION: Xaa = Beta-3 homo- Arginine
<220> FEATURE:
<221> NAME/KEY: MISC_FEATURE
<222> LOCATION: (24)..(24)
<223> OTHER INFORMATION: Xaa = Beta-3 homo- Glutamine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 59

His Xaa Asp Ala Val Phe Thr Asn Ser Tyr Arg Lys Val Leu Lys Arg
1               5                   10                  15

Xaa Ser Ala Xaa Lys Leu Leu Xaa Asp Ile Xaa
            20                  25

<210> SEQ ID NO 60
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (29)..(29)
<223> OTHER INFORMATION: Xaa = Beta-3 homo- Glycine

<400> SEQUENCE: 60

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Xaa Gly Thr
            20                  25                  30

<210> SEQ ID NO 61
<211> LENGTH: 31
```

```
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (29)..(29)
<223> OTHER INFORMATION: Xaa = Beta-3 homo- Glycine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 61

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Xaa Xaa Thr
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
```

```
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (31)..(31)
<223> OTHER INFORMATION: Xaa = Beta-3 homo- Threonine

<400> SEQUENCE: 62

His Xaa Asp Ala Xaa Phe Thr Glu Xaa Xaa Thr Lys Leu Arg Lys Xaa
 1               5                  10                  15

Leu Ala Ala Xaa Lys Tyr Xaa Asn Asp Leu Xaa Lys Gly Gly Xaa
                20                  25                  30

<210> SEQ ID NO 63
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
```

```
<222> LOCATION: (29)..(29)
<223> OTHER INFORMATION: Xaa = Beta-3 homo- Glycine
<220> FEATURE:
<221> NAME/KEY: MISC_FEATURE
<222> LOCATION: (31)..(31)
<223> OTHER INFORMATION: Xaa = Beta-3 homo- Threonine

<400> SEQUENCE: 63

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Xaa Gly Xaa
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine
<220> FEATURE:
<221> NAME/KEY: MISC_FEATURE
<222> LOCATION: (31)..(31)
<223> OTHER INFORMATION: Xaa = Beta-3 homo- Threonine

<400> SEQUENCE: 64

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Gly Xaa Xaa
            20                  25                  30

<210> SEQ ID NO 65
<211> LENGTH: 27
<212> TYPE: PRT
```

<213> ORGANISM: Homo sapiens

<400> SEQUENCE: 65

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25

<210> SEQ ID NO 66
<211> LENGTH: 28
<212> TYPE: PRT
<213> ORGANISM: Homo sapiens

<400> SEQUENCE: 66

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 67
<211> LENGTH: 9
<212> TYPE: PRT
<213> ORGANISM: Artificial Sequence
<220> FEATURE:
<223> OTHER INFORMATION: VIP analog polypeptide

<400> SEQUENCE: 67

His Ser Asp Ala Val Phe Thr Asp Asn
1               5

<210> SEQ ID NO 68
<211> LENGTH: 10
<212> TYPE: PRT
<213> ORGANISM: Artificial Sequence
<220> FEATURE:
<223> OTHER INFORMATION: VIP analog polypeptide

<400> SEQUENCE: 68

His Ser Asp Ala Val Phe Thr Asp Asn Tyr
1               5                   10

<210> SEQ ID NO 69
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine

<400> SEQUENCE: 69

His Xaa Asp Ala Val Phe Thr Asn Ser Tyr Arg Lys Val Leu Lys Arg
1               5                   10                  15

Leu Ser Ala Arg Lys Leu Leu Gln Asp Ile Leu
            20                  25

<210> SEQ ID NO 70
<211> LENGTH: 10
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE -continued

```
<222> LOCATION: (2)..(2)
<223> OTHER INFORMATION: Xaa = d-Phenylalanine

<400> SEQUENCE: 70

His Xaa Asp Ala Val Phe Thr Asn Ser Tyr
1               5                   10

<210> SEQ ID NO 71
<211> LENGTH: 9
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine

<400> SEQUENCE: 71

His Xaa Asp Ala Val Phe Thr Asp Asn
1               5

<210> SEQ ID NO 72
<211> LENGTH: 10
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine

<400> SEQUENCE: 72

His Xaa Asp Ala Val Phe Thr Asp Asn Tyr
1               5                   10

<210> SEQ ID NO 73
<211> LENGTH: 9
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine

<400> SEQUENCE: 73

His Xaa Asp Ala Val Phe Thr Asn Ser
1               5

<210> SEQ ID NO 74
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (11)..(11)
<223> OTHER INFORMATION: Xaa = 3-Aminopyrrolidine-4-carboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
```

```
<221> NAME/KEY: MISC_FEATURE
<222> LOCATION: (18)..(18)
<223> OTHER INFORMATION: Xaa = 2-aminocyclopentanecarboxylic Acid

<400> SEQUENCE: 74

His Xaa Asp Ala Val Phe Thr Asn Ser Tyr Xaa Lys Val Xaa Lys Arg
1               5                   10                  15

Leu Xaa Ala Arg Lys Leu Leu Gln Asp Ile Leu
            20                  25

<210> SEQ ID NO 75
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid

<400> SEQUENCE: 75

His Xaa Asp Ala Val Phe Thr Asn Ser Tyr Arg Lys Val Xaa Lys Arg
1               5                   10                  15

Leu Xaa Ala Arg Xaa Leu Leu Gln Asp Ile Leu
            20                  25

<210> SEQ ID NO 76
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 76

His Xaa Asp Ala Val Phe Thr Asn Ser Tyr Arg Lys Val Xaa Lys Arg
1               5                   10                  15

Leu Xaa Ala Arg Lys Leu Leu Gln Xaa Ile Leu
            20                  25

<210> SEQ ID NO 77
<211> LENGTH: 27
```

```
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (11)..(11)
<223> OTHER INFORMATION: Xaa = 3-Aminopyrrolidine-4-carboxylic Acid
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 77

His Xaa Asp Ala Val Phe Thr Asn Ser Tyr Xaa Lys Val Xaa Lys Arg
1               5                   10                  15

Leu Xaa Ala Arg Xaa Leu Leu Gln Xaa Ile Leu
            20                  25

<210> SEQ ID NO 78
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 78

His Xaa Asp Ala Val Phe Thr Asn Ser Tyr Arg Lys Val Leu Xaa Arg
1               5                   10                  15

Leu Xaa Ala Arg Lys Leu Leu Gln Xaa Ile Leu
            20                  25

<210> SEQ ID NO 79
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
```

```
<223> OTHER INFORMATION: Xaa = d-Phenylalanine
<220> FEATURE:
<221> NAME/KEY: MISC_FEATURE
<222> LOCATION: (11)..(11)
<223> OTHER INFORMATION: Xaa = 3-Aminopyrrolidine-4-carboxylic Acid
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 79

His Xaa Asp Ala Val Phe Thr Asn Ser Tyr Xaa Lys Val Leu Xaa Arg
1               5                   10                  15

Leu Xaa Ala Arg Lys Leu Leu Gln Xaa Ile Leu
            20                  25

<210> SEQ ID NO 80
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 80

His Xaa Asp Ala Val Phe Thr Asn Ser Tyr Arg Lys Val Xaa Lys Arg
1               5                   10                  15

Leu Ser Ala Arg Xaa Leu Leu Xaa Asp Ile Leu
            20                  25

<210> SEQ ID NO 81
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
```

```
<222> LOCATION: (24)..(24)
<223> OTHER INFORMATION: Xaa = 2-aminocyclopentanecarboxylic Acid

<400> SEQUENCE: 81

His Xaa Asp Ala Val Phe Thr Asn Ser Tyr Arg Lys Val Xaa Lys Arg
1               5                   10                  15

Xaa Ser Ala Arg Lys Leu Leu Xaa Asp Ile Leu
            20                  25

<210> SEQ ID NO 82
<211> LENGTH: 27
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = d-Phenylalanine
<220> FEATURE:
<221> NAME/KEY: MISC_FEATURE
<222> LOCATION: (14)..(14)
<223> OTHER INFORMATION: Xaa = 2-aminocyclopentanecarboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 82

His Xaa Asp Ala Val Phe Thr Asn Ser Tyr Arg Lys Val Xaa Lys Arg
1               5                   10                  15

Xaa Ser Ala Arg Xaa Leu Leu Xaa Asp Ile Leu
            20                  25

<210> SEQ ID NO 83
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (25)..(25)
<223> OTHER INFORMATION: Xaa = Beta-3 homo- Alanine

<400> SEQUENCE: 83

His Ser Asp Ala Val Phe Thr Asp Asn Tyr Thr Arg Leu Arg Lys Gln
1               5                   10                  15

Xaa Ala Val Lys Lys Tyr Leu Asn Xaa Ile Leu Asn
            20                  25

<210> SEQ ID NO 84
<211> LENGTH: 28
<212> TYPE: PRT
<213> ORGANISM: Artificial Sequence
<220> FEATURE:
<223> OTHER INFORMATION: VIP analog polypeptide
<220> FEATURE:
```

```
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (14)..(14)
<223> OTHER INFORMATION: Xaa = Beta-3 homo- Arginine
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MISC_FEATURE
<222> LOCATION: (21)..(21)
<223> OTHER INFORMATION: Xaa = Beta-3 homo- Lysine
<220> FEATURE:
<221> NAME/KEY: MISC_FEATURE
<222> LOCATION: (25)..(25)
<223> OTHER INFORMATION: Xaa = Beta-3 homo- Alanine
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 84

His Ser Asp Ala Val Phe Thr Asp Asn Tyr Xaa Arg Leu Xaa Lys Gln
1               5                   10                  15

Leu Xaa Val Lys Xaa Tyr Leu Asn Xaa Ile Xaa Xaa
            20                  25

<210> SEQ ID NO 85
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (18)..(18)
<223> OTHER INFORMATION: Xaa = Beta-3 homo- Alanine
<220> FEATURE:
<221> NAME/KEY: MISC_FEATURE
<222> LOCATION: (22)..(22)
<223> OTHER INFORMATION: Xaa = Beta-3 homo- Tyrosine
<220> FEATURE:
<221> NAME/KEY: MISC_FEATURE
<222> LOCATION: (25)..(25)
<223> OTHER INFORMATION: Xaa = Beta-3 homo- Alanine

<400> SEQUENCE: 85

His Ser Asp Ala Val Phe Thr Asp Asn Tyr Xaa Arg Leu Arg Xaa Gln
1               5                   10                  15

Leu Xaa Val Lys Lys Xaa Leu Asn Xaa Ile Leu Asn
            20                  25

<210> SEQ ID NO 86
<211> LENGTH: 28
<212> TYPE: PRT
<213> ORGANISM: Artificial Sequence
<220> FEATURE:
<223> OTHER INFORMATION: VIP analog polypeptide
```

```
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = Beta-3 homo- Arginine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (21)..(21)
<223> OTHER INFORMATION: Xaa = Beta-3 homo- Lysine
<220> FEATURE:
<221> NAME/KEY: MISC_FEATURE
<222> LOCATION: (24)..(24)
<223> OTHER INFORMATION: Xaa = Beta-3 homo- Asparagine
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 86

His Ser Asp Ala Val Phe Thr Asp Asn Xaa Thr Arg Leu Xaa Lys Gln
1               5                   10                  15

Xaa Ala Val Lys Xaa Tyr Leu Xaa Ala Ile Xaa Xaa
            20                  25

<210> SEQ ID NO 87
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = Beta-3 homo- Lysine
<220> FEATURE:
<221> NAME/KEY: MISC_FEATURE
<222> LOCATION: (25)..(25)
<223> OTHER INFORMATION: Xaa = 2-aminocyclopentanecarboxylic Acid
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 87

His Ser Asp Ala Val Phe Thr Asp Asn Tyr Xaa Arg Leu Xaa Lys Gln
1               5                   10                  15

Leu Xaa Val Lys Xaa Tyr Leu Asn Xaa Ile Leu Xaa
            20                  25

<210> SEQ ID NO 88
```

```
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 88

His Ser Asp Ala Val Phe Thr Asp Asn Tyr Xaa Arg Leu Xaa Lys Gln
1               5                   10                  15

Leu Xaa Val Lys Xaa Tyr Leu Asn Xaa Ile Xaa Xaa
            20                  25

<210> SEQ ID NO 89
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = Beta-3 homo- Lysine
<220> FEATURE:
<221> NAME/KEY: MISC_FEATURE
<222> LOCATION: (25)..(25)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 89
```

```
His Ser Asp Ala Val Phe Thr Asp Asn Tyr Xaa Arg Leu Xaa Lys Gln
1               5                   10                  15

Leu Xaa Val Lys Xaa Tyr Leu Asn Xaa Ile Xaa Xaa
            20                  25

<210> SEQ ID NO 90
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 90

His Ser Asp Ala Val Phe Thr Asp Asn Tyr Xaa Arg Leu Xaa Lys Gln
1               5                   10                  15

Leu Xaa Val Lys Xaa Tyr Leu Asn Xaa Ile Xaa Xaa
            20                  25

<210> SEQ ID NO 91
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (22)..(22)
<223> OTHER INFORMATION: Xaa = Beta-3 homo- Tyrosine
<220> FEATURE:
<221> NAME/KEY: MISC_FEATURE
<222> LOCATION: (25)..(25)
<223> OTHER INFORMATION: Xaa = 2-aminocyclopentanecarboxylic Acid
```

```
<400> SEQUENCE: 91

His Ser Asp Ala Val Phe Thr Asp Asn Tyr Xaa Arg Leu Arg Xaa Gln
1               5                   10                  15

Leu Xaa Val Lys Lys Xaa Leu Asn Xaa Ile Leu Asn
            20                  25

<210> SEQ ID NO 92
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (22)..(22)
<223> OTHER INFORMATION: Xaa = Beta-3 homo- Tyrosine
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 92

His Ser Asp Ala Val Phe Thr Asp Asn Tyr Xaa Arg Leu Arg Xaa Gln
1               5                   10                  15

Leu Xaa Val Lys Lys Xaa Leu Asn Xaa Ile Leu Asn
            20                  25

<210> SEQ ID NO 93
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine
```

```
<400> SEQUENCE: 93

His Ser Asp Ala Val Phe Thr Asp Asn Xaa Thr Arg Leu Xaa Lys Gln
1               5                   10                  15

Xaa Ala Val Lys Xaa Tyr Leu Xaa Ala Ile Xaa Xaa
            20                  25

<210> SEQ ID NO 94
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = Beta-3 homo- Lysine
<220> FEATURE:
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 94

His Ser Asp Ala Val Phe Thr Asp Asn Xaa Thr Arg Leu Xaa Lys Gln
1               5                   10                  15

Xaa Ala Val Lys Xaa Tyr Leu Xaa Ala Ile Xaa Xaa
            20                  25

<210> SEQ ID NO 95
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
```

```
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Leucine
<220> FEATURE:
<221> NAME/KEY: MISC_FEATURE
<222> LOCATION: (28)..(28)
<223> OTHER INFORMATION: Xaa = Beta-3 homo- Asparagine

<400> SEQUENCE: 95

His Ser Asp Ala Val Phe Thr Asp Asn Xaa Thr Arg Leu Xaa Lys Gln
1               5                   10                  15

Xaa Ala Val Lys Xaa Tyr Leu Xaa Ala Ile Xaa Xaa
            20                  25

<210> SEQ ID NO 96
<211> LENGTH: 31
<212> TYPE: PRT
<213> ORGANISM: Artificial Sequence
<220> FEATURE:
<223> OTHER INFORMATION: VIP analog polypeptide

<400> SEQUENCE: 96

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid

<400> SEQUENCE: 97

His Ser Asp Ala Val Phe Thr Asp Asn Tyr Xaa Arg Leu Xaa Lys Gln
1               5                   10                  15

Val Xaa Ala Lys Lys Tyr Leu Gln Ser Ile Lys Asn Lys Arg Tyr
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
```

<222> LOCATION: (21)..(21)
<223> OTHER INFORMATION: Xaa = 3-Aminopyrrolidine-4-carboxylic Acid

<400> SEQUENCE: 98

His Ser Asp Ala Val Phe Thr Asp Asn Tyr Thr Arg Leu Xaa Lys Gln
1               5                   10                  15

Val Xaa Ala Lys Xaa Tyr Leu Gln Ser Ile Lys Asn Lys Arg Tyr
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 99

His Ser Asp Ala Val Phe Thr Asp Asn Tyr Thr Arg Leu Xaa Lys Gln
1               5                   10                  15

Val Xaa Ala Lys Lys Tyr Leu Gln Xaa Ile Lys Asn Lys Arg Tyr
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid
<220> FEATURE:
<221> NAME/KEY: MISC_FEATURE
<222> LOCATION: (28)..(28)
<223> OTHER INFORMATION: Xaa = 2-aminocyclopentanecarboxylic Acid

<400> SEQUENCE: 100

His Ser Asp Ala Val Phe Thr Asp Asn Tyr Xaa Arg Leu Xaa Lys Gln
1               5                   10                  15

Val Xaa Ala Lys Xaa Tyr Leu Gln Xaa Ile Lys Xaa Lys Arg Tyr
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 101

His Ser Asp Ala Val Phe Thr Asp Asn Tyr Thr Arg Leu Arg Xaa Gln
1               5                   10                  15

Val Xaa Ala Lys Lys Tyr Leu Gln Xaa Ile Lys Asn Lys Arg Tyr
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (11)..(11)
<223> OTHER INFORMATION: Xaa = 2-aminocyclopentanecarboxylic Acid
<220> FEATURE:
<221> NAME/KEY: MISC_FEATURE
<222> LOCATION: (15)..(15)
<223> OTHER INFORMATION: Xaa = 3-Aminopyrrolidine-4-carboxylic Acid
<220> FEATURE:
<221> NAME/KEY: MISC_FEATURE
<222> LOCATION: (18)..(18)
<223> OTHER INFORMATION: Xaa = 2-aminocyclopentanecarboxylic Acid
<220> FEATURE:
<221> NAME/KEY: MISC_FEATURE
<222> LOCATION: (25)..(25)
<223> OTHER INFORMATION: Xaa = 2-aminocyclopentanecarboxylic Acid

<400> SEQUENCE: 102

His Ser Asp Ala Val Phe Thr Asp Asn Tyr Xaa Arg Leu Arg Xaa Gln
1               5                   10                  15

Val Xaa Ala Lys Lys Tyr Leu Gln Xaa Ile Lys Asn Lys Arg Tyr
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

```
<400> SEQUENCE: 103

His Ser Asp Ala Val Phe Thr Asp Asn Tyr Thr Arg Leu Xaa Lys Gln
1               5                   10                  15

Val Ser Ala Lys Xaa Tyr Leu Xaa Ser Ile Lys Asn Lys Arg Tyr
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 104

His Ser Asp Ala Val Phe Thr Asp Asn Tyr Thr Arg Leu Xaa Lys Gln
1               5                   10                  15

Xaa Ser Ala Lys Lys Tyr Leu Xaa Ser Ile Lys Asn Lys Arg Tyr
            20                  25                  30

<210> SEQ ID NO 105
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 105

His Ser Asp Ala Val Phe Thr Asp Asn Tyr Thr Arg Leu Xaa Lys Gln
1               5                   10                  15

Xaa Ser Ala Lys Xaa Tyr Leu Xaa Ser Ile Lys Asn Lys Arg Tyr
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
```

```
<223> OTHER INFORMATION: Xaa = 3-Aminopyrrolidine-4-carboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 106

His Ser Asp Ala Val Phe Thr Asp Asn Tyr Thr Arg Leu Xaa Lys Gln
1               5                   10                  15

Val Ala Ala Lys Xaa Tyr Leu Xaa Ser Ile Lys Asn Lys Arg Tyr
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 107

His Ser Asp Ala Val Phe Thr Asp Asn Tyr Thr Arg Leu Xaa Lys Gln
1               5                   10                  15

Xaa Ala Ala Lys Lys Tyr Leu Xaa Ser Ile Lys Asn Lys Arg Tyr
            20                  25                  30

<210> SEQ ID NO 108
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (14)..(14)
<223> OTHER INFORMATION: Xaa = 3-Aminopyrrolidine-4-carboxylic Acid
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (21)..(21)
<223> OTHER INFORMATION: Xaa = 3-Aminopyrrolidine-4-carboxylic Acid
<220> FEATURE:
<221> NAME/KEY: MISC_FEATURE
<222> LOCATION: (24)..(24)
<223> OTHER INFORMATION: Xaa = 2-aminocyclopentanecarboxylic Acid

<400> SEQUENCE: 108

His Ser Asp Ala Val Phe Thr Asp Asn Tyr Thr Arg Leu Xaa Lys Gln
1               5                   10                  15

Xaa Ala Ala Lys Xaa Tyr Leu Xaa Ser Ile Lys Asn Lys Arg Tyr
            20                  25                  30
```

<210> SEQ ID NO 109
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (19)..(19)
<223> OTHER INFORMATION: Xaa = 2-aminocyclopentanecarboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (26)..(26)
<223> OTHER INFORMATION: Xaa = Beta-3 homo- Leucine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 109

His Ser Asp Ala Val Phe Thr Glu Asn Tyr Thr Lys Leu Arg Lys Gln
1               5                   10                  15

Leu Ala Xaa Lys Lys Tyr Xaa Asn Asp Xaa Lys Lys Gly Xaa Thr
            20                  25                  30

<210> SEQ ID NO 110
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 110

His Ser Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (17)..(17)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:

```
<221> NAME/KEY: MISC_FEATURE
<222> LOCATION: (24)..(24)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine

<400> SEQUENCE: 111

His Ser Asp Ala Val Phe Thr Glu Asn Tyr Thr Lys Leu Arg Lys Gln
1               5                   10                  15

Xaa Ala Ala Xaa Lys Tyr Leu Xaa Asp Leu Xaa Lys Gly Gly Thr
            20                  25                  30

<210> SEQ ID NO 112
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 112

His Xaa Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 113
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
```

<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 113

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MOD_RES
<222> LOCATION: (2)..(2)
<223> OTHER INFORMATION: Xaa = AIB
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 114

His Xaa Asp Ala Xaa Phe Thr Glu Xaa Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 115
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)

```
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 115

His Xaa Asp Ala Val Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 116

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 117
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
```

```
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 117

His Xaa Asp Ala Xaa Phe Thr Glu Xaa Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 118
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 118

His Xaa Asp Ala Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
```

<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 119

His Phe Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 120

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Phenylalanine

```
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 121

His Xaa Asp Ala Xaa Phe Thr Asp Xaa Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (3)..(3)
<223> OTHER INFORMATION: Xaa = Beta-3 homo- Aspartic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 122

His Phe Xaa Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
```

```
                    20                  25

<210> SEQ ID NO 123
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 123

His Xaa Asp Ala Xaa Phe Thr Glu Asn Tyr Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 124
```

```
His Xaa Asp Ala Xaa Phe Thr Glu Asn Tyr Thr Lys Leu Arg Lys Gln
1               5                   10                  15

Xaa Ala Ala Xaa Lys Tyr Xaa Asn Asp Leu Xaa Lys Gly Xaa Thr
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 125

His Xaa Asp Ala Xaa Phe Thr Glu Asn Tyr Thr Lys Leu Arg Lys Xaa
1               5                   10                  15

Leu Ala Ala Xaa Lys Tyr Xaa Asn Asp Leu Xaa Lys Gly Xaa Thr
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
```

<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 126

His Xaa Asp Ala Xaa Phe Thr Glu Asn Tyr Thr Lys Leu Arg Xaa Gln
1               5                   10                  15

Leu Ala Ala Xaa Lys Tyr Xaa Asn Asp Leu Xaa Lys Gly Xaa Thr
            20                  25                  30

<210> SEQ ID NO 127
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (14)..(14)
<223> OTHER INFORMATION: Xaa = Beta-3 homo- Arginine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 127

His Xaa Asp Ala Xaa Phe Thr Glu Asn Tyr Thr Lys Leu Xaa Lys Gln
1               5                   10                  15

Leu Ala Ala Xaa Lys Tyr Xaa Asn Asp Leu Xaa Lys Gly Xaa Thr
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (13)..(13)
<223> OTHER INFORMATION: Xaa = Beta-3 homo- Leucine

```
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 128

His Xaa Asp Ala Xaa Phe Thr Glu Asn Tyr Thr Lys Xaa Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 129

His Xaa Asp Ala Xaa Phe Thr Glu Xaa Xaa Thr Lys Leu Arg Lys Gln
1               5                   10                  15

Leu Ala Ala Xaa Lys Tyr Xaa Asn Asp Leu Xaa Lys Gly Xaa Thr
            20                  25                  30

<210> SEQ ID NO 130
<211> LENGTH: 31
<212> TYPE: PRT
<213> ORGANISM: Artificial Sequence
<220> FEATURE:
```

```
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (17)..(17)
<223> OTHER INFORMATION: Xaa = Beta-3 homo- Leucine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 130

His Xaa Asp Ala Xaa Phe Thr Glu Xaa Xaa Thr Lys Leu Arg Lys Gln
1               5                   10                  15

Xaa Ala Ala Xaa Lys Tyr Xaa Asn Asp Leu Xaa Lys Gly Xaa Thr
            20                  25                  30

<210> SEQ ID NO 131
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (16)..(16)
<223> OTHER INFORMATION: Xaa = Beta-3 homo- Glutamine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
```

<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 131

His Xaa Asp Ala Xaa Phe Thr Glu Xaa Xaa Thr Lys Leu Arg Lys Xaa
1               5                   10                  15

Leu Ala Ala Xaa Lys Tyr Xaa Asn Asp Leu Xaa Lys Gly Xaa Thr
            20                  25                  30

<210> SEQ ID NO 132
<211> LENGTH: 31
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = 2-aminocyclopentanecarboxylic Acid
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (9)..(9)
<223> OTHER INFORMATION: Xaa = 2-aminocyclopentanecarboxylic Acid
<220> FEATURE:
<221> NAME/KEY: MISC_FEATURE
<222> LOCATION: (10)..(10)
<223> OTHER INFORMATION: Xaa = Beta-3 homo- Tyrosine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (20)..(20)
<223> OTHER INFORMATION: Xaa = 3-Aminopyrrolidine-4-carboxylic Acid
<220> FEATURE:
<221> NAME/KEY: MISC_FEATURE
<222> LOCATION: (23)..(23)
<223> OTHER INFORMATION: Xaa = 2-aminocyclopentanecarboxylic Acid
<220> FEATURE:
<221> NAME/KEY: MISC_FEATURE
<222> LOCATION: (27)..(27)
<223> OTHER INFORMATION: Xaa = Beta-3 homo- Lysine
<220> FEATURE:
<221> NAME/KEY: MISC_FEATURE
<222> LOCATION: (30)..(30)
<223> OTHER INFORMATION: Xaa = Beta-3 homo- Glycine

<400> SEQUENCE: 132

His Xaa Asp Ala Xaa Phe Thr Glu Xaa Xaa Thr Lys Leu Arg Xaa Gln
1               5                   10                  15

Leu Ala Ala Xaa Lys Tyr Xaa Asn Asp Leu Xaa Lys Gly Xaa Thr
            20                  25                  30

<210> SEQ ID NO 133
<211> LENGTH: 10
<212> TYPE: PRT
<213> ORGANISM: Artificial Sequence
<220> FEATURE:
<223> OTHER INFORMATION: VIP fragment 1

<400> SEQUENCE: 133

His Ser Asp Ala Val Phe Thr Asp Asn Tyr
1               5                   10

<210> SEQ ID NO 134
<211> LENGTH: 9
<212> TYPE: PRT
<213> ORGANISM: Artificial Sequence
<220> FEATURE:
<223> OTHER INFORMATION: VIP fragment 2

<400> SEQUENCE: 134

His Ser Asp Ala Val Phe Thr Asp Asn
1               5

<210> SEQ ID NO 135
<211> LENGTH: 27
<212> TYPE: PRT
<213> ORGANISM: Artificial Sequence
<220> FEATURE:
<223> OTHER INFORMATION: VIP analog with D-phe
<220> FEATURE:
<221> NAME/KEY: MISC_FEATURE
<222> LOCATION: (2)..(2)
<223> OTHER INFORMATION: Xaa= D-phenylalanine

<400> SEQUENCE: 135

His Xaa Asp Ala Val Phe Thr Asn Ser Tyr Arg Lys Val Leu Lys Arg
1               5                   10                  15

Leu Ser Ala Arg Lys Leu Leu Gln Asp Ile Leu
            20                  25

<210> SEQ ID NO 136
<211> LENGTH: 10
<212> TYPE: PRT
<213> ORGANISM: Artificial Sequence
<220> FEATURE:
<223> OTHER INFORMATION: VIP analog fragment with D-phe
<220> FEATURE:
<221> NAME/KEY: MISC_FEATURE
<222> LOCATION: (2)..(2)
<223> OTHER INFORMATION: Xaa= D-phenylalanine

<400> SEQUENCE: 136

His Xaa Asp Ala Val Phe Thr Asn Ser Tyr
1               5                   10

<210> SEQ ID NO 137
<211> LENGTH: 9
<212> TYPE: PRT
<213> ORGANISM: Artificial Sequence
<220> FEATURE:
<223> OTHER INFORMATION: VIP analog fragment 2 with D-Phe
<220> FEATURE:
<221> NAME/KEY: MISC_FEATURE
<222> LOCATION: (2)..(2)
<223> OTHER INFORMATION: Xaa= D-Phe

<400> SEQUENCE: 137

His Xaa Asp Ala Val Phe Thr Asp Asn
1               5

<210> SEQ ID NO 138
<211> LENGTH: 10
<212> TYPE: PRT
<213> ORGANISM: Artificial Sequence
<220> FEATURE:
<223> OTHER INFORMATION: VIP analog fragment 3

<400> SEQUENCE: 138

Phe Thr Glu Asn Tyr Thr Lys Leu Arg Lys
1               5                   10

<210> SEQ ID NO 139
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Phenylalanine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 139

His Xaa Asp Ala Val Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Phenylalanine
<220> FEATURE:
<221> NAME/KEY: MISC_FEATURE
<222> LOCATION: (5)..(5)
<223> OTHER INFORMATION: Xaa = 2-aminocyclopentanecarboxylic Acid
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 140

His Phe Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Phenylalanine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 141

His Xaa Asp Ala Xaa Phe Thr Asp Asn Tyr Xaa Arg Leu Arg Xaa Gln
1               5                   10                  15

Leu Ala Xaa Lys Lys Tyr Xaa Asn Ala Ile Xaa Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Serine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:

```
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 142

His Xaa Asp Ala Xaa Phe Thr Asp Asn Tyr Xaa Arg Leu Arg Xaa Gln
 1               5                  10                  15

Leu Ala Xaa Lys Lys Tyr Xaa Asn Ala Ile Xaa Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Serine
<220> FEATURE:
<221> NAME/KEY: MISC_FEATURE
<222> LOCATION: (5)..(5)
<223> OTHER INFORMATION: Xaa = Beta-3 homo- Valine
<220> FEATURE:
<221> NAME/KEY: MISC_FEATURE
<222> LOCATION: (9)..(9)
<223> OTHER INFORMATION: Xaa = Beta-3 homo- Asparagine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 143

His Xaa Asp Ala Xaa Phe Thr Asp Xaa Tyr Xaa Arg Leu Arg Xaa Gln
 1               5                  10                  15

Leu Ala Xaa Lys Lys Tyr Xaa Asn Ala Ile Xaa Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: VIP analog polypeptide
<220> FEATURE:
<221> NAME/KEY: MISC_FEATURE
<222> LOCATION: (2)..(2)
<223> OTHER INFORMATION: Xaa = Beta-3 homo- Phenylalanine
```

```
<220> FEATURE:
<221> NAME/KEY: MISC_FEATURE
<222> LOCATION: (3)..(3)
<223> OTHER INFORMATION: Xaa = Beta-3 homo- Aspartic Acid
<220> FEATURE:
<221> NAME/KEY: MISC_FEATURE
<222> LOCATION: (7)..(7)
<223> OTHER INFORMATION: Xaa = Beta-3 homo- Threonine
<220> FEATURE:
<221> NAME/KEY: MISC_FEATURE
<222> LOCATION: (11)..(11)
<223> OTHER INFORMATION: Xaa = Beta-3 homo- Threonine
<220> FEATURE:
<221> NAME/KEY: MISC_FEATURE
<222> LOCATION: (15)..(15)
<223> OTHER INFORMATION: Xaa = Beta-3 homo- Lysine
<220> FEATURE:
<221> NAME/KEY: MISC_FEATURE
<222> LOCATION: (19)..(19)
<223> OTHER INFORMATION: Xaa = Beta-3 homo- Valine
<220> FEATURE:
<221> NAME/KEY: MISC_FEATURE
<222> LOCATION: (23)..(23)
<223> OTHER INFORMATION: Xaa = Beta-3 homo- Leucine
<220> FEATURE:
<221> NAME/KEY: MISC_FEATURE
<222> LOCATION: (27)..(27)
<223> OTHER INFORMATION: Xaa = Beta-3 homo- Leucine

<400> SEQUENCE: 144

His Xaa Xaa Ala Val Phe Xaa Asp Asn Tyr Xaa Arg Leu Arg Xaa Gln
1               5                   10                  15

Leu Ala Xaa Lys Lys Tyr Xaa Asn Ala Ile Xaa Asn
            20                  25
```